US012655160B2

(12) United States Patent
Wang et al.

(10) Patent No.: US 12,655,160 B2
(45) Date of Patent: Jun. 16, 2026

(54) KRAS G12D INHIBITORS

(71) Applicants: Mirati Therapeutics, Inc., Princeton, NJ (US); Array BioPharma Inc., Boulder, CO (US)

(72) Inventors: Xiaolun Wang, San Diego, CA (US); Matthew Arnold Marx, San Diego, CA (US); John David Lawson, Carlsbad, CA (US); Shelley Allen, Loveland, CO (US); Patrick Michael Barbour, Westminster, CO (US); James Francis Blake, Longmont, CO (US); Joshua Ryan Dahlke, Longmont, CO (US); Donghua Dai, Superior, CO (US); Jay Bradford Fell, Longmont, CO (US); John Peter Fischer, Longmont, CO (US); Sherif Hosam Hassanien, Westminster, CO (US); Michael Christopher Hilton, Fort Collins, CO (US); Macedonio Junior Mejia, Denver, CO (US); Jacob Matthew O'Leary, Denver, CO (US); Tony Pisal Tang, Boulder, CO (US)

(73) Assignees: Mirati Therapeutics, Inc., Princeton, NJ (US); Array BioPharma Inc., Boulder, CO (US)

( * ) Notice: Subject to any disclaimer, the term of this patent is extended or adjusted under 35 U.S.C. 154(b) by 568 days.

(21) Appl. No.: 18/020,013

(22) PCT Filed: Aug. 3, 2021

(86) PCT No.: PCT/US2021/044308
§ 371 (c)(1),
(2) Date: Feb. 6, 2023

(87) PCT Pub. No.: WO2022/031678
PCT Pub. Date: Feb. 10, 2022

(65) Prior Publication Data

US 2023/0339976 A1 Oct. 26, 2023

Related U.S. Application Data

(60) Provisional application No. 63/060,926, filed on Aug. 4, 2020.

(51) Int. Cl.
*C07D 519/00* (2006.01)
*C07D 471/04* (2006.01)

(52) U.S. Cl.
CPC ......... *C07D 519/00* (2013.01); *C07D 471/04* (2013.01)

(58) Field of Classification Search
CPC ............................ C07D 519/00; C07D 471/04
See application file for complete search history.

(56) References Cited

U.S. PATENT DOCUMENTS

| | | | |
|---|---|---|---|
| 6,924,284 | B2 | 8/2005 | Beaton et al. |
| 8,163,763 | B2 | 4/2012 | Bergeron et al. |
| 8,426,401 | B2 | 4/2013 | Bian et al. |
| 9,562,019 | B2 | 2/2017 | Djaballah et al. |
| 9,840,516 | B2 | 12/2017 | Li et al. |
| 10,125,134 | B2 | 11/2018 | Blake et al. |
| 2003/0191143 | A1 | 10/2003 | Pitts et al. |
| 2006/0229307 | A1 | 10/2006 | Blurton et al. |
| 2007/0021445 | A1 | 1/2007 | Berthel et al. |
| 2009/0312342 | A1 | 12/2009 | Wilson et al. |
| 2010/0081654 | A1 | 4/2010 | Stockwell et al. |
| 2011/0269244 | A1 | 11/2011 | Petter et al. |
| 2013/0029978 | A1 | 1/2013 | Kamino et al. |
| 2014/0288045 | A1 | 9/2014 | Ren et al. |
| 2015/0175558 | A1 | 6/2015 | Stockwell et al. |
| 2015/0239900 | A1 | 8/2015 | Li et al. |
| 2016/0031898 | A1 | 2/2016 | Ren et al. |
| 2016/0108019 | A1 | 4/2016 | Li et al. |
| 2016/0166571 | A1 | 6/2016 | Janes et al. |
| 2016/0229836 | A1 | 8/2016 | Stockwell et al. |
| 2016/0264627 | A1 | 9/2016 | Henning et al. |
| 2016/0297774 | A1 | 10/2016 | Li et al. |
| 2017/0022184 | A1 | 1/2017 | Li et al. |
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2017/0275289 | A1 | 9/2017 | Albrecht et al. |
| 2018/0015087 | A1 | 1/2018 | Liu et al. |
| 2018/0072723 | A1 | 3/2018 | Blake et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |

(Continued)

FOREIGN PATENT DOCUMENTS

| | | | |
|---|---|---|---|
| CN | 113999226 | A | 2/2022 |
| WO | 02/053558 | A1 | 7/2002 |

(Continued)

OTHER PUBLICATIONS

European Search Report Issued in European Application No. 21853488.1, Mailed on Jul. 22, 2024, 8 Pages.
International Search Report and Written Opinion Issued in International Application No. PCT/US2021/044308, Mailed on Dec. 30, 2021, 10 Pages.
PubChem-SID-132593111, Modify Date: May 31, 2019 (May 31, 2019), p. 2, figure, this is a purchasable chemical.
JP 2015-124211 A (Dainippon Sumitomo Pharma Co L TD) Jul. 6, 2015 (Jul. 6, 2015), especially: original document, p. 58, Table, formula 93.

(Continued)

*Primary Examiner* — Alicia L Otton
(74) *Attorney, Agent, or Firm* — Mintz, Levin, Cohn, Ferris, Glovsky and Popeo, P.C.

(57) ABSTRACT

The present invention relates to compounds that inhibit KRas G12D. In particular, the present invention relates to compounds that inhibit the activity of KRas G12D, pharmaceutical compositions comprising the compounds and methods of use therefor.

50 Claims, No Drawings

(56) References Cited

U.S. PATENT DOCUMENTS

| | | | |
|---|---|---|---|
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |
| 2018/0282308 | A1 | 10/2018 | Li et al. |
| 2018/0289683 | A1 | 10/2018 | Mccormick et al. |
| 2019/0144444 | A1 | 5/2019 | Blake et al. |
| 2019/0374542 | A1 | 12/2019 | Allen et al. |
| 2020/0069657 | A1 | 3/2020 | Lanman et al. |
| 2020/0262837 | A1 | 8/2020 | Marx et al. |
| 2020/0331911 | A1 | 10/2020 | Marx et al. |
| 2020/0399297 | A1 | 12/2020 | Campbell et al. |
| 2021/0024501 | A1 | 1/2021 | Liansheng et al. |
| 2021/0139517 | A1 | 5/2021 | Gill et al. |

FOREIGN PATENT DOCUMENTS

| | | | |
|---|---|---|---|
| WO | 02/087513 | A2 | 11/2002 |
| WO | 2007/146122 | A2 | 12/2007 |
| WO | 2008/009078 | A2 | 1/2008 |
| WO | 2009/047255 | A1 | 4/2009 |
| WO | 2010/014939 | A1 | 2/2010 |
| WO | 2010/120996 | A1 | 10/2010 |
| WO | 2013/155223 | A1 | 10/2013 |
| WO | 2014/143659 | A1 | 9/2014 |
| WO | 2014/152588 | A1 | 9/2014 |
| WO | 2016/049568 | A1 | 3/2015 |
| WO | 2015/054572 | A1 | 4/2015 |
| WO | 2016/025650 | A1 | 2/2016 |
| WO | 2016/044772 | A1 | 3/2016 |
| WO | 2016/049565 | A1 | 3/2016 |
| WO | 2016130460 | A2 | 8/2016 |
| WO | 2016/168540 | A1 | 10/2016 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/079864 | A1 | 5/2017 |
| WO | 2017/080980 | A1 | 5/2017 |
| WO | 2017/087528 | A1 | 5/2017 |
| WO | 2017/100546 | A1 | 6/2017 |
| WO | 2018/064510 | A1 | 4/2018 |
| WO | 2018/068017 | A1 | 4/2018 |
| WO | 2018/102452 | A2 | 6/2018 |
| WO | 2018/102453 | A1 | 6/2018 |
| WO | 2018/112420 | A1 | 6/2018 |
| WO | 2018/115380 | A1 | 6/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/195439 | A2 | 10/2018 |
| WO | 2018218070 | A2 | 11/2018 |
| WO | 2019/051291 | A1 | 3/2019 |
| WO | 2019099524 | A1 | 5/2019 |
| WO | 202063594 | | 4/2020 |
| WO | 202098488 | | 5/2020 |
| WO | 2020097537 | A2 | 5/2020 |
| WO | 2020118066 | A1 | 6/2020 |
| WO | 2020123395 | A1 | 6/2020 |
| WO | 2020146613 | A1 | 7/2020 |
| WO | 202027202 | | 8/2020 |
| WO | 2020163598 | | 8/2020 |
| WO | 2020165670 | | 8/2020 |
| WO | 2020169838 | | 8/2020 |
| WO | 2020171499 | | 8/2020 |
| WO | 2020172332 | | 8/2020 |
| WO | 2016164675 | A1 | 9/2020 |
| WO | 2020176693 | | 9/2020 |
| WO | 2020176963 | | 9/2020 |
| WO | 2020177629 | | 9/2020 |
| WO | 2020178282 | | 9/2020 |
| WO | 2020181142 | | 9/2020 |
| WO | 2020198125 | | 10/2020 |
| WO | 2020204359 | | 10/2020 |
| WO | 2020205473 | | 10/2020 |
| WO | 2020205486 | | 10/2020 |
| WO | 2020212895 | | 10/2020 |
| WO | 2020214537 | | 10/2020 |
| WO | 2020221239 | | 11/2020 |
| WO | 2020230028 | | 11/2020 |
| WO | 2020230091 | | 11/2020 |
| WO | 2020231806 | | 11/2020 |
| WO | 2020231808 | | 11/2020 |
| WO | 2020232130 | | 11/2020 |
| WO | 2020233592 | | 11/2020 |
| WO | 2020234103 | | 11/2020 |
| WO | 2020236940 | | 11/2020 |
| WO | 2020236947 | | 11/2020 |
| WO | 2020236948 | | 11/2020 |
| WO | 2020247914 | | 12/2020 |
| WO | 2020252336 | | 12/2020 |
| WO | 2020252353 | | 12/2020 |
| WO | 2021000885 | | 1/2021 |
| WO | 2021023154 | | 2/2021 |
| WO | 2021023247 | | 2/2021 |
| WO | 2021027911 | | 2/2021 |
| WO | 2021027943 | | 2/2021 |
| WO | 2021031952 | | 2/2021 |
| WO | 2021034992 | | 2/2021 |
| WO | 2021037018 | | 3/2021 |
| WO | 2021041671 | | 3/2021 |
| WO | 2021043322 | | 3/2021 |
| WO | 2021045279 | | 3/2021 |
| WO | 2021050732 | | 3/2021 |
| WO | 2021051034 | | 3/2021 |
| WO | 2021052499 | | 3/2021 |
| WO | 2021055728 | | 3/2021 |
| WO | 2021057832 | | 4/2021 |
| WO | 2021058018 | | 4/2021 |
| WO | 2021061515 | | 4/2021 |
| WO | 2021061749 | | 4/2021 |
| WO | 2021063346 | | 4/2021 |
| WO | 2021068898 | | 4/2021 |
| WO | 2021075147 | | 4/2021 |
| WO | 2021076655 | | 4/2021 |
| WO | 2021078285 | | 4/2021 |
| WO | 2021078312 | | 4/2021 |
| WO | 2021080359 | | 4/2021 |
| WO | 2021081212 | | 4/2021 |
| WO | 2021083167 | | 5/2021 |
| WO | 2021084765 | | 5/2021 |
| WO | 2021085653 | | 5/2021 |
| WO | 2021086833 | | 5/2021 |
| WO | 2021088458 | | 5/2021 |
| WO | 2021088938 | | 5/2021 |
| WO | 2021091956 | | 5/2021 |
| WO | 2021091967 | | 5/2021 |
| WO | 2021091982 | | 5/2021 |
| WO | 2021093758 | A1 | 5/2021 |
| WO | 2021104431 | A1 | 6/2021 |
| WO | 2021106230 | A1 | 6/2021 |
| WO | 2021106231 | A1 | 6/2021 |
| WO | 2021107160 | A1 | 6/2021 |
| WO | 2021108683 | A1 | 6/2021 |
| WO | 2021109737 | A1 | 6/2021 |
| WO | 2021113595 | A1 | 6/2021 |
| WO | 2021120045 | A1 | 6/2021 |
| WO | 2021121330 | A1 | 6/2021 |
| WO | 2021121367 | A1 | 6/2021 |

(56) References Cited

FOREIGN PATENT DOCUMENTS

| | | | |
|---|---|---|---|
| WO | 2021121371 | A1 | 6/2021 |
| WO | 2021121397 | A1 | 6/2021 |
| WO | 2021126120 | A1 | 6/2021 |
| WO | 2021126799 | A1 | 6/2021 |
| WO | 2021127404 | A1 | 6/2021 |
| WO | 2021129820 | A1 | 7/2021 |
| WO | 2021129824 | A1 | 7/2021 |
| WO | 2021139678 | A1 | 7/2021 |
| WO | 2021139748 | A1 | 7/2021 |
| WO | 2021141628 | A1 | 7/2021 |
| WO | 2021142252 | A1 | 7/2021 |
| WO | 2021143693 | A1 | 7/2021 |
| WO | 2021145520 | A1 | 7/2021 |
| WO | 2021145521 | A1 | 7/2021 |
| WO | 2021147965 | A1 | 7/2021 |
| WO | 2021147967 | A1 | 7/2021 |
| WO | 2021150613 | A1 | 7/2021 |
| WO | 2021152149 | A1 | 8/2021 |
| WO | 2021168193 | A1 | 8/2021 |
| WO | 2021169963 | A1 | 9/2021 |
| WO | 2021169990 | A1 | 9/2021 |
| WO | 2021173923 | A1 | 9/2021 |
| WO | 2021175199 | A1 | 9/2021 |
| WO | 2021177721 | A1 | 9/2021 |
| WO | 2021178740 | A2 | 9/2021 |
| WO | 2021178741 | A1 | 9/2021 |
| WO | 2021180181 | A1 | 9/2021 |
| WO | 2021185233 | A1 | 9/2021 |
| WO | 2021190467 | A2 | 9/2021 |
| WO | 2021197499 | A1 | 10/2021 |
| WO | 2021203768 | A1 | 10/2021 |
| WO | 2021207172 | A1 | 10/2021 |
| WO | 2021211864 | A1 | 10/2021 |
| WO | 2021215544 | A1 | 10/2021 |
| WO | 2021216770 | A1 | 10/2021 |
| WO | 2021217019 | A1 | 10/2021 |
| WO | 2021090855 | A1 | 11/2021 |
| WO | 2021218110 | A1 | 11/2021 |
| WO | 2021219072 | A1 | 11/2021 |
| WO | 2021219090 | A2 | 11/2021 |
| WO | 2021219091 | A1 | 11/2021 |
| WO | 2021228161 | A1 | 11/2021 |
| WO | 2021231526 | A1 | 11/2021 |
| WO | 2021236475 | A1 | 11/2021 |
| WO | 2021239058 | A1 | 12/2021 |
| WO | 2021243280 | A1 | 12/2021 |
| WO | 2021244603 | A1 | 12/2021 |
| WO | 2021245051 | A1 | 12/2021 |
| WO | 2021245055 | A1 | 12/2021 |
| WO | 2021245499 | A1 | 12/2021 |
| WO | 2021248079 | A1 | 12/2021 |
| WO | 2021248082 | A1 | 12/2021 |
| WO | 2021248083 | A1 | 12/2021 |
| WO | 2021248090 | A1 | 12/2021 |
| WO | 2021248095 | A1 | 12/2021 |
| WO | 2021249563 | A1 | 12/2021 |
| WO | 2021252339 | A1 | 12/2021 |
| WO | 2021257828 | A1 | 12/2021 |
| WO | 2021259331 | A1 | 12/2021 |
| WO | 2022002102 | A1 | 1/2022 |
| WO | 2022015375 | A1 | 1/2022 |
| WO | 2022017339 | A1 | 1/2022 |
| WO | 2022028346 | A1 | 2/2022 |
| WO | 2022028492 | A1 | 2/2022 |
| WO | 2022031678 | A1 | 2/2022 |
| WO | 2022036176 | A1 | 2/2022 |
| WO | 2022258974 | A1 | 12/2022 |
| WO | 2023039240 | A1 | 3/2023 |

OTHER PUBLICATIONS

Bakalova et al. "Electronic absorption and emission spectra and computational studies of some 2-aryl, 2-styryl, and 2-(40-aryl)butadienyl quinazolin-4-ones", Journal of Molecular Structure (Theochem). 2004. 710, 229-234, especially: p. 230, Scheme 2.

Orlov et al. "Rapid Improvement of the Performance Status and Reduction of the Tumor Size in KRAS-Mutated Colorectal Cancer Patient Receiving Binimetinib, Hydroxychloroquine, and Bevacizumab", Case Rep Oncol. 2020. 13: pp. 985-989, para 3; p. 988, para 4.

Canon et al. "The clinical KRAS(G12C) inhibitor AMG 510 drives anti-tumour immunity", Nature. 2019. vol 575, pp. 217-223, especially: abstract; p. 218, Fig. 1a, formula AMG 510; p. 220, col. 2, para 2.

Lanman et al. "Discovery of a Covalent Inhibitor of KRASG12C (AMG 510) for the Treatment of Solid Tumors" Journal of Medicinal Chemistry. Dec. 10, 2019 (Dec. 10, 2019) vol. 63, p. 52-65; p. 52, abstract.

Abe, H et al. Discovery of a Highly Potent and Selective MEK Inhibitor: GSK1120212 (JTP-74057 DMSO Solvate). ACS Medicinal Chemistry Letters, vol. 2, No. 4, Feb. 28, 2011, doi: 10.1021/ml200004g, pp. 320-324; p. 321, figure 1.

Sung, Y. et al., "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436 , Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 . Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

Singh et al., A Gene Expression Signature Associated with "K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.

Simanshu et al., "RAS Proteins and Their Regulators in Human Disease", Cell 170, p. 17, Jun. 29, 2017.

Pacold et al., "Crystal Structure and Functional Analysis of Ras Binding to Its Effector Phosphoinositide 3-Kinase gamma", Cell, vol. 103, p. 931-943, Dec. 8, 2000.

Lech-Gustav et al., "The Renaissance of Ras", ACS Chem. Biol., 2014, 9, 2447-2458.

Karachaliou et al., "KRAS Mutations in Lung Cancer", Clinical Lung Cancer, vol. 14, No. 3, p. 2015-14, 2013.

(56) References Cited

OTHER PUBLICATIONS

Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Serafimova et al., "Reversible targeting of noncatalytic cysteines with chemically tuned electrophiles", Nat Chem Biol.; 8(5):471-476. doi:10.1038/nchembio.925.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", Plos One, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi: 10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 mailed Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K Inhibition, Downloaded from clincancerres.aacrjournals.org on Oct. 22, 2018. © 2018 American Association for Cancer Research.
Nabet, B. et al., "It Takes Two To Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ross, S. et al., "Targeting KRAS-dependent tumors with AZD4785, a high-affinity therapeutic antisense bligonucleotide inhibitor of KRAS", Sci. Transl. Med. 9, eaal5253 (2017) Jun. 14, 2017.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancerres.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer A Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic

(56) References Cited

OTHER PUBLICATIONS molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", Plos One | DOI: 10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of July 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi: 10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi: 10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: Kras G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.

(56) References Cited

OTHER PUBLICATIONS

Rudoni, S. et al., "Role of guanine nucleotides in the regulation of the Ras/cAMP pathway in *Saccharomyces cerevisiae*", Biochimica et Biophysica Acta 1538 (2001) 181^189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag Gmbh & Co. KGaA, Weinheim.
Sun, Q., et al., "A method for the second-site screening of K-Ras in the presence of a covalently attached first-site igand", J Biomol NMR (2014) 60:11-14 DOI 10.1007/s10858-014-9849-8.

KRAS G12D INHIBITORS

FIELD OF THE INVENTION

The present invention relates to compounds that inhibit KRas G12D. In particular, the present invention relates to compounds that inhibit the activity of KRas G12D, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma. KRAS G12D mutation is present in 25.0% of all pancreatic ductal adenocarcinoma patients, 13.3% of all colorectal carcinoma patients, 10.1% of all rectal carcinoma patients, 4.1% of all non-small cell lung carcinoma patients and 1.7% of all small cell lung carcinoma patients (e.g., see The AACR Project GENIE Consortium, (2017) Cancer Discovery; 7(8):818-831. Dataset Version 4).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants, especially KRas G12D.

Thus, there is a need to develop new KRas G12D inhibitors that demonstrate sufficient efficacy for treating KRas G12D-mediated cancer.

SUMMARY OF THE INVENTION

In one aspect of the invention, compounds are provided that inhibit KRas G12D activity. In certain embodiments, the compounds are represented by Formula (I):

Formula (I)

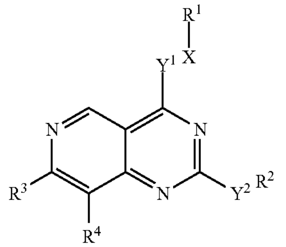

or a pharmaceutically acceptable salt thereof:

wherein:

$R^1$ is hydroxy, —$N(R^5)_2$, cycloalkyl, or heterocycyl, wherein the cycloalkyl or the heterocyclyl is optionally substituted with one or more $R^X$;

X is a bond or C1-C4 alkylene;

$Y^1$ and $Y^2$ are each independently a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(=NH)$NH_2$, -L-C(O)$N(R^5)_2$, -L-C1-C6 haloalkyl, -L-$OR^5$, -L-$(CH_2OR^5)(CH_2)_n$ $OR^5$, -L-$NR^5$C(O)-aryl, or -L-COOH, wherein the heterocyclyl and the aryl portion of -L-$NR^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more $R^8$;

$R^4$ is hydrogen, halogen or C1-C3 alkyl;

each $R^5$ and $R^{5a}$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2F$, —NHC(O)phenyl, —NHC(O)phenyl$SO_2F$, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(=O)—, oxo, (C1-C3 haloalkyl)C(=O)—, —$SO_2F$, (C1-C3 alkoxy)C1-C3 alkoxy, -L-OC(O)$N(R^5)_2$ or -L-OC(O)heterocyclyl;

each Q is independently a bond or O;

each $R^7$ is independently halogen, hydroxy, HC(=O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, cycloalkyl, C1-C3 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, or —S—C1-C3 haloalkyl; and each $R^X$ is independently C1-C3 alkyl, hydroxy, —$N(R^5)_2$. —$CH_2N(R^5)_2$, cyanomethyl, or heterocyclyl.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12D activity in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12D-associated disease or disorder in a patient in need of such treatment, the method comprising administering to the patient a therapeutically effective amount of a compound of Formula (I), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of KRas G12D.

Also provided herein is a compound of Formula (I), or a pharmaceutically acceptable salt thereof or a pharmaceutical composition thereof as defined herein, for use in the treatment of a KRas G12D-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of KRas G12D.

Also provided herein is the use of a compound of Formula (I), or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that the cancer is associated with a KRas G12D mutation (i.e., a KRas G12D-associated cancer); and (b) administering to the patient a therapeutically effective amount of a compound of Formula (I), or a pharmaceutically acceptable salt thereof, or a pharmaceutical composition thereof.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of KRas G12D. In particular, the present invention relates to compounds that inhibit the activity of KRas G12D, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.

As used herein, a "KRas G12D inhibitor" refers to compounds of the present invention that are represented by Formula (I), as described herein. These compounds are capable of negatively modulating or inhibiting all or a portion of the enzymatic activity of KRas G12D.

A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12D mutation (e.g., as determined using a regulatory agency-approved, e.g., FDA-approved, assay or kit). In some embodiments, the subject has a tumor that is positive for a KRas G12D mutation (e.g., as determined using a regulatory agency-approved assay or kit). The subject can be a subject with a tumor(s) that is positive for a KRas G12D mutation (e.g., identified as positive using a regulatory agency-approved, e.g., FDA-approved, assay or kit). The subject can be a subject whose tumors have a KRas G12D mutation (e.g., where the tumor is identified as such using a regulatory agency-approved, e.g., FDA-approved, kit or assay). In some embodiments, the subject is suspected of having a KRas G12D gene-associated cancer. In some embodiments, the subject has a clinical record indicating that the subject has a tumor that has a KRas G12D mutation (and optionally the clinical record indicates that the subject should be treated with any of the compositions provided herein).

In some embodiments of any of the methods or uses described herein, an assay is used to determine whether the patient has KRas G12D mutation using a sample (e.g., a biological sample or a biopsy sample (e.g., a paraffin-embedded biopsy sample) from a patient (e.g., a patient suspected of having a KRas G12D-associated cancer, a patient having one or more symptoms of a KRas G12D-associated cancer, and/or a patient that has an increased risk of developing a KRas G12D-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "acyl" refers to —C(O)$CH_3$.

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl" and "C1-C4 haloalkyl" refer to a C1-C3 alkyl chain or C1-C4 alkyl chain, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, 2-2-dimethyl ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more $R^X$ groups as defined herein. The cycloalkyl may be a monocyclic, a bicyclic, a spirocyclic or a bridged ring system. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a C6-C14 aromatic moiety comprising one to three aromatic rings, which is optionally substituted with one or more $R^6$ or with one or more $R^7$ as defined herein. As one embodiment, the aryl group is a $C_6$-$C_{10}$ aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

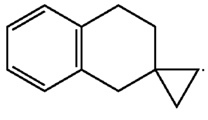 [SMILES: c1ccc2c(c1)CCC1(CC1)C2]

An "araC1-C6 alkyl" or "arylalkyl" group comprises an aryl group covalently linked to an alkyl group, either of which may independently be optionally substituted or unsubstituted. An example of an aralkyl group is ($C_6$-$C_{10}$) aryl($C_1$-$C_6$)alkyl-, including, without limitation, benzyl, phenethyl, and naphthylmethyl. Another example of an aralkyl group is (C6-C10)aryl(C1-C3)alkyl-, again including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or $SO_2$, the remainder of the ring atoms being carbon. The heterocyclyl may be a monocyclic, a bicyclic, a spirocyclic or a bridged ring system. The heterocyclic group is optionally substituted with one or more $R^6$ on ring carbon or ring nitrogen at one or more positions, wherein $R^6$ is as defined for Formula I. The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, tetrahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4(1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms per ring selected from the group consisting of N, O, and S in which one ring system may be saturated or partially saturated.

As used herein, "an effective amount" of a compound is an amount that is sufficient to negatively modulate or inhibit the activity of KRas G12D. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12D. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by Formula (I):

Formula (I)

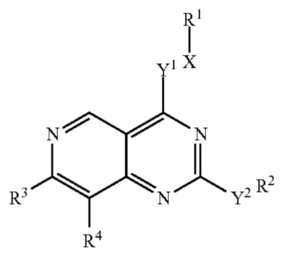

or a pharmaceutically acceptable salt thereof:

wherein:

$R^1$ is hydroxy, —$N(R^5)_2$, cycloalkyl, or heterocyclyl, wherein the cycloalkyl or the heterocyclyl is optionally substituted with one or more $R^X$;

X is a bond or C1-C4 alkylene;

$Y^1$ and $Y^2$ are each independently a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(═NH)$NH_2$, -L-C(O)$N(R^5)_2$, -L-C1-C6 haloalkyl, -L-$OR^5$, -L-($CH_2OR^5$)$(CH_2)_n$ $OR^5$, -L-$NR^5$C(O)-aryl, or -L-COOH, wherein the heterocyclyl and the aryl portion of -L-$NR^5$C(O)-aryl and the heterocyclyl portion of -L-heterocyclyl and the cycloalkyl portion of the -L-cycloalkyl may each be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more $R^8$ $R^4$ is hydrogen, halogen or C1-C3 alkyl;

each $R^5$ and $R^{5a}$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2F$, —NHC(O)phenyl, —NHC(O)phenyl$SO_2F$, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(═O)—, oxo, (C1-C3 haloalkyl)C(═O)—, —$SO_2F$, (C1-C3 alkoxy)C1-C3 alkoxy, -L-OC(O)$N(R^5)_2$ or -L-OC(O)heterocyclyl;

each Q is independently a bond or O;

each $R^7$ is independently halogen, hydroxy, HC(═O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, cycloalkyl, C1-C3 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, or —S—C1-C3 haloalkyl; and each $R^X$ is independently C1-C3 alkyl, hydroxy, —$N(R^5)_2$. —$CH_2N(R^5)_2$, cyanomethyl, or heterocyclyl.

In one embodiment, $Y^1$ is $NR^5$.

In certain embodiments, $R^5$ is hydrogen. In certain embodiments, $R^5$ is C1-C3 alkyl. In certain embodiments, the C1-C3 alkyl is methyl. In one embodiment, $Y^1$ is $NR^5$ and X is methylene or ethylene.

In one embodiment of the compounds of Formula (I), $Y^1$ is $NR^5$, X is methylene or ethylene and $R^1$ is —$N(R^5)_2$. In one embodiment, each $R^5$ of the —$N(R^5)_2$ is C1-C3 alkyl. In one embodiment, one $R^5$ of the —$N(R^5)_2$ is hydrogen and the other $R^5$ is C1-C3 alkyl. In one embodiment, each $R^5$ of the —$N(R^5)_2$ is hydrogen.

In one embodiment of the compounds of Formula (I), $Y^1$ is $NR^5$, X is methylene or ethylene and $R^1$ is cycloalkyl optionally substituted with one or more $R^X$. In certain embodiments, the cycloalkyl is cyclopropyl, cyclobutyl, cyclopentyl, cyclohexyl, or spiro[3.3]heptanyl each optionally substituted with one $R^X$. In certain embodiments, the cycloalkyl is cyclobutyl optionally substituted with one $R^X$. In certain embodiments, the $R^X$ is —$N(R^5)_2$, hydroxy, C1-C3 alkyl, or heterocyclyl.

In one embodiment of the compounds of Formula (I), $Y^1$ is $NR^5$, X is methylene or ethylene and $R^1$ is heterocyclyl optionally substituted with one or more $R^X$. In certain embodiments, the heterocyclyl is azetidinyl, pyrrolidinyl, piperidinyl, piperazinyl, tetrahydropyranyl, 2-azabicyclo[3.1.0]hexanyl or diazapanyl, each optionally substituted with one or more $R^X$. In certain embodiments, the heterocyclyl is substituted with one $R^X$, wherein the one $R^X$ is hydroxy, C1-C3 alkyl, —$N(R^5)_2$. —$CH_2N(R^5)_2$, or cyanomethyl. In certain embodiments, the heterocyclyl is pyrrolidinyl and the one $R^X$ is C1-C3 alkyl. In certain embodiments, the heterocyclyl is azetidinyl and the one $R^X$ is hydroxyl or C1-C3 alkyl. In certain embodiments, the heterocyclyl is tetrahydropyranyl and the one $R^X$ is —$N(R^5)_2$.

In one embodiment of the compounds of Formula (I), $Y^1$ is $NR^5$, X is butylene and $R^1$ is hydroxy. In one embodiment of the compounds of Formula (I), $Y^1$ is $NR^5$ and X is a bond.

In one embodiment of the compounds of Formula (I), $Y^1$ is $NR^5$, X is a bond and $R^1$ is cycloalkyl optionally substituted with one or more $R^X$. In certain embodiments, the cycloalkyl is cyclobutyl substituted with one $R^X$. In one embodiment, the one $R^X$ is —$N(R^5)_2$.

In one embodiment of the compounds of Formula (I), $Y^1$ is $NR^5$, X is a bond and $R^1$ is heterocyclyl optionally substituted with one or more $R^X$. In one embodiment, the heterocyclyl is azetidinyl optionally substituted with one $R^X$. In one embodiment, the heterocyclyl is pyrrolidinyl substituted with one $R^X$. In one embodiment, the one $R^X$ is C1-C3 alkyl. In certain embodiments, the heterocyclyl is 3-azabicyclo[3.2.0]hexanyl substituted with one $R^X$. In one embodiment, the one $R^X$ is —$N(R^5)_2$.

In one embodiment of the compounds of Formula (I), $Y^2$ is a bond and $R^2$ is hydrogen, —$N(R^5)_2$, or heterocyclyl optionally substituted with one or more $R^6$.

In certain embodiments, $R^2$ is —$N(R^5)_2$. In one embodiment, each $R^5$ is hydrogen. In one embodiment, each $R^5$ is an independently selected from C1-C3 alkyl. In one embodiment, one $R^5$ is hydrogen and the second $R^5$ is C1-C3 alkyl. In certain embodiments, $Y^2$ is a bond and is a bond and $R^2$ is —$N(R^5)_2$.

In other embodiments, $R^2$ is heterocyclyl. In one embodiment $R^2$ is heterocyclyl and the heterocyclyl is azetidinyl, pyrrolidinyl, tetrahydro-2H-thiopyran 1,1-dioxide or 1,6λ 2-diazaspiro[3.3]heptanyl. In certain embodiments, $Y^2$ is a bond and $R^2$ is heterocyclyl.

In certain embodiments, the heterocyclyl is azetidinyl substituted with one $R^6$. In certain embodiments, the heterocyclyl is azetidinyl substituted with one $R^6$, wherein $R^6$ is hydroxy, hydroxyalkyl, or —$N(R^5)_2$. In certain embodiments, the heterocyclyl is azetidinyl substituted with two $R^6$ groups independently selected from —$N(R^5)_2$ and C1-C3 alkyl. In certain embodiments, $Y^2$ and is a bond and the heterocyclyl is azetidinyl substituted with one $R^6$, wherein $R^6$ is hydroxy, hydroxyalkyl, or —$N(R^5)_2$. In certain embodiments, $Y^2$ is a bond and the heterocyclyl is azetidinyl substituted with two $R^6$ groups independently selected from —$N(R^5)_2$ and C1-C3 alkyl.

In one embodiment, $Y^2$ is O.

In one embodiment, $Y^2$ is O and $R^2$ is C1-C6 alkyl, -L-heterocyclyl optionally substituted with one or more $R^6$, -L-heteroaryl, wherein the heteroaryl portion is optionally substituted with one or more $R^7$, -L-aryl, wherein the aryl portion is optionally substituted with one or more $R^7$, -L-cycloalkyl, wherein the cycloalkyl portion is optionally substituted with one or more $R^6$, -L-$N(R^5)_2$, -L-NC(=NH)—$NH_2$, -L-C(O)$N(R^5)_2$, -L-C1-C6 haloalkyl, -L-$COR^5$, -L-$(CH_2OR^5)(CH_2)_nOR^5$, or -L-$NR^5$C(O)-aryl.

In one embodiment of the compounds of Formula (I), $Y^2$ is O and $R^2$ is C1-C6 alkyl. In certain embodiments, the C1-C6 alkyl is methyl, ethyl, isopropyl or isobutyl.

In one embodiment of the compounds of Formula (I), $Y^2$ is O and $R^2$ is -L-heterocyclyl optionally substituted with one or more $R^6$.

In one embodiment, $Y^2$ is O and $R^2$ is heterocyclyl wherein the heterocyclyl is tetrahydropyranyl optionally substituted with two halogens. In certain embodiment, the two halogens are both fluoro.

In another embodiment, $Y^2$ is O and $R^2$ is -L-heterocyclyl wherein L is methylene and the heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4(1H)-oxide, azetidinyl, pyrrolidinyl, pyrrolidin-2-one, oxetanyl, piperidinyl, 1-azabicyclo[2.2.1]heptanyl, morpholinyl, oxa-5-azabicyclo[2.2.1]heptan-5-yl, thiopyranyl, 6-oxa-2λ$^2$-azaspiro[3.4]octanyl, 7-oxa-2λ$^2$-azaspiro[3.5]nonanyl, 2',3'-dihydrospiro[cyclopropane-1,1'-indenyl], (2S)-1-azabicyclo[2.2.1]heptan-2-yl or tetrahydrofuranyl.

In certain embodiments, $Y^2$ is O and $R^2$ is -L-heterocyclyl wherein L is methylene and the heterocyclyl is hexahydro-1H-pyrrolizinyl.

In certain embodiments, $Y^2$ is O and $R^2$ is -L-heterocyclyl wherein L is methylene and the heterocyclyl is hexahydro-1H-pyrrolizinyl is optionally substituted with one $R^6$, wherein $R^6$ is halogen, hydroxy, C1-C3 hydroxyalkyl, C1-C3 haloalkyl, C1-C3 alkyl, C1-C3 alkoxy, phenyl, tert-butyldimethylsilyloxy$CH_2$—, -L-OC(O)$N(R^5)_2$, -L-OC(O)heterocyclyl or pyrazolyl, wherein the pyrazolyl is optionally substituted with C1-C3 alkyl or wherein the pyrazolyl is substituted with C1-C3 alkyl. In one embodiment, the C1-C3 haloalkyl is chloromethyl. In another embodiment, the pyrazolyl is substituted with C1-C3 alkyl. In one embodiment, $R^6$ is -L-OC(O)$N(R^5)_2$. In one embodiment, L is methylene and each $R^5$ of the —$N(R^5)_2$ is C1-C3 alkyl. In one embodiment, L is methylene and one $R^5$ of the —$N(R^5)_2$ is hydrogen and the other $R^5$ is C1-C3 alkyl. In one embodiment, $R^6$ is -L-OC(O)heterocyclyl.

In one embodiment, L is methylene and the heterocyclyl is pyrrolidinyl or piperidinyl. In certain embodiments, $Y^2$ is O and $R^2$ is -L-heterocyclyl wherein L is methylene and the heterocyclyl is hexahydro-1H-pyrrolizinyl is optionally substituted with one $R^6$, wherein $R^6$ is halogen. In one embodiment, the halogen is fluoro.

In other embodiments, the hexahydro-1H-pyrrolizinyl is substituted with two $R^6$ groups, wherein each $R^6$ is an independently selected C1-C3 alkyl. In certain embodiments, the heterocyclyl is hexahydro-1H-pyrrolizinyl which is unsubstituted.

In certain embodiments, $Y^2$ is O and $R^2$ is -L-heterocyclyl wherein L is methylene and the heterocyclyl is azetidinyl substituted with one $R^6$, wherein $R^6$ is C1-C3 alkyl.

In certain embodiments, $Y^2$ is O and $R^2$ is -L-heterocyclyl wherein L is methylene and the heterocyclyl is pyrrolidinyl substituted with one $R^6$, wherein $R^6$ is C1-C3 hydroxyalkyl, C1-C3 haloalkyl, C1-C3 alkyl, C1-C3 alkoxy, C1-C3 aralkyl, or -Q-phenyl, wherein Q is O, and —NHC(O)phenyl. In one embodiment, the phenyl group of the -Q-phenyl is substituted with $SO_2F$. In another embodiment, the phenyl group of the —NHC(O)phenyl is substituted with $SO_2F$. In one embodiment, the C1-C3 aralkyl is benzyl.

In other embodiments, $Y^2$ is O and $R^2$ is -L-heterocyclyl wherein L is methylene and the pyrrolidinyl is substituted with two $R^6$ groups, wherein one $R^6$ is C1-C3 alkyl and the other $R^6$ is C1-C3 alkoxy or halogen.

In certain embodiments, $Y^2$ is O and $R^2$ is -L-heterocyclyl wherein L is methylene and the heterocyclyl is pyrrolidin-2-one substituted with one $R^6$, wherein $R^6$ is C1-C3 alkyl.

In certain embodiments, $Y^2$ is O and $R^2$ is -L-heterocyclyl wherein L is methylene and the heterocyclyl is piperidinyl substituted with one $R^6$, wherein $R^6$ is acetyl, (C1-C3 alkoxy)C1-C3 alkoxy, or —C(O)$CH_2$Cl.

In certain embodiments, $Y^2$ is O and $R^2$ is -L-heterocyclyl wherein L is methylene and the heterocyclyl is (2S)-1-azabicyclo[2.2.1]heptan-2-yl.

In one embodiment of the compounds of Formula (I), $Y^2$ is O, $R^2$ is -L-heterocyclyl wherein L is ethylene or propylene and the heterocyclyl is morpholinyl or oxa-5-azabicyclo[2.2.1]heptan-5-yl.

In one embodiment of the compounds of Formula (I), $Y^2$ is O and $R^2$ is -L-heteroaryl, wherein the heteroaryl portion is optionally substituted with one or more $R^7$. In certain embodiments, L is ethylene and the heteroaryl is benzimidazolyl, optionally substituted with one or more $R^7$. In one embodiment, $R^7$ is C1-C4 alkyl.

In certain embodiments, $Y^2$ is O and $R^2$ is -L-heteroaryl.

In certain embodiments, $Y^2$ is O and $R^2$ is -L-heteroaryl, wherein L is methylene or ethylene. In certain embodiments, $Y^2$ is O and $R^2$ is -L-heteroaryl, wherein L is methylene or ethylene and the heteroaryl is pyridyl, pyrazolyl, imidazolyl, triazolyl, 4,5,6,7-tetrahydro-1H-indazolyl, benzimidazolyl, imidazo[1,2-a]pyridinyl, or pyrimidinyl.

In certain embodiments, $Y^2$ is O and $R^2$ is -L-heteroaryl, wherein the heteroaryl is pyridyl substituted with one $R^7$. In certain embodiments, $Y^2$ is O and $R^2$ is -L-heteroaryl, wherein the heteroaryl is pyridyl substituted with one $R^7$ wherein $R^7$ is halogen, C1-C4 haloalkyl, C1-C4 hydroxyalkyl, C1-C4 alkyl, $—N(R^5)_2$, or C1-C4 alkoxy.

In certain embodiments, $Y^2$ is O and $R^2$ is -L-heteroaryl, wherein L is methylene or ethylene and the heteroaryl is pyrazolyl substituted with one $R^7$. In certain embodiments, $Y^2$ is O and $R^2$ is -L-heteroaryl, wherein L is methylene or ethylene and the heteroaryl is pyrazolyl substituted with one $R^7$ wherein $R^7$ is halogen, C1-C4 haloalkyl, C1-C4 hydroxyalkyl, C1-C4 alkyl, C1-C4 alkoxy or $—N(R^5)_2$.

In certain embodiments, $Y^2$ is O and $R^2$ is -L-heteroaryl, wherein L is methylene or ethylene and the heteroaryl is imidazolyl substituted with one $R^7$. In certain embodiments, $Y^2$ is O and $R^2$ is -L-heteroaryl, wherein L is methylene or ethylene and the heteroaryl is imidazolyl substituted with one $R^7$ wherein $R^7$ is C1-C4 alkyl, C1-C4 haloalkyl, or C1-C4 hydroxyalkyl.

In certain embodiments, $Y^2$ is O and $R^2$ is -L-heteroaryl, wherein L is methylene or ethylene and the heteroaryl is triazolyl substituted with one $R^7$. In certain embodiments, $Y^2$ is O and $R^2$ is -L-heteroaryl, wherein L is methylene or ethylene and the heteroaryl is triazolyl substituted with one $R^7$, wherein $R^7$ is C1-C4 alkyl.

In one embodiment of the compounds of Formula (I), $Y^2$ is O and $R^2$ is -L-aryl, wherein the aryl portion is optionally substituted with one or more $R^7$. In certain embodiments, L is ethylene and the aryl is phenyl. In one embodiment, the phenyl is substituted with one $R^7$. In one embodiment, the phenyl is substituted with one $R^7$, wherein $R^7$ is halogen. In one embodiment, the phenyl is substituted with two $R^7$ groups. In one embodiment, the phenyl is substituted with two $R^7$ groups wherein one $R^7$ is hydroxy and one $R^7$ is HC(═O)—.

In one embodiment of the compounds of Formula (I), $Y^2$ is O and $R^2$ is -L-cycloalkyl, wherein the cycloalkyl portion is optionally substituted with one or more $R^6$. In one embodiment, L is methylene. In one embodiment, the cycloalkyl is cyclopropyl, cyclobutyl, cyclopentyl or cyclohexyl. In certain embodiments, the cyclopropyl and cyclopentyl are each substituted with one $R^6$. In certain embodiments, the cyclopropyl and cyclopentyl are each substituted with one $R^6$, wherein $R^6$ is C1-C3 haloalkyl. In certain embodiments, the cyclobutyl and cyclohexyl are each substituted with two $R^6$ groups. In certain embodiments, the cyclobutyl and cyclohexyl are each substituted with two $R^6$ groups, wherein each $R^6$ group is halogen.

In one embodiment of the compounds of Formula (I), $Y^2$ is O, and $R^2$ is $-L-N(R^5)_2$. In certain embodiments, L is ethylene. In certain embodiments, $R^5$ is C1-C3 alkyl.

In one embodiment of the compounds of Formula (I), $Y^2$ is O, and $R^2$ is $-L-NC(═NH)—NH_2$. In certain embodiments, L is ethylene or propylene.

In one embodiment of the compounds of Formula (I), $Y^2$ is O, and $R^2$ is $-L-C(O)N(R^5)_2$. In certain embodiments, L is ethylene and each $R^5$ is C1-C3 alkyl.

In one embodiment of the compounds of Formula (I), $Y^2$ is O, and $R^2$ is -L-C1-C6 haloalkyl. In certain embodiments, L is methylene. In certain embodiments, the haloalkyl is 1,1,3,3-tetrafluoropropanoyl or trifluoromethyl. In other embodiments, L is ethylene or propylene and the haloalkyl is trifluoromethyl.

In one embodiment of the compounds of Formula (I), $Y^2$ is O, and $R^2$ is $-L-COR^5$. In certain embodiments, L is propylene and $R^5$ is hydrogen or C1-C3 alkyl. In certain embodiments, L is propylene that is substituted with hydroxy, hydroxyalkyl or heteroaryl and $R^5$ is hydrogen or C1-C3 alkyl. In one embodiment, the heteroaryl is pyridyl.

In one embodiment of the compounds of Formula (I), $Y^2$ is O, and $R^2$ is $-L-(CH_2OR^5)(CH_2)_nOR^5$. In certain embodiments, L is methylene, each $R^5$ is independently hydrogen or C1-C3 alkyl, and n is one or two.

In one embodiment of the compounds of Formula (I), $Y^2$ is O, and $R^2$ is $-L-NR^5C(O)$-aryl. In certain embodiments, L is methylene, $R^5$ is hydrogen. In one embodiment the aryl is phenyl. In one embodiment, the phenyl is substituted with one $R^6$, wherein $R^6$ is $—SO_2F$.

In one embodiment of the compounds of Formula (I), $R^3$ is aryl optionally substituted with one or more $R^8$. In certain embodiments, the aryl is selected from the group consisting of phenyl, naphthyl, 1,2,3,4-tetrahydronaphthalenyl and 2,3-dihydro-1H-indenyl, wherein each is optionally substituted with one or more $R^8$.

In one embodiment, the aryl is phenyl substituted with one or more $R^8$ groups. In one embodiment, the aryl is phenyl substituted with one or more $R^8$ groups independently selected from halogen, C1-C3 alkyl and cycloalkyl. In certain embodiments the phenyl is substituted with two $R^8$ groups. In certain embodiments the phenyl is substituted with two $R^8$ groups, wherein the one $R^8$ group is halogen and the other $R^8$ group is C1-C3 alkyl or cycloalkyl.

In one embodiment, the aryl is 2,3-dihydro-1H-indenyl optionally substituted with one or more $R^8$. In one embodiment, the aryl is 2,3-dihydro-1H-indenyl optionally substituted with one $R^8$. In one embodiment, $R^8$ is C1-C alkyl.

In one embodiment, the aryl is naphthyl substituted with one or more $R^8$ groups. In one embodiment, the aryl is naphthyl substituted with one or more $R^8$ groups independently selected from halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, cycloalkyl, triazolyl, C1-C3 haloalkyl and —O—C1-C3 haloalkyl.

In one embodiment, the aryl is naphthyl substituted with hydroxy. In one embodiment, the aryl is naphthyl substituted with halogen. In certain embodiments, the halogen is chlorine, fluorine or bromine. In other embodiments, the halogen is chlorine. In other embodiments, the halogen is fluorine.

In one embodiment, the aryl is naphthyl substituted with C1-C3 alkyl, wherein the C1-C3 alkyl is methyl or ethyl.

In one embodiment, the aryl is naphthyl substituted with C2-C4 alkenyl. In certain embodiments, the C2-C4 alkenyl is prop-2-enyl.

In one embodiment, the aryl is naphthyl substituted with C2-C4 alkynyl. In certain embodiments, the C2-C4 alkynyl is ethyne or prop-2-ynyl.

In one embodiment, the aryl is naphthyl substituted with cycloalkyl. In certain embodiments, the cycloalkyl is cyclopropyl.

In one embodiment, the aryl is naphthyl substituted with one or two $R^8$, wherein each $R^8$ is halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, or triazolyl. In one embodiment, the aryl is naphthyl substituted with two $R^8$ groups independently selected from halogen, hydroxy, C1-C3 alkyl and C2-C4 alkynyl. In one embodiment, the aryl is naphthyl substituted with three $R^8$ groups wherein the first $R^8$ group is halogen, the second $R^8$ group is hydroxy, and the third $R^8$ group is C1-C3 alkyl or C2-C4 alkynyl.

In one embodiment of the compounds of Formula (I), $R^3$ is heteroaryl optionally substituted with one or more $R^8$. In one embodiment, the heteroaryl is isoquinolinyl, indazolyl, or benzo[d][1,3]dioxolyl optionally substituted with one or more $R^8$. In one embodiment, the heteroaryl is indazolyl optionally substituted with one or more $R^8$. In one embodiment, the heteroaryl is indazolyl optionally substituted with C1-C3 alkyl or C1-C3 alkyl and halogen. In other embodiments, the heteroaryl is isoquinolinyl optionally substituted with one or more $R^8$. In other embodiments, the heteroaryl is isoquinolinyl optionally substituted with halogen or C2-C4 alkynyl. In certain embodiments, the heteroaryl is benzo[d][1,3]dioxolyl optionally substituted with two $R^8$ groups. In certain embodiments, the heteroaryl is benzo[d][1,3]dioxolyl optionally substituted with two $R^8$ groups, wherein each $R^8$ group is an independently selected halogen. In one embodiment, the two halogens are gem-difluoro substitutions.

In one embodiment of the compounds of Formula (I), $R^4$ is hydrogen.

In one embodiment of the compounds of Formula (I), $R^4$ is halogen. In one embodiment, $R^4$ is fluorine. In one embodiment, $R^4$ is chlorine.

In one embodiment of the compounds of Formula (I), $R^4$ is C1-C3 alkyl. In one embodiment, $R^4$ is methyl.

Nonlimiting examples of compounds of Formula (I) are selected from the group consisting of:

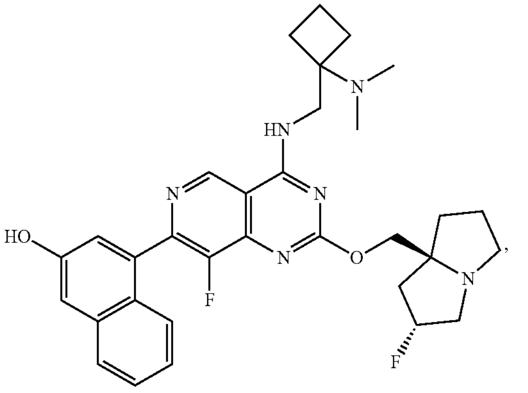

-continued

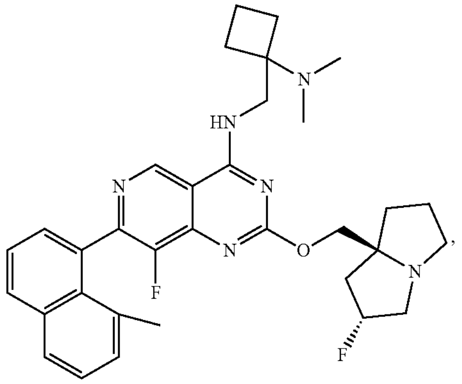

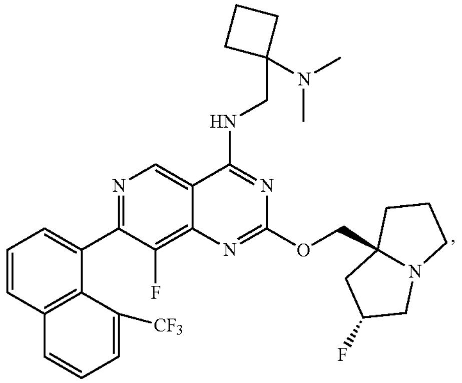

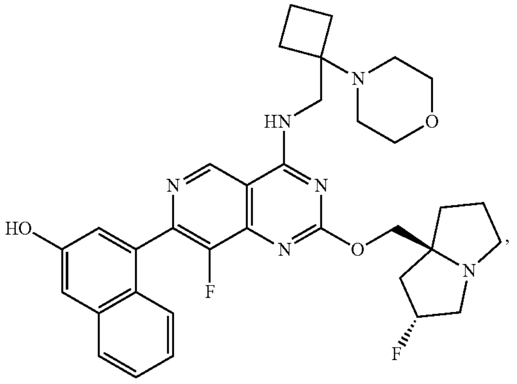

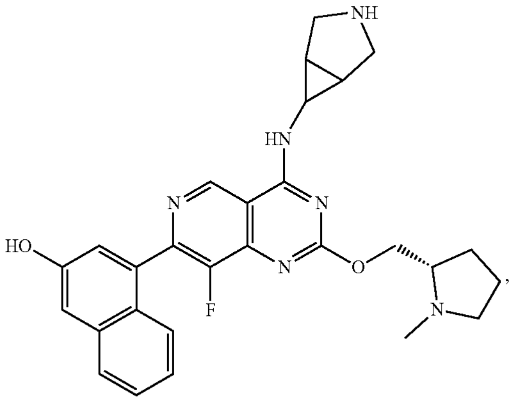

-continued
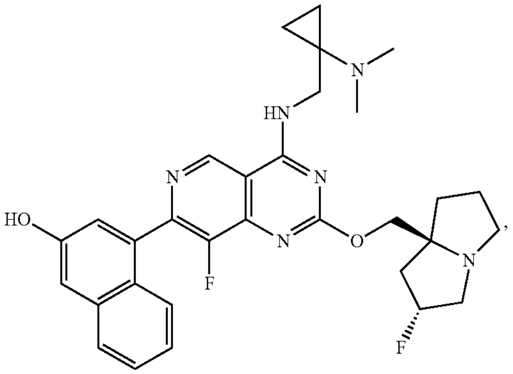
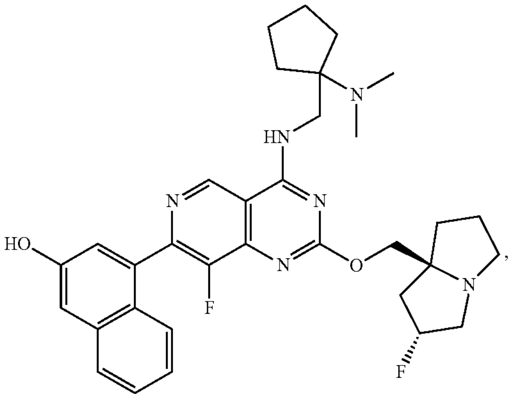
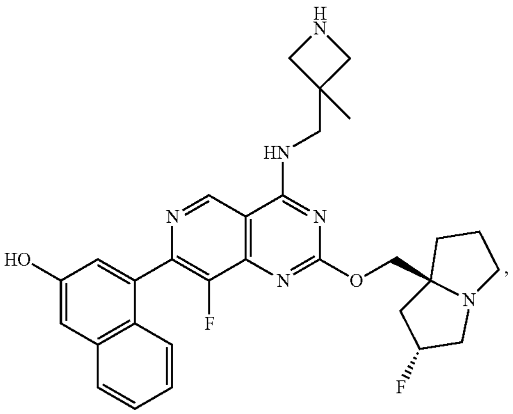
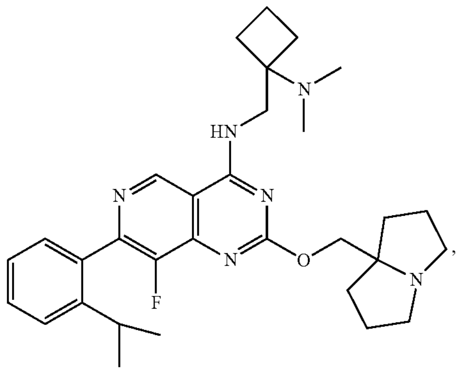
-continued
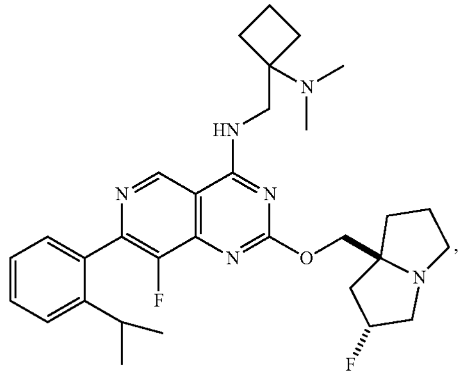
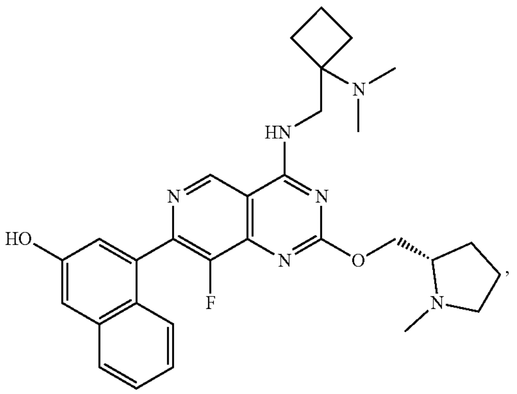
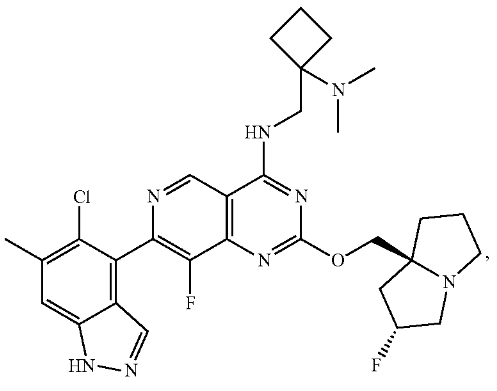
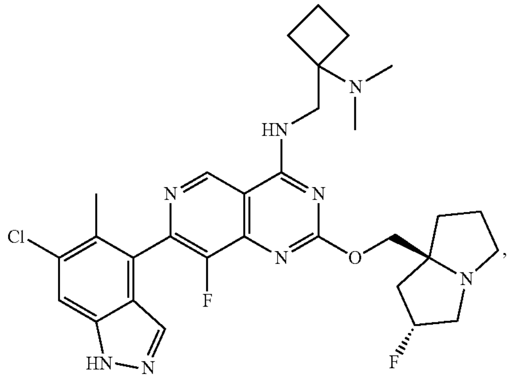

-continued
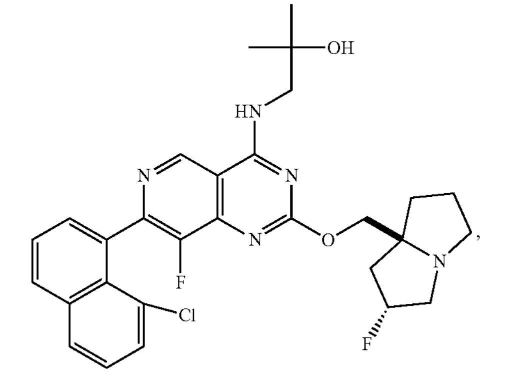
,
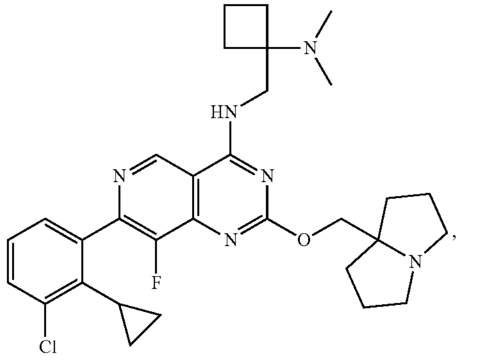
,
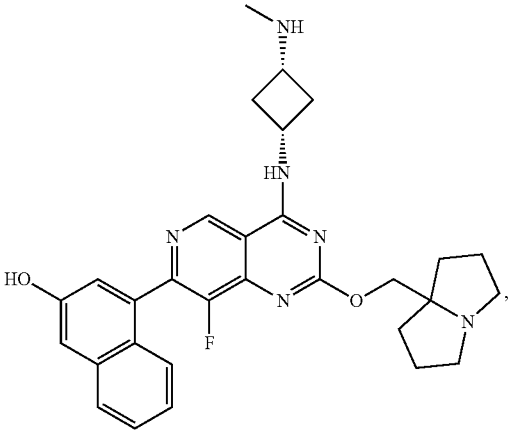
,
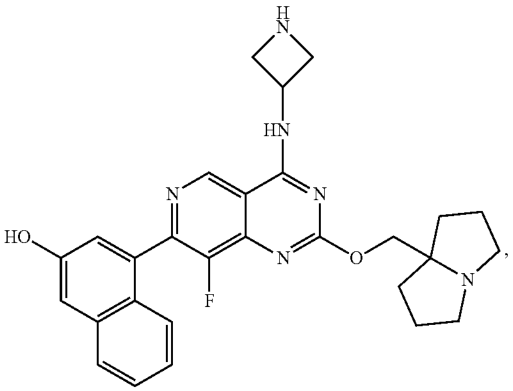
,
-continued
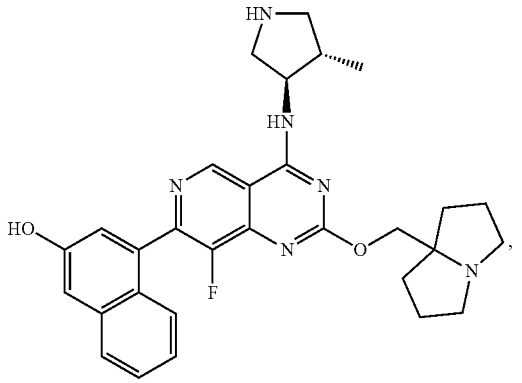
,
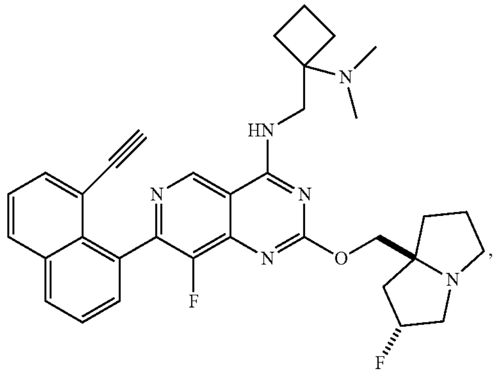
,
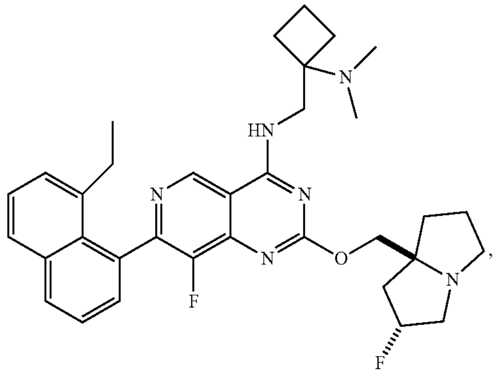
,
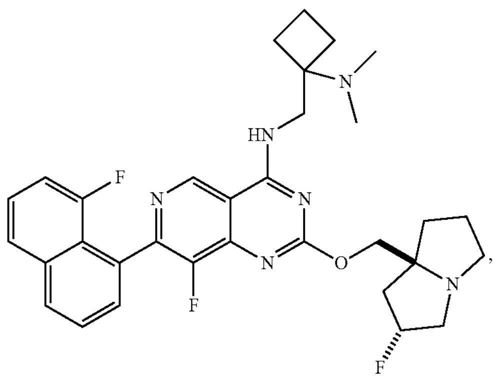
, -continued
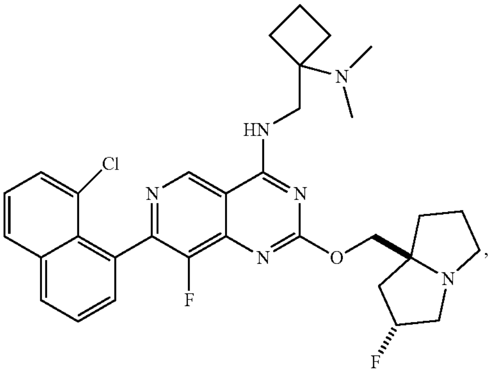
,
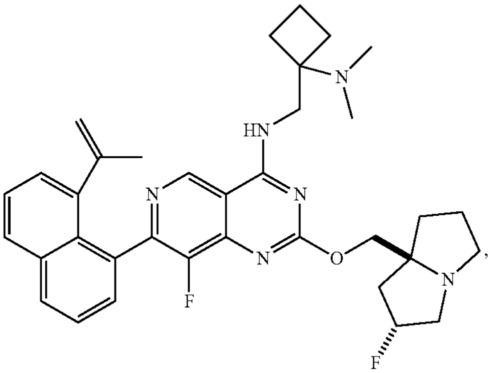
,
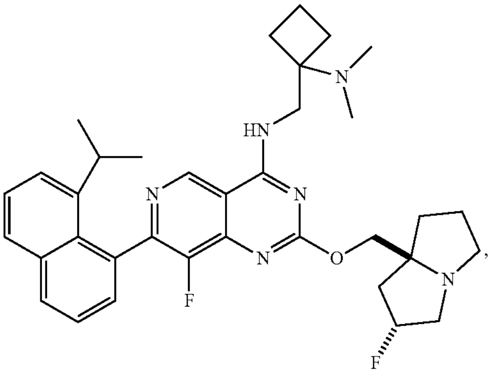
,
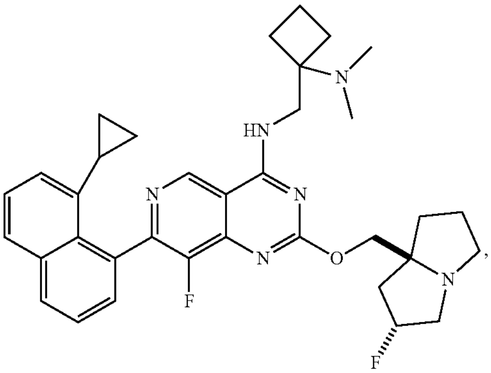
,
-continued
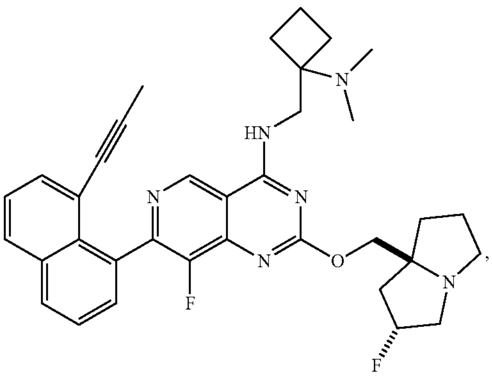
,
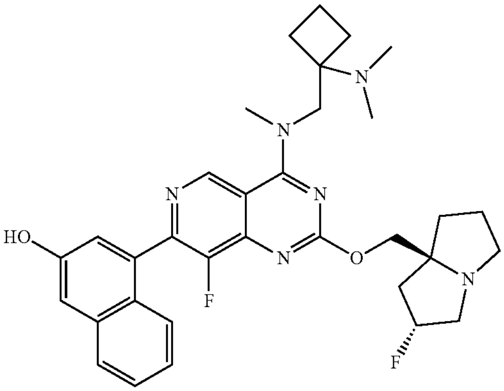
,
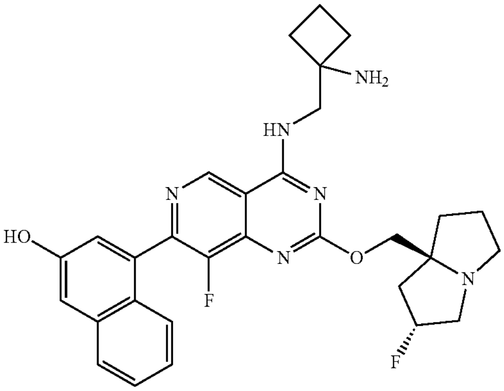
,
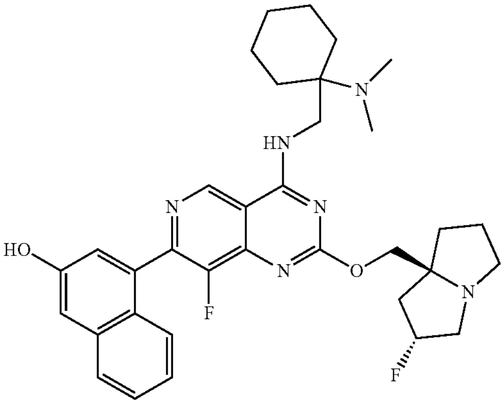
, -continued
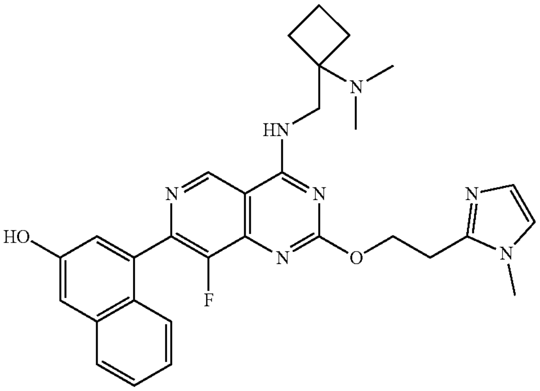
,
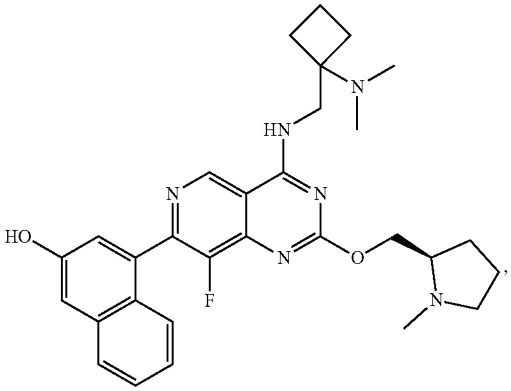
,
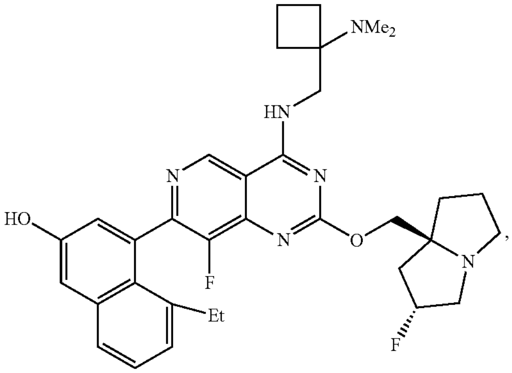
,
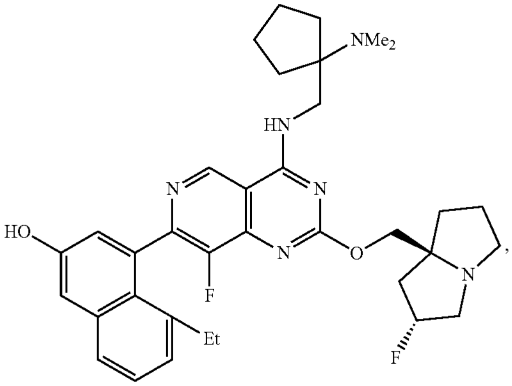
,
-continued
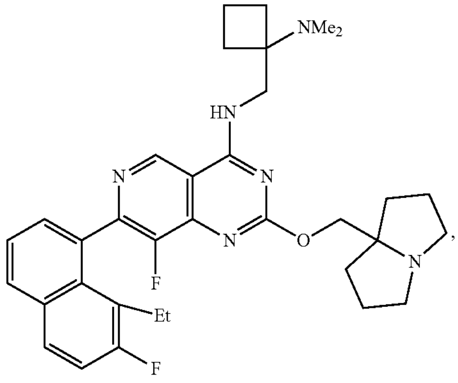
,
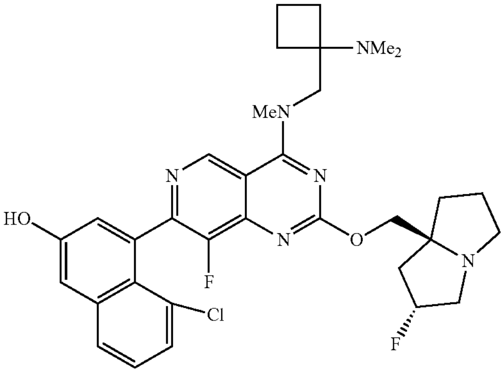
,
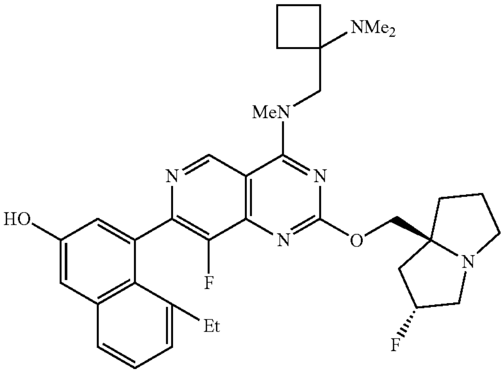
,
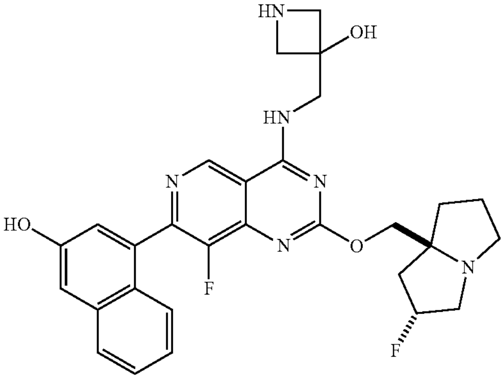
,

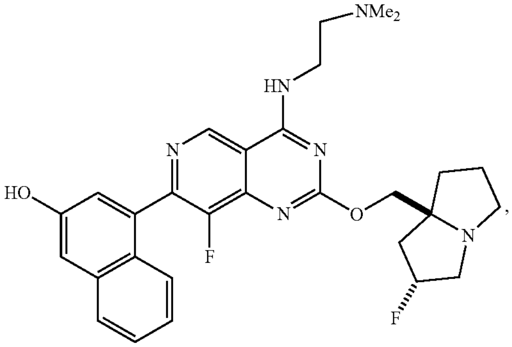
,
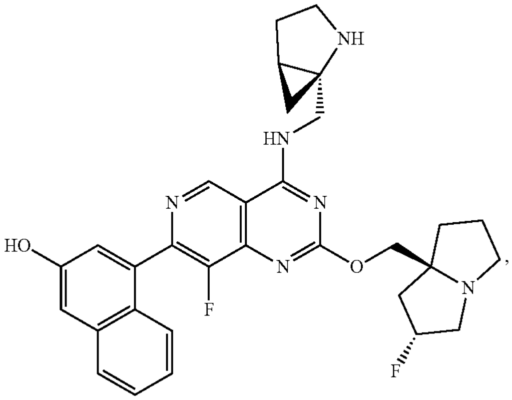
,
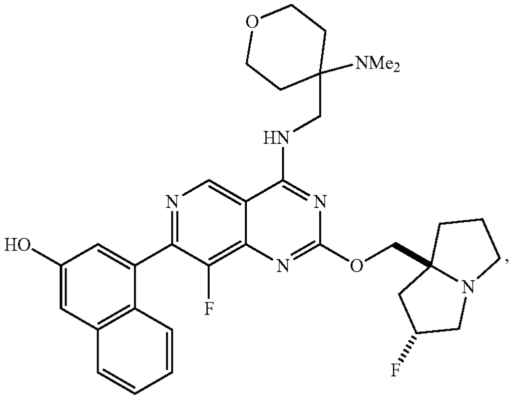
,
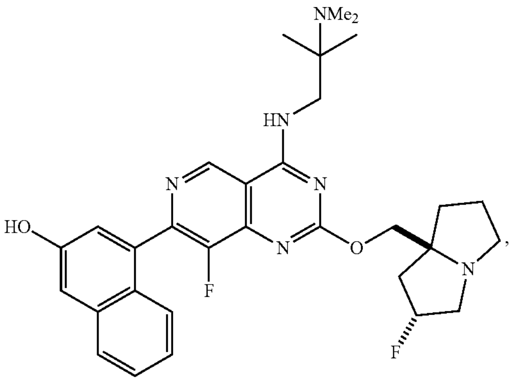
,
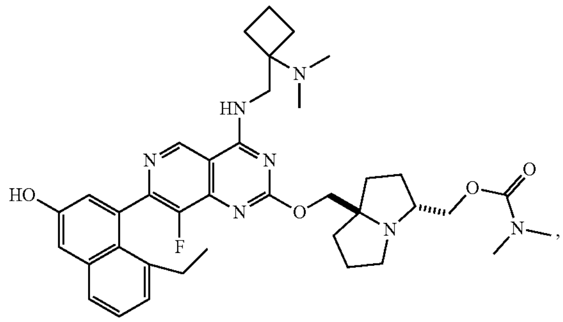
,
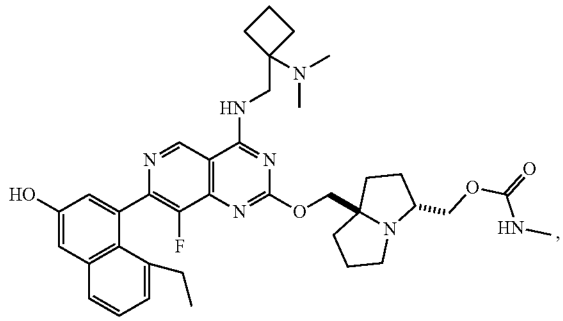
,
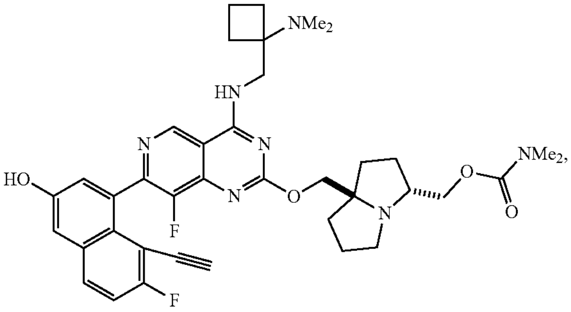
,
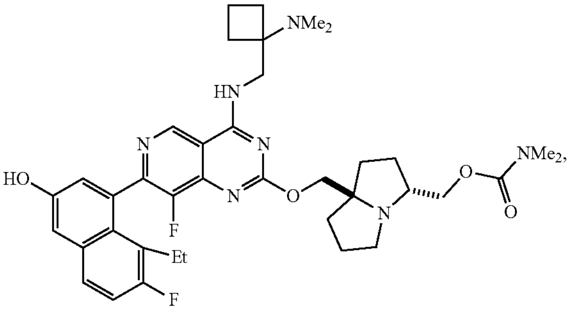
,
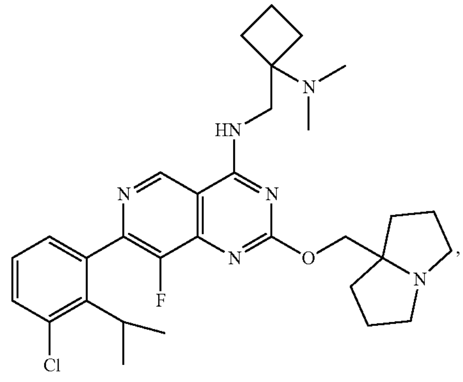
, -continued
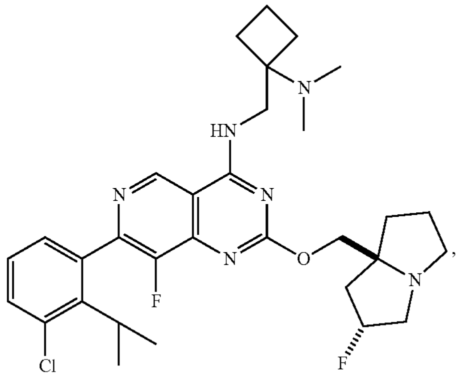
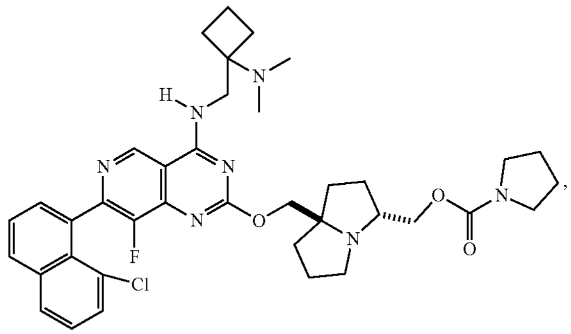
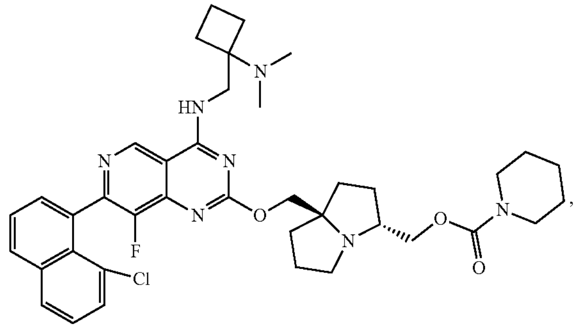
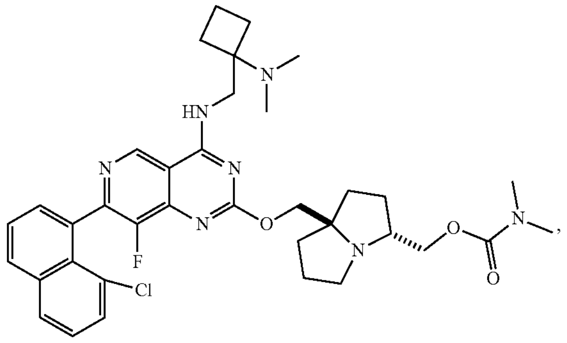
-continued
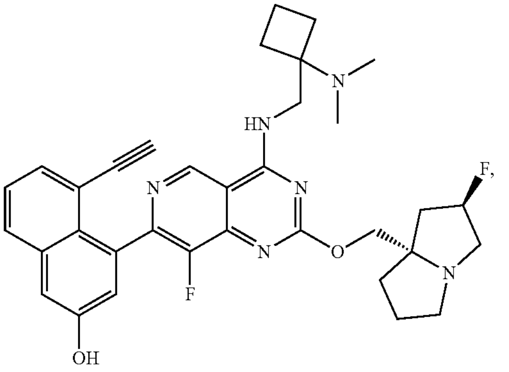
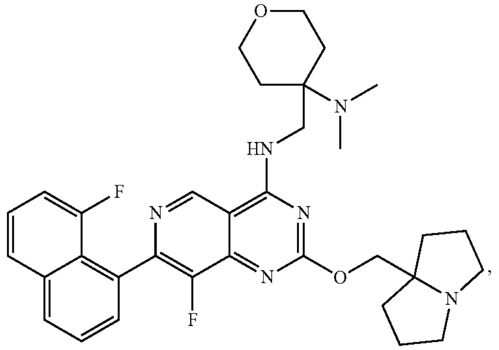
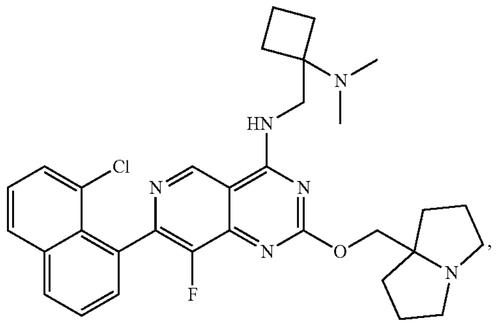
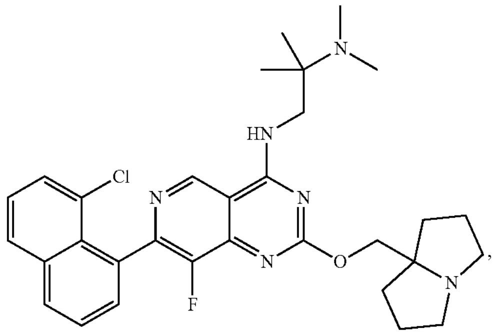
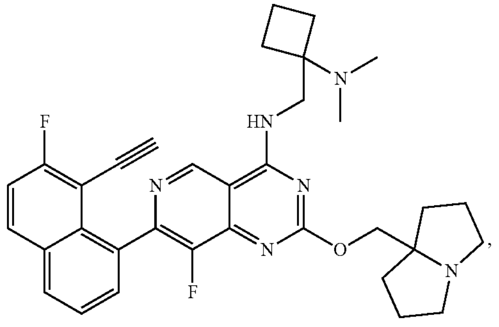

-continued

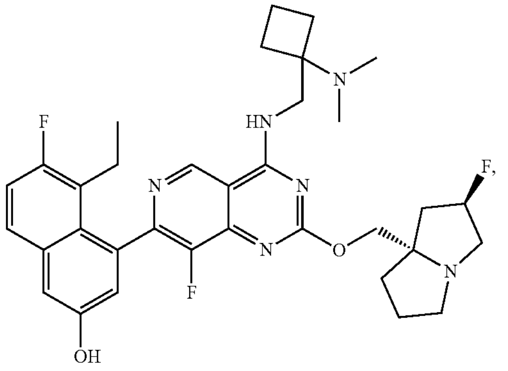

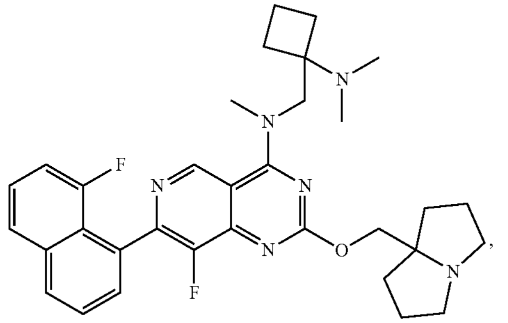

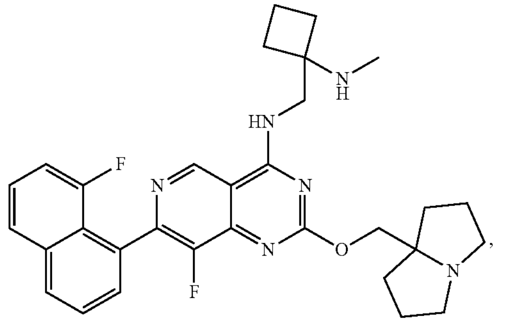

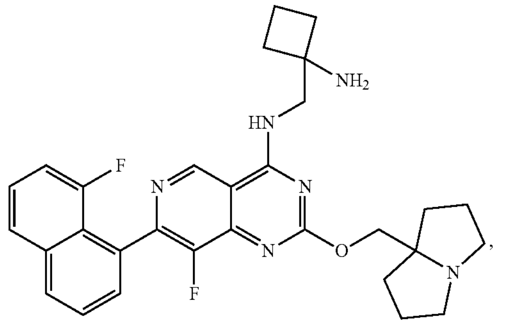

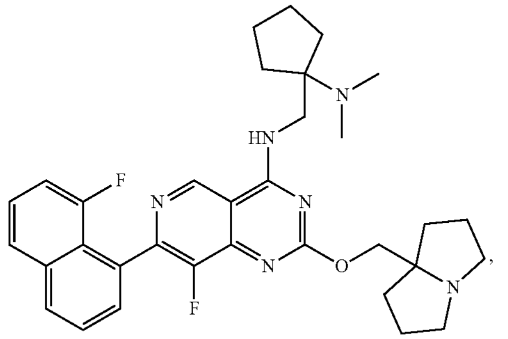

-continued

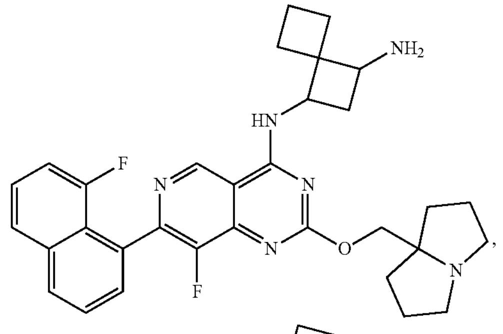

or

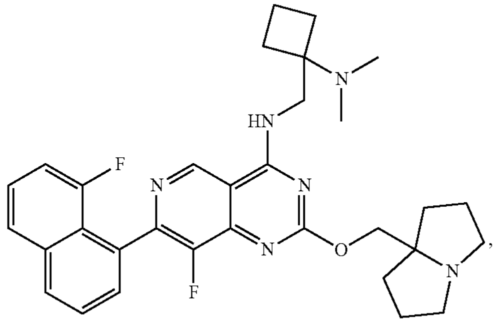

and pharmaceutically acceptable salts thereof.

In one embodiment, the compounds of Formula (I) include bis-hydrochloride, formic acid, bis-formic acid, tris-hydrochloride, trifluoroacetic acid, bis-trifluoroacetic acid, and tris-trifluoracetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a KRas G12D inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalene-disulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12D activity in a cell, comprising contacting the cell in which inhibition of KRas G12D activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12D with a compound provided herein includes the administration of a compound provided herein to an individual or patient, such as a human, having KRas G12D, as well as, for example, introducing a compound provided herein into a sample containing a cellular or purified preparation containing the KRas G12D.

In one embodiment, a cell in which inhibition of KRas G12D activity is desired is contacted with an effective amount of a compound of Formula (I) or pharmaceutically acceptable salt thereof to negatively modulate the activity of KRas G12D.

By negatively modulating the activity of KRas G12D, the methods described herein are designed to inhibit undesired cellular proliferation resulting from enhanced KRas G12D activity within the cell. The cells may be contacted in a single dose or multiple doses in accordance with a particular treatment regimen to effect the desired negative modulation of KRas G12D. The ability of compounds to bind KRas G12D may be monitored in vitro using well known methods, including those described in Examples A and B below. In addition, the inhibitory activity of exemplary compounds in cells may be monitored, for example, by measuring the inhibition of KRas G12D activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a KRas G12D-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the KRas G12D-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of KRas G12D.

Also provided herein is a compound of Formula (I) or a pharmaceutically acceptable salt thereof, or a pharmaceutical composition thereof as defined herein, for use in the treatment of a KRas G12D-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of KRas G12D.

Also provided herein is the use of a compound of Formula (I) or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that cancer is associated with a KRas G12D mutation (e.g., a KRas G12D-associated cancer) (e.g., as determined using a regulatory agency-approved, e.g., FDA-approved, assay or kit); and (b) administering to the patient a therapeutically effective amount of a compound of Formula (I), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I-III.

General Reaction Schemes

GENERAL REACTION SCHEME I

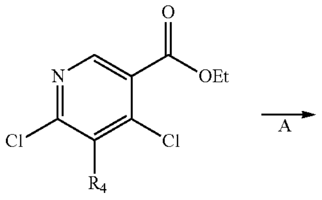

1

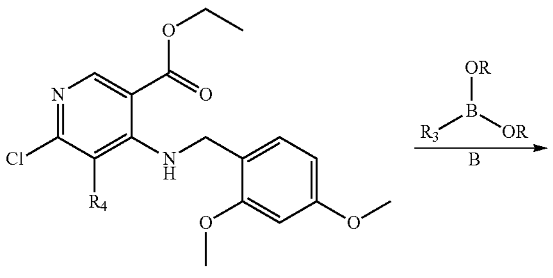

2

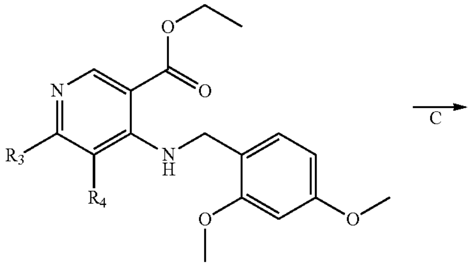

3

-continued

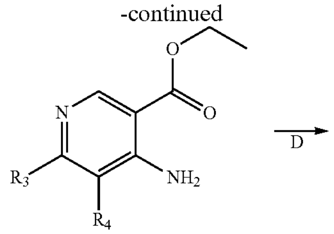

4

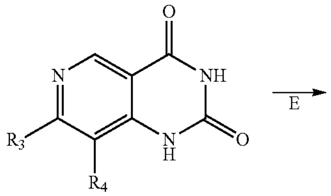

5

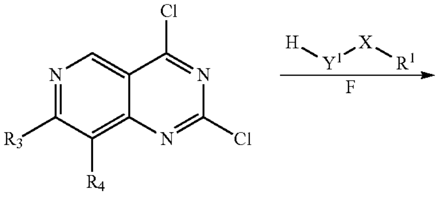

6

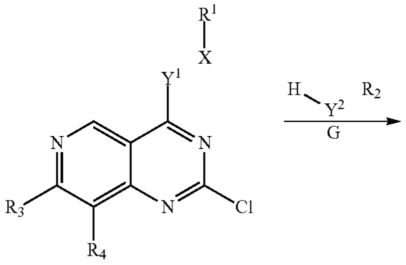

7

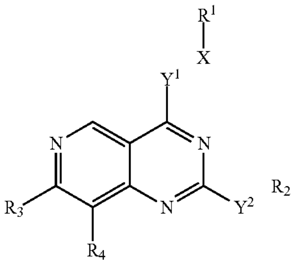

I

Compounds of Formula (I) wherein $Y^1$, X, $R^1$, $R^3$, and $R^4$ are as defined for Formula I, $Y^2$ and $R^2$ are as defined for Formula I with the exception that —$Y^2$—$R^2$ is other than hydrogen, can be prepared according to Scheme I. In step A, the 4-chlorine of nicotinate derivative (1) is substituted with 2,4-dimethoxybenzylamine in a polar solvent such as dioxane and in the presence of a base such as N-ethyl-N-isopropylpropan-2-amine to give compound (2). In step B, compound (2) is coupled with an aryl boronic acid ester under the Suzuki reaction conditions to give compound (3). In step C, the 2,4-dimethoxybenzyl group of compound (3) is removed with trifluoroacetic acid and in a solvent such as dichloromethane to give compound (4). In step D, compound (4) is treated with trichloroacetyl isocyanate in THE and then ammonia in methanol, and the cyclization is facilitated with heat to give pyridopyrimidinedione (5). In step E, dichloroazaquinazoline (6) is prepared from compound (5) with phosphoryl trichloride and N-ethyl-N-isopropylpropan-2-amine. In step F, the substituent —$Y^1$—X—$R^1$ is introduced by substitution of the chlorine with a nucleophile having the formula H—$Y^1$—X—$R^1$ in a polar solvent such as dioxane in the presence of a base such as cesium carbonate to provide compound (7). In step G, compound (7) undergoes a $S_NAr$ reaction with a nucleophile having the formula H—$Y^2$—$R^2$ in a solvent such as N,N-dimethylacetamide and in the presence of a base such as N-ethyl-N-isopropylpropan-2-amine to give compound (I). In some cases, the species $R^1$, $R^2$ and/or $R^3$ will also contain protecting group(s), which can be removed before or after step G in the synthetic sequence.

Compounds (1), (2), (3), (4), (5), (6), and (7) as shown and described above for Scheme I are useful as intermediates for preparing compounds of Formula (I) and are provided as further aspects of the invention.

GENERAL REACTION SCHEME II

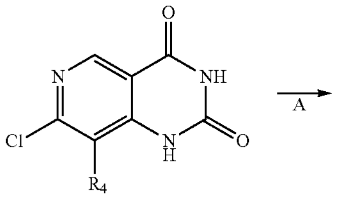

8

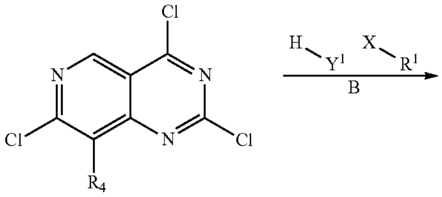

9

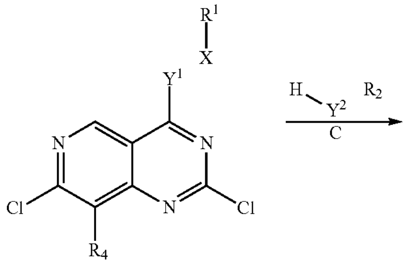

10

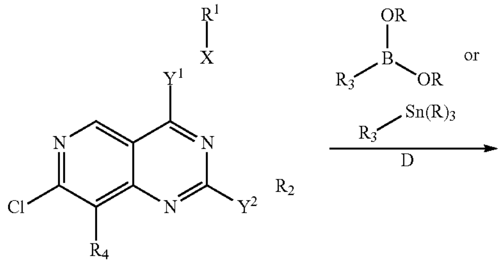

11

-continued

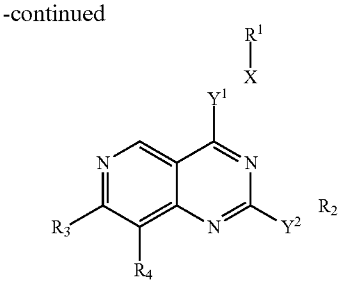

I

Compounds of Formula (I) wherein $Y^1$, X, $R^1$, $R^3$, and $R^4$ are as defined for Formula I, $Y^2$ and $R^2$ are as defined for Formula I with the exception that —$Y^2$—$R^2$ is other than hydrogen, can be prepared according to Scheme II. In step A, trichloroazaquinazoline (9) is prepared from compound (8) with phosphoryl trichloride and N-ethyl-N-isopropylpropan-2-amine. In step B, compound (9) undergoes a $S_NAr$ reaction with a nucleophile having the formula H—$Y^1$—X—$R^1$ to give compound (10) in a solvent such as N,N-dimethylacetamide and in the presence of a base such as N-ethyl-N-isopropylpropan-2-amine. In step C, the substituent —$Y^2$—X—$R^2$ is introduced by substitution of the chlorine with a nucleophile having the formula H—$Y^2$—$R^2$ in a polar solvent such as dioxane in the presence of a base such as cesium carbonate to provide compound (11). In step D, compound (11) is coupled with an aryl boronic acid ester or aryl stannane under the Suzuki or Stille reaction conditions to give compound (I). In some cases, the species $R^1$, $R^2$ and/or $R^3$ will also contain protecting group(s), which can be removed before or after step D in the synthetic sequence.

Compounds (8), (9), (10), and (11) as shown and described above for Scheme II are useful as intermediates for preparing compounds of Formula (I) and are provided as further aspects of the invention.

GENERAL REACTION SCHEME III

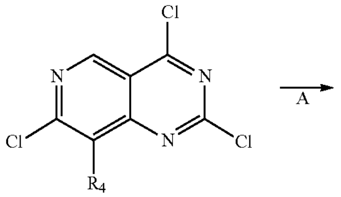

9

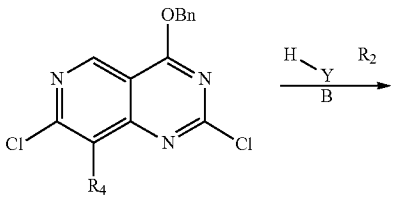

12

-continued

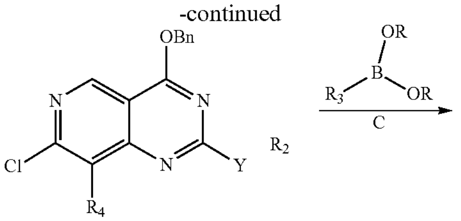

13

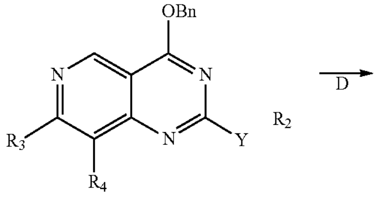

14

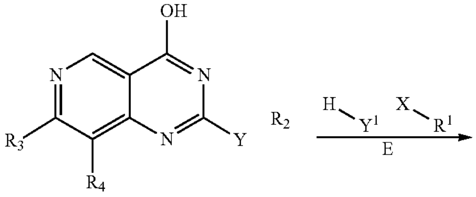

15

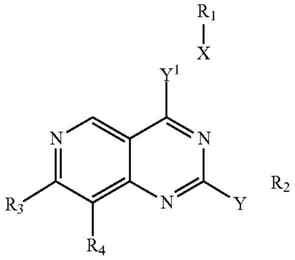

I

Compounds of Formula (I) wherein $Y^1$, X, $R^1$, $R^3$, and $R^4$ are as defined for Formula I, $Y^2$ and $R^2$ are as defined for Formula I with the exception that —$Y^2$—$R^2$ is other than hydrogen, can be prepared according to Scheme III. In step A, 4-chlorine of trichloroazaquinazoline (9) is substituted with a benzyl alcohol in a polar solvent such as dioxane and in the presence of a base such as N-ethyl-N-isopropylpropan-2-amine to provide compound (12). In step B, the substituent —$Y^2$—$R^2$ is introduced by substitution of 2-chlorine of compound (12) with a nucleophile having the formula H—$Y^2$—$R^2$ in a polar solvent such as dioxane and in the presence of a base such as cesium carbonate to provide compound (13). In step C, compound (13) is coupled with an aryl boronic acid ester under the Suzuki reaction conditions to give compound (14). In step D, the benzyl group of compound (14) is removed under the palladium-catalyzed hydrogenation condition in a solvent such as ethyl acetate to give compound (15). In step E, compound (15) is coupled with a nucleophile having the formula H—$Y^1$—X—$R^1$ to provide compound (I). This reaction proceeds with an activating reagent such as 2-(3H-[1,2,3]triazolo[4,5-b]pyridin-3-yl)-1,1,3,3-tetramethylisouronium hexafluorophosphate (V) in a polar solvent such as N,N-dimethylacetamide. In some cases, the species $R^1$, $R^2$ and/or $R^3$ will also contain protecting group(s), which can be removed before or after step E in the synthetic sequence.

Compounds (12), (13), (14), and (15) as shown and described above for Scheme III are useful as intermediates for preparing compounds of Formula (I) and are provided as further aspects of the invention.

The compounds of the present invention may be in anhydrous, solvated or hydrated forms, and all such forms are included within the scope of the invention.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic IPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

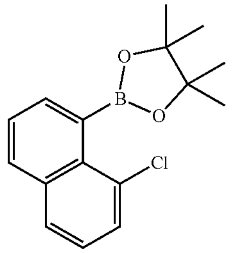

2-(8-chloronaphthalen-1-yl)-4,4,5,5-tetramethyl-1,3,2-dioxaborolane

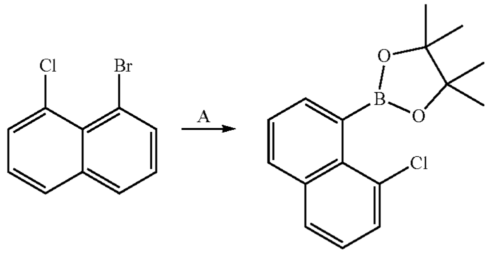

Step A. To a solution of 1-bromo-8-chloronaphthalene (20.0 g, 82.81 mmol) in dioxane (414 ml, 82.8 mmol) was added KOAc (24.38 g, 248.4 mmol) and 4,4,4',4',5,5,5',5'-octamethyl-2,2'-bi(1,3,2-dioxaborolane) (63.09 g, 248.4 mmol) and the reaction was degassed with Ar for 15 minutes followed by the addition of $PdCl_2$(dppf) (6.059 g, 8.281 mmol). The reaction was heated to 95° C. for 18 hrs. The dark mixture was filtered, and the filtrate was partitioned between water (400 mL) and EtOAc (400 mL). The aqueous layer was extracted with EtOAc (2×200 mL) and the combined organic phases were washed with brine (200 mL), dried over $Na_2SO_4$, filtered and concentrated to afford a black solid. The solid was filtered through a silica gel plug in a 2 L fritted funnel eluting with hexanes to 10% EtOAc/hexanes to afford partially purified product as a bright yellow solid. This was further purified by dividing in half and purifying on a 330 g Redisep cartridge (Isolera) eluting with 0-8% EtOAc/hexanes. Clean fractions from both lots were combined and concentrated to afford the product as a pale yellow solid. (14.8 g, 62%). $^1$H NMR (400 MHz, $(CDCl_3)$ δ 7.86 (dd, J=8.0, 1.2 Hz, 1H), 7.75 (dd, J=7.7, 1.2 Hz, 1H), 7.66 (dd, J=7.0, 1.2 Hz, 1H), 7.57 (dd, J=7.5, 1.1 Hz, 1H), 7.50 (dd, J=7.1, 6.9 Hz, 1H), 7.36 (dd, J=8.2, 7.4 Hz, 1H), 1.44 (s, 12H).

Intermediate 2

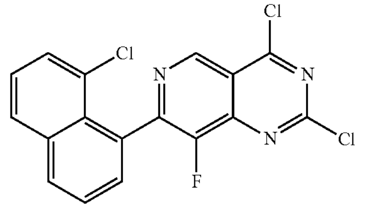

2,4-dichloro-7-(8-chloro-1-naphthyl)-8-fluoro-pyrido[4,3-d] pyrimidine

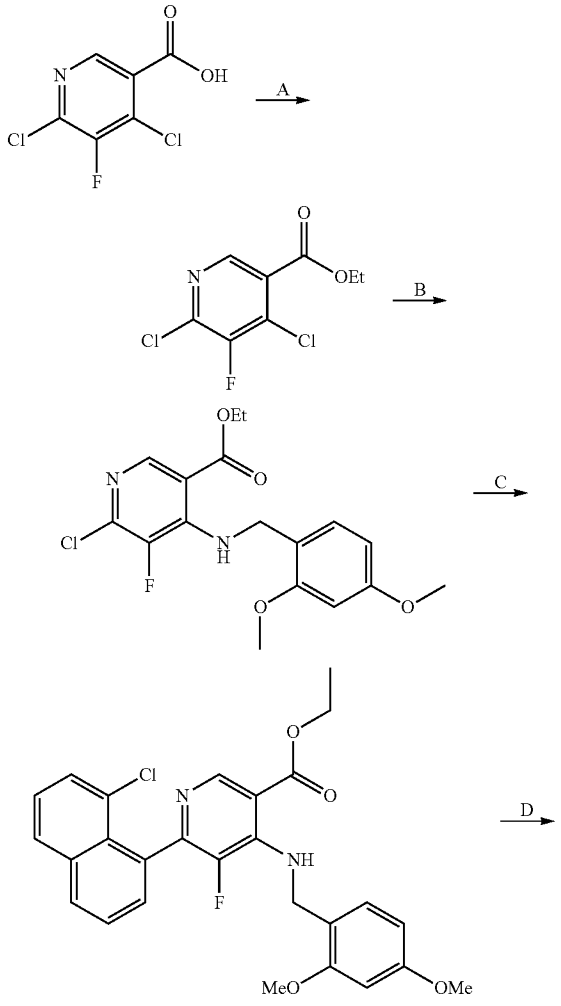

-continued

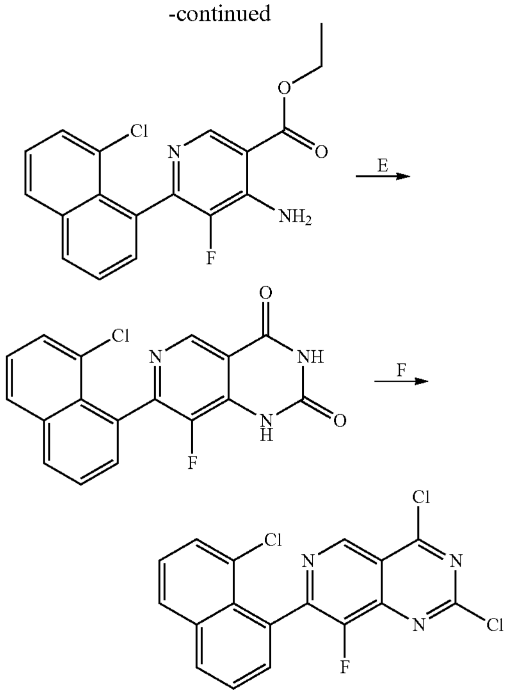

Step A. Ethyl 4,6-dichloro-5-fluoronicotinate. A solution of 4,6-dichloro-5-fluoro-3-pyridinecarboxylic acid (10.0 g, 47.6 mmol) in ethanol (238 ml, 47.6 mmol) was heated at 80° C. and thionyl chloride (6.95 ml, 95.2 mmol) was added dropwise through the condenser. The mixture was stirred at 65° C. overnight. The reaction was concentrated in vacuo and the residue was partitioned between EtOAc/water. The organic layer washed with $NaHCO_3$, dried, and concentrated to give a residue that was purified by flash chromatography eluting with a 0-100 ethyl acetate/hexanes gradient. The product fractions were collected and concentrated to give the desired product (9.61 g, 40.4 mmol, 85%). LCMS (MM-ES+APCI, Pos): m/z 237.9 (100%), 240.1 (50%) (M, M+2).

Step B. Ethyl 6-chloro-4-((2,4-dimethoxybenzyl)amino)-5-fluoronicotinate. To a mixture of ethyl 4,6-dichloro-5-fluoronicotinate (750 mg, 3.15 mmol) and N-ethyl-N-isopropylpropan-2-amine (1.38 ml, 7.88 mmol) in dioxane (15.8 ml, 3.15 mmol) was added 2,4-dimethoxybenzylamine (521 μl, 3.47 mmol) and the mixture heated at 40° C. for 18 h. The mixture was diluted with EtOAc and water and the layers were separated. The aqueous layer was extracted with EtOAc (3×). The combined organic layers were dried over $Na_2SO_4$, filtered, and concentrated. The residue was purified by flash chromatography eluting with 0-25% EtOAc/hexanes to give ethyl 6-chloro-4-((2,4-dimethoxybenzyl)amino)-5-fluoronicotinate (862 mg, 2.34 mmol, 74% yield). LCMS (MM-ES+APCI, Pos): m/z 369.1 (M+H).

Step C. ethyl6-(8-chloronaphthalen-1-yl)-4-((2,4-dimethoxybenzyl) amino)-5-fluoronicotinate. Ethyl 6-chloro-4-((2,4-dimethoxybenzyl)amino)-5-fluoronicotinate (6.1 g, 16 mmol), 2-(8-chloronaphthalen-1-yl)-4,4,5,5-tetramethyl-1,3,2-dioxaborolane (11.8 g, 41.0 mmol), $K_2CO_3$ (11.3 g, 82 mmol) and $Pd(PPh_3)_4$ (1.9 g, 1.6 mmol) were combined in toluene (120 mL), EtOH (60 mL) and water (30 mL) in a sealed vessel and stirred at 100° C. for 2.5 hours. The reaction stirred at room temperature overnight. The mixture was partitioned between water (300 mL) and EtOAc (300 mL) and the aqueous phase was extracted with EtOAc (2×200 mL). The combined organic phases were washed with brine (200 mL), dried over $Na_2SO_4$, filtered, and concentrated in vacuo. The residue was purified with silica gel column eluting with 0-40% EtOAc/hexanes to afford ethyl6-(8-chloronaphthalen-1-yl)-4-((2,4-dimethoxybenzyl) amino)-5-fluoronicotinate (4.3 g, 53% yield). LCMS (MM-ES+APCI, Pos): m/z 495.1 (M+H).

Step D. ethyl 4-amino-6-(8-chloronaphthalen-1-yl)-5-fluoronicotinate. To a solution of ethyl 6-(8-chloronaphthalen-1-yl)-4-((2,4-dimethoxybenzyl)amino)-5-fluoronicotinate (4.3 g, 8.7 mmol) in DCM (60 mL) at 0° C. was added TFA (13 mL, 173 mmol). The mixture was stirred for 2 hours. The mixture was carefully basified with 1M $K_3PO_4$ then filtered through GF paper to remove solids which were washed thoroughly with DCM. The filtrate was extracted with DCM (3×100 mL) and the combined organic phases were washed with brine (100 mL), dried over $Na_2SO_4$, filtered, and concentrated in vacuo. The residue was purified by silica gel column eluting with 0-30% EtOAc/hexanes to afford ethyl 4-amino-6-(8-chloronaphthalen-1-yl)-5-fluoronicotinate (2.1 g, 69% yield). LCMS (MM-ES+APCI, Pos): m/z 345.1 (M+H).

Step E. 7-(8-chloronaphthalen-1-yl)-8-fluoropyrido[4,3-d] pyrimidine-2,4(1H,3H)-dione. To a suspension of ethyl 4-amino-6-(8-chloronaphthalen-1-yl)-5-fluoronicotinate (2.1 g, 6.0 mmol) in THE (12 mL) cooled to 0° C. was added trichloro acetyl isocyanate (0.85 mL, 7.1 mmol) and the mixture was stirred for 30 minutes. The mixture was concentrated, suspended in MeOH (30 mL), cooled to 0° C. and treated with ammonia (7M in MeOH, 17 mL, 119 mmol). The mixture was stirred at room temperature for 16 hours, and then solids were filtered, washed with minimal methanol, and dried in vacuo to afford 7-(8-chloronaphthalen-1-yl)-8-fluoropyrido[4,3-d]pyrimidine-2,4(1H,3H)-dione (1.7 g, 82% yield). LCMS (MM-ES+APCI, Pos): m/z 342.1 (M+H).

Step F. 2,4-dichloro-7-(8-chloronaphthalen-1-yl)-8-fluoropyrido[4,3-d] pyrimidine. To a suspension of 7-(8-chloronaphthalen-1-yl)-8-fluoropyrido[4,3-d]pyrimidine-2,4(1H,3H)-dione (0.10 g, 0.29 mmol) in $POCl_3$ (1.5 mL) was carefully added DIEA (0.15 mL). The mixture was warmed to 110° C. and stirred for 2 hours. The cooled mixture was concentrated and dried in vacuo for 16 hours. The residue was partitioned between EtOAc (10 mL) and water (10 mL) and then $NaHCO_3$ was added until basic. The aqueous layer was extracted with EtOAc (2×10 mL) and the combined organic phases were washed with $NaHCO_3$ (10 mL) and brine (10 mL) then dried over $Na_2SO_4$, filtered, and concentrated to afford 2,4-dichloro-7-(8-chloronaphthalen-1-yl)-8-fluoropyrido[4,3-d]pyrimidine. Used directly in the next reaction assuming 100% yield. LCMS (MM-ES+APCI, Pos): m/z 378.1 (M+H).

Intermediate 3

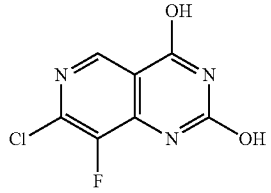

7-chloro-8-fluoro-pyrido[4,3-*d*] pyrimidine-2,4-diol

-continued

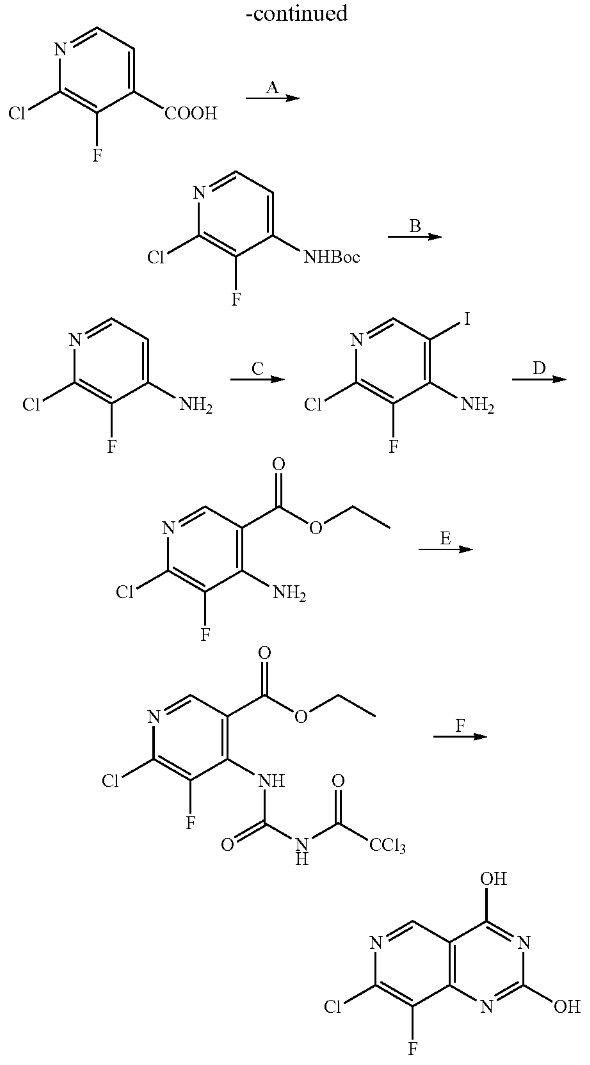

Step A. tert-butyl N-(2-chloro-3-fluoro-4-pyridyl)carbamate. A mixture of 2-chloro-3-fluoro-pyridine-4-carboxylic acid (180 g, 1.03 mol, 1.0 eq), 4 Å molecular sieve (300 g) and $Et_3N$ (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen. The mixture was cooled to 25° C. and diphenylphosphoryl azide (423 g, 1.54 mol, 333 mL, 1.5 eq) was added. The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography ($SiO_2$, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191. $^1$H NMR (400 MHz, methanol-$d_4$) δ=8.11 (t, J=5.6 Hz, 1H), 7.99 (d, J=5.6 Hz, 1H), 1.52 (s, 9H).

Step B. 2-chloro-3-fluoro-pyridin-4-amine. To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered, and the filter cake was diluted with saturated $NaHCO_3$ solution (2000 mL) and extracted with ethyl acetate (2×2000 mL). The combined organic layers were dried over sodium sulfate, filtered and concentrated under vacuum. 2-chloro-3-fluoro-pyridin-4-amine (107 g, 731 mmol, 91% yield, 99.9% purity) was obtained as a yellow solid and used in the next step without further purification. LCMS [ESI, M+1]: 147. $^1$H NMR (400 MHz, methanol-$d_4$) δ=7.61 (d, J=5.6 Hz, 1H), 6.67 (t, J=6.0 Hz, 1H).

Step C. 2-chloro-3-fluoro-5-iodo-pyridin-4-amine. To a solution of 2-chloro-3-fluoro-pyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL). The organic layer was washed with saturated $Na_2CO_3$ solution (2×1500 mL), saturated $Na_2SO_3$ (1×2000 mL) solution and brine (1×1500 mL), dried over $Na_2SO_4$, filtered and concentrated under vacuum. 2-chloro-3-fluoro-5-iodo-pyridin-4-amine (190 g, 676 mmol, 93% yield, 97.2% purity) was obtained as a yellow solid and used for next steps without further purification. LCMS [ESI, M+1]: 273. $^1$H NMR (400 MHz, methanol-$d_4$) δ=8.06 (s, 1H).

Step D. ethyl 4-amino-6-chloro-5-fluoro-pyridine-3-carboxylate. To a solution of 2-chloro-3-fluoro-5-iodo-pyridin-4-amine (78.4 g, 288 mmol, 1.0 eq) in EtOH (1500 mL) was added $Pd(PPh_3)_2Cl_2$ (20.2 g, 28.8 mmol, 0.1 eq) and $Et_3N$ (105 g, 1.04 mol, 144 mL, 3.61 eq) under nitrogen. The suspension was degassed under vacuum and purged with nitrogen several times. The mixture was stirred under $CO_2$ (15.0 psi) at 80° C. for 15 hours. Upon completion, the mixture was filtered, and the filtrate was concentrated under vacuum to remove 70% of MeOH and the residue was filtered. The combined filter cakes were concentrated under vacuum. ethyl 4-amino-6-chloro-5-fluoro-pyridine-3-carboxylate (142 g, crude) was obtained as a yellow solid. LCMS [ESI, M+1]: 219. $^1$H NMR (400 MHz, dmso-$d_6$) δ=8.36 (s, 1H), 7.49-7.42 (m, 2H), 4.31 (q, J=7.2 Hz, 2H), 1.31 (t, J=7.2 Hz, 3H).

Step E. ethyl-6-chloro-5-fluoro-4-[(2,2,2-trichloroacetyl)carbamoylamino]pyridine-3-carboxylate. To a solution of ethyl 4-amino-6-chloro-5-fluoro-pyridine-3-carboxylate (20.3 g, 73.2 mmol, 1.0 eq) in THE (60 mL) was added 2,2,2-trichloroacetyl isocyanate (20.7 g, 110 mmol, 13.0 mL, 1.5 eq) at 25° C. The mixture was stirred at 25° C. for 10 min. Upon completion, the mixture was concentrated under vacuum. The crude product was triturated with MTBE (200 mL) at 25° C. for 5 min. Ethyl 6-chloro-5-fluoro-4-[(2,2,2-trichloroacetyl)carbamoylamino]pyridine-3-carboxylate (29.3 g, 67.74 mmol, 92% yield, 94.1% purity) was obtained as a gray solid. LCMS [ESI, M+1]: 408.

Step F. 7-chloro-8-fluoro-pyrido[4,3-d]pyrimidine-2,4-diol. To a solution of ethyl 6-chloro-5-fluoro-4-[(2,2,2-trichloroacetyl)carbamoylamino]pyridine-3-carboxylate (29.3 g, 63.1 mmol, 1.0 eq) in MeOH (290 mL) was added $NH_3$MeOH (29 mL, 20% purity) at 25° C. The mixture was stirred at 25° C. for 1 h. Upon completion, the mixture was concentrated under vacuum. The crude product was triturated with MTBE (200 mL) at 25° C. for 10 min. 7-Chloro-8-fluoro-pyrido[4,3-d]pyrimidine-2,4-diol (18 g, crude) was obtained as a brown solid. LCMS [ESI, M+1]: 216. $^1$H NMR (400 MHz, dmso-$d_6$) δ=8.35 (br s, 1H).

Intermediate 4

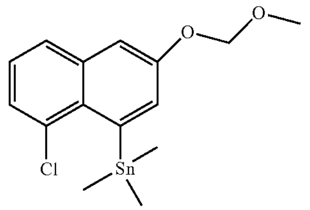

(8-chloro-3-(methoxymethoxy)naphthalen-1-yl)trimethylstannane

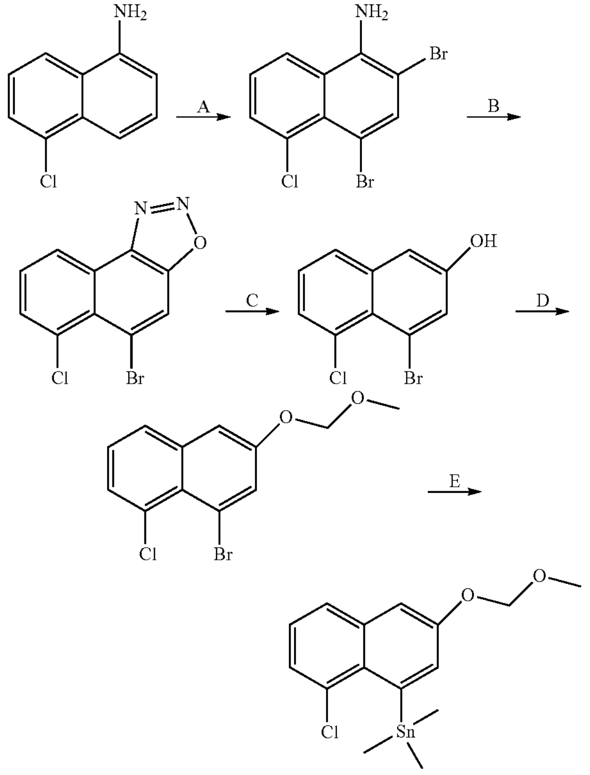

Step A. 2,4-dibromo-5-chloronaphthalen-1-amine: To a solution of 5-chloronaphthalen-1-amine (1.0 g, 5.6 mmol) in chloroform (30 mL) was added bromine (0.58 mL, 11 mmol) in chloroform (30 mL) dropwise. The mixture was heated at 50° C. for 16 hours. Additional bromine (0.58 mL, 11 mmol) in 30 mL of chloroform was added dropwise at room temperature and the mixture was warmed to 50° C. for 4 additional hours. The reaction was cooled to room temperature and concentrated in vacuo. Water was added to the residue and the aqueous layer extracted three times with ethyl acetate. Pooled organic layers were dried over magnesium sulfate, filtered, and concentrated. The residue was purified by silica gel column to afford 2,4-dibromo-5-chloronaphthalen-1-amine. $^1$H NMR 400 MHz, ($CDCl_3$) δ 7.94 (s, 1H), 7.76 (d, 1H, J=8.0 Hz), 7.64 (d, 1H, J=8.0 Hz), 7.36 (t, 1H, J=8.0 Hz), 4.46 (bs, 2H).

Step B. 5-bromo-6-chloronaphtho[1,2-d][1,2,3]oxadiazole: 2,4-dibromo-5-chloronaphthalen-1-amine (0.90 g, 2.7 mmol) was dissolved in acetic acid (22 mL) and propionic acid (2 mL) and cooled in an ice bath followed by addition of sodium nitrite (0.28 g, 4.1 mmol). The reaction was stirred at 0° C. for one hour and room temperature for one hour. Water was added to the reaction and the aqueous layer was extracted three times with ethyl acetate. The pooled organic layers were dried over magnesium sulfate, filtered, and concentrated. The residue was purified by silica gel column to afford 5-bromo-6-chloronaphtho[1,2-d][1,2,3]oxadiazole. $^1$H NMR 400 MHz, ($CDCl_3$) δ 7.45-7.38 (m, 2H), 7.31 (s, 1H), 7.22 (dd, 1H, J=8.0, 4.0 Hz).

Step C. 4-bromo-5-chloronaphthalen-2-ol: 5-bromo-6-chloronaphtho[1,2-d][1,2,3]oxadiazole (0.28 g, 1.0 mmol) was dissolved in ethanol (15 mL) and THE (15 mL) at 0° C. Sodium borohydride (0.87 g, 2.3 mmol) was added and the reaction was warmed up to room temperature over 2 hours. The solvent was removed in vacuo and water was added to the residue. The mixture was acidified with 2 M HCl (aq.) and extracted two times with ethyl acetate. Pooled organic layers were dried over magnesium sulfate, filtered, and concentrated. The residue was purified by silica gel column to give 4-bromo-5-chloronaphthalen-2-ol. $^1$H NMR 500 MHz, ($CDCl_3$) δ 7.61-7.58 (m, 2H), 7.48 (d, 1H, J=10.0 Hz), 7.30 (d, 1H, J=10.0 Hz), 7.15 (s, 1H), 5.02 (s, 1H).

Step D. 1-bromo-8-chloro-3-(methoxy methoxy) naphthalene: To a solution of 4-bromo-5-chloronaphthalen-2-ol (0.20 g, 0.79 mmol) in THE (4 mL, 0.79 mmol) at 0° C. was added sodium hydride (47 mg, 1.2 mmol). The mixture was stirred at 0° C. for 30 minutes followed by addition of chloromethyl methyl ether (78 μL, 1.02 mmol) and the mixture was warmed to room temperature over 2 hours. The reaction was concentrated in vacuo and partitioned between EtOAc and water. The layers were separated. The aqueous layer was extracted with additional ethyl acetate. Pooled organic layers were dried over magnesium sulfate, filtered, and concentrated. The residue was purified by silica gel column eluting with 0→10% EtOAc/Hex to afford 1-bromo-8-chloro-3-(methoxymethoxy)naphthalene. $^1$H NMR 500 MHz, ($CDCl_3$) δ 7.68 (s, 1H), 7.65 (d, 1H, J=10.0 Hz), 7.49 (d, 1H, J=10.0 Hz), 7.36 (s, 1H), 7.29 (t, 1H, J=10.0 Hz), 5.26 (s, 2H), 3.51 (s, 3H).

Step E. (8-chloro-3-(methoxymethoxy)naphthalen-1-yl) trimethylstannane: A mixture of 1-bromo-8-chloro-3-(methoxymethoxy)naphthalene (200 mg, 0.66 mmol), 1,1,1,2,2,2-hexamethyldistannane (0.69 ml, 3.3 mmol) and toluene (4.0 mL, 0.66 mmol) was sparged with argon for 5 minutes. Tetrakis(triphenylphosphine) Pd(0) (77 mg, 0.07 mmol) was added and the reaction sparged with argon for a few more minutes and the mixture was heated at 110° C. for 16 hours. The reaction was diluted with water and the aqueous layer extracted 2× with hexane. The pooled organic layers were washed with brine, dried over magnesium sulfate, filtered, and concentrated. The residue was purified by silica gel column eluting with 0→5% EtOAc/Hex to afford (8-chloro-3-(methoxymethoxy)naphthalen-1-yl)trimethylstannane. $^1$H NMR 500 MHz, ($CDCl_3$) δ 7.67 (d, 1H, J=10.0 Hz), 7.56 (s, 1H), 7.46 (d, 1H, J=10.0 Hz), 7.37 (s, 1H), 7.31 (t, 1H, J=10.0 Hz), 5.30 (s, 2H), 3.53 (s, 3H), 0.42 (s, 9H).

Intermediate 5

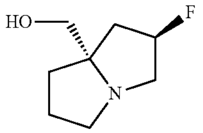

((2R,7aS)-2-fluorotetrahydro-1H-pyrrolizin-7a(5H)-yl)methanol

-continued

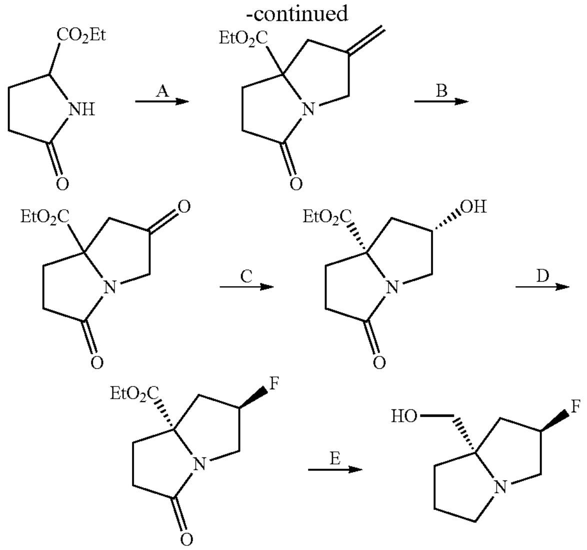

Step A. Ethyl 2-methylene-5-oxotetrahydro-1H-pyrrolizine-7a(5H)-carboxylate. To a mixture of ethyl 5-oxopyrrolidine-2-carboxylate (1.50 kg, 9.54 mol, 1.00 eq) and 3-chloro-2-(chloromethyl)prop-1-ene (1.91 kg, 15.3 mol, 1.77 L, 1.60 eq) in THE (7.50 L) was added LiHMDS (1 M, 19.1 L, 2.00 eq) drop-wise at −40° C. under $N_2$. The mixture was stirred at 25° C. for 20 hrs. The reaction mixture was poured into HCl (1 M, 2.50 L) and pH was adjusted to 7 with HCl (2 M) at 0° C. The mixture was extracted with EtOAc (4.50 L×3). The combined organic layers were washed with brine (4.50 L), dried over $Na_2SO_4$, filtered and concentrated under reduced pressure to give a residue. The residue was purified by column chromatography ($SiO_2$, Petroleum ether/Ethyl acetate=10/1 to 1/1, Rf=0.40) to afford the title compound (898 g, 3.88 mol, 40.6% yield, 82% purity) as a yellow oil. LCMS: Rt=0.716 min, m/z=210.1 (M+H). $^1H$ NMR: 400 MHz $CDCl_3$ δ: 5.02-5.07 (m, 2H), 4.28 (m, 1H), 4.16-4.22 (m, 2H), 3.71 (dd, J=15.6, 1.6 Hz, 1H), 3.04 (m, 1H), 2.73-2.80 (m, 1H), 2.57-2.64 (m, 1H), 2.41-2.49 (m, 2H), 2.03-2.17 (m, 2H), 1.24-1.30 (m, 3H).

Step B. ethyl 2,5-dioxotetrahydro-1H-pyrrolizine-7a(5H)-carboxylate. To a mixture of ethyl 2-methylene-5-oxotetrahydro-1H-pyrrolizine-7a(5H)-carboxylate (165 g, 646 mmol, 1.00 eq) in DCM (1650 mL) and MeOH (165 mL) was added $O_3$ (15 psi) at −70° C. under $N_2$. The solution became pale blue, and then the mixture was purged by $N_2$ for 30 min. $Me_2S$ (80.4 g, 1.29 mol, 95.0 mL, 2.00 eq) was added to the mixture at −70° C. The mixture was stirred at 25° C. for 16 hours. The reaction mixture was concentrated under reduced pressure to give a residue. The residue was purified by column chromatography ($SiO_2$, Petroleum ether/Ethyl acetate=10/1 to 1/1, Rf=0.50) to afford the title compound (821 g, 3.62 mol, 93.3% yield, 93.1% purity) as a yellow oil. LCMS: Rt=0.543 min, m/z=212.1 (M+H). $^1H$ NMR: 400 MHz $CDCl_3$ δ: 4.23 (m, 2H), 4.12 (m, 1H), 3.56 (m, 1H), 2.96-3.01 (m, 2H), 2.77-2.86 (m, 1H), 2.43-2.50 (m, 2H), 2.14-2.22 (m, 1H), 1.28 (m, 1H).

Step C. ethyl 2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (257 g, 1.22 mol, 1.00 eq) in EtOH (1300 mL) was slowly added $NaBH_4$ (13.8 g, 365 mmol, 0.30 eq) at 0° C. under $N_2$. The mixture was stirred at 0° C. for 10 min. The reaction was quenched with saturated $NH_4Cl$ (65.0 mL) at 5° C. and stirred at 5° C. for 0.5 hr, then the mixture was concentrated under reduced pressure to give a residue. The residue was purified by column chromatography ($SiO_2$, Petroleum ether/Ethyl acetate=10/1 to 1/1) to afford the title compound (56.8% yield) as a yellow oil. $^1H$ NMR: 400 MHz $CDCl_3$ δ: 4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

Step D. ethyl (2S,7aR)-2-fluoro-5-oxotetrahydro-1H-pyrrolizine-7a(5H)-carboxylate. To a solution of ethyl 2-hydroxy-5-oxotetrahydro-1H-pyrrolizine-7a(5H)-carboxylate (150 g, 642 mmol, 1.00 eq) in DCM (750 mL) was added a solution of DAST (131 g, 813 mmol, 107 mL, 1.50 eq) drop-wise at −70° C. under $N_2$. The reaction mixture was warmed to 25° C. stirred at 25° C. for 16 hours. The reaction mixture was quenched with MeOH (40.0 mL) at 10° C., then diluted with water (750 mL) and extracted with DCM (750 mL×3). The combined organic layers were washed with brine (750 mL), dried over $Na_2SO_4$, filtered and concentrated under reduced pressure to give a residue. The residue was purified by column chromatography ($SiO_2$, Petroleum ether/Ethyl acetate=1/0 to 0/1, Rf=0.30) to afford ethyl 2-fluoro-5-oxotetrahydro-1H-pyrrolizine-7a(5H)-carboxylate (50.6% yield, 74.7% purity) as a yellow oil. This compound (61 g, 283.43 mmol, 1.00 eq) was further purified by HPLC (column: Welch ultimate XB—$NH_2$ 250*50*10 um; mobile phase: [Heptane-EtOH(0.1% $NH_3H_2O$)]; B %: 10%-10%, 10 min) to give a yellow oil (49.0 g, 226.08 mmol, 99.3% purity). $^1H$ NMR: 400 MHz $CDCl_3$ δ: 5.30 (m, 1H), 4.10-4.23 (m, 3H), 3.11-3.14 (m, 1H), 2.67-2.76 (m, 3H), 2.41-2.45 (m, 1H), 2.03-2.12 (m, 2H), 1.23-1.29 (m, 3H). SFC separation (column: DAICEL CHIRALPAK IC (250 mm*50 mm, 10 um); mobile phase: [0.1% $NH_3{\cdot}H_2O$ IPA]; B %: 40%-40%, 4.7 min; 200 minmin, desired product: Peak 2, Rt=1.959 min) of the racemic material (280 g, 1.22 mol, 1 eq) gave the title compound (114 g, 96.0% purity).

Step E. ((2R,7aS)-2-fluorotetrahydro-1H-pyrrolizin-7a(5H)-yl)methanol. To a suspension of $LiAlH_4$ (33.1 g, 871 mmol, 1.50 eq) in THE (625 mL) was added a solution of ethyl (2S,7aR)-2-fluoro-5-oxotetrahydro-1H-pyrrolizine-7a(5H)-carboxylate (125 g, 581 mmol, 1.00 eq) in THE (375 mL) drop-wise at 0° C. under $N_2$. The reaction mixture was warmed to 70° C. and stirred at 70° C. for 3 hours. The mixture was cooled to 0° C. Then to the mixture was added water (33.0 mL), NaOH (15%, 99.0 mL) and water (99 mL) dropwise in sequence 0° C. After addition, the mixture was stirred at 0° C. stirred for 5 min. The mixture was filtered, and the filtered cake was washed with EtOAc (1000 mL×2). The filtrate was dried with $MgSO_4$, filtered, and concentrated under reduced pressure to give a residue. The residue was purified by column chromatography ($SiO_2$, DCM: MeOH=100/1 to 10/1) to afford the title compound (180 g, 1.10 mol, 94.7% yield, 97.3% purity) as a yellow oil. $^1H$ NMR: 400 MHz $CDCl_3$ δ: 5.12-5.27 (m, 1H), 3.25 (s, 2H), 3.14-3.18 (m, 2H), 3.12-3.13 (m, 1H), 3.02-3.09 (m, 1H), 2.01-2.11 (m, 2H), 1.75-1.86 (m, 4H). Racemic material was made from the racemic ethyl (2S,7aR)-2-fluoro-5-oxotetrahydro-1H-pyrrolizine-7a(5H)-carboxylate without SFC separation.

Intermediate 6

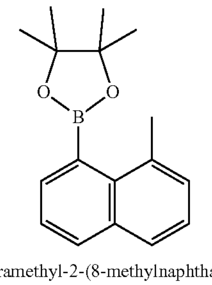

4,4,5,5-tetramethyl-2-(8-methylnaphthalen-1-yl)-1,3,2-dioxaborolane

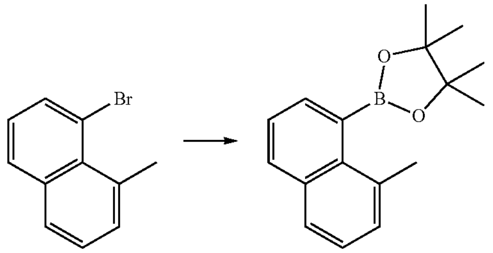

Step A. 4,4,5,5-tetramethyl-2-(8-methylnaphthalen-1-yl)-1,3,2-dioxaborolane. To a solution of 1-bromo-8-methyl-naphthalene (0.700 g, 3.17 mmol) in dioxane (15.8 ml) was added potassium acetate (0.932 g, 9.50 mmol) and 4,4,4',4',5,5,5',5'-octamethyl-2,2'-bi(1,3,2-dioxaborolane) (2.41 g, 9.50 mmol) and the reaction sparged with $N_2$ for 15 minutes, followed by the addition of $PdCl_2$(dppf) (0.232 g, 0.317 mmol). The reaction was heated to 95° C. for 18 hrs. The reaction was concentrated in vacuo and taken up in DCM. The slurry was filtered through GF/F filter paper and the organics was concentrated in vacuo. The material was chromatographed twice using 10→100% Ethyl acetate/hexane as eluent to give 4,4,5,5-tetramethyl-2-(8-methyl-naphthalen-1-yl)-1,3,2-dioxaborolane (576 mg, 2.15 mmol, 68% yield). HPLC (5-95% ACN/$H_2O$+0.1% TFA) 3.701 min.

Intermeidate 7

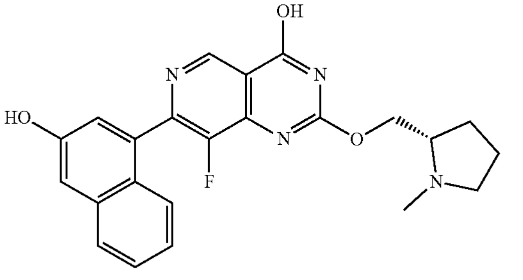

(S)-8-fluoro-7-(3-hydroxynaphthalen-1-yl)-2-((1-methylpyrrolidin-2-yl)methoxy)pyrido[4,3-d]pyrimidin-4-ol

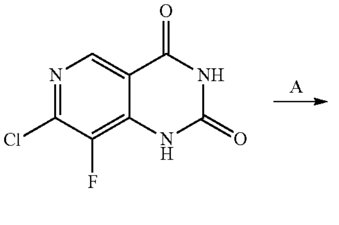

-continued

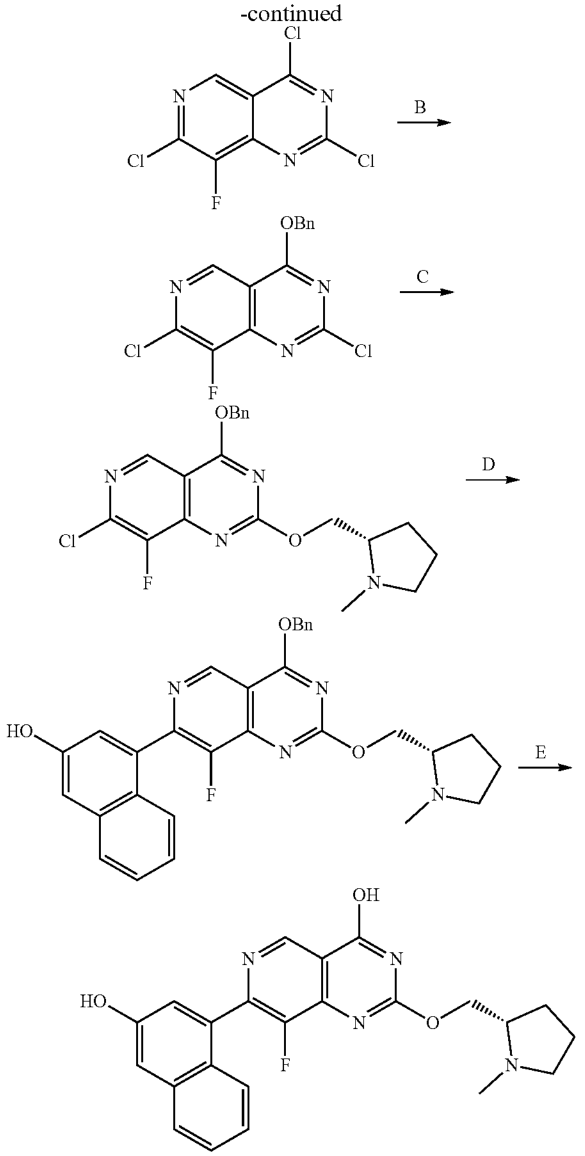

Step A. 2,4,7-trichloro-8-fluoropyrido[4,3-d]pyrimidine. To a flask containing 7-chloro-8-fluoropyrido[4,3-d]pyrimi-dine-2,4(1H,3H)-dione (0.93 g, 4.3 mmol) was added $POCl_3$ (8 mL, 86 mmol). The mixture was cooled with an ice bath and DIPEA (2 mL, 13 mmol) was added. The ice bath was removed and the mixture was stirred at 100° C. for 20 hours. The solution was cooled and concentrated to give a brown oil. The oil was dissolved in DCM and the solution was quenched with a mixture of $K_3PO_4$ (37%, 10 mL) and ice (20 g). The mixture was stirred for 10 minutes. The two layers were separated, and the organic layer was further washed with brine, dried over $Na_2SO_4$, and concentrated to give crude 2,4,7-trichloro-8-fluoropyrido[4,3-d]pyrimidine which was used immediately without purification assuming 100% yield.

Step B. 4-(benzyloxy)-2,7-dichloro-8-fluoropyrido[4,3-d]pyrimidine. To a flask containing crude 2,4,7-trichloro-8-fluoropyrido[4,3-d]pyrimidine (1.5 g, 4.3 mmol) were added molecular sieves (3 Å, 0.4 g), 1,4-dioxane (22 mL), benzyl alcohol (0.50 mL, 4.7 mmol) and DIPEA (2.0 mL, 13 mmol). The mixture was stirred at 60° C. under $N_2$ for 7 hours. The mixture was concentrated to dryness and diluted with EtOAc. The mixture was filtered through a pad of Celite, and the filtrate was concentrated in vacuo. The residue was purified by flash chromatography eluting with 0-25% ethyl acetate/hexanes to afford 4-(benzyloxy)-2,7-dichloro-8-fluoropyrido[4,3-d]pyrimidine (0.68 g, 49%). LCMS (MM-ES+APCI, Pos): m/z 324.1 (M+H).

Step C. (S)-4-(benzyloxy)-7-chloro-8-fluoro-2-((1-methylpyrrolidin-2-yl)methoxy)pyrido[4,3-d]pyrimidine. To a solution of 4-(benzyloxy)-2,7-dichloro-8-fluoropyrido[4,3-d]pyrimidine (1.3 g, 4.0 mmol) in 1,4-dioxane (40 mL) was added (S)-(1-methylpyrrolidin-2-yl)methanol (0.67 mL, 5.6 mmol) followed by $Cs_2CO_3$ (3.27 g, 10 mmol). The mixture was heated at 80° C. under $N_2$ for 3 hours followed by stirring at room temperature for 15 hours. The mixture was diluted with ethyl acetate and filtered through a pad of Celite. The filtrate was concentrated, and the residue was purified by preparative C18 HPLC (Gilson, 0-95% $CH_3CN$/$H_2O$ with 0.1% TFA as modifier). The desired fractions were combined, basified with $Na_2CO_3$ (2 M), and extracted with EtOAc. The combined organic extract was washed with brine, dried over $Na_2SO_4$ and concentrated to afford (S)-4-(benzyloxy)-7-chloro-8-fluoro-2-((1-methylpyrrolidin-2-yl)methoxy)pyrido[4,3-d]pyrimidine (0.91 g, 56%). LCMS (MM-ES+APCI, Pos): m/z 403.1 (M+H).

Step D. (S)-4-(4-(benzyloxy)-8-fluoro-2-((1-methylpyrrolidin-2-yl)methoxy)pyrido[4,3-d]pyrimidin-7-yl)naphthalen-2-ol. A flask containing a solution of 4-(4,4,5,5-tetramethyl-1,3,2-dioxaborolan-2-yl)naphthalen-2-ol (0.58 g, 2.1 mmol), (S)-4-(benzyloxy)-7-chloro-8-fluoro-2-((1-methylpyrrolidin-2-yl)methoxy)pyrido[4,3-d]pyrimidine (0.66 g, 1.6 mmol), $Na_2CO_3$ (2 mL, 4 mmol), $Pd(PPh_3)_4$ (0.19 g, 0.16 mmol) in dioxane (16 mL) was sparged with $N_2$. The mixture was heated under $N_2$ at 80° C. for 7 hours and cooled to room temperature. The resulting mixture was quenched with water and extracted with EtOAc. The combined EtOAc extract was dried over $Na_2SO_4$, concentrated, and purified by preparative C18 HPLC (Gilson, 5-95% $CH_3CN/H_2O$ with 0.1% TFA). The desired fractions were combined, basified with $NaHCO_3$(Sat.) and extracted with DCM. The combined DCM extract was dried over $Na_2SO_4$, filtered and concentrated to afford (S)-4-(4-(benzyloxy)-8-fluoro-2-((1-methylpyrrolidin-2-yl)methoxy)pyrido[4,3-d]pyrimidin-7-yl)naphthalen-2-ol (0.39 g, 46% yield). LCMS (MM-ES+APCI, Pos): m/z 511.2 (M+H).

Step E. (S)-8-fluoro-7-(3-hydroxynaphthalen-1-yl)-2-((1-methylpyrrolidin-2-yl)methoxy)pyrido[4,3-d]pyrimidin-4-ol. To a flask with a stir bar was added Pd/C (160 mg, 0.15 mmol). A solution of (S)-4-(4-(benzyloxy)-8-fluoro-2-((1-methylpyrrolidin-2-yl)methoxy)pyrido[4,3-d]pyrimidin-7-yl)naphthalen-2-ol (0.39 g, 0.75 mmol) in EtOAc (15 mL) was added. The flask was closed with a septum and stirred under a balloon of $H_2$ at room temperature for 15 hours. The mixture was filtered through Celite and the Celite was further washed with DCM/MeOH (2:1, 200 mL). The combined organics were concentrated and dried to afford (S)-8-fluoro-7-(3-hydroxynaphthalen-1-yl)-2-((1-methylpyrrolidin-2-yl)methoxy)pyrido[4,3-d]pyrimidin-4-ol (0.29 g, 92% yield). LCMS (MM-ES+APCI, Pos): m/z 421.2 (M+H).

Intermediate 8

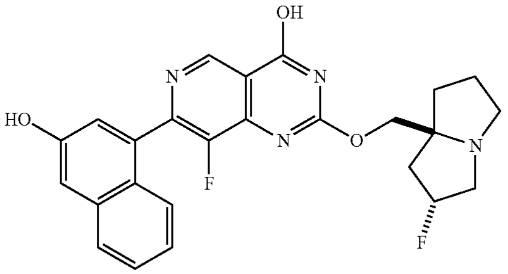

8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (racemic, trans)

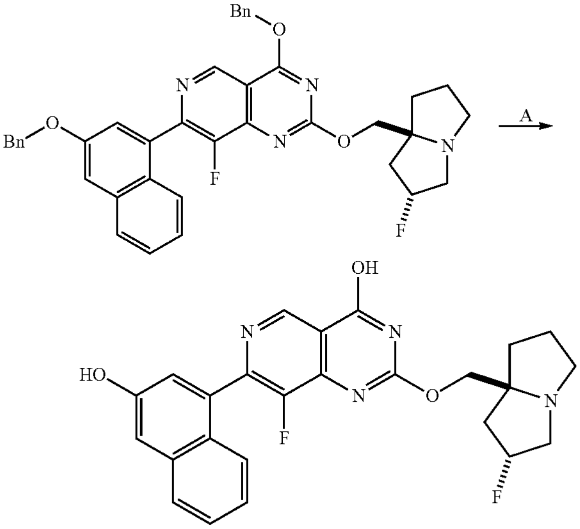

4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine. Synthesized according to Intermediate 7 substituting racemic ((2R,7aS)-2-fluorotetrahydro-1H-pyrrolizin-7a(5H)-yl)methanol for (S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 645.3 (M+H).

Step A. 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol. To 4-(benzyloxy)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidine (1.0 g, 1.6 mmol) in DCM (200 mL) at −70° C. were added 1,2,3,4,5-pentamethylbenzene (1.2 g, 7.8 mmol) and dropwise trichloroborane (8.0 mL, 7.7 mmol). The reaction was stirred at −70° C. for 30 minutes and warmed to 0° C. The reaction was stirred at 0° C. for two hours and quenched with sat. $NaHCO_3$ (150 mL). The aqueous layer was extracted with IPA/DCM (20%, 3×). The combined organic phases were then dried over $Na_2SO_4$, filtered, and concentrated. The material was triturated with ether and the solids filtered to give 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (0.59 g, 82% yield). LCMS (MM-ES+APCI, Pos): m/z 465.1 (M+H).

Intermediate 9

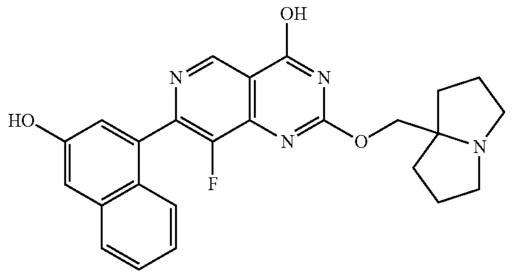

8-fluoro-7-(3-hydroxynaphthalen-1-yl)-2-((tetrahydro-1H-pyrrolizin-7a(5H)-yl)methoxy)pyrido[4,3-d]pyrimidin-4-ol

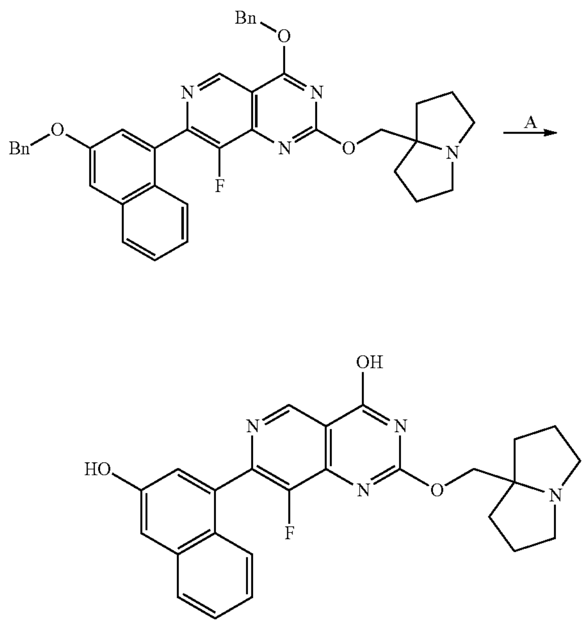

4-(benzyloxy)-7-(3-(benzyloxy)naphthalen-1-yl)-8-fluoro-2-((tetrahydro-1H-pyrrolizin-7a(5H)-yl)methoxy) pyrido[4,3-d]pyrimidine. Synthesized according to Intermediate 7 substituting tetrahydro-1H-pyrrolizin-7a(5H)-yl) methanol for (S)-(1-methylpyrrolidin-2-yl)methanol in step C and 2-(3-(benzyloxy)naphthalen-1-yl)-4,4,5,5-tetramethyl-1,3,2-dioxaborolane for 4-(4,4,5,5-tetramethyl-1,3,2-dioxaborolan-2-yl)naphthalen-2-ol in step D. LCMS (MM-ES+APCI, Pos): m/z 627.3 (M+H).

Step A. 8-fluoro-7-(3-hydroxynaphthalen-1-yl)-2-((tetrahydro-1H-pyrrolizin-7a(5H)-yl)methoxy)pyrido[4,3-d]pyrimidin-4-ol. To 4-(benzyloxy)-7-(3-(benzyloxy)naphthalen-1-yl)-8-fluoro-2-((tetrahydro-1H-pyrrolizin-7a(5H)-yl) methoxy)pyrido[4,3-d]pyrimidine (5.3 g, 8.38 mmol) in THF/MeOH (10 mL/6 mL) was added $Pd(OH)_2/C$ (4.7 g, 3.4 mmol). The mixture was flushed with $N_2$ and $H_2$, and then stirred at 45 psi $H_2$ for 16 hours. The reaction was filtered through Celite and the Celite was washed with 20% MeOH/DCM. The filtrate was concentrated to afford 8-fluoro-7-(3-hydroxynaphthalen-1-yl)-2-((tetrahydro-1H-pyrrolizin-7a (5H)-yl)methoxy)pyrido[4,3-d]pyrimidin-4-ol (2.1 g, 56% yield). LCMS (MM-ES+APCI, Pos): m/z 447.3 (M+H).

Intermediate 10

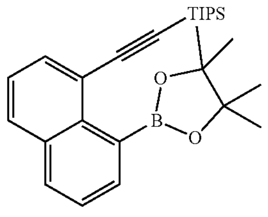

triisopropyl((8-(4,4,5,5-tetramethyl-1,3,2-dioxaborolan-Z-yl)naphthalen-1-yl)ethynyl)silane

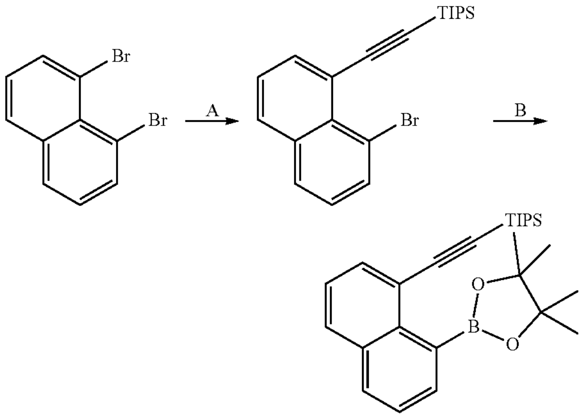

Step A. 2-(8-bromo-1-naphthyl) ethynyl-triisopropyl-silane. A mixture of 1,8-dibromonaphthalene (7.0 g, 25 mmol), ethynyl(triisopropyl)silane (4.9 g, 27 mmol), CuI (0.47 g, 2.5 mmol), $PPh_3$ (0.64 g, 2.5 mmol) and $Pd(PPh_3)_2Cl_2$ (0.86 g, 1.2 mmol) in TEA (100 mL) was stirred at 80° C. for 3 hours under $N_2$. The mixture was diluted with water (50 mL) and extracted with ethyl acetate (2×50 mL). The combined organic layers were washed with brine (50 mL), dried over $Na_2SO_4$, filtered, and concentrated in vacuo. The residue was purified by column chromatography ($SiO_2$, petroleum ether) to give 2-(8-bromo-1-naphthyl) ethynyl-triisopropyl-silane (7.0 g, 74% yield). $^1H$ NMR (400 MHz, chloroform-d) δ=7.87 (dd, J=1.2, 7.2 Hz, 1H), 7.82-7.73 (m, 3H), 7.41-7.34 (m, 1H), 7.25 (t, J=7.6 Hz, 1H), 1.19-1.16 (m, 21H).

Step B. triisopropyl((8-(4,4,5,5-tetramethyl-1,3,2-dioxaborolan-2-yl) naphthalen-1-yl) ethynyl) silane. To a mixture of 4,4,4',4',5,5,5',5'-octamethyl-2,2'-bi(1,3,2-dioxaborolane) (0.25 g, 1.0 mmol), Palladium (II) Acetate (11 mg, 0.050 mmol), Cyclohexyl diphenyl phosphine (27 mg, 0.10 mmol), and potassium acetate (0.20 g, 2.0 mmol) in a vial was added a solution of ((8-bromonaphthalen-1-yl)ethynyl) triisopropylsilane (194 mg, 0.5 mmol) in toluene (2 mL) under $N_2$. The vial was closed and heated at 110° C. for 24 hours. The reaction was cooled to room temperature, diluted with EtOAc, and filtered through a filter paper. The filtrate was concentrated and purified using hexanes as eluent to give triisopropyl((8-(4,4,5,5-tetramethyl-1,3,2-dioxaborolan-2-yl) naphthalen-1-yl) ethynyl) silane (0.20 g, 90% yield). LCMS (MM-ES+APCI, Pos): m/z 435.3 (M+H).

Intermediate 11

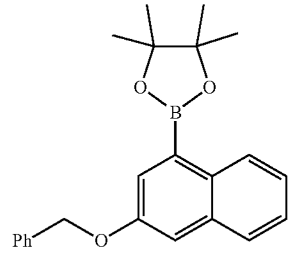

2-(3-(benzyloxy) naphthalen-1-yl)-4,4,5,5-tetramethyl-1,3,2-dioxaborolane

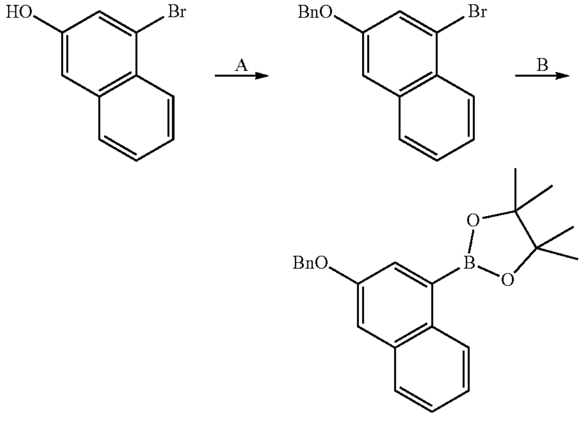

Step A. 3-(benzyloxy)-1-bromonaphthalene. A solution of 4-bromonaphthalen-2-ol (5.0 g, 22 mmol) in DMF (50 mL) was treated with sodium hydride (0.99 g, 60%, 25 mmol) and heated to 50° C. for 1 hour under $N_2$. After the mixture was cooled to room temperature, benzyl bromide (3.5 mL, 29 mmol) was added, followed by tetrabutylammonium iodide (0.82 g, 2.2 mmol). The mixture was stirred for 16 hours, and then partitioned between water (200 mL) and EtOAc (200 mL). The aqueous layer was extracted with EtOAc (2×100 mL) and the combined organic phases were washed with water (4×100 mL) and brine (50 mL) then dried over $Na_2SO_4$, filtered, and concentrated. The residue was purified by silica column chromatography eluting with 0-15% EtOAc/hexanes, and for a second time eluting with 0-5% EtOAc/hexanes to afford 3-(benzyloxy)-1-bromonaphthalene (6.2 g, 88% yield).

Intermediate 12

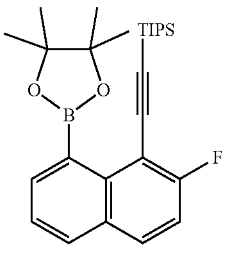

((2-fluoro-8-(4,4,5,5-tetramethyl-1,3,2-dioxaborolan-Z-yl)naphthalen-1-yl)ethynyl)triisopropylsilane -continued

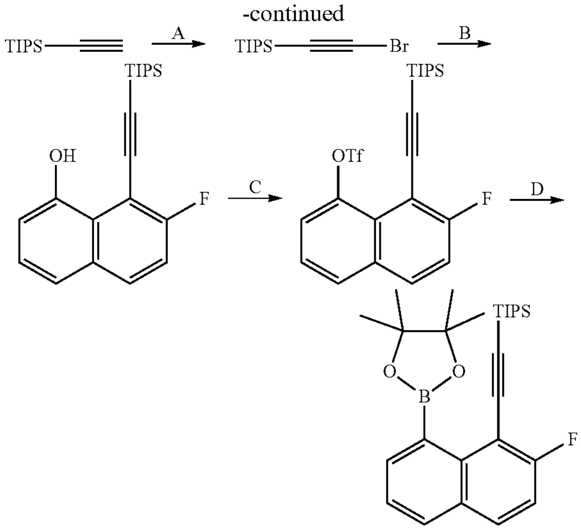

Step A. (bromoethynyl)triisopropylsilane. To a solution of ethynyltriisopropylsilane (1.00 g, 5.48 mmol, 1.23 mL, 1.00 eq) in acetone (30.0 mL) was added NBS (1.13 g, 6.36 mmol, 1.16 eq) followed by silver nitrate (93.1 mg, 548 μmol, 0.10 eq), and the reaction was stirred at 25° C. for 12 hours. Then the mixture was poured into ice. After ice being allowed to melt, the aqueous layer was extracted with petroleum ether (3×30 mL). The combined organic layers were dried over sodium sulfate, filtered and concentrated in vacuum affording (bromoethynyl)triisopropylsilane (1.20 g, 84% yield) as a brown oil; $^1$H NMR (400 MHz, $CDCl_3$) δ 1.25-0.83 (m, 21H).

Step B. 7-fluoro-8-(2-triisopropylsilylethynyl)naphthalen-1-ol. To a solution of (bromoethynyl)triisopropylsilane (445 mg, 1.70 mmol, 1.20 eq) and 7-fluoronaphthalen-1-ol (230 mg, 1.42 mmol, 1.00 eq) in DCE (4.00 mL) was added potassium carbonate (196 mg, 1.42 mmol, 1.00 eq), sodium acetate (23.3 mg, 284 μmol, 0.20 eq) and Dichloro(p-cymene)ruthenium(II) dimer (217 mg, 355 μmol, 0.25 eq). The mixture was stirred at 40° C. for 12 hours. The reaction was cooled to 25° C. and filtered, and the filtrate was concentrated in vacuum to give a residue. The residue was purified by preparative TLC (petroleum ether/ethyl acetate=10/1) affording 7-fluoro-8-(2-triisopropylsilylethynyl)naphthalen-1-ol (450 mg, 93% yield) as a brown solid; LCMS [ESI, 2M+1]: 685.1.

Step C. [7-fluoro-8-(2-triisopropylsilylethynyl)-1-naphthyl] trifluoromethanesulfonate. To a solution of 7-fluoro-8-(2-triisopropylsilylethynyl)naphthalen-1-ol (450 mg, 1.31 mmol, 1.00 eq) in DCM (5.00 mL) were added DIEA (509 mg, 3.94 mmol, 687 μL, 3.00 eq) and trifluoromethanesulfonic anhydride (556 mg, 1.97 mmol, 325 μL, 1.50 eq.) at −40° C. The mixture was stirred at 25° C. for 0.5 hour. The mixture was purified by column chromatography ($SiO_2$, petroleum ether/ethyl acetate=1/0 to 100/1) affording [7-fluoro-8-(2-triisopropylsilylethynyl)-1-naphthyl]trifluoromethanesulfonate (560 mg, 90% yield). Yellow oil; $^1$H NMR (400 MHz, DMSO-$d_6$) δ 8.25 (dd, J=5.6, 9.2 Hz, 1H), 8.19 (dd, J=0.8, 8.0 Hz, 1H), 7.80-7.75 (m, 1H), 7.74-7.70 (m, 1H), 7.69-7.66 (m, 1H), 1.22-1.10 (m, 21H).

Step D. 2-[2-fluoro-8-(4,4,5,5-tetramethyl-1,3,2-dioxaborolan-2-yl)-1-naphthyl]ethynyl-triisopropyl-silane. To a solution of [7-fluoro-8-(2-triisopropylsilylethynyl)-1-naphthyl]trifluoromethanesulfonate (250 mg, 527 μmol, 1.00 eq) and 4,4,5,5-tetramethyl-2-(4,4,5,5-tetramethyl-1,3,2-dioxaborolan-2-yl)-1,3,2-dioxaborolane (200 mg, 790 μmol, 1.50 eq) in dioxane (6.00 mL) were added Pd(dppf)C12 (38.5 mg, 52.7 μmol, 0.10 eq) and dry potassium acetate (103 mg, 1.05 mmol, 2.00 eq) under nitrogen atmosphere. The mixture was stirred at 110° C. for 12 hours under nitrogen atmosphere. The mixture was concentrated in vacuum to give a residue. The residue was purified by column chromatography by preparative TLC ($SiO_2$, petroleum ether/ethyl acetate=100/1) affording 2-[2-fluoro-8-(4,4,5,5-tetramethyl-1,3,2-dioxaborolan-2-yl)-1-naphthyl]ethynyl-triisopropyl-silane (80.0 mg, crude) as a red solid; $^1H$ NMR (400 MHz, DMSO-$d_6$) δ 8.07 (dd, J=6.0, 9.2 Hz, 1H), 8.04 (dd, J=1.2, 8.2 Hz, 1H), 7.73 (d, J=6.4 Hz, 1H), 7.57-7.53 (m, 1H), 7.52 (dd, J=1.6, 6.8 Hz, 1H), 1.34 (s, 12H), 1.24-1.21 (m, 2H), 1.14-1.09 (m, 19H).

Intermediate 13

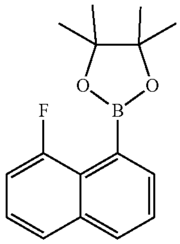

2-(8-fluoronaphthalan-1-yl)-4,4,5,5-tetramethyl-1,3,2-dioxaborolane

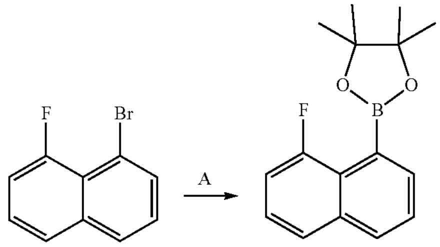

Step A. 2-(8-fluoronaphthalen-1-yl)-4,4,5,5-tetramethyl-1,3,2-dioxaborolane. A solution of 1-bromo-8-fluoronaphthalene (55.0 g, 244 mmol, 1.00 eq) in THE (850 mL) was degassed and purged with $N_2$ for 3 times, and then n-BuLi (2.5 M, 117 mL, 1.20 eq) was added drop-wise at −70° C. The mixture was stirred at −70° C. for 1 hr under $N_2$ atmosphere. Then added a solution of 2-isopropoxy-4,4,5,5-tetramethyl-1,3,2-dioxaborolane (63.6 g, 342 mmol, 69.8 mL, 1.40 eq) in THF (150 mL) at −70° C. The resulting mixture was stirred at −70° C. for 1 hr. LCMS showed 1-bromo-8-fluoronaphthalene was consumed completely and one main peak with desired mass (RT=1.073 min) was detected. The reaction mixture was quenched by $NH_4Cl$ solution (500 mL) at 10° C., then diluted with $H_2O$ (300 mL) and extracted with PE (500 mL×3). The combined organic layers were washed with brine (500 mL×2), dried over $Na_2SO_4$, filtered and concentrated under reduced pressure to give a residue. The residue was purified by flash silica gel chromatography (ISCO®; 100 g SepaFlash® Silica Flash Column, Eluent of 0~4% Ethyl acetate/Petroleum ether, TLC:Petroleum ether/Ethyl acetate=10/1, Rf=0.67) to give compound the title compound (30.0 g, 110 mmol, 45.1% yield, 100% purity) as a light yellow solid. LCMS: M+1, 273.

Intermediate 14

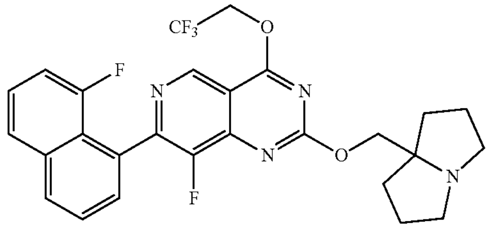

8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimdine

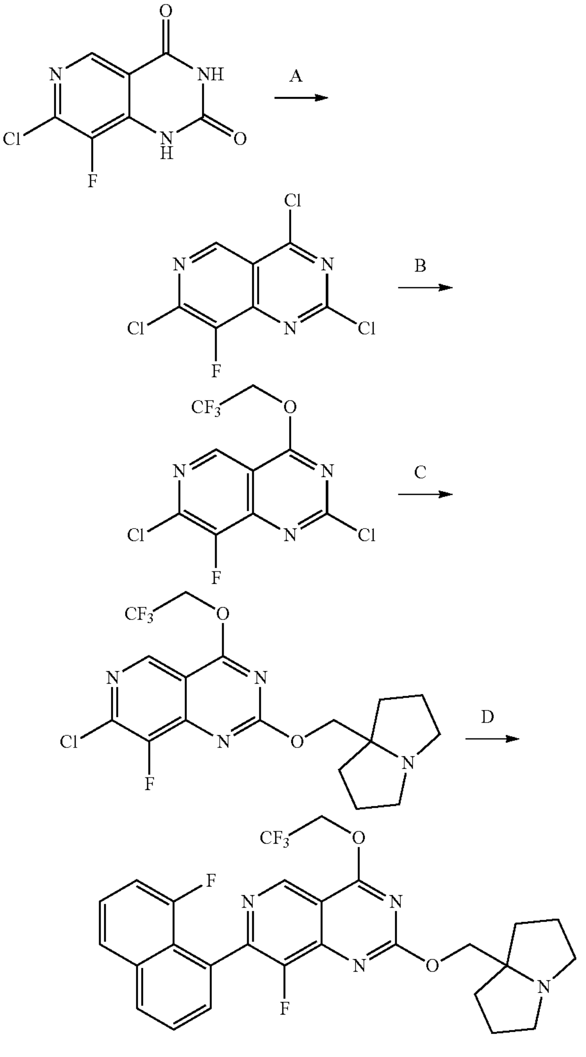

Step A. 2,4,7-trichloro-8-fluoropyrido[4,3-d]pyrimidine. To a solution of 7-chloro-8-fluoropyrido[4,3-d]pyrimidine-2,4(1H,3H)-dione (100 g, 463 mmol, 1.00 eq) in toluene (500 mL) were added $POCl_3$ (213 g, 1.39 mol, 129 mL, 3.00 eq) and DIEA (179 g, 1.39 mol, 242 mL, 3.00 eq) at 0° C. The mixture was stirred at 110° C. for 5 h. The reaction was distilled in vacuum (80° C., water pump) to give 2,4,7-trichloro-8-fluoropyrido[4,3-d]pyrimidine (100 g, 396.10 mmol, 85.39% yield) as brown oil.

Step B. 2,7-dichloro-8-fluoro-4-(2,2,2-trifluoroethoxy) pyrido[4,3-d]pyrimidine. To a solution of 2,4,7-trichloro-8-fluoropyrido[4,3-d]pyrimidine (100 g, 396 mmol, 1.00 eq) and 2,2,2-trifluoroethanol (59.4 g, 594 mmol, 42.7 mL, 1.50 eq) in toluene (2 L) was added t-BuONa (152 g, 1.58 mol, 4.00 eq) at 25° C. The mixture was stirred at 25° C. for 2 hr. The reaction mixture was filtered through a pad of Celite, washed with brine (3 L×2) and concentrated under reduced pressure to give a residue, which was purified by reversed-phase HPLC (0.1% FA condition) to give 2,7-dichloro-8-fluoro-4-(2,2,2-trifluoroethoxy)pyrido[4,3-d]pyrimidine (45.0 g, 140 mmol, 35.5% yield, 99.0% purity) as a brown solid. LCMS: M+1, 316.

Step C. 7-chloro-8-fluoro-2-((tetrahydro-1H-pyrrolizin-7a(5H)-yl)methoxy)-4-(2,2,2-trifluoroethoxy)pyrido[4,3-d]pyrimidine. A mixture of (tetrahydro-1H-pyrrolizin-7a(5H)-yl)methanol (35.7 g, 253 mmol, 2.00 eq), DIEA (32.7 g, 253 mmol, 44.0 mL, 2.00 eq) and 4 A MS (40.0 g) in 2-methyltetrahydrofuran (400 mL) was stirred at 25° C. for 1 hr. Then a solution of 2,7-dichloro-8-fluoro-4-(2,2,2-trifluoroethoxy)pyrido[4,3-d]pyrimidine (40.0 g, 126 mmol, 1.00 eq) in 2-methyltetrahydrofuran (400 mL) was added and the resulting mixture was stirred at 25° C. for 2 hrs. The reaction mixture was filtered. The filtrate was washed with sat. aq. $NH_4Cl$ solution (1 L×2), dried over $Na_2SO_4$, filtered and concentrated under reduced pressure to give a residue. The residue was triturated with acetonitrile (300 mL) at 25° C. for 30 min to give 7-chloro-8-fluoro-2-((tetrahydro-1H-pyrrolizin-7a(5H)-yl)methoxy)-4-(2,2,2-trifluoroethoxy)pyrido[4,3-d]pyrimidine (26.0 g, 61.1 mmol, 48.3% yield, 99.0% purity) as a light yellow solid. LCMS: M+1, 421.

Step D. 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine. A mixture of 7-chloro-8-fluoro-2-((tetrahydro-1H-pyrrolizin-7a(5H)-yl)methoxy)-4-(2,2,2-trifluoroethoxy)pyrido[4,3-d]pyrimidine (17.0 g, 40.4 mmol, 1.00 eq), 2-(8-fluoronaphthalen-1-yl)-4,4,5,5-tetramethyl-1,3,2-dioxaborolane (16.4 g, 60.6 mmol, 1.50 eq), BrettPhos Pd G3 (4.25 g, 4.69 mmol, 1.16e-1 eq), $K_3PO_4$ (1.5 M, 80.8 mL, 3.00 eq) in toluene (170 mL) was degassed and purged with $N_2$ for 3 times, and then the mixture was stirred at 65° C. for 4 hrs under $N_2$ atmosphere. The reaction mixture was filtered. The filtrate was extracted with toluene (170 mL×3). The combined organic layers were dried over $Na_2SO_4$, filtered and concentrated under reduced pressure to give a residue. The residue was purified by reversed-phase HPLC (0.1% FA condition) to give 8-fluoro-7-(8-fluoronaphthalen-1-yl)-2-((tetrahydro-1H-pyrrolizin-7a(5H)-yl)methoxy)-4-(2,2,2-trifluoroethoxy)pyrido[4,3-d]pyrimidine (10.85 g, 16.6 mmol, 41.2% yield, 95.8% purity) as a yellow solid. NMR: δ 9.28 (s, 1H), 8.23 (d, J=8.1 Hz, 1H), 7.97 (d, J=8.1 Hz, 1H), 7.81-7.76 (m, 1H), 7.68 (dd, J=0.9, 7.2 Hz, 1H), 7.61 (dt, J=5.1, 7.9 Hz, 1H), 7.34 (dd, J=7.1, 13.3 Hz, 1H), 5.47-5.37 (m, 2H), 4.77-4.67 (m, 2H), 3.56-3.49 (m, 2H), 3.22 (td, J=6.0, 11.7 Hz, 2H), 2.27-2.00 (m, 8H); LCMS: M+1, 531.

Intermediate 15

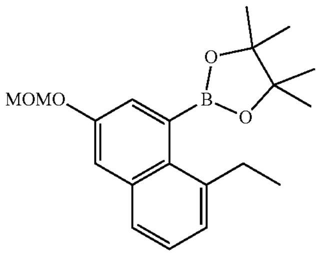

2-[8-ethyl-3-(methoxymethoxy)-1-napthyl]-4,4,5,5-tetramethyl-1,3,2-dioxaborolane -continued

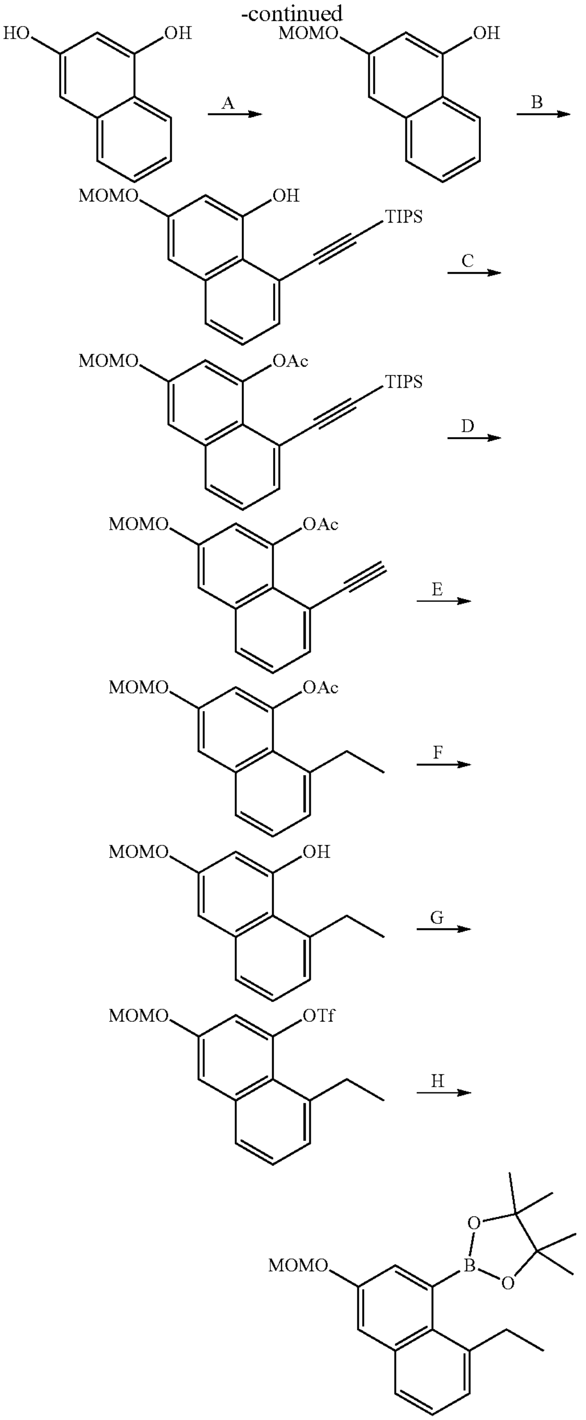

Step A. 3-(methoxymethoxy)naphthalen-1-ol. To a solution of naphthalene-1,3-diol (50 g, 312 mmol, 1.0 eq) and DIEA (120 g, 935 mmol, 163 mL, 3.0 eq) in dichloromethane (400 mL) was added chloro(methoxy)methane (27.5 g, 342 mmol, 1.1 eq) dropwise at 0-5° C. over 30 minutes. The mixture was stirred at 25° C. for 16 hours. The reaction mixture was quenched with saturated $NaHCO_3$ aqueous solution (100 mL) below 5° C. and diluted with $H_2O$ (300 mL). The organic layer was separated and $H_2O$ (100 mL) was added. The pH of the mixture was adjusted to 3~4 with 2N HCl below 10° C. The organic layer was separated, dried over $Na_2SO_4$, filtered and concentrated under reduced pressure to give a residue. The residue was purified by silica gel column chromatography (petroleum ether/ethyl acetate=10/1, 8/1) to give the title compound (31.3 g, 49% yield). Red brown liquid. $^1$H NMR (400 MHz, chloroform-d) δ=8.17-8.08 (m, 1H), 7.71-7.61 (m, 1H), 7.45-7.30 (m, 2H), 7.02-6.63 (m, 2H), 5.38-5.28 (m, 2H), 3.56-3.53 (m, 3H).

Step B. 3-(methoxymethoxy)-8-(2-triisopropylsilylethynyl)naphthalen-1-ol. A mixture of 3-(methoxymethoxy) naphthalen-1-ol (20 g, 97.9 mmol, 1.0 eq), (bromoethynyl) triisopropylsilane (32 g, crude), $K_2CO_3$ (13.6 g, 98.4 mmol, 1.0 eq), sodium acetate (2 g, 24.4 mmol, 0.25 eq) and dichlororuthenium; 1-isopropyl-4-methyl-benzene (9.00 g, 14.7 mmol, 0.15 eq) in DCE (200 mL) was degassed and purged with $N_2$ for 3 times. The mixture was stirred at 40° C. for 13 hours under $N_2$ atmosphere. The reaction mixture was filtered through a pad of Celite. The filtrate was concentrated under reduced pressure to give a residue. The residue was purified by silica gel column chromatography ($SiO_2$, petroleum ether/ethyl acetate=1/0 to 50/1) to give the title compound (10.6 g, 28% yield). Yellow liquid. $^1$H NMR (400 MHz, chloroform-d) δ=9.26 (s, 1H), 7.69 (dd, J=0.8, 8.4 Hz, 1H), 7.50 (dd, J=1.2, 7.2 Hz, 1H), 7.33-7.29 (m, 1H), 6.97 (d, J=2.4 Hz, 1H), 6.77 (d, J=2.4 Hz, 1H), 5.27 (s, 2H), 3.52 (s, 3H), 1.29-1.14 (m, 21H).

Step C. 3-(methoxymethoxy)-8-(2-triisopropylsilylethynyl)-1-naphthyl]acetate. To a mixture of 3-(methoxymethoxy)-8-(2-triisopropylsilylethynyl)naphthalen-1-ol (10 g, 26.0 mmol, 1.0 eq) and DIEA (8.40 g, 65.0 mmol, 11.3 mL, 2.5 eq) in dichloromethane (100 mL) was added acetyl chloride (3.06 g, 39.0 mmol, 2.78 mL, 1.5 eq) at 0° C. The mixture was stirred at 0° C. for 0.5 hour. After completion, the mixture was diluted with water (100 mL) and separated. The water phase was extracted with dichloromethane (50 mL). The combined organic layer was washed with brine (70 mL), dried over $Na_2SO_4$, filtered and concentrated under vacuum. The residue was purified by column chromatography ($SiO_2$, petroleum ether/ethyl acetate=3/1.) to give the title compound (9 g, 80% yield). Yellow oil. Rf=0.28 (petroleum ether/ethyl acetate=3/1). $^1$H NMR (400 MHz, chloroform-d) δ=7.72 (dd, J=0.8, 8.4 Hz, 1H), 7.67 (dd, J=1.2, 7.2 Hz, 1H), 7.36 (dd, J=7.2, 8.4 Hz, 1H), 7.32 (d, J=2.4 Hz, 1H), 6.96 (d, J=2.4 Hz, 1H), 5.28 (s, 2H), 3.52 (s, 3H), 2.44 (s, 3H), 1.19 (s, 21H).

Step D. 8-ethynyl-3-(methoxymethoxy)naphthalen-1-yl acetate. A mixture of 3-(methoxymethoxy)-8-(2-triisopropylsilylethynyl)-1-naphthyl]acetate (9.3 g, 21.8 mmol, 1 eq) and CsF (23.2 g, 153 mmol, 5.63 mL, 7 eq) in DMF (90 mL) was stirred at 25° C. for 1 hour. After completion, the mixture was diluted with ethyl acetate (150 mL), washed with brine (3×100 mL), dried over $Na_2SO_4$, filtered and concentrated under vacuum. The residue was purified by column chromatography ($SiO_2$, petroleum ether/ethyl acetate=3/1) to give the title compound (2.5 g, 42% yield). Yellow oil. Rf=0.21 (petroleum ether/ethyl acetate=3/1). [ESI, M+1]: 271.2.

Step E. [8-ethyl-3-(methoxymethoxy)-1-naphthyl] acetate. A mixture of [8-ethynyl-3-(methoxymethoxy)-1-naphthyl]acetate (2.5 g, 9.25 mmol, 1 eq) and Pd/C (60 mg, 10% purity) in methanol (10 mL) was stirred at 25° C. for 10 minutes under $H_2$ at 15 psi. After completion, the mixture was filtered and concentrated under vacuum to give the title compound (2.1 g, 83% yield) and used in the next step without further purification. Yellow oil. [ESI, M−41]: 233.3.

Step F. 8-ethyl-3-(methoxymethoxy)naphthalen-1-ol. A mixture of [8-ethyl-3-(methoxymethoxy)-1-naphthyl]acetate (2 g, 7.29 mmol, 1 eq) and LiOH (873 mg, 36.5 mmol, 5 eq) in THF (20 mL) and $H_2O$ (6 mL) was stirred at 25° C. for 1 hour. After completion, the mixture was diluted with water (50 mL), and extracted with ethyl acetate (2×50 mL). The combined organic layer was washed with brine. The residue was purified by column chromatography ($SiO_2$, petroleum ether/ethyl acetate=5/1) to give the title compound (1.42 g, 84% yield). Yellow oil. Rf=0.26 (petroleum ether/ethyl acetate=5/1). $^1$H NMR (400 MHz, chloroform-d) δ=7.53 (d, J=8.0 Hz, 1H), 7.3 (t, J=3.6 Hz, 1H), 7.11 (d, J=7.2 Hz, 1H), 7.00 (d, J=2.4 Hz, 1H), 6.55 (d, J=2.4 Hz, 1H), 5.27 (s, 2H), 3.53 (s, 3H), 3.30 (q, J=7.4 Hz, 2H), 1.33 (t, J=7.2 Hz, 3H).

Step G. [8-ethyl-3-(methoxymethoxy)-1-naphthyl] trifluoromethanesulfonate. To a mixture of 8-ethyl-3-(methoxymethoxy)naphthalen-1-ol (1.4 g, 6.03 mmol, 1 eq) and DIEA (3.12 g, 24.1 mmol, 4.20 mL, 4 eq) in dichloromethane (20 mL) was added $Tf_2O$ (2.55 g, 9.04 mmol, 1.49 mL, 1.5 eq) at −40° C. The mixture was stirred at −40° C. for 0.5 hour. After completion, the mixture was diluted with water (20 mL) and separated. The water phase was extracted with dichloromethane (10 mL), and the combined organic layer was washed with brine (20 mL), dried over $Na_2SO_4$, filtered and concentrated under vacuum. The residue was purified by column chromatography ($SiO_2$, petroleum ether/ethyl acetate=5/1, Rf=0.67) to give the title compound (1.87 g, 83% yield). Yellow oil. Rf=0.67 (petroleum ether/ethyl acetate=5/1).

Step H. 2-[8-ethyl-3-(methoxymethoxy)-1-naphthyl]-4,4,5,5-tetramethyl-1,3,2-dioxaborolane. A mixture of [8-ethyl-3-(methoxymethoxy)-1-naphthyl]trifluoromethanesulfonate (1.8 g, 4.94 mmol, 1 eq), 4,4,5,5-tetramethyl-2-(4,4,5,5-tetramethyl-1,3,2-dioxaborolan-2-yl)-1,3,2-dioxaborolane (3.14 g, 12.4 mmol, 2.5 eq), KOAc (1.21 g, 12.4 mmol, 2.5 eq) and Pd(dppf)$Cl_2$ (362 mg, 494 μmol, 0.1 eq) in dioxane (20 mL) was stirred at 110° C. for 2 hours. After completion, the mixture was diluted with water (20 mL), and extracted with ethyl acetate (2×20 mL). The combined organic layer was washed with brine (20 mL), dried over $Na_2SO_4$, filtered and concentrated under vacuum. The residue was purified by column chromatography ($SiO_2$, petroleum ether/ethyl acetate=30/1) to give the title compound (810 mg, 46% yield). Yellow oil. Rf=0.7 (petroleum ether/ethyl acetate=10/1). $^1$H NMR (400 MHz, chloroform-d) δ=7.60 (dd, J=0.8, 8.0 Hz, 1H), 7.42 (d, J=2.8 Hz, 1H), 7.40-7.33 (m, 2H), 7.27-7.24 (m, 1H), 5.30 (s, 2H), 3.52 (s, 3H), 3.19 (q, J=7.2 Hz, 2H), 1.45 (s, 12H), 1.36 (t, J=7.2 Hz, 3H).

Intermediate 16

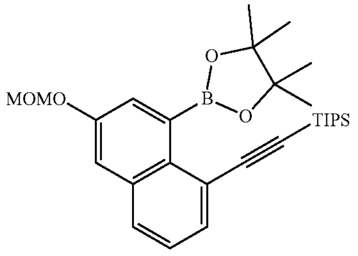

triisopropyl-[2-[6-(methoxymethoxy)-8-(4,4,5,5-tetramethyl-1,3,2-dioxaborolan-2-yl)-1-naphthyl]ethynyl]silane

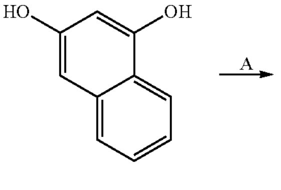

-continued

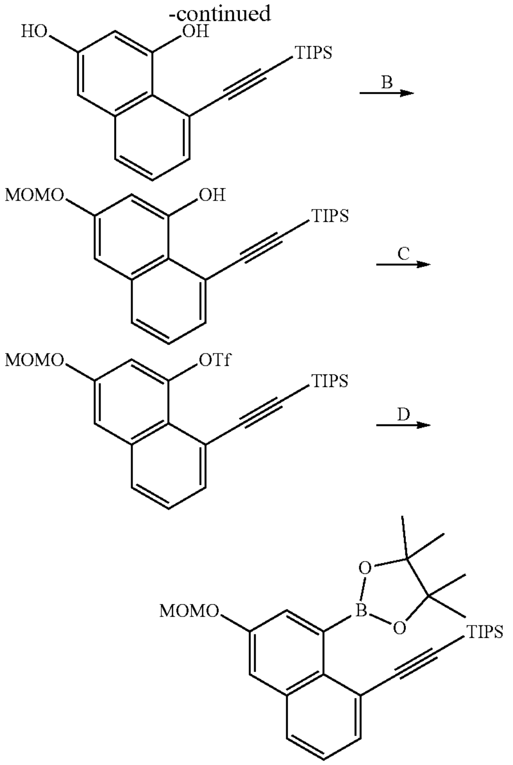

Step A. 8-(2-triisopropylsilylethynyl)naphthalene-1,3-diol. A mixture of naphthalene-1,3-diol (50 g, 312 mmol, 1 eq), 2-bromoethynyl(triisopropyl)silane (97.9 g, 375 mmol, 1.2 eq), dichlororuthenium; 1-isopropyl-4-methyl-benzene (19.1 g, 31.2 mmol, 0.1 eq), AcOK (61.3 g, 624 mmol, 2 eq) in dioxane (600 mL) was stirred at 110° C. for 12 hours. After completion, the mixture was filtered, diluted with water (1 L), and extracted with ethyl acetate (2×1 L). The combined organic layer was washed with brine (1 L), dried over $Na_2SO_4$, filtered and concentrated under vacuum. The residue was purified by column chromatography ($SiO_2$, petroleum ether/ethyl acetate=3/1, Rf=0.68) to give the title compound (100 g, 89% yield). Yellow oil. Rf=0.68 (petroleum ether/ethyl acetate=3/1). LCMS [ESI, M+1]: 341.3.

Step B. 3-(methoxymethoxy)-8-(2-triisopropylsilylethynyl)naphthalen-1-ol. To a mixture of 8-(2-triisopropylsilylethynyl)naphthalene-1,3-diol (180 g, 529 mmol, 1 eq) and DIEA (205 g, 1.59 mol, 276 mL, 3 eq) in dichloromethane (1500 mL) was added MOMCl (63.8 g, 793 mmol, 60.2 mL, 1.5 eq) at 0° C. After stirred at 0° C. for 0.5 hour, the mixture was diluted with water (1 L) and separated. The water phase was extracted with dichloromethane (500 mL). The combined organic layer was washed with brine (1 L), dried over $Na_2SO_4$, filtered and concentrated under vacuum. The residue was purified by column chromatography ($SiO_2$, petroleum ether/ethyl acetate=3/1, Rf=0.6) to give the title compound (126 g, 60% yield). Black solid. LCMS [ESI, M+1]: 285.3. $^1H$ NMR (400 MHz, chloroform-d) δ=9.25 (s, 1H), 7.69 (dd, J=0.8, 8.0 Hz, 1H), 7.50 (dd, J=1.2, 7.2 Hz, 1H), 7.31 (dd, J=7.2, 8.4 Hz, 1H), 6.98 (d, J=2.4 Hz, 1H), 6.78 (d, J=2.4 Hz, 1H), 5.27 (s, 2H), 3.51 (s, 3H), 1.20-1.16 (m, 21H).

Step C. [3-(methoxymethoxy)-8-(2-triisopropylsilylethynyl)-1-naphthyl]trifluoromethanesulfonate. To a mixture of 3-(methoxymethoxy)-8-(2-triisopropylsilylethynyl)naphthalen-1-ol (200 g, 520.04 mmol, 1 eq) and DIEA (202 g, 1.56 mol, 272 mL, 3 eq) in dichloromethane (2000 mL) was added $Tf_2O$ (220 g, 780 mmol, 129 mL, 1.5 eq) at −40° C. After stirred at −40° C. for 0.5 hour, the mixture was quenched with water (2 L) and separated. The water phase was extracted with dichloromethane (500 mL). The combined organic layer was washed with brine (1 L), dried over $Na_2SO_4$, filtered and concentrated under vacuum. The residue was purified by column chromatography ($SiO_2$, petroleum ether/ethyl acetate=5/1, Rf=0.24), to give the title compound (250 g, 92% yield). Yellow oil.

Step D. triisopropyl-[2-[6-(methoxymethoxy)-8-(4,4,5,5-tetramethyl-1,3,2-dioxaborolan-2-yl)-1-naphthyl]ethynyl]silane. A mixture of [3-(methoxymethoxy)-8-(2-triisopropylsilylethynyl)-1-naphthyl]trifluoromethanesulfonate (230 g, 445 mmol, 1 eq), 4,4,5,5-tetramethyl-2-(4,4,5,5-tetramethyl-1,3,2-dioxaborolan-2-yl)-1,3,2-dioxaborolane (226 g, 890 mmol, 2 eq), Pd(dppf)C12 (32.6 g, 44.5 mmol, 0.1 eq) and KOAc (152.92 g, 1.56 mol, 3.5 eq) in toluene (2 L) was stirred at 110° C. for 3 hours under $N_2$. After completion, the mixture was filtered and concentrated under vacuum. The residue was diluted with water (1 L) and extracted with ethyl acetate (1 L×2). The combined organic layer was washed with brine (1 L), dried over $Na_2SO_4$, filtered and concentrated under vacuum. The residue was purified by column chromatography ($SiO_2$, petroleum ether/ethyl acetate=20/1, Rf=0.39). The compound was triturated with acetonitrile (500 mL) to give 98 g pure product. The filtrate was purified by reversed phase flash chromatography [water (FA, 0.1%)/acetonitrile] to further give 27 g product. Total of the title compound is 125 g (57% yield). Yellow solid. $^1H$ NMR (400 MHz, chloroform-d) δ=7.72-7.67 (m, 2H), 7.48 (d, J=2.4 Hz, 1H), 7.40-7.32 (m, 2H), 5.29 (s, 2H), 3.51 (s, 3H), 1.44 (s, 12H), 1.19-1.15 (m, 21H).

Intermediate 17

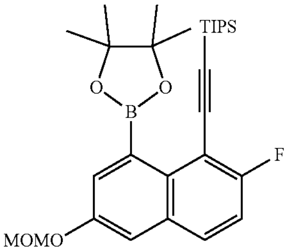

((2-fluoro-6-(methoxymethoxy)-8-(4,4,5,5-tetramethyl-1,3,2-dioxaborolan-Z-yl)naphthalen-1-yl)ethynyl)triisopropylsilane

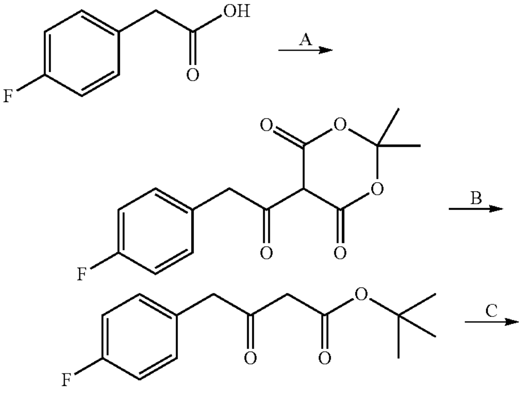

-continued

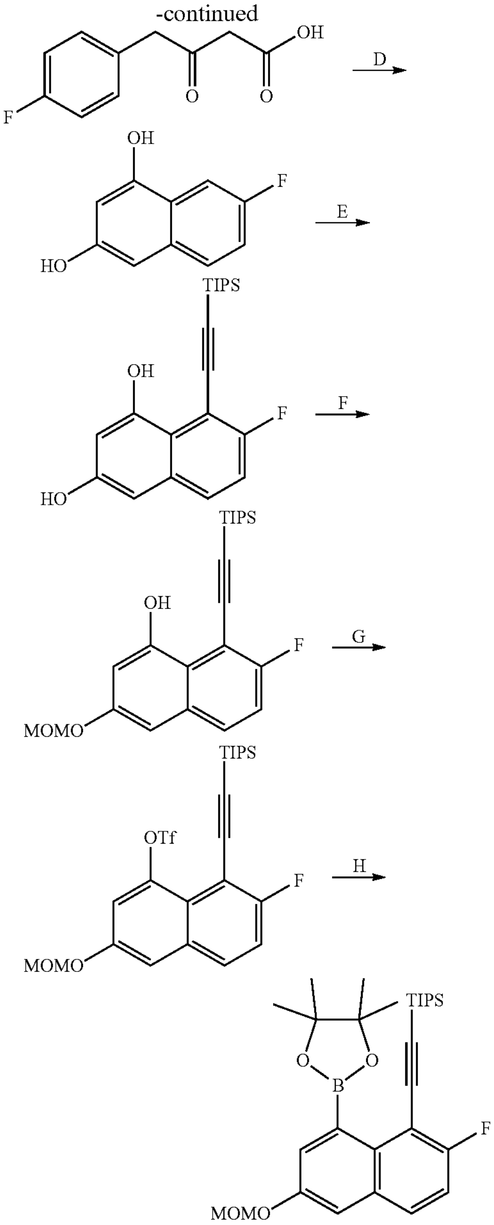

Step A. 5-(2-(4-fluorophenyl)acetyl)-2,2-dimethyl-1,3-dioxane-4,6-dione. To a solution of 2-(4-fluorophenyl)acetic acid (500 g, 3.24 mol, 1 eq), Meldrum's acid (514 g, 3.57 mol, 1.1 eq), DMAP (33.7 g, 275 mmol, 0.085 eq) in $CH_3CN$ (1500 mL) was added DIPEA (901 g, 6.97 mol, 1.21 L, 2.15 eq) while maintaining the temperature below 45° C., and then pivaloyl chloride (430 g, 3.57 mol, 439 mL, 1.1 eq) was slowly added over 3 hours while maintaining the temperature below 45° C. The resulted solution was stirred at 45° C. for 3 hours. The mixture solution was cooled to 0° C., then 1N HCl (5 L) was slowly added, and the resulted solution was stirred at 0° C. for 2 hours. Many of solid was generated, and the mixture was filtered to give the crude yellow solid. The crude was washed with $CH_3CN/H_2O$ (3 L/12 L) to give 5-(2-(4-fluorophenyl)acetyl)-2,2-dimethyl-1,3-dioxane-4,6-dione (800 g, 88% yield). White Solid; $^1H$ NMR (400 MHz, DMSO-d6) δ=15.35 (s, 1H), 7.40-7.38 (m, 2H), 7.05-7.01 (m, 2H), 4.40 (s, 2H), 1.72 (s, 6H).

Step B. tert-butyl 4-(4-fluorophenyl)-3-oxobutanoate. A solution of 5-(2-(4-fluorophenyl)acetyl)-2,2-dimethyl-1,3-dioxane-4,6-dione in t-BuOH (3 L) was stirred at 90° C. for 2 hours, then the mixture solution was concentrated to give the crude solid, and the crude solid was washed with petroleum ether (350 mL) to give tert-butyl 4-(4-fluorophenyl)-3-oxobutanoate (850 g, 94% yield). Light-yellow Solid; $^1H$ NMR (400 MHz, DMSO-d6) δ=7.27-7.18 (m, 2H), 7.18-7.08 (m, 2H), 3.86 (s, 2H), 3.55 (s, 2H), 1.40 (s, 9H).

Step C. 4-(4-fluorophenyl)-3-oxobutanoic acid. A solution of tert-butyl 4-(4-fluorophenyl)-3-oxobutanoate (800 g, 3.17 mol, 1 eq) and TFA (2.46 kg, 21.6 mol, 1.6 L, 6.81 eq) in DCM (1.6 L) was stirred at 20° C. for 1 hour. The mixture was concentrated to dryness. The residue was washed with petroleum ether (500 mL) to give 4-(4-fluorophenyl)-3-oxobutanoic acid (760 g, 83% yield). White Solid; $^1H$ NMR (400 MHz, $CDCl_3$-d) δ=10.01 (s, 1H), 7.20-7.17 (m, 2H), 7.07-7.03 (m, 2H), 3.84 (s, 2H), 3.54-3.52 (m, 2H).

Step D. 7-fluoronaphthalene-1,3-diol. A solution of 4-(4-fluorophenyl)-3-oxobutanoic acid (450 g, 2.29 mol, 1 eq) in $CF_3SO_3H$ (8.5 kg, 56 mol, 5 L, 25 eq) was stirred at 25° C. for 24 hours, the reaction was cooled to 0° C., and slowly added to ice-water (15 L). Precipitates were formed, and the mixture was filtered to give the crude product. Then the crude was slurred with petroleum ether (1 L), and filtered to give the 7-fluoronaphthalene-1,3-diol (325 g, 76% yield). Light-yellow Solid;

Step E. 7-fluoro-8-((triisopropylsilyl)ethynyl)naphthalene-1,3-diol. To the mixture of 7-fluoronaphthalene-1,3-diol (120 g, 673 mmol, 1 eq), 2-bromoethynyl(triisopropyl)silane (184 g, 707 mmol, 1.05 eq), AcOK (132 g, 1.34 mol, 2 eq) in dioxane (800 mL) was added dichlororuthenium; 1-isopropyl-4-methyl-benzene (41.3 g, 67.4 mmol, 0.1 eq) under $N_2$. The mixture was stirred at 110° C. for 2 hours. The mixture was filtered and concentrated to give a residue. Then the residue was purified by column chromatography ($SiO_2$, Petroleum ether/Ethyl acetate=1/0 to 5/1) to give 7-fluoro-8-((triisopropylsilyl)ethynyl)naphthalene-1,3-diol (213 g, 88% yield) was obtained. Black Oil; LCMS [ESI, M+1]: 359.2

Step F. 7-fluoro-3-(methoxymethoxy)-8-((triisopropylsilyl)ethynyl)naphthalen-1-ol. To the mixture of 7-fluoro-8-((triisopropylsilyl)ethynyl)naphthalene-1,3-diol (170 g, 474 mmol, 1 eq), DIEA (184 g, 1.42 mol, 3 eq) in DCM (1700 mL) was added MOMCl (49.8 g, 618 mmol, 1.3 eq) at 0° C. The mixture was warmed to 15° C. and stirred for 0.5 hour. The reaction mixture was diluted with ice-water (1000 mL) and extracted with ethyl acetate (500 mL×2). The combined organic phase was washed with brine (1000 mL), dried over anhydrous sodium sulfate, filtered and concentrated to give a residue. The residue was purified by column chromatography ($SiO_2$, Petroleum ether/Ethyl acetate=1/0 to 50/1) to give 7-fluoro-3-(methoxymethoxy)-8-((triisopropylsilyl)ethynyl)naphthalen-1-ol (96 g, 50% yield). Yellow Solid; $^1H$ NMR (400 MHz, $CDCl_3$-d) δ=9.13 (s, 1H), 7.68-7.64 (m, 1H), 7.21-7.16 (m, 1H), 6.97-6.96 (m, 1H), 6.81-6.80 (m, 1H), 5.26 (s, 2H), 3.51 (s, 3H), 1.24-1.17 (m, 21H). LCMS [ESI, M+1]: 403.2.

Step G: 7-fluoro-3-(methoxymethoxy)-8-((triisopropylsilyl)ethynyl)naphthalen-1-yl trifluoromethanesulfonate. To the solution of 7-fluoro-3-(methoxymethoxy)-8-((triisopropylsilyl)ethynyl)naphthalen-1-ol (80 g, 198 mmol, 1 eq), DIEA (77.0 g, 596 mmol, 104 mL, 3 eq) in DCM (1200 mL) was added $Tf_2O$ (84.1 g, 298 mmol, 49.2 mL, 1.5 eq) at −40° C., and the mixture was stirred at −40° C. for 0.5 hour. The reaction mixture was diluted with ice-water (500 mL), and then extracted with DCM (300 mL). The combined organic phase was dried over $Na_2SO_4$ and concentrated to dryness. The residue was purified by column chromatography ($SiO_2$, Petroleum ether/Ethyl acetate=1/0 to 60/1) to afford 7-fluoro-3-(methoxymethoxy)-8-((triisopropylsilyl)ethynyl) naphthalen-1-yl trifluoromethanesulfonate (100 g, 94% yield). Yellow oil.

Step H. ((2-fluoro-6-(methoxymethoxy)-8-(4,4,5,5-tetramethyl-1,3,2-dioxaborolan-2-yl)naphthalen-1-yl)ethynyl)triisopropylsilane. To the mixture of 7-fluoro-3-(methoxymethoxy)-8-((triisopropylsilyl)ethynyl)naphthalen-1-yl trifluoromethanesulfonate (105 g, 196 mmol, 1 eq), 4,4,5,5-tetramethyl-2-(4,4,5,5-tetramethyl-1,3,2-dioxaborolan-2-yl)-1,3,2-dioxaborolane (100 g, 393 mmol, 2 eq), AcOK (57.8 g, 589 mmol, 3 eq) in toluene (1100 mL) was added Pd(dppf)$Cl_2$ (14.4 g, 20 mmol, 0.1 eq). The mixture was degassed and stirred at 130° C. for 3 hours. The reaction mixture was filtered and concentrated to give a residue. To the residue was added EtOAc (1000 mL) and water (800 mL). The organic phase was washed with brine (500 mL), dried over anhydrous sodium sulfate, filtered and concentrated to give a residue. The residue was purified by column chromatography ($SiO_2$, Petroleum ether/Ethyl acetate=100/1 to 3/1) and triturated with MeCN (40 mL) to give ((2-fluoro-6-(methoxymethoxy)-8-(4,4,5,5-tetramethyl-1,3,2-dioxaborolan-2-yl)naphthalen-1-yl)ethynyl)triisopropylsilane (41 g, 43% yield). Yellow Solid; $^1H$ NMR (400 MHz, $CDCl_3$-d) δ=7.69-7.65 (m, 1H), 7.51 (d, J=2.4 Hz, 1H), 7.38 (d, J=2.4 Hz, 1H), 7.25 (t, J=8.8 Hz, 1H), 5.28 (s, 2H), 3.50 (s, 3H), 1.44 (s, 12H), 1.18-1.16 (m, 21H); LCMS [ESI, M+1]: 513.4.

Intermediate 18

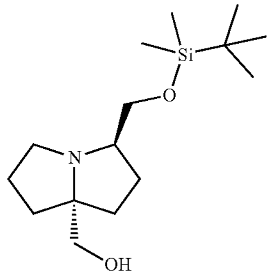

((3R,7aR)-3-(((tert-butyldimethylsilyl)oxy)methyl)tetrahydro-1H-pyrrolizin-7a(5H)-yl)methanol

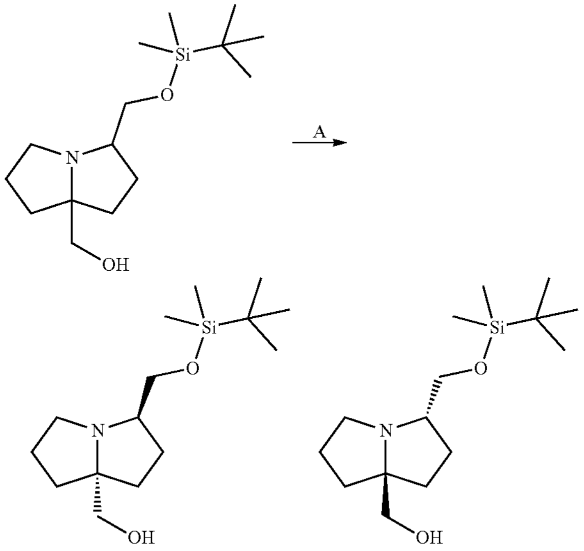

A mixture of (3-(((tert-butyldimethylsilyl)oxy)methyl)tetrahydro-1H-pyrrolizin-7a(5H)-yl)methanol was separated by Lotus Separations using chiral SFC using an AD-H (3×25 cm) column injecting with 1 mL of a 20 mg/mL solution of compound in methanol eluting with 20% methanol/$CO_2$ at 100 bar of pressure with 70 mL/min. flow rate and monitoring 220 nM.

The following Examples are intended to illustrate further certain embodiments of the invention and are not intended to limit the scope of the invention.

Example 1

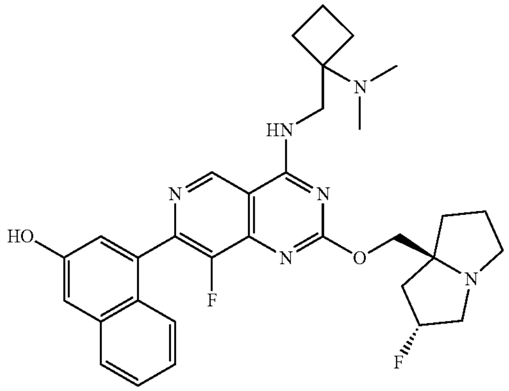

4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol

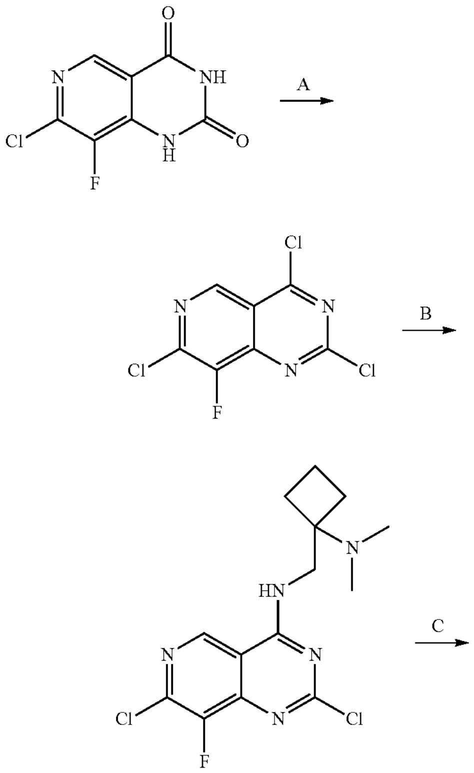

-continued

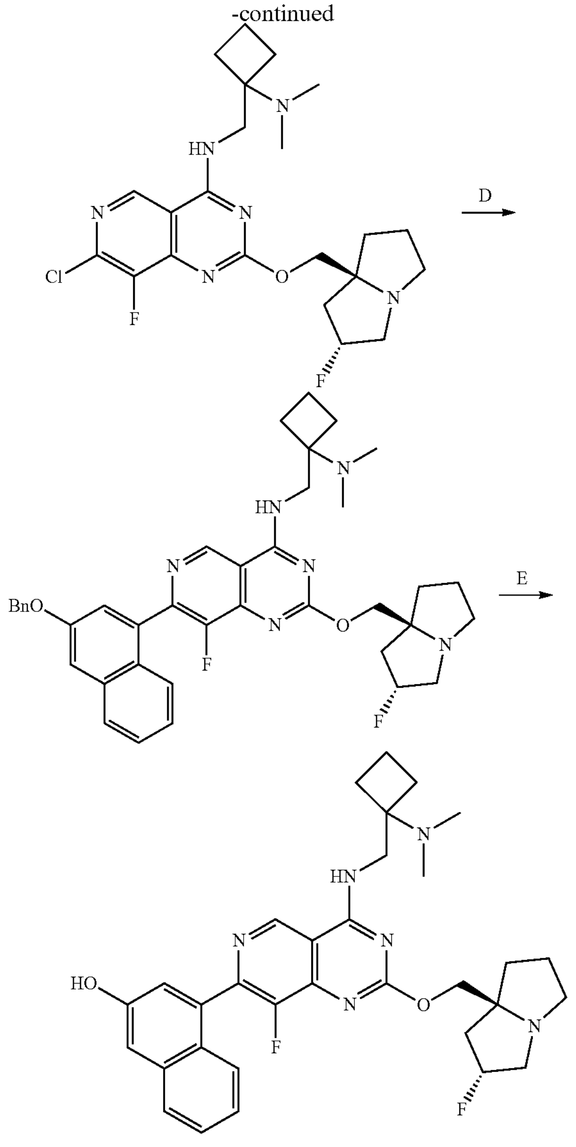

Step A. 2,4,7-trichloro-8-fluoropyrido[4,3-d]pyrimidine: 7-Chloro-8-fluoropyrido[4,3-d]pyrimidine-2,4(1H,3H)-dione (1.1 g, 5.1 mmol) was suspended in $POCl_3$ (14 mL, 153 mmol) and treated with DIEA (1 mL, 8.16 mmol). The mixture was heated to 110° C. and stirred for 2 hours. The cooled mixture was concentrated in vacuo. The residue was partitioned between DCM (50 mL) and water (50 mL). After 15 minutes, sat. $NaHCO_3$ (50 mL) was added and the layers were separated. The aqueous layer was extracted with DCM (2×50 mL) and the combined organic phases were washed with sat. $NaHCO_3$ (50 mL) and brine (50 mL), dried over $Na_2SO_4$, filtered, and concentrated to afford 2,4,7-trichloro-8-fluoropyrido[4,3-d]pyrimidine (1.3 g, 100% yield). LCMS (MM-ES+APCI, Pos): m/z 253.8 [M+H].

Step B. 2,7-dichloro-N-((1-(dimethylamino)cyclobutyl)methyl)-8-fluoropyrido[4,3-d]pyrimidin-4-amine: To a solution of 2,4,7-trichloro-8-fluoropyrido[4,3-d]pyrimidine (0.26 g, 1.0 mmol) in DCM (10 mL) was added 1-(aminomethyl)-N,N-dimethylcyclobutan-1-amine (0.12 g, 0.93 mmol) followed by $Et_3N$ (0.43 mL, 3.1 mmol). The mixture was stirred at ambient temperature for 16 hours and partitioned between sat. $NaHCO_3$ (30 mL) and DCM (30 mL). The aqueous layer was extracted with DCM (2×20 mL) and the combined organic phases were washed with brine (20 mL), dried over $Na_2SO_4$, filtered, and concentrated. The residue was purified by silica column chromatography eluting with 0-10% MeOH/DCM to afford 2,7-dichloro-N-((1-(dimethylamino)cyclobutyl)methyl)-8-fluoropyrido[4,3-d]pyrimidin-4-amine (0.27 g, 76% yield). LCMS (MM-ES+APCI, Pos): m/z 345.9 [M+H].

Step C. 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine: A mixture of 2,7-dichloro-N-((1-(dimethylamino)cyclobutyl)methyl)-8-fluoropyrido[4,3-d]pyrimidin-4-amine (0.50 g, 1.5 mmol) in 1,4-dioxane (14 mL) was treated with ((2S,7aR)-2-fluorotetrahydro-1H-pyrrolizin-7a(5H)-yl)methanol (0.35 g, 2.2 mmol) and cesium carbonate (1.4 g, 4.4 mmol), and then 4 Å powdered mol sieves (0.4 g) were added. The mixture was stirred at 95° C. for 16 hours, then cooled, diluted with EtOAc (50 mL), and filtered. The filtrate was washed with water (90 mL) and the aqueous layer was extracted with EtOAc (2×20 mL). The combined organic layers were washed with brine (40 mL), dried over $Na_2SO_4$, filtered, and concentrated in vacuo. The residue was purified by silica column chromatography eluting with 10-20% MeOH/DCM to afford 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (0.22 g, 32% yield). LCMS (MM-ES+APCI, Pos): m/z 468.2 [M+H].

Step D. 7-(3-(benzyloxy)naphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine: 2-(3-(benzyloxy)naphthalen-1-yl)-4,4,5,5-tetramethyl-1,3,2-dioxaborolane (64 mg, 0.18 mmol), 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (55 mg, 0.12 mmol), and $Pd(Ph_3P)_4$ (14 mg, 0.01 mmol) were suspended in 1,4-dioxane (1 mL) and aqueous $K_2CO_3$ (0.18 mL, 0.35 mmol). After degassing with argon, the mixture was heated to 90° C. for 16 hours. The cooled mixture was concentrated and the residue was purified by reverse phase IPLC (Gilson, 5-95% ACN/water with 0.1% TFA as modifier) to afford 7-(3-(benzyloxy)naphthalen-1-yl)-N-((1-(dimethylamino) cyclobutyl) methyl)-8-fluoro-2-(((2R,7aS)-2-fluorotetrahydro-1H-pyrrolizin-7a(5H)-yl) methoxy) pyrido[4,3-d]pyrimidin-4-amine (23 mg, 29% yield). LCMS (MM-ES+APCI, Pos): m/z 665.9 [M+H].

Step E. 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol: 7-(3-(benzyloxy)naphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (23 mg, 0.04 mmol) was dissolved in methanol (2 mL). After degassing with nitrogen, $Pd(OH)_2/C$ (9.7 mg, 0.01 mmol) was added and the mixture was hydrogenated under balloon atmosphere for 1 hour. The mixture was filtered through Celite and the filtrate was concentrated. The residue was purified by reverse phase HPLC (Gilson, 5-95% ACN/water with 0.1% TFA as modifier) and the desired fractions were lyophilized to afford 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis-TFA salt (10 mg, 50% yield). LCMS (MM-ES+APCI, Pos): m/z 575.1 [M+H].

Example 2

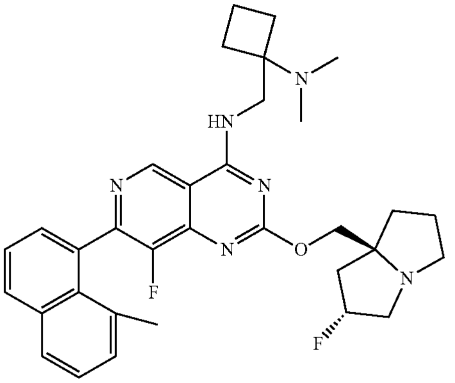

N-((1-(dimethylamino)cyclobutyl)methyl)-8-fluoro-2-(((2R,7aS)-2-fluorotetrahydro-1H-pyrrolizin-7a(5H)-yl)methoxy)-7-(8-methylnaphthalen-1-yl)pyrido[4,3-d]pyrimidin-4-amine

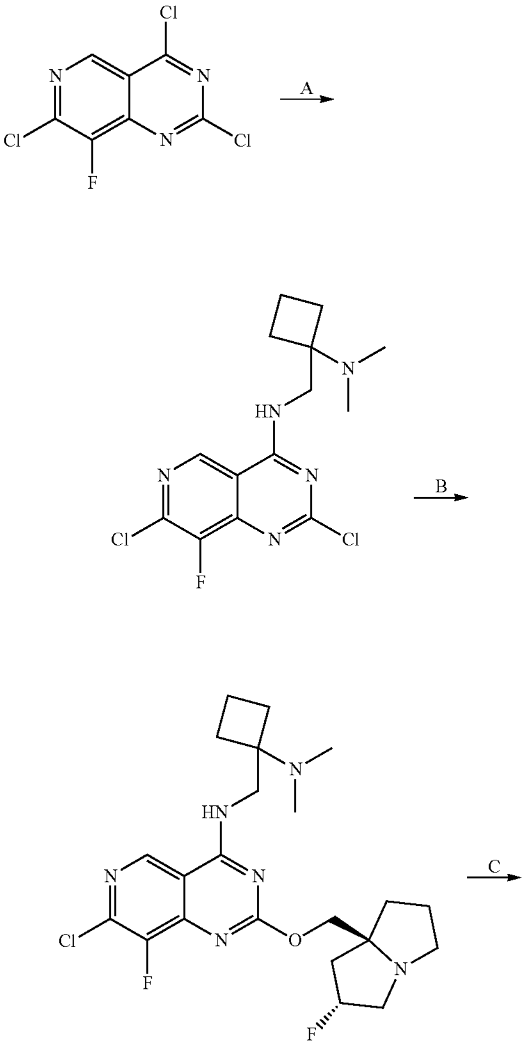

-continued

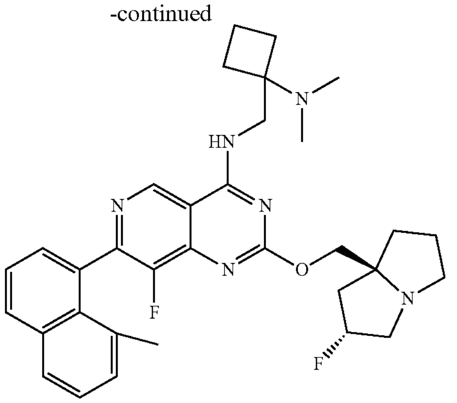

Step A. 2,7-dichloro-N-((1-(dimethylamino)cyclobutyl)methyl)-8-fluoropyrido[4,3-d]pyrimidin-4-amine. 2,4,7-trichloro-8-fluoropyrido[4,3-d]pyrimidine (265 mg, 1.05 mmol) was dissolved in dichloromethane (2 mL) and cooled in an ice/water bath. To the reaction mixture was added a solution of 1-(aminomethyl)-N,N-dimethylcyclobutan-1-amine (1.0 mL, 1.0 mmol) in dichloromethane and N-ethyl-N-isopropylpropan-2-amine (0.36 mL, 2.1 mmol). The reaction was stirred for 1 hour and then concentrated to afford 2,7-dichloro-N-((1-(dimethylamino)cyclobutyl)methyl)-8-fluoropyrido[4,3-d]pyrimidin-4-amine that was used directly in the next step without further purification. LCMS (MM-ES+APCI, Pos): m/z 344.1 (M+H).

Step B. 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine. 2,7-dichloro-N-((1-(dimethylamino)cyclobutyl)methyl)-8-fluoropyrido[4,3-d]pyrimidin-4-amine (361 mg, 1.05 mmol) was dissolved in 1,4-dioxane (2 mL). To the reaction mixture were added cesium carbonate (683 mg, 2.1 mmol), activated 4 Å mol sieves (200 mg) and a solution of ((2R,7aS)-2-fluorotetrahydro-1H-pyrrolizin-7a(5H)-yl)methanol (1.1 M solution, 1 mL, 175 mg, 1.1 mmol) in 1,4-dioxane. The reaction mixture was heated under nitrogen atmosphere at 90° C. for 16 hours. The reaction was cooled to ambient temperature, diluted with ethyl acetate (75 mL), passed through filter paper, and concentrated. The residue was purified by reverse-phase C-18 flash chromatography eluting with 5-95% acetonitrile in water+0.1% trifluoroacetic acid as a modifier. The fractions containing product were combined and diluted with saturated aqueous sodium bicarbonate solution (25 mL) and extracted with ethyl acetate (3×50 mL). The organic extracts were combined and stirred over sodium sulfate, filtered, and concentrated to afford 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (0.24 g, 49% yield). LCMS (MM-ES+APCI, Pos): m/z 467.3 (M+H).

Step C. N-((1-(dimethylamino)cyclobutyl)methyl)-8-fluoro-2-(((2R,7aS)-2-fluorotetrahydro-1H-pyrrolizin-7a(5H)-yl)methoxy)-7-(8-methylnaphthalen-1-yl)pyrido[4,3-d]pyrimidin-4-amine bis(2,2,2-trifluoroacetate). 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (17 mg, 0.04 mmol), tetrakis(triphenylphosphine)palladium(0) (8.4 mg, 0.01 mmol), 4,4,5,5-tetramethyl-2-(8-methylnaphthalen-1-yl)-1,3,2-dioxaborolane (15 mg, 0.06 mmol), were suspended in 1,4-dioxane (1 mL) and aqueous potassium carbonate (60 μL, 0.12 mmol). The reaction mixture was sparged with argon for 5 minutes, then sealed, and heated to 100° C. for 16 hours. The reaction was cooled to ambient temperature, diluted with ethyl acetate (15 mL), and washed with water (15 mL), saturated aqueous sodium bicarbonate solution (3×15 mL), and brine (15 mL). The organic phase was separated, stirred over sodium sulfate, filtered, and concentrated. The reaction mixture was purified by HPLC eluting with a gradient from 5-95% acetonitrile in water+ 0.1% trifluoroacetic acid as a modifier to afford N-((1-(dimethylamino)cyclobutyl)methyl)-8-fluoro-2-(((2R,7aS)-2-fluorotetrahydro-1H-pyrrolizin-7a(5H)-yl)methoxy)-7-(8-methylnaphthalen-1-yl)pyrido[4,3-d]pyrimidin-4-amine bis (2,2,2-trifluoroacetate) (6.0 mg, 21% yield) after lyophilization. LCMS (MM-ES+APCI, Pos): m/z 573.3 (M+H).

Example 3

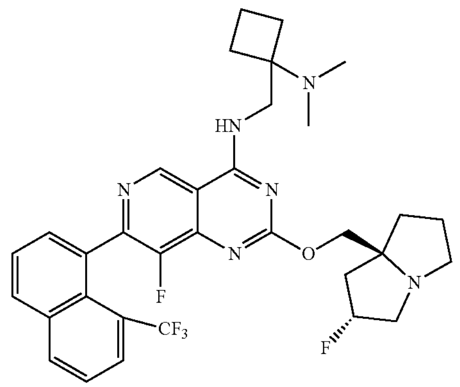

N-((1-(dimethylamino)cyclobutyl)methyl)-8-fluoro-2-(((2R,7aS)-2-fluorotetrahydro-1H-pyrrolizin-7a(5H)-yl)methoxy)-7-(8-(trifluoromethyl)naphthalen-1-yl)pyrido[4,3-d]pyrimidin-4-amine

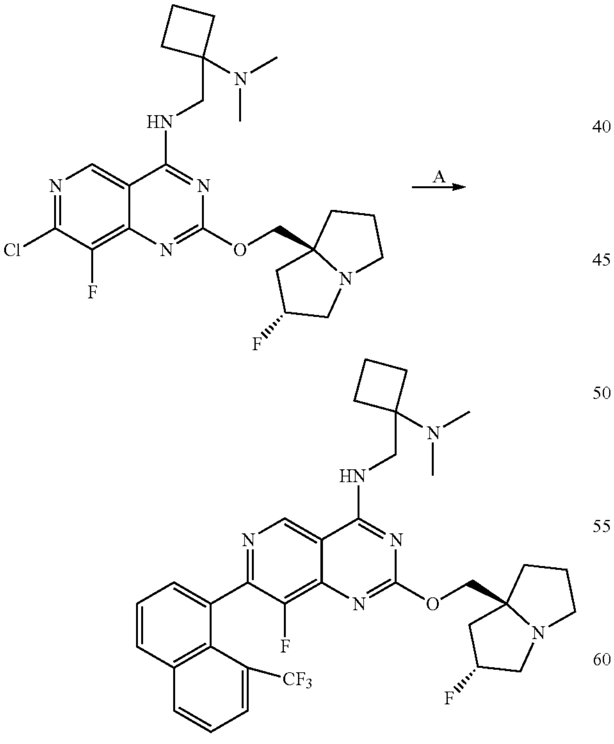

Step A. N-((1-(dimethylamino)cyclobutyl)methyl)-8-fluoro-2-(((2R,7aS)-2-fluorotetrahydro-1H-pyrrolizin-7a (5H)-yl)methoxy)-7-(8 (trifluoromethyl)naphthalen-1-yl) pyrido[4,3-d]pyrimidin-4-amine bis(2,2,2-trifluoroacetate): 7-chloro-N-((1-(dimethylamino)cyclobutyl)methyl)-8-fluoro-2-(((2R,7aS)-2-fluorotetrahydro-1H-pyrrolizin-7a (5H)-yl)methoxy)pyrido[4,3-d]pyrimidin-4-amine (50 mg, 0.11 mmol), 4,4,5,5-tetramethyl-2-(8-(trifluoromethyl) naphthalen-1-yl)-1,3,2-dioxaborolane (52 mg, 0.16 mmol) and [(di(1-adamantyl)-butylphosphine)-2-(2'-amino-1,1'-bi-phenyl)]palladium(II) methanesulfonate (16 mg, 0.02 mmol) were suspended in tetrahydrofuran (1 mL) and aqueous tri-potassium phosphate (0.30 mL, 0.30 mmol). The reaction mixture was sparged with argon for 5 minutes, sealed and heated at 60° C. for 16 hours. The reaction was cooled to ambient temperature and diluted with ethyl acetate (25 mL). The organic phase was washed with water (15 mL), saturated aqueous sodium bicarbonate solution (3×15 mL), and brine (15 mL). The organic phase was separated, stirred over sodium sulfate, filtered, and concentrated. The reaction mixture was purified by silica gel chromatography eluting with a gradient from 0-10% methanol in dichloromethane (methanol contains 0.1% ammonium hydroxide modifier). The residue was further purified by HPLC eluting with a gradient from 5-95% acetonitrile in water with 0.1% trifluoroacetic acid as a modifier to afford N-((1-(dimethyl-amino)cyclobutyl)methyl)-8-fluoro-2-(((2R,7aS)-2-fluoro-tetrahydro-1H-pyrrolizin-7a(5H)-yl)methoxy)-7-(8-(trifluoromethyl)naphthalen-1-yl)pyrido[4,3-d]pyrimidin-4-amine as the bis TFA salt (10 mg, 15% yield) after lyophilization. LCMS (MM-ES+APCI, Pos): m/z 627.3 (M+H).

Example 4

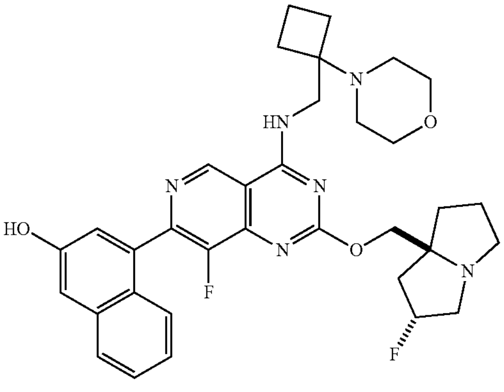

4-(8-fluoro-2-(((2R,7aS)-2-fluorotetrahydro-1H-pyrrolizin-7a(5H)-yl)methoxy)-4-(((1-morpholinocyclobutyl)methyl)amino)pyrido[4,3-d]pyrimidin-7-yl)naphthalen-2-ol (racemic, trans)

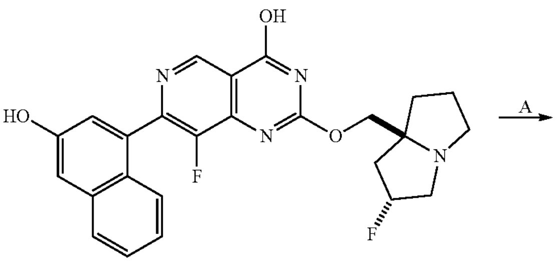

-continued

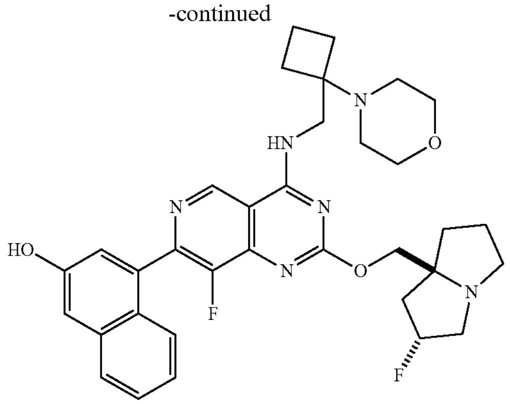

Step A. 4-(8-fluoro-2-(((2R,7aS)-2-fluorotetrahydro-1H-pyrrolizin-7a(5H)-yl)methoxy)-4-(((1-morpholinocyclobutyl)methyl)amino)pyrido[4,3-d]pyrimidin-7-yl)naphthalen-2-ol. To a solution of 8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-ol (23 mg, 0.05 mmol) and 2-(3H-[1,2,3]triazolo[4,5-b]pyridin-3-yl)-1,1,3,3-tetramethylisouronium hexafluorophosphate(V) (75 mg, 0.20 mmol) in DMA (0.5 mL) was added DIPEA (70 μL, 0.4 mmol). The solution was stirred at room temperature for 15 minutes and (1-morpholinocyclobutyl) methanamine (17 mg, 0.1 mmol) was added. The solution was stirred at room temperature for 1 hour and the mixture was quenched with $NH_3 \cdot H_2O$ (0.1 mL). The mixture was purified by preparative C18 HPLC (Gilson, 0-95% $CH_3CN/H_2O$ with 0.1% formic acid modifier). The desired fractions were combined, basified with $NaHCO_3$(Sat.), and extracted with DCM. The combined extract was dried over $Na_2SO_4$ and concentrated to afford 4-(8-fluoro-2-(((2R,7aS)-2-fluorotetrahydro-1H-pyrrolizin-7a(5H)-yl)methoxy)-4-(((1-morpholinocyclobutyl)methyl)amino)pyrido[4,3-d]pyrimidin-7-yl)naphthalen-2-ol (4 mg, 13% yield). LCMS (MM-ES+APCI, Pos): m/z 617.3 (M+H).

Example 5

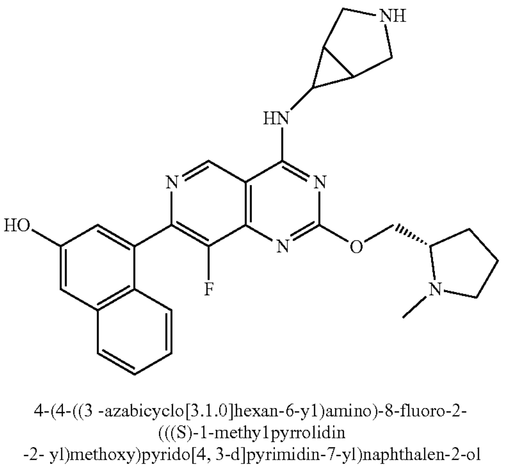

4-(4-((3 -azabicyclo[3.1.0]hexan-6-yl)amino)-8-fluoro-2-(((S)-1-methylpyrrolidin -2- yl)methoxy)pyrido[4, 3-d]pyrimidin-7-yl)naphthalen-2-ol -continued

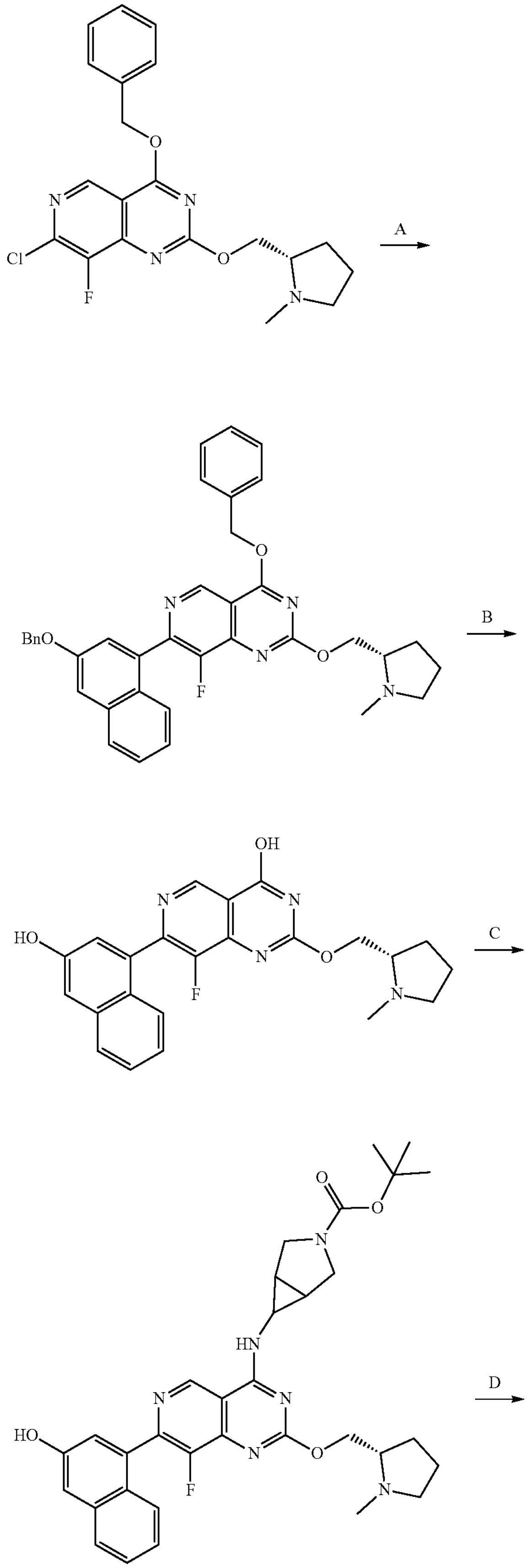

-continued

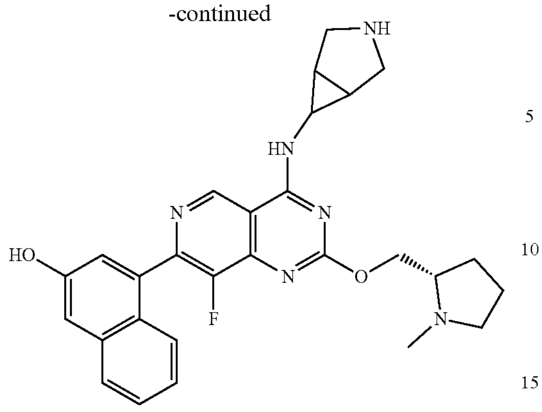

Step A. (S)-4-(benzyloxy)-7-(3-(benzyloxy)naphthalen-1-yl)-8-fluoro-2-((1-methylpyrrolidin-2-yl)methoxy)pyrido[4,3-d]pyrimidine. To a solution of 2-(3-(benzyloxy)naphthalen-1-yl)-4,4,5,5-tetramethyl-1,3,2-dioxaborolane (2.6 g, 7.3 mmol) in dioxane (50 mL) were added (S)-4-(benzyloxy)-7-chloro-8-fluoro-2-((1-methylpyrrolidin-2-yl)methoxy)pyrido[4,3-d]pyrimidine (2.0 g, 4.9 mmol), $K_2CO_3$ in water (7.0 mL, 14 mmol), and $Pd(PPh_3)_4$ (0.56 g, 0.49 mmol). The reaction was sparged with argon and heated at 85° C. After 6 hours, 2-(3-(benzyloxy)naphthalen-1-yl)-4,4,5,5-tetramethyl-1,3,2-dioxaborolane (0.49 g) was added to the reaction. At 7 hours, $Pd(PPh_3)_4$ (0.25 g) was added and the reaction was stirred for 16 hours at 85° C. The mixture was diluted with water (150 mL) and extracted with EtOAc (3×100 mL). The combined organic layers were washed with brine (100 mL), dried over sodium sulfate, filtered, and concentrated in vacuo. The residue was purified by silica column chromatography eluting with 0-10% MeOH/DCM to afford (S)-4-(benzyloxy)-7-(3-(benzyloxy)naphthalen-1-yl)-8-fluoro-2-((1-methylpyrrolidin-2-yl)methoxy)pyrido[4,3-d]pyrimidine (1.5 g, 51% yield). LCMS (MM-ES+APCI, Pos): m/z 601.3 (M+H).

Step B. (S)-8-fluoro-7-(3-hydroxynaphthalen-1-yl)-2-((1-methylpyrrolidin-2-yl)methoxy)pyrido[4,3-d]pyrimidin-4-ol. A stirred mixture of (S)-4-(benzyloxy)-7-(3-(benzyloxy)naphthalen-1-yl)-8-fluoro-2-((1-methylpyrrolidin-2-yl)methoxy)pyrido[4,3-d]pyrimidine (1.5 g, 2.47 mmol) and palladium on carbon, 5%, Degussa type (0.75 g, 7.1 mmol) in methanol (12 mL) and DCM (4 mL) was degassed with nitrogen. The mixture was stirred under $H_2$ atmosphere for 16 hours. The reaction was filtered through G/F paper and the filter paper washed with MeOH. The combined filtrate was concentrated in vacuo to afford (S)-8-fluoro-7-(3-hydroxynaphthalen-1-yl)-2-((1-methylpyrrolidin-2-yl)methoxy)pyrido[4,3-d]pyrimidin-4-ol (0.65 g, 62% yield). LCMS (MM-ES+APCI, Pos): m/z 421.1 (M+H).

Step C. tert-butyl 6-((8-fluoro-7-(3-hydroxynaphthalen-1-yl)-2-(((S)-1-methylpyrrolidin-2-yl)methoxy)pyrido[4,3-d]pyrimidin-4-yl)amino)-3-azabicyclo[3.1.0]hexane-3-carboxylate. A vial was charged with (S)-8-fluoro-7-(3-hydroxynaphthalen-1-yl)-2-((1-methylpyrrolidin-2-yl)methoxy)pyrido[4,3-d]pyrimidin-4-ol (50 mg, 0.12 mmol), N,N-dimethylacetamide (0.50 mL) and N-ethyl-N-isopropylpropan-2-amine (0.10 mL, 0.60 mmol) and the reaction stirred for 15 minutes. 2-(3H-[1,2,3]triazolo[4,5-b]pyridin-3-yl)-1,1,3,3-tetramethylisouronium hexafluorophosphate (V) (0.18 g, 0.48 mmol) was added and the reaction was stirred for 10 minutes. The suspension was cooled in an ice bath and tert-butyl 6-amino-3-azabicyclo[3.1.0]hexane-3-carboxylate (71 mg, 0.36 mmol) was charged to the suspension. The ice bath was removed, and the reaction was warmed to room temperature over 3.5 hours. The mixture was diluted with water (20 mL) and extracted with EtOAc (3×15 mL). The combined organic layers were washed with water (3×20 mL), brine (20 mL), dried over sodium sulfate, filtered, and concentrated in vacuo. The residue was purified by silica column chromatography eluting with 0-5% MeOH/DCM to afford tert-butyl 6-((8-fluoro-7-(3-hydroxynaphthalen-1-yl)-2-(((S)-1-methylpyrrolidin-2-yl)methoxy)pyrido[4,3-d]pyrimidin-4-yl)amino)-3-azabicyclo[3.1.0]hexane-3-carboxylate (21 mg, 29% yield). LCMS (MM-ES+APCI, Pos): m/z 601.3 (M+H).

Step D. 4-(4-((3-azabicyclo[3.1.0]hexan-6-yl)amino)-8-fluoro-2-(((S)-1-methylpyrrolidin-2-yl)methoxy)pyrido[4,3-d]pyrimidin-7-yl)naphthalen-2-ol bis(2,2,2-trifluoroacetate). To a solution of tert-butyl 6-((8-fluoro-7-(3-hydroxynaphthalen-1-yl)-2-(((S)-1-methylpyrrolidin-2-yl)methoxy)pyrido[4,3-d]pyrimidin-4-yl)amino)-3-azabicyclo[3.1.0]hexane-3-carboxylate (21 mg, 0.040 mmol) in DCM (1 mL, 0.04 mmol) was added TFA (54 μL, 0.70 mmol). The mixture was stirred at room temperature for 2 hours. The reaction was concentrated in vacuo. The residue was purified by reverse phase chromatography eluting with 5-95% ACN/water to afford 4-(4-((3-azabicyclo[3.1.0]hexan-6-yl)amino)-8-fluoro-2-(((S)-1-methylpyrrolidin-2-yl)methoxy)pyrido[4,3-d]pyrimidin-7-yl)naphthalen-2-ol bis(2,2,2-trifluoroacetate) (8.0 mg, 31% yield) as a pale yellow solid. LCMS (MM-ES+APCI, Pos): m/z 501.2 (M+H).

Example 6

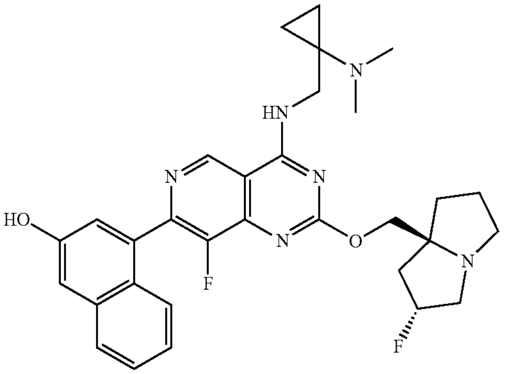

4-(4-(((1-(dimethylamino)cyclopropyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol Synthesized according to Example 1, Step A-E substituting 1-(aminomethyl)-N,N-dimethylcyclopropan-1-amine in place of 1-(aminomethyl)-N,N-dimethylcyclobutan-1-amine in Step B to afford 4-(4-(((1-(dimethylamino)cyclopropyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-bis(2,2,2-trifluoroacetate) (41 mg, 74% yield). LCMS (MM-ES+APCI, Pos): m/z 561.1 (M+H).

Example 7

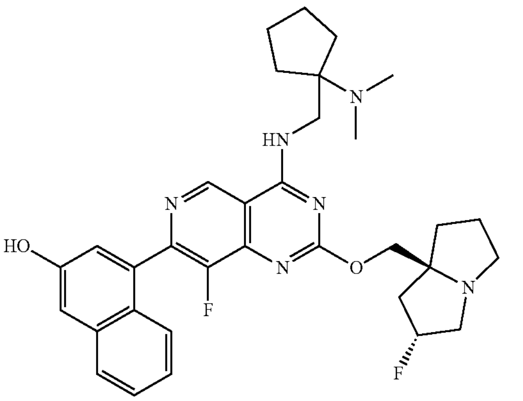

4-(4-(((1-(dimethylamino)cyclopentyl)methyl)amino)-8-fluoro-2-(((2R, 7aS)-2-fluorotetrahydro-1H-pyrrolizin-7a(5H)-yl)methoxy)pyrido[4,3-d]pyrimidin-7-yl)naphthalen-2-ol Synthesized according to Example 1, Steps A-E substituting 1-(aminomethyl)-N,N-dimethylcyclopentan-1-amine in place of 1-(aminomethyl)-N,N-dimethylcyclobutan-1-amine in Step B to afford 4-(4-(((1-(dimethylamino)cyclopentyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate) (30 mg, 57% yield). LCMS (MM-ES+APCI, Pos): m/z 589.1 (M+H).

Example 8

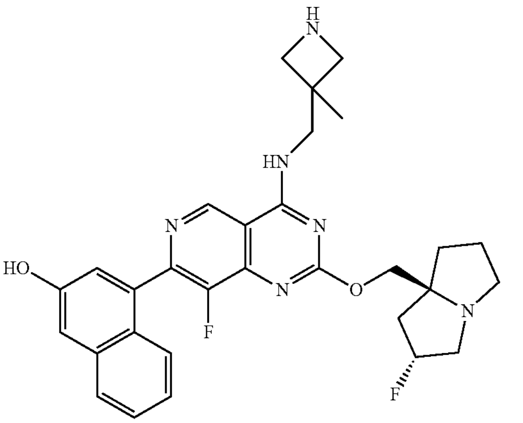

4-(8-fluoro-2-(((2R, 7aS)-2-fluorotetrahydro-1H-pyrrolizin-7a(5H)-yl)methoxy)-4-(((3-methylazetidin-3-yl)methyl)amino)pyrido[4, 3-d]pyrimidin-7-yl)naphthalen-2-ol -continued

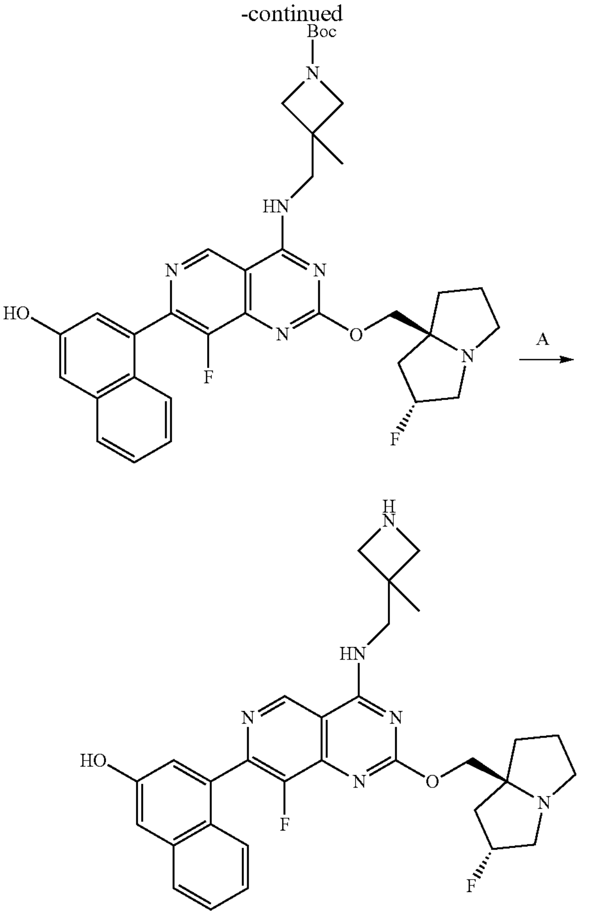

tert-butyl 3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-methylazetidine-1-carboxylate bis(2,2,2-trifluoroacetate). Synthesized according to Example 1, Steps A-E substituting tert-butyl 3-(aminomethyl)-3-methylazetidine-1-carboxylate in place of 1-(aminomethyl)-N,N-dimethylcyclobutan-1-amine in Step B to afford tert-butyl 3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-methylazetidine-1-carboxylate bis(2,2,2-trifluoroacetate) (52 mg, 76% yield). LCMS (MM-ES+APCI, Pos): m/z 647.1 (M+H).

Step A. 4-(8-fluoro-2-(((2R,7aS)-2-fluorotetrahydro-1H-pyrrolizin-7a(5H)-yl)methoxy)-4-(((3-methylazetidin-3-yl)methyl)amino)pyrido[4,3-d]pyrimidin-7-yl)naphthalen-2-ol. To solution of tert-butyl 3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-methylazetidine-1-carboxylate bis(2,2,2-trifluoroacetate) (52 mg, 0.06 mmol) in DCM (1 ml) was added 4 M HCl in dioxane (1.5 ml, 6.0 mmol). After stirring for 1 hour at room temperature the reaction was concentrated to dryness, the solids triturated with ether, and filtered to afford 4-(8-fluoro-2-(((2R,7aS)-2-fluorotetrahydro-1H-pyrrolizin-7a(5H)-yl)methoxy)-4-(((3-methylazetidin-3-yl)methyl)amino)pyrido[4,3-d]pyrimidin-7-yl)naphthalen-2-ol (34 mg, 84% yield). LCMS (MM-ES+APCI, Pos): m/z 547.1 (M+H).

Example 9

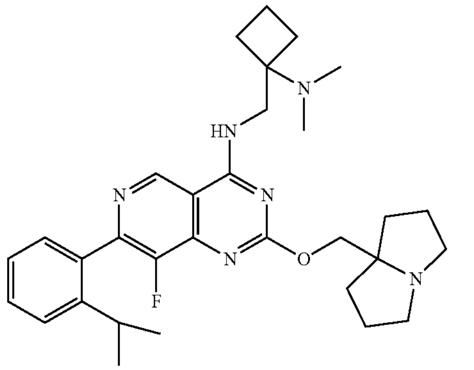

N-((1-(dimethylamino)cyclobutyl)methyl)-8-fluoro-7-(2-isopropylphenyl)-2-((tetrahydro-1H-pyrrolizin-7a(5H)-yl)methoxy) pyrido[4,3-d]pyrimidin-4-amine Synthesized according to Example 1, Steps A-D substituting (tetrahydro-1H-pyrrolizin-7a(5H)-yl)methanol in place of ((2S,7aR)-2-fluorotetrahydro-1H-pyrrolizin-7a (5H)-yl)methanol in Step C and substituting (2-isopropylphenyl)boronic acid in place of 2-(3-(benzyloxy)naphthalen-1-yl)-4,4,5,5-tetramethyl-1,3,2-dioxaborolane in Step D to afford N-((1-(dimethylamino)cyclobutyl)methyl)-8-fluoro-7-(2-isopropylphenyl)-2-((tetrahydro-1H-pyrrolizin-7a(5H)-yl)methoxy)pyrido[4,3-d]pyrimidin-4-amine bis(2,2,2-trifluoroacetate) (7.4 mg, 15% yield). LCMS (MM-ES+APCI, Pos): m/z 533.3 (M+H).

Example 10

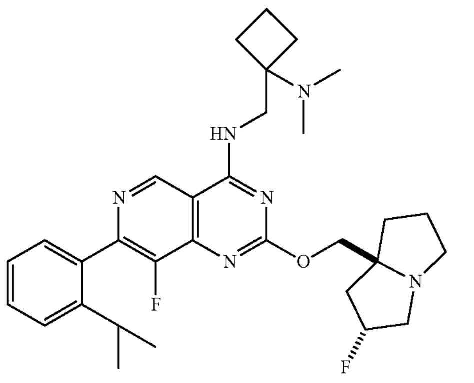

N-((1-(dimethylamino)cyclobutyl)methyl)-8-fluoro-2-(((2R,7aS)-2-fluorotetrahydro-1H- pyrrolizin-7a(5H)-yl)methoxy)-7-(2-isopropylphenyl)pyrido[4,3-d]pyrimidin-4-amine (racemic, trans)

Synthesized according to Example 1, Steps A-D substituting (2-isopropylphenyl)boronic acid in place of 2-(3-(benzyloxy)naphthalen-1-yl)-4,4,5,5-tetramethyl-1,3,2-dioxaborolane in Step D to afford N-((1-(dimethylamino) cyclobutyl)methyl)-8-fluoro-2-(((2R,7aS)-2-fluorotetrahydro-1H-pyrrolizin-7a(5H)-yl)methoxy)-7-(2-isopropylphenyl)pyrido[4,3-d]pyrimidin-4-amine bis(2,2,2-trifluoroacetate) (19 mg, 38% yield). LCMS (MM-ES+APCI, Pos): m/z 551.3 (M+H).

Example 11

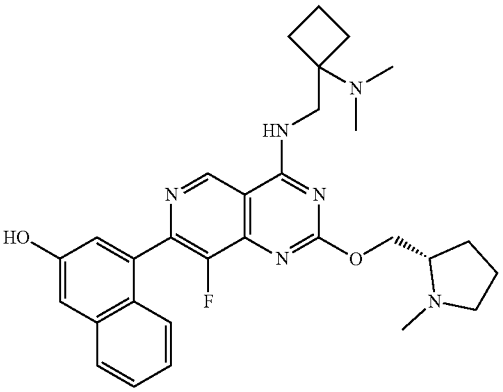

(S)-4-(4-(((1-(dimethylamino)cyclobutyl)methyl)amino)-8-fluoro-2-((1-methylpyrrolidin-2-yl)methoxy)pyrido[4,3-d]pyrimidin-7yl)naphthalen-2-ol Synthesized according to Example 1, Steps A-E substituting (S)-(1-methylpyrrolidin-2-yl)methanol in place of ((2S,7aR)-2-fluorotetrahydro-1H-pyrrolizin-7a(5H)-yl) methanol in Step C to afford (S)-4-(4-(((1-(dimethylamino) cyclobutyl)methyl)amino)-8-fluoro-2-((1-methylpyrrolidin-2-yl)methoxy)pyrido[4,3-d]pyrimidin-7-yl)naphthalen-2-ol bis(2,2,2-trifluoroacetate) (3.5 mg, 44% yield). LCMS (MM-ES+APCI, Pos): m/z 531.3 (M+H).

Example 12

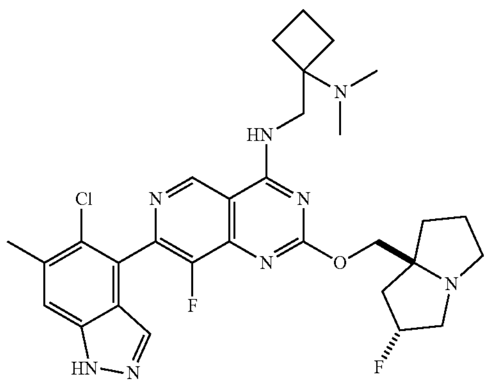

7-(5-chloro-6-methyl-1H-indazol-4-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (racemic, trans)

Synthesized according to Example 1, Steps A-D substituting 5-chloro-6-methyl-1-(tetrahydro-2H-pyran-2-yl)-4-(4,4,5,5-tetramethyl-1,3,2-dioxaborolan-2-yl)-1H-indazole in place of 2-(3-(benzyloxy)naphthalen-1-yl)-4,4,5,5-tetramethyl-1,3,2-dioxaborolane in Step D followed by deprotection using Example 8, Step A to afford 7-(5-chloro-6-methyl-1H-indazol-4-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine bis(2,2,2-trifluoroacetate) (18 mg, 29% yield). LCMS (MM-ES+APCI, Pos): m/z 597.3 (M+H).

Example 13

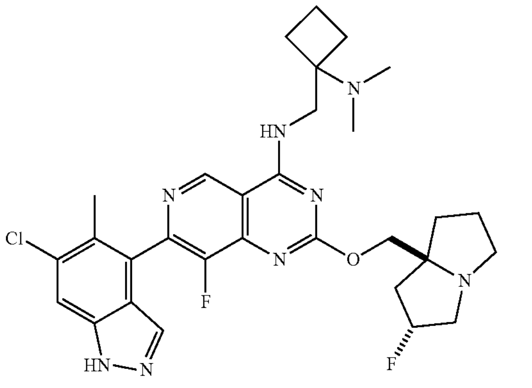

7-(6-chloro-5-methyl-1H-indazol-4-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (racemic, trans)

Synthesized according to Example 1, Steps A-D substituting 6-chloro-5-methyl-1-(tetrahydro-2H-pyran-2-yl)-4-(4,4,5,5-tetramethyl-1,3,2-dioxaborolan-2-yl)-1H-indazole in place of 2-(3-(benzyloxy)naphthalen-1-yl)-4,4,5,5-tetramethyl-1,3,2-dioxaborolane in Step D followed by deprotection using Example 8, Step A to afford 7-(6-chloro-5-methyl-1H-indazol-4-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine bis(2,2,2-trifluoroacetate) (20 mg, 40% yield). LCMS (MM-ES+APCI, Pos): m/z 597.3 (M+H).

Example 14

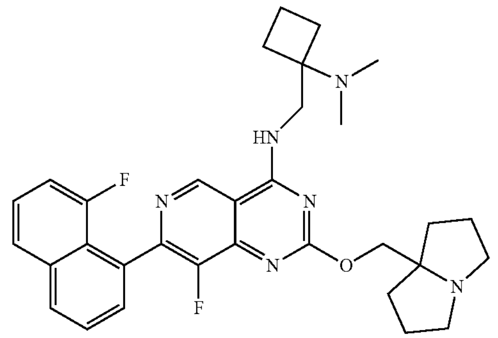

N-((1-(dimethylamino)cyclobutyl)methyl)-8-fluoro-7-(8-fluoronaphthalen-1-yl)-2-((hexahydro-1H-pyrrolizin-7a-yl)methoxy)pyrido[4, 3-d]pyrimidin-4-amine

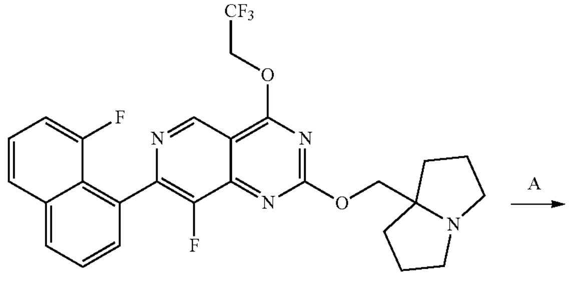

-continued

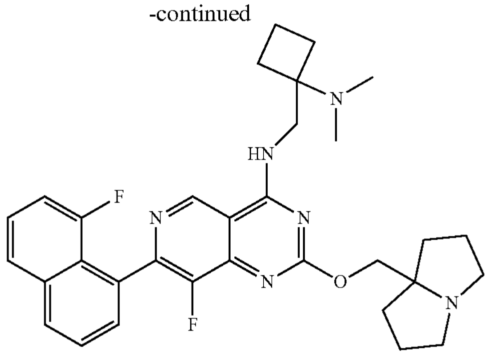

Step A. N-((1-(dimethylamino)cyclobutyl)methyl)-8-fluoro-7-(8-fluoronaphthalen-1-yl)-2-((hexahydro-1H-pyrrolizin-7a-yl)methoxy)pyrido[4,3-d]pyrimidin-4-amine. To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 μmol, 1.00 eq), 4 Å molecular sieve (50 mg) and 1-(aminomethyl)-N,N-dimethyl-cyclobutanamine (29.0 mg, 226 μmol, 1.2 eq) in DMF (1.0 mL) was added DIEA (73.0 mg, 565 μmol, 98.5 μL, 3.00 eq). The mixture was stirred at 40° C. for 2 hours. After completion, the reaction mixture was filtered. The filtrate was purified by prep-HPLC (column: Shim-pack C18 150*25*10 um; mobile phase: [water (0.225% FA)-ACN]; B %: 10%-30%, 10 min) and lyophilized affording the title compound (63.2 mg, 53% yield, 1.5 FA). Off-white solid; $^1$H NMR (400 MHz, Methanol-$d_4$) δ=9.30 (s, 1H), 8.16-8.11 (m, 1H), 7.89-7.84 (m, 1H), 7.74-7.69 (m, 1H), 7.60 (dd, J=1.2, 7.2 Hz 1H), 7.57-7.51 (m, 1H), 7.25-7.15 (m, 1H), 4.71 (s, 2H), 4.32-4.19 (m, 2H), 3.72-3.64 (m, 2H), 3.30-3.24 (m, 2H), 2.76 (s, 6H), 2.48-2.37 (m, 2H), 2.37-2.26 (m, 4H), 2.26-2.07 (m, 6H), 2.05-1.90 (m, 2H); [ESI, M/2+1, M+1]: 280.3, 559.3.

Example 15

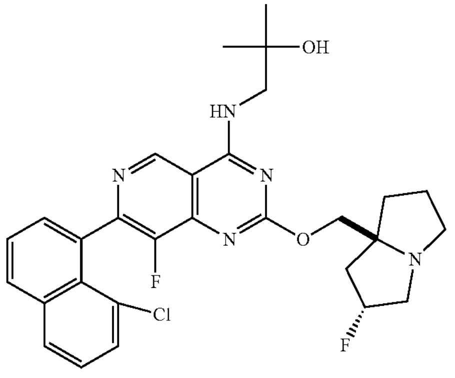

1-((7-(8-chloronaphthalen-1-yl)-8-fluoro-2-(((2R,7aS)-2-fluorotetrahydro-lH-pyrrolizin-7a(5H)-yl)methoxy)pyrido[4,3-d]pyrimidin-4-yl)amino)-2-methylpropan-2-ol (racemic, trans)

Synthesized according to Example 14 substituting 1-amino-2-methylpropan-2-ol in place of 1-(aminomethyl) cyclohexan-1-ol hydrochloride in step A to afford 1-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpropan-2-ol (5.7 mg, 2% yield). LCMS (MM-ES+APCI, Pos): m/z 554.2 (M+H).

Example 16

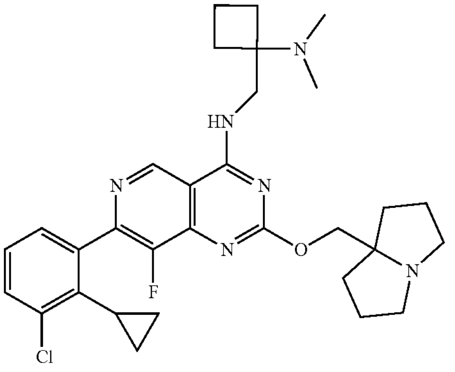

7-(3-chloro-2-cyclopropylphenyl)-N-((1-(dimethylamino) cyclobutyl) methyl)-8-fluoro-2-((tetrahydro-1H-pyrrolizin-7a (5H)-yl) methoxy) pyrido[4, 3-d] pyrimidin-4-amine

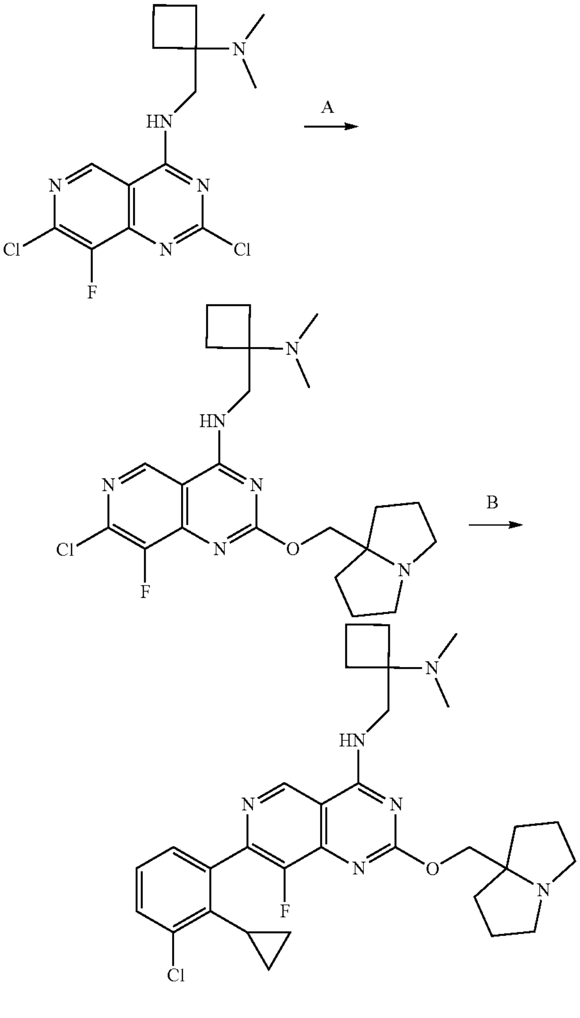

Step A. 7-chloro-N-((1-(dimethylamino) cyclobutyl) methyl)-8-fluoro-2-((tetrahydro-1H-pyrrolizin-7a(5H)-yl) methoxy) pyrido[4,3-d]pyrimidin-4-amine: A mixture of 2,7-dichloro-N-((1-(dimethylamino)cyclobutyl)methyl)-8-fluoropyrido[4,3-d]pyrimidin-4-amine (0.14 g, 0.40 mmol, synthesized according to Example 1, Step A-B) in 1,4-dioxane (4 mL) was treated with (tetrahydro-1H-pyrrolizin-7a(5H)-yl) methanol (56 mg, 0.40 mmol) and Cesium Carbonate (0.39 g, 1.2 mmol) at room temperature. 3 Å powdered mol sieves (0.2 g) were added and the mixture was stirred at 95° C. overnight. The cooled mixture was diluted with EtOAc and filtered. The filtrate was concentrated in vacuo and purified by silica column chromatography eluting with 0%-10% DCM/MeOH+2% $NH_4OH$ as modifier to afford 7-chloro-N-((1-(dimethylamino)cyclobutyl)methyl)-8-fluoro-2-((tetrahydro-1H-pyrrolizin-7a (5H)-yl)methoxy)pyrido[4,3-d]pyrimidin-4-amine (92 mg, 51% yield). LCMS (MM-ES+APCI, Pos): m/z 449.3 (M+H).

Step B. 7-(3-chloro-2-cyclopropylphenyl)-N-((1-(dimethylamino) cyclobutyl) methyl)-8-fluoro-2-((tetrahydro-1H-pyrrolizin-7a(5H)-yl) methoxy) pyrido[4,3-d] pyrimidin-4-amine: 7-chloro-N-((1-(dimethylamino)cyclobutyl)methyl)-8-fluoro-2-((tetrahydro-1H-pyrrolizin-7a(5H)-yl)methoxy) pyrido[4,3-d]pyrimidin-4-amine (46 mg, 0.10 mmol) was dissolved in dioxane (0.50 mL, 0.1 mmol). The reaction was purged with argon and treated with Potassium phosphate tribasic (0.20 mL, 0.21 mmol) and 2-(3-chloro-2-cyclopropylphenyl)-4,4,5,5-tetramethyl-1,3,2-dioxaborolane (43 mg, 0.15 mmol). After 5 minutes of argon sparging [(Di(1-adamantyl)-butylphosphine)-2-(2'-amino-1,1'-biphenyl)] palladium (II) methanesulfonate (CatXcium) (8 mg, 0.01 mmol) was added. The reaction was heated to 65° C. for 3 hours. The mixture was cooled to room temperature and partitioned between water and EtOAc. The layers were separated. The combined organics were washed with brine, dried over sodium sulfate, filtered, and concentrated in vacuo. The residue was purified by prep HPLC (Gilson, 5-95% ACN/water with 0.1% TFA as modifier). Fractions containing product were pooled, frozen, and lyophilized. The solid was resuspended in 1 mL of methanol and free based by passing through PL-$HCO_3$ MP SPE cartridge. The combined organics were concentrated in vacuo to give 7-(3-chloro-2-cyclopropylphenyl)-N-((1-(dimethylamino) cyclobutyl)methyl)-8-fluoro-2-((tetrahydro-1H-pyrrolizin-7a(5H)-yl)methoxy)pyrido[4,3-d]pyrimidin-4-amine (7.3 mg, 13% yield). LCMS (MM-ES+APCI, Pos): m/z 565.3 (M+H).

Example 17

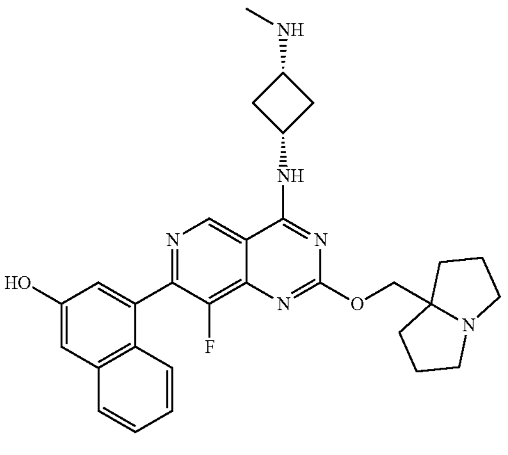

4-(8-fluoro-4-(((1s, 3s)-3-(methylamino) cyclobutyl)amino)-2-((tetrahydro-1H-pyrrolizin-7a(5H)- yl)methoxy)pyrido[4, 3-d] pyrimidin-7-yl)naphthalen-2-ol -continued

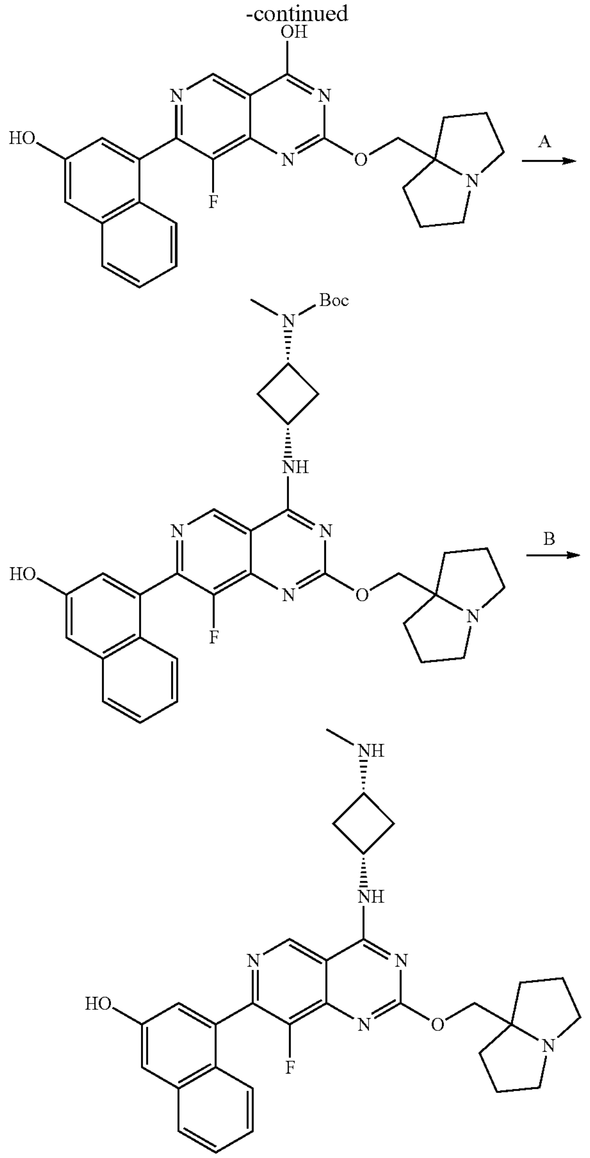

Step A. 4-(8-fluoro-4-(((1s,3s)-3-(methylamino)cyclobutyl)amino)-2-((tetrahydro-1H-pyrrolizin-7a(5H)-yl)methoxy)pyrido[4,3-d]pyrimidin-7-yl)naphthalen-2-ol bis(2,2,2-trifluoroacetate). To a solution of 8-fluoro-7-(3-hydroxynaphthalen-1-yl)-2-((tetrahydro-1H-pyrrolizin-7a(5H)-yl)methoxy)pyrido[4,3-d]pyrimidin-4-ol (11 mg, 0.03 mmol) in DMA (0.12 mL) were added Hunig's base (22 µL, 0.12 mmol) and HATU (37 mg, 0.1 mmol). The reaction was stirred for 5 minutes. tert-Butyl ((1s,3s)-3-aminocyclobutyl)(methyl)carbamate (9.9 mg, 0.05 mmol) was added and the reaction was stirred overnight. The mixture was purified by reverse-phase chromatography (5-95% MeCN/water with 0.1% TFA as modifier). The product was partitioned between dichloromethane and saturated $NaHCO_3$. The organics were washed with brine, dried with $Na_2SO_4$, filtered, and concentrated to give tert-butyl ((1s,3s)-3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)cyclobutyl)(methyl)carbamate (2.5 mg, 16% yield). LCMS (MM-ES+APCI, Pos): m/z 629.3 [M+H].

Step B. 4-(8-fluoro-4-(((1s,3s)-3-(methylamino)cyclobutyl)amino)-2-((tetrahydro-1H-pyrrolizin-7a(5H)-yl)methoxy)pyrido[4,3-d]pyrimidin-7-yl)naphthalen-2-ol bis(2,2,2-trifluoroacetate): A solution of tert-butyl ((1s,3s)-3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)cyclobutyl)(methyl)carbamate (2.5 mg, 0.004 mmol) in dichloromethane (0.1 mL) and 4M HCl in dioxane (0.1 mL, 0.004 mmol) was stirred for 45 minutes. The mixture was diluted with 1 mL of MeOH and purified by reverse-phase chromatography (5-95% MeCN/water with 0.1% TFA as modifier). The product was lyophilized to give 4-(8-fluoro-4-(((1s,3s)-3-(methylamino)cyclobutyl)amino)-2-((tetrahydro-1H-pyrrolizin-7a(5H)-yl)methoxy)pyrido[4,3-d]pyrimidin-7-yl)naphthalen-2-ol bis(2,2,2-trifluoroacetate) (1.6 mg, 53% yield). LCMS (MM-ES+APCI, Pos): m/z 529.3 [M+H].

Example 18

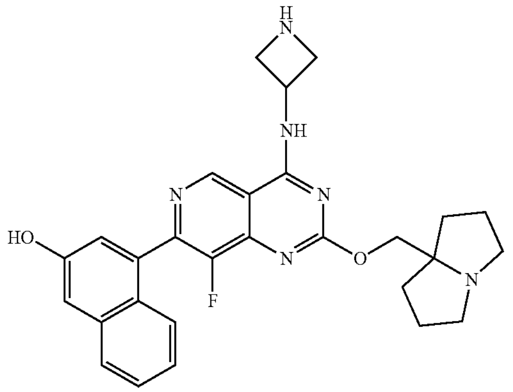

4-(4-(azetidin-3-ylamino)-8-fluoro-2-((tetrahydro-1H-pyrrolizin-7a(5H)-yl)methoxy)pyrido[4,3-d]pyrimidin-7-yl)naphthalen-2-ol

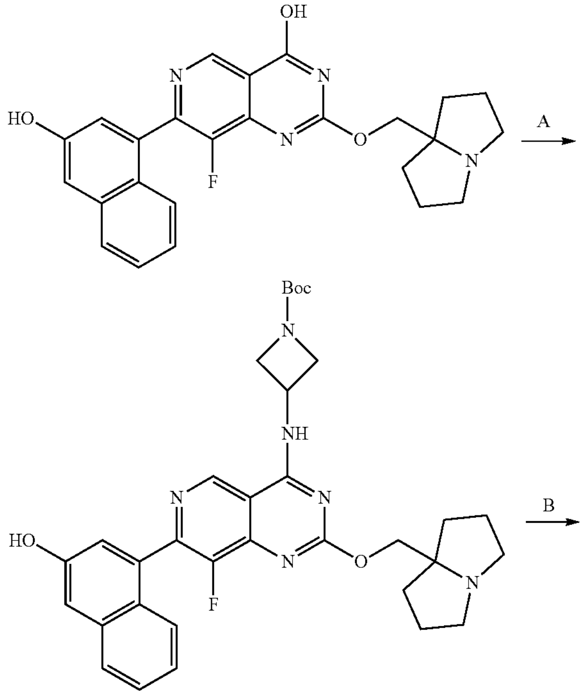

-continued

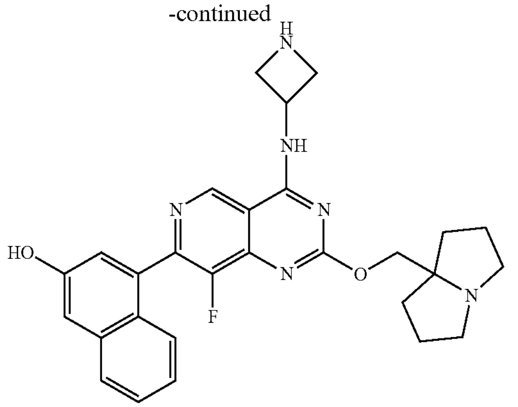

Step A. tert-butyl 3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)azetidine-1-carboxylate: To a solution of 8-fluoro-7-(3-hydroxynaphthalen-1-yl)-2-((tetrahydro-1H-pyrrolizin-7a(5H)-yl)methoxy)pyrido[4,3-d]pyrimidin-4-ol (13 mg, 0.03 mmol) in DMA (0.15 mL) was added Hunig's base (25 μL, 0.15 mmol) and HATU (44 mg, 0.12 mmol) and the reaction was stirred for 10 minutes. Tert-butyl 3-aminoazetidine-1-carboxylate (10 mg, 0.06 mmol) was added and the reaction was stirred overnight followed by addition of 0.2 mL of $NaHCO_3$. The reaction was stirred for an additional night. The solution was partitioned between dichloromethane and water. The organics were concentrated and purified by silica gel chromatography eluting with 1-20% MeOH/DCM with 1% $NH_4OH$ as modifier to give tert-butyl 3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)azetidine-1-carboxylate (10 mg, 26% yield). LCMS (MM-ES+APCI, Pos): m/z 601.4 [M+H].

Step B. 4-(4-(azetidin-3-ylamino)-8-fluoro-2-((tetrahydro-1H-pyrrolizin-7a(5H)-yl)methoxy)pyrido[4,3-d]pyrimidin-7-yl)naphthalen-2-ol: A solution of tert-butyl 3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)azetidine-1-carboxylate (5 mg, 0.01 mmol) in dichloromethane (0.2 mL) and TFA (0.2 mL) was stirred for 45 minutes. The solution was concentrated and purified by reverse-phase chromatography eluting with 5-95% MeCN/water+0.1% TFA modifier. The product was lyophilized to give 4-(4-(azetidin-3-ylamino)-8-fluoro-2-((tetrahydro-1H-pyrrolizin-7a(5H)-yl)methoxy)pyrido[4,3-d]pyrimidin-7-yl)naphthalen-2-ol (1.4 mg, 34% yield). LCMS (MM-ES+APCI, Pos): m/z 501.2 [M+H].

Example 19

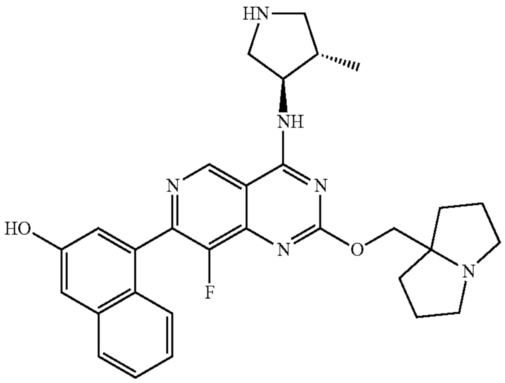

4-(8-fluoro-4-(((3R, 4S)-4-methylpyrrolidin-3-yl)amino)-2-((tetrahydro-1H-pyrrolizin-7a(5H)-yl)methoxy)pyrido[4, 3-d]pyrimidin-7-yl)naphthalen-2-ol

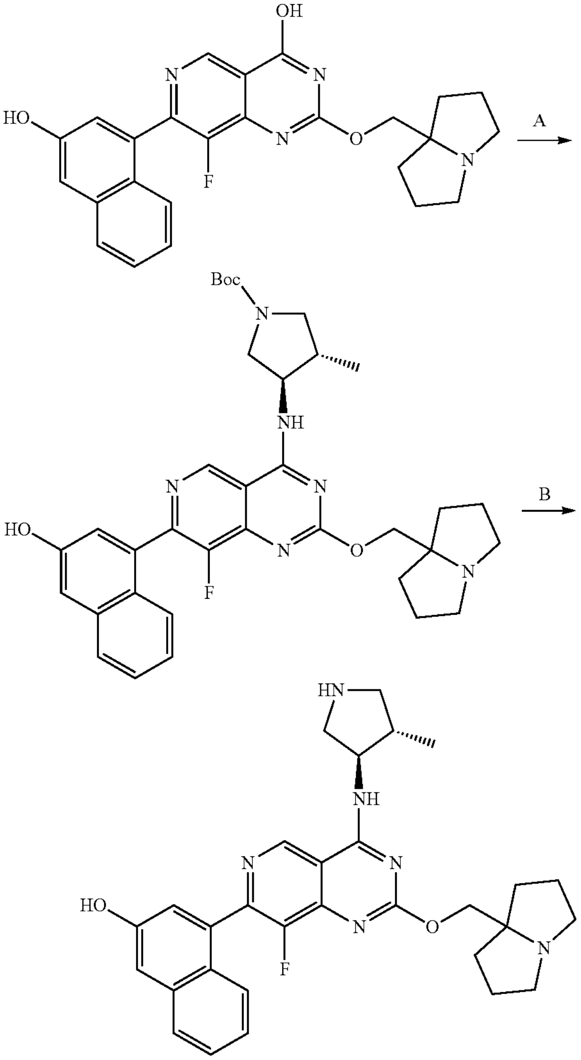

Step A. tert-butyl (3R,4S)-3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)-4- methylpyrrolidine-1-carboxylate: To a solution of 8-fluoro-7-(3-hydroxynaphthalen-1-yl)-2-((tetrahydro-1H-pyrrolizin-7a(5H)-yl)methoxy)pyrido[4,3-d]pyrimidin-4-ol (18 mg, 0.04 mmol) in DMA (0.2 mL) was added Hunig's base (35 μL, 0.2 mmol) and HATU (61 mg, 0.16 mmol) and the reaction was stirred for 10 minutes followed by addition of tert-butyl (3R,4S)-3-amino-4-methylpyrrolidine-1-carboxylate (16 mg, 0.08 mmol). The reaction was stirred overnight. $NaHCO_3$ (0.2 mL) was added and the reaction was stirred for 6 hours. The mixture was partitioned between dichloromethane and water. The organics were concentrated and purified by silica gel chromatography (1-20% MeOH/DCM with 1% $NH_4OH$ as modifier) to give tert-butyl (3R,4S)-3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)-4-methylpyrrolidine-1-carboxylate (4 mg, 16% yield). LCMS (MM-ES+APCI, Pos): m/z 629.3 [M+H].

Step B. 4-(8-fluoro-4-(((3R,4S)-4-methylpyrrolidin-3-yl)amino)-2-((tetrahydro-1H-pyrrolizin-7a(5H)-yl)methoxy)pyrido[4,3-d]pyrimidin-7-yl)naphthalen-2-ol: A solution of tert-butyl (3R,4S)-3-((8-fluoro-7-(3-hydroxynaphthalen-1-yl)-2-((tetrahydro-1H-pyrrolizin-7a(5H)-yl)methoxy)pyrido[4,3-d]pyrimidin-4-yl)amino)-4-methylpyrrolidine-1-carboxylate (4 mg, 0.01 mmol) in dichloromethane (0.15 mL) and TFA (0.15 mL) was stirred for 45 minutes. The solution was concentrated and purified by reverse-phase chromatography (5-95% MeCN/water with 0.1% TFA as modifier). The product was then lyophilized to give 4-(8-fluoro-4-(((3R,4S)-4-methylpyrrolidin-3-yl)amino)-2-((tetrahydro-1H-pyrrolizin-7a(5H)-yl)methoxy)pyrido[4,3-d]pyrimidin-7-yl)naphthalen-2-ol (2.9 mg, 86% yield). LCMS (MM-ES+APCI, Pos): m/z 529.2 [M+H].

Example 20

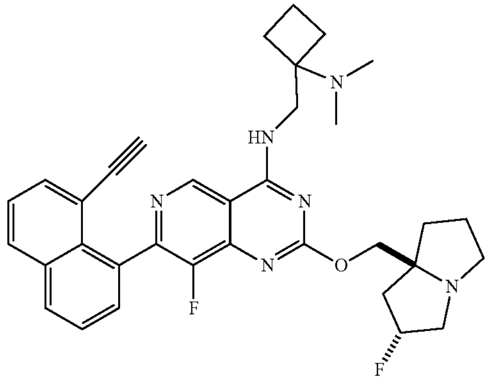

N-((1-(dimethylamino)cyclobutyl)methyl)-7-(8-ethynylnaphthalen-1-yl)-8-fluoro-2-(((2R, 7aS)-2-fluorotetrahydro-1H-pyrrolizin-7a(5H)-yl)methoxy)pyrido[4, 3-d]pyrimidin-4-amine (racemic, trans)

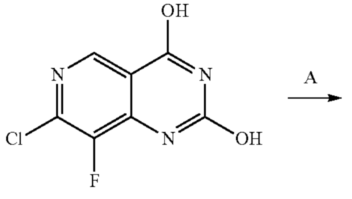

-continued

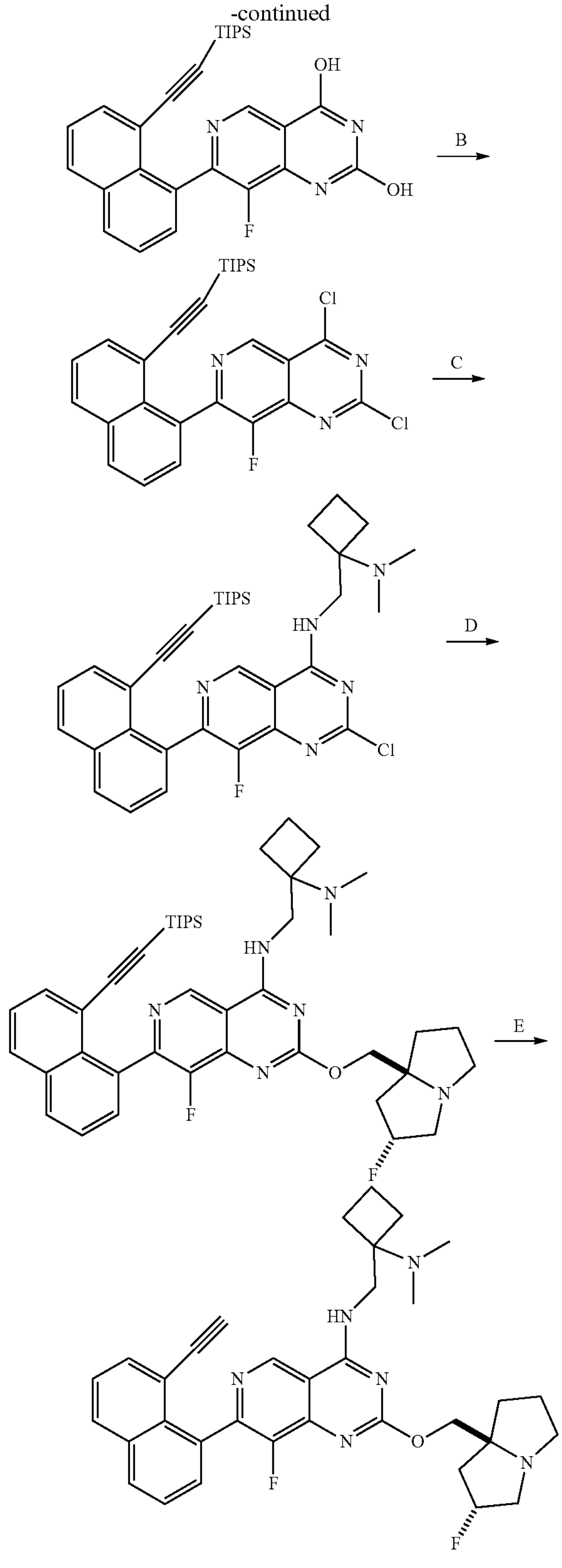

Step A. 8-fluoro-7-(8-((triisopropylsilyl)ethynyl)naphthalen-1-yl)pyrido[4,3-d]pyrimidine-2,4(1H,3H)-dione: 7-chloro-8-fluoropyrido[4,3-d]pyrimidine-2,4(1H,3H)-dione (1.49 g, 6.91 mmol) was dissolved in 4:1 THF/Water (70 mL, 0.1 M) and treated with triisopropyl((8-(4,4,5,5-tetramethyl-1,3,2-dioxaborolan-2-yl)naphthalen-1-yl)ethynyl)silane (3.3 g, 7.6 mmol), potassium phosphate tribasic (2.9 g, 14 mmol). The mixture was sparged with argon for several minutes and treated with X-Phos-G2 precatalyst (0.54 g, 0.69 mmol). The reaction was sealed and heated to 45° C. overnight. Additional X-Phos-G2 (0.27 g) was added and the reaction was sparged with argon for several minutes, sealed and heated to 45° C. for 24 hours.

The mixture was cooled to room temperature and poured into 500 mL water. The mixture was extracted with EtOAc (3×), the combined organics washed with brine (lx), dried over $Na_2SO_4$, filtered, concentrated, and purified by silica gel chromatography eluting with 5-70% DCM/EtOAc to give 8-fluoro-7-(8-((triisopropylsilyl)ethynyl)naphthalen-1-yl)pyrido[4,3-d]pyrimidine-2,4(1H,3H)-dione (1.4 g, 41% yield). LCMS (MM-ES+APCI, Pos): m/z 488.2 [M+H].

Step B. 2,4-dichloro-8-fluoro-7-(8-((triisopropylsilyl)ethynyl)naphthalen-1-yl)pyrido[4,3-d]pyrimidine: To a suspension of 8-fluoro-7-(8-((triisopropylsilyl)ethynyl)naphthalen-1-yl)pyrido[4,3-d]pyrimidine-2,4(1H,3H)-dione (0.15 g, 0.31 mmol) in $POCl_3$ (1.5 mL) was added DIEA (0.15 mL, 0.31 mmol) and the mixture was warmed to 110° C. and stirred for 1 hour. The cooled mixture was concentrated and partitioned between EtOAc and $NaHCO_3$. The organics were washed with brine, dried with $Na_2SO_4$, filtered, and concentrated to give 2,4-dichloro-8-fluoro-7-(8-((triisopropylsilyl)ethynyl) naphthalen-1-yl) pyrido[4,3-d] pyrimidine (0.16 g, 96% yield). LCMS (MM-ES+APCI, Pos): m/z 525.1 [M+H].

Step C. 2-chloro-N-((1-(dimethylamino)cyclobutyl) methyl)-8-fluoro-7-(8-((triisopropylsilyl)ethynyl)naphthalen-1-yl)pyrido[4,3-d]pyrimidin-4-amine: To a solution of 2,4-dichloro-8-fluoro-7-(8-((triisopropylsilyl)ethynyl)naphthalen-1-yl)pyrido[4,3-d]pyrimidine (20 mg, 0.04 mmol) and 1-(aminomethyl)-N,N-dimethylcyclobutan-1-amine (4.9 mg, 0.04 mmol) in dichloromethane (0.38 mL) at 0° C. was added DIEA (20 μL, 0.11 mmol) and stirred for 1 hour. The solution was purified by silica gel chromatography (1-10% MeOH/DCM with 1% $NH_4OH$ as modifier) to give 2-chloro-N-((1-(dimethylamino)cyclobutyl)methyl)-8-fluoro-7-(8-((triisopropylsilyl)ethynyl)naphthalen-1-yl) pyrido[4,3-d]pyrimidin-4-amine (10 mg, 43% yield). LCMS (MM-ES+APCI, Pos): m/z 616.3 [M+H].

Step D. N-((1-(dimethylamino)cyclobutyl)methyl)-8-fluoro-2-(((2R,7aS)-2-fluorotetrahydro-1H-pyrrolizin-7a (5H)-yl)methoxy)-7-(8-((triisopropylsilyl)ethynyl)naphthalen-1-yl)pyrido[4,3-d]pyrimidin-4-amine: A suspension of 2-chloro-N-((1-(dimethylamino)cyclobutyl)methyl)-8-fluoro-7-(8-((triisopropylsilyl)ethynyl)naphthalen-1-yl) pyrido[4,3-d]pyrimidin-4-amine (10 mg, 0.02 mmol), ((2R, 7aS)-2-fluorotetrahydro-1H-pyrrolizin-7a(5H)-yl)methanol (13 mg, 0.08 mmol), $Cs_2CO_3$ (16 mg, 0.05 mmol), and 4 Å molecular sieves (15 mg) in 1,4-dioxane (0.16 mL) was heated to 85° C. in a sealed vial and stirred for two days. The reaction was then filtered, concentrated and purified by silica gel chromatography (1-10% MeOH/DCM with 1% $NH_4OH$ as modifier) to give N-((1-(dimethylamino)cyclobutyl) methyl)-8-fluoro-2-(((2R,7aS)-2-fluorotetrahydro-1H-pyrrolizin-7a(5H)-yl)methoxy)-7-(8-((triisopropylsilyl)ethynyl)naphthalen-1-yl)pyrido[4,3-d]pyrimidin-4-amine (6 mg, 50% yield). LCMS (MM-ES+APCI, Pos): m/z 739.4 [M+H].

Step E. N-((1-(dimethylamino)cyclobutyl)methyl)-7-(8-ethynylnaphthalen-1-yl)-8-fluoro-2-(((2R,7aS)-2-fluorotetrahydro-1H-pyrrolizin-7a(5H)-yl)methoxy)pyrido[4,3-d] pyrimidin-4-amine bis(2,2,2-trifluoroacetate): To a solution of N-((1-(dimethylamino)cyclobutyl)methyl)-8-fluoro-2-(((2R,7aS)-2-fluorotetrahydro-1H-pyrrolizin-7a(5H)-yl) methoxy)-7-(8-((triisopropylsilyl)ethynyl)naphthalen-1-yl) pyrido[4,3-d]pyrimidin-4-amine (6 mg, 0.01 mmol) in tetrahydrofuran (80 μL) was added 1M TBAF (41 μL. 0.04 mmol) and the reaction was stirred for 45 minutes. The mixture was purified by reverse-phase chromatography (5-95% MeCN/water with 0.1% TFA as modifier). Fractions containing product were pooled, frozen and lyophilized to give N-((1-(dimethylamino)cyclobutyl)methyl)-7-(8-ethynylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine bis(2,2,2-trifluoroacetate) (4.2 mg, 64% yield). LCMS (MM-ES+APCI, Pos): m/z 583.3 [M+H].

Example 21

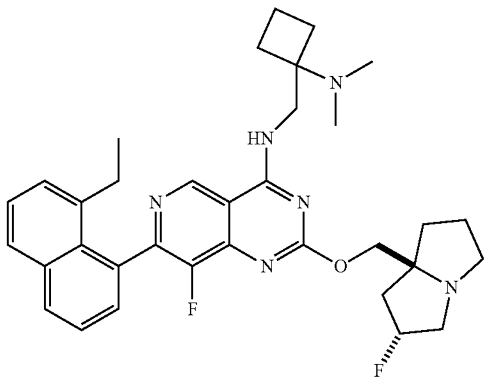

N-((1-(dimethylamino)cyclobutyl)methyl)-7-(8-ethylnaphthalen-1-yl)-8-fluoro-2-(((2R, 7aS)-2-fluorotetrahydro-1H-pyrrolizin-7a(5H)-yl)methoxy)pyrido[4, 3-d]pyrimidin-4-amine (racemic, trans)

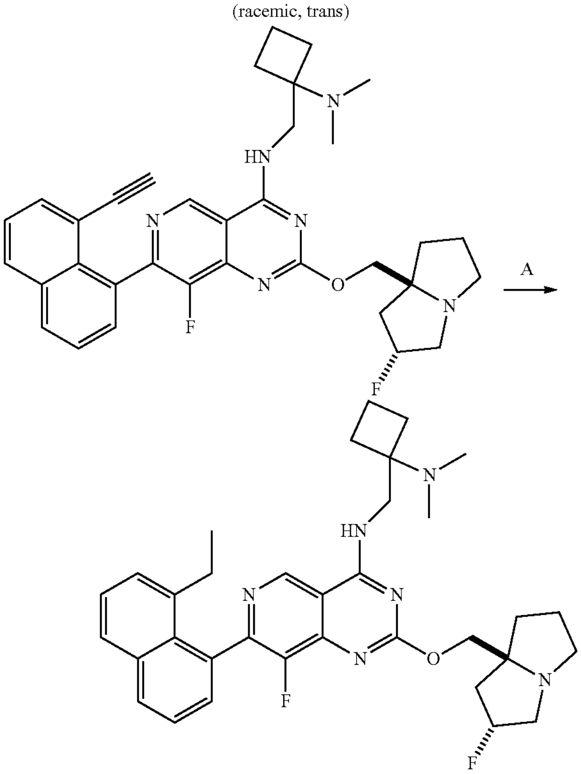

Step A. N-((1-(dimethylamino)cyclobutyl)methyl)-7-(8-ethylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine. A solution of N-((1-(dimethylamino)cyclobutyl)methyl)-7-(8-ethynylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (11 mg, 0.02 mmol) and Pd/C (2 mg, 0.02 mmol) in ethanol (0.2 mL) was purged with hydrogen and stirred under hydrogen atmosphere for 1 hour. The solution was filtered, concentrated, and purified by reverse-phase chromatography (5-95% MeCN/water with 0.1% TFA as modifier). The product was lyophilized to give N-((1-(dimethylamino)cyclobutyl)methyl)-7-(8-ethylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (5 mg, 45% yield). LCMS (MM-ES+APCI, Pos): m/z 587.4 [M+H].

Example 22

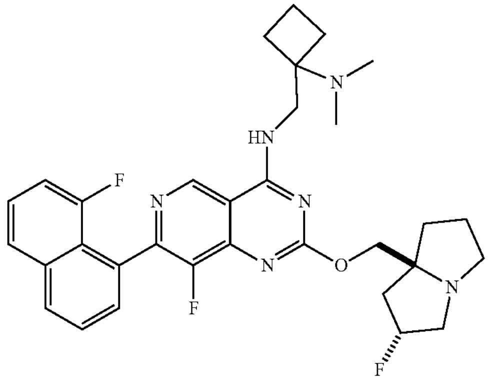

N-((1-(dimethylamino)cyclobutyl)methyl)-8-fluoro-7-(8-fluoronaphthalen-1-yl)-2-(((2R, 7aS)-2-fluorotetrahydro-1H-pyrrolizin-7a(5H)-yl)methoxy)pyrido[4, 3-d]pyrimidin-4-amine (racemic, trans)

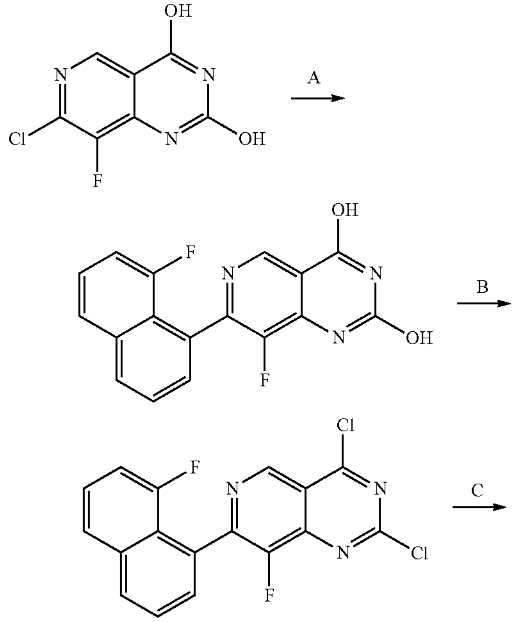

-continued

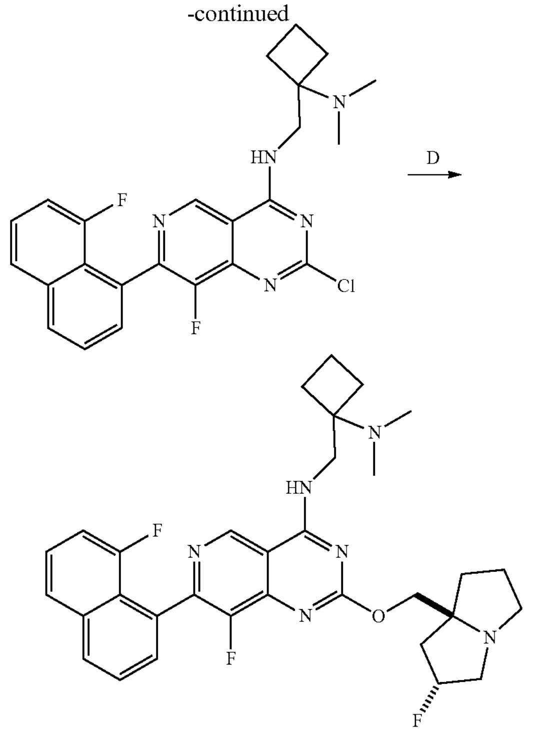

Step A. 8-fluoro-7-(8-fluoronaphthalen-1-yl)pyrido[4,3-d]pyrimidine-2,4(1H,3H)-dione: A mixture of 7-chloro-8-fluoropyrido[4,3-d]pyrimidine-2,4(1H,3H)-dione (25 mg, 0.12 mmol), 2-(8-fluoronaphthalen-1-yl)-4,4,5,5-tetramethyl-1,3,2-dioxaborolane (50 mg, 0.18 mmol), and potassium phosphate tribasic (49 mg, 0.23 mmol) in THF (0.7 mL) and water (0.2 mL) was sparged with argon for 5 minutes and X-Phos-G2 (9.1 mg, 0.01 mmol) was added and the vial was sealed and heated to 45° C. overnight. The mixture was partitioned between DCM and water. The organics were concentrated and purified by silica gel chromatography eluting with 1-10% MeOH/DCM with 1% $NH_4OH$ as modifier. The impure product was concentrated and re-purified by reverse-phase chromatography eluting with 5-95% MeCN/water with 0.1% TFA as modifier. The product was partitioned between DCM and saturated $NaHCO_3$. The organics were washed with brine, dried with $Na_2SO_4$, filtered, and concentrated to give 8-fluoro-7-(8-fluoronaphthalen-1-yl)pyrido[4,3-d]pyrimidine-2,4(1H,3H)-dione (4 mg, 11% yield). LCMS (MM-ES+APCI, Pos): m/z 326.1 [M+H].

Step B. 2,4-dichloro-8-fluoro-7-(8-fluoronaphthalen-1-yl)pyrido[4,3-d]pyrimidine: To a suspension of 8-fluoro-7-(8-fluoronaphthalen-1-yl)pyrido[4,3-d]pyrimidine-2,4(1H,3H)-dione (4 mg, 0.01 mmol) in $POCl_3$ (60 μL) was added DIEA (6 μL, 0.01 mmol) and the mixture was warmed to 110° C. and stirred for 1 hour. The cooled mixture was concentrated and partitioned between DCM and saturated $NaHCO_3$. The organics were washed with brine, dried with $Na_2SO_4$, filtered, and concentrated to give 2,4-dichloro-8-fluoro-7-(8-fluoronaphthalen-1-yl)pyrido[4,3-d]pyrimidine (4 mg, 90% yield). LCMS (MM-ES+APCI, Pos): m/z 362.1 [M+H].

Step C. 2-chloro-N-((1-(dimethylamino)cyclobutyl)methyl)-8-fluoro-7-(8-fluoronaphthalen-1-yl)pyrido[4,3-d]pyrimidin-4-amine: To a solution of 2,4-dichloro-8-fluoro-7-(8-fluoronaphthalen-1-yl)pyrido[4,3-d]pyrimidine (4 mg, 0.01 mmol) and 1-(aminomethyl)-N,N-dimethylcyclobutan-1-amine (1.4 mg, 0.01 mmol) in dichloromethane (0.1 mL) at 0° C. was added DIEA (6 μL, 0.03 mmol) and the reaction was stirred for 90 minutes at 0° C. The solution was partitioned between DCM and saturated $NaHCO_3$. The organics were washed with brine, dried with $Na_2SO_4$, filtered, and concentrated to give 2-chloro-N-((1-(dimethylamino)cyclobutyl)methyl)-8-fluoro-7-(8-fluoronaphthalen-1-yl)pyrido[4,3-d]pyrimidin-4-amine (4 mg, 80% yield). LCMS (MM-ES+APCI, Pos): m/z 454.1 [M+H].

Step D. N-((1-(dimethylamino)cyclobutyl)methyl)-8-fluoro-7-(8-fluoronaphthalen-1-yl)-2-(((2R,7aS)-2-fluoro-tetrahydro-1H-pyrrolizin-7a(5H)-yl)methoxy)pyrido[4,3-d]pyrimidin-4-amine: A suspension of 2-chloro-N-((1-(dimethylamino)cyclobutyl)methyl)-8-fluoro-7-(8-fluoronaphthalen-1-yl)pyrido[4,3-d]pyrimidin-4-amine (4 mg, 0.01 mmol), ((2R,7aS)-2-fluorotetrahydro-1H-pyrrolizin-7a(5H)-yl)methanol (7 mg, 0.04 mmol), $Cs_2CO_3$ (8.6 mg, 0.03 mmol), and 4 Å molecular sieves (15 mg) in 1,4-dioxane (0.1 mL) was heated to 85° C. in a sealed vial overnight. The product was filtered, concentrated, and purified by reverse-phase chromatography (5-95% MeCN/water with 0.1% TFA as modifier. The product was lyophilized to give N-((1-(dimethylamino)cyclobutyl)methyl)-8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-amine (1 mg, 20% yield) as the TFA salt. LCMS (MM-ES+APCI, Pos): m/z 577.3 [M+H].

Example 23

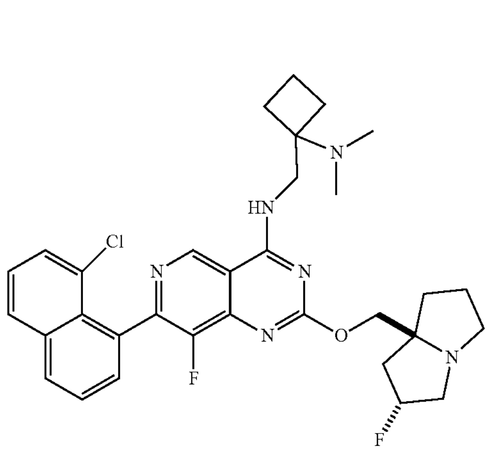

7-(8-chloronaphthalen-1-yl)-N-((1-(dimethylamino)cyclobutyl)methyl)-8-fluoro-2-(((2R, 7aS)-2-fluorotetrahydro-1H-pyrrolizin-7a(5H)-yl)methoxy)pyrido[4, 3-d]pyrimidin-4-amine (racemic, trans)

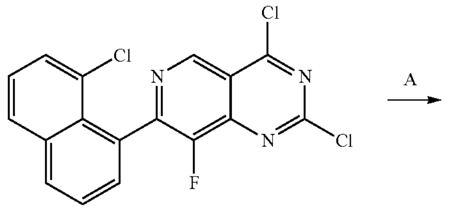

-continued

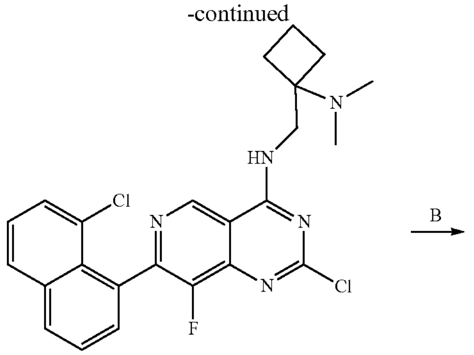

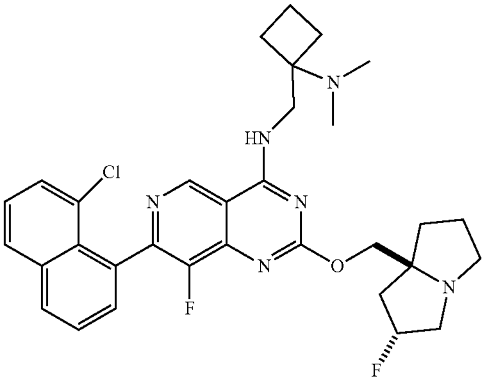

Step A. 2-chloro-7-(8-chloronaphthalen-1-yl)-N-((1-(dimethylamino)cyclobutyl)methyl)-8-fluoropyrido[4,3-d]pyrimidin-4-amine: To a solution of 2,4-dichloro-7-(8-chloronaphthalen-1-yl)-8-fluoropyrido[4,3-d]pyrimidine (0.31 g, 0.82 mmol) and 1-(aminomethyl)-N,N-dimethylcyclobutan-1-amine (0.11 g, 0.82 mmol) in dichloromethane (8 mL) at 0° C. was added DIEA (0.43 mL, 2.5 mmol) and the reaction was stirred at 0° C. for 1 hour. The solution was partitioned between DCM and saturated $NaHCO_3$. The organics were washed with brine, dried with $Na_2SO_4$, filtered, concentrated, and purified by silica gel chromatography (1-20% MeOH/DCM with 1% $NH_4OH$ as modifier) to give 2-chloro-7-(8-chloronaphthalen-1-yl)-N-((1-(dimethylamino) cyclobutyl)methyl)-8-fluoropyrido[4,3-d]pyrimidin-4-amine (0.28 g, 73% yield). LCMS (MM-ES+APCI, Pos): m/z 470.1 [M+H].

Step B. 7-(8-chloronaphthalen-1-yl)-N-((1-(dimethylamino)cyclobutyl)methyl)-8-fluoro-2-(((2R,7aS)-2-fluoro-tetrahydro-1H-pyrrolizin-7a(5H)-yl)methoxy)pyrido[4,3-d]pyrimidin-4-amine: A suspension of 2-chloro-7-(8-chloronaphthalen-1-yl)-N-((1-(dimethylamino)cyclobutyl)methyl)-8-fluoropyrido[4,3-d]pyrimidin-4-amine (0.28 g, 0.60 mmol), ((2R,7aS)-2-fluorotetrahydro-1H-pyrrolizin-7a(5H)-yl)methanol (0.47 g, 3.0 mmol), $Cs_2CO_3$ (0.58 g, 1.8 mmol), and 4 Å molecular sieves (0.25 g) in 1,4-dioxane (6 mL) was heated to 90° C. in a sealed vial and stirred overnight. The product was filtered, concentrated, and purified by silica gel chromatography (1-20% MeOH/DCM with 1% $NH_4OH$ as modifier) to give 7-(8-chloronaphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (0.32 g, 90% yield). LCMS (MM-ES+APCI, Pos): m/z 593.2 [M+H].

Example 24

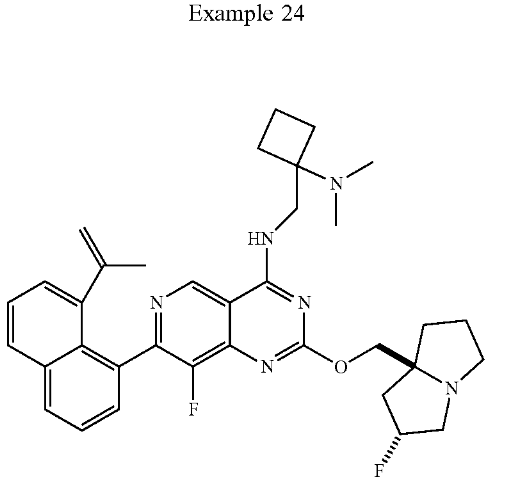

N-((1-(dimethylamino)cyclobutyl)methyl)-8-fluoro-2-(((2R, 7aS)-2-fluorotetrahydro-1H-pyrrolizin-7a(5H)-yl)methoxy)-7-(8-(prop-1-en-2-yl)naphthalen-1-yl)pyrido[4, 3-d]pyrimidin-4-amine (racemic, trans)

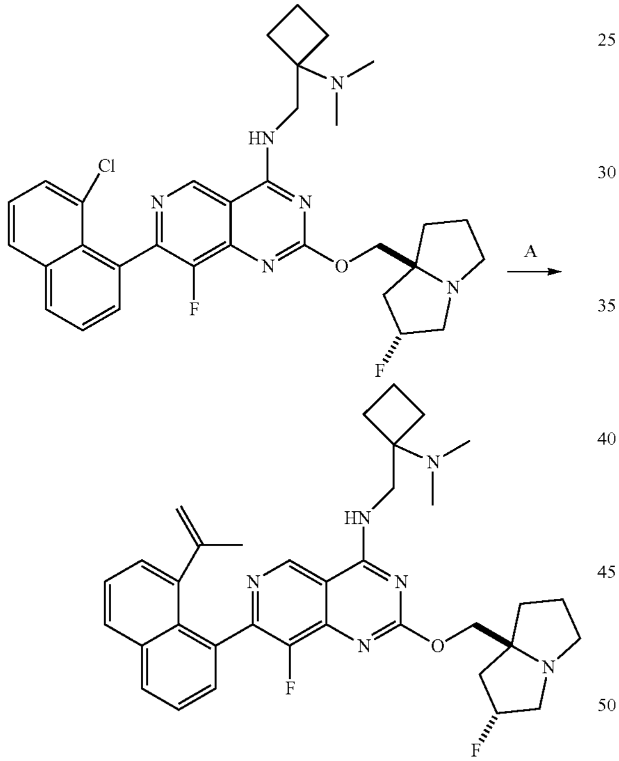

Step A. N-((1-(dimethylamino)cyclobutyl)methyl)-8-fluoro-2-(((2S,7aR)-2-fluorotetrahydro-1H-pyrrolizin-7a(5H)-yl)methoxy)-7-(8-(prop-1-en-2-yl)naphthalen-1-yl)pyrido[4,3-d]pyrimidin-4-amine: A solution of 7-(8-chloronaphthalen-1-yl)-N-((1-(dimethylamino)cyclobutyl)methyl)-8-fluoro-2-(((2S,7aR)-2-fluorotetrahydro-1H-pyrrolizin-7a(5H)-yl)methoxy)pyrido[4,3-d]pyrimidin-4-amine (10 mg, 0.01 mmol), 4,4,5,5-tetramethyl-2-(prop-1-en-2-yl)-1,3,2-dioxaborolane (16 μL, 0.08 mmol), $Pd(Ph_3P)_4$ (3.9 mg, 0.003 mmol), and 2.0 M $K_2CO_3$ (25 μL, 0.05 mmol) in dioxane (0.2 mL) was sparged with argon and stirred at 100° C. in a sealed vial for 36 hours. The solution was purified by reverse-phase chromatography (5-95% MeCN/water with 0.1% TFA as modifier). Fractions containing product were pooled, frozen, and lyophilized to give N-((1-(dimethylamino)cyclobutyl)methyl)-8-fluoro-2-(((2S,7aR)-2-fluorotetrahydro-1H-pyrrolizin-7a(5H)-yl)methoxy)-7-(8-(prop-1-en-2-yl)naphthalen-1-yl)pyrido[4,3-d]pyrimidin-4-amine (5 mg, 50% yield) as the bis TFA salt. LCMS (MM-ES+APCI, Pos): m/z 599.3 [M+H].

Example 25

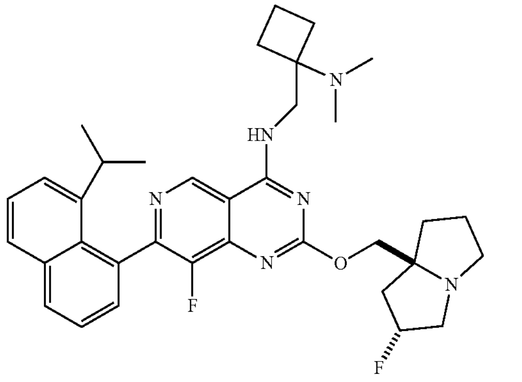

N-((1-(dimethylamino)cyclobutyl)methyl)-8-fluoro-2-(((2R, 7aS)-2-fluorotetrahydro-1H-pyrrolizin-7a(5H)-yl)methoxy)-7-(8-isopropylnaphthalen-1-yl)pyrido[4, 3-d]pyrimidin-4-amine (racemic, trans)

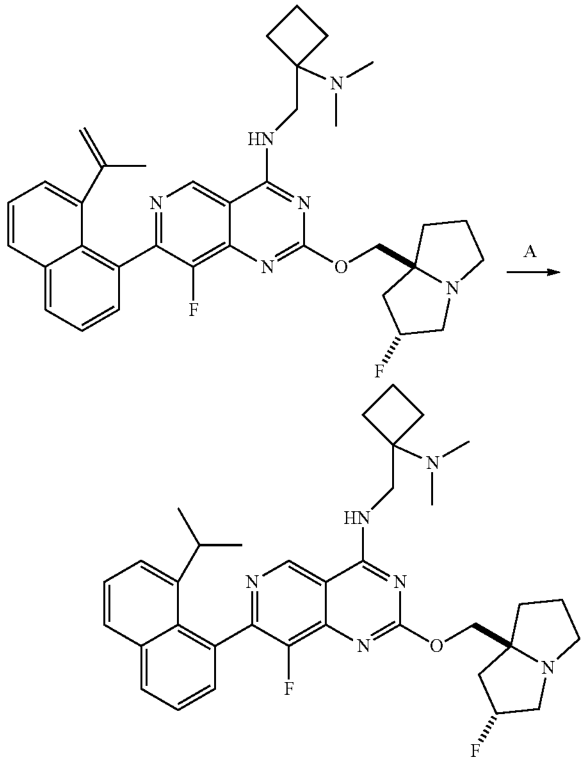

Step A. N-((1-(dimethylamino)cyclobutyl)methyl)-8-fluoro-2-(((2S,7aR)-2-fluorotetrahydro-1H-pyrrolizin-7a(5H)-yl)methoxy)-7-(8-isopropylnaphthalen-1-yl)pyrido[4,3-d]pyrimidin-4-amine: A suspension of N-((1-(dimethylamino)cyclobutyl)methyl)-8-fluoro-2-(((2S,7aR)-2-fluorotetrahydro-1H-pyrrolizin-7a(5H)-yl)methoxy)-7-(8-(prop-1-en-2-yl)naphthalen-1-yl)pyrido[4,3-d]pyrimidin-4- amine (12 mg, 0.02 mmol) and Pd/C (0.4 mg, 0.002 mmol) in methanol (0.2 mL) was stirred under hydrogen overnight. The mixture was filtered and purified by reverse-phase chromatography (5-95% MeCN/water with 0.1% TFA as modifier). Fractions containing product were pooled, frozen, and lyophilized to give N-((1-(dimethylamino)cyclobutyl)methyl)-8-fluoro-2-(((2S,7aR)-2-fluorotetrahydro-1H-pyrrolizin-7a(5H)-yl)methoxy)-7-(8-isopropylnaphthalen-1-yl)pyrido[4,3-d]pyrimidin-4-amine (1.6 mg, 13% yield) as the bis TFA salt. LCMS (MM-ES+APCI, Pos): m/z 601.3 [M+H].

Example 26

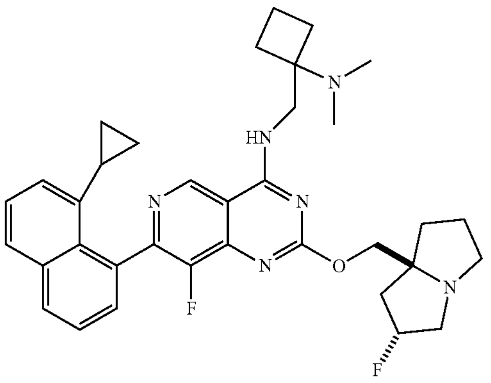

7-(8-cyclopropylnaphthalen-1-yl)-N-((1-(dimethylamino)cyclobutyl)methyl)-8-fluoro-2-(((2S, 7aR)-2-fluorotetrahydro-1H-pyrrolizin-7a(5H)-yl)methoxy)pyrido[4, 3-d]pyrimidin-4-amine
(racemic, trans)

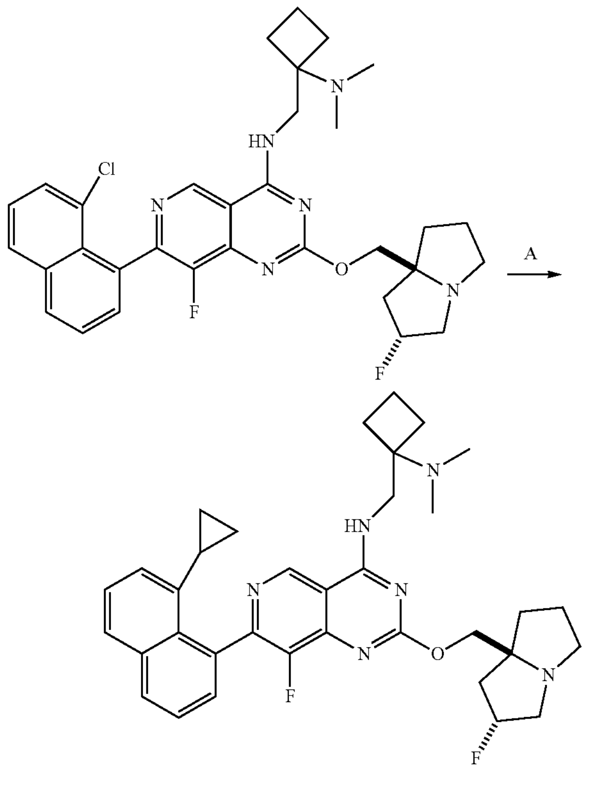

Step A. 7-(8-cyclopropylnaphthalen-1-yl)-N-((1-(dimethylamino)cyclobutyl)methyl)-8-fluoro-2-(((2S,7aR)-2-fluorotetrahydro-1H-pyrrolizin-7a(5H)-yl)methoxy)pyrido[4,3-d]pyrimidin-4-amine: A mixture of 7-(8-chloronaphthalen-1-yl)-N-((1-(dimethylamino)cyclobutyl)methyl)-8-fluoro-2-(((2S,7aR)-2-fluorotetrahydro-1H-pyrrolizin-7a(5H)-yl)methoxy)pyrido[4,3-d]pyrimidin-4-amine (30 mg, 0.05 mmol), cyclopropylboronic acid (22 mg, 0.25 mmol), Pd-XPhos-G2 (4 mg, 0.01 mmol), $PdCl_2(dppf)$ (13 mg, 0.02 mmol), and $Cs_2CO_3$ (40 mg, 0.13 mmol) in 1,4-dioxane (0.34 mL) and water (84 μL) was sparged with argon and heated in a sealed vial to 100° C. overnight. The mixture was filtered and purified by reverse-phase chromatography (5-95% MeCN/water with 0.1% TFA as modifier). Fractions containing product were pooled, frozen, and lyophilized to give 7-(8-cyclopropylnaphthalen-1-yl)-N-((1-(dimethylamino)cyclobutyl)methyl)-8-fluoro-2-(((2S,7aR)-2-fluorotetrahydro-1H-pyrrolizin-7a(5H)-yl)methoxy)pyrido[4,3-d]pyrimidin-4-amine (3 mg, 10% yield) as the bis TFA salt. LCMS (MM-ES+APCI, Pos): m/z 599.3 [M+H].

Example 27

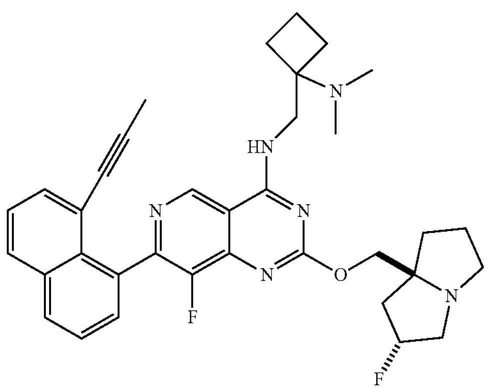

N-((1-(dimethylamino)cyclobutyl)methyl)-8-fluoro-2-(((2R, 7aS)-2-fluorotetrahydro-1H-pyrrolizin-7a(5H)-yl)methoxy)-7-(8-(prop-1-yn-1-yl)naphthalen-1-yl)pyrido[4, 3-d]pyrimidin-4-amine
(racemic, trans)

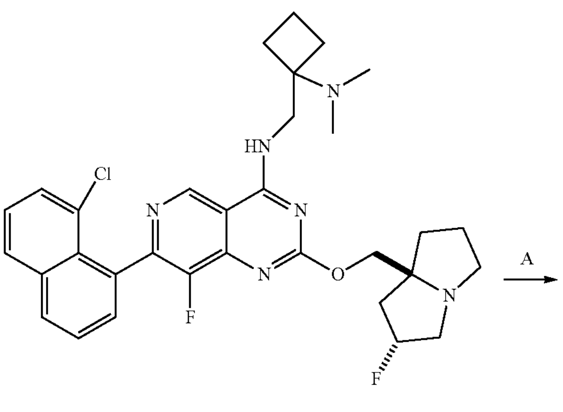

-continued

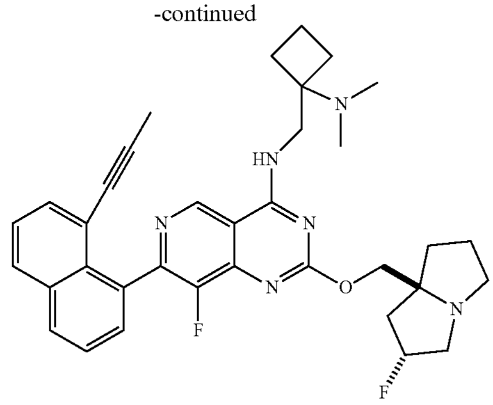

Step A. N-((1-(dimethylamino)cyclobutyl)methyl)-8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-amine: A mixture of 7-(8-chloronaphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (20 mg, 0.03 mmol), trimethyl(prop-2-yn-1-yl)silane (50 μL, 0.34 mmol), $PdCl_2(MeCN)_2$ (8.7 mg, 0.03 mmol), XPhos (16 mg, 0.03 mmol), and $Cs_2CO_3$ (33 mg, 0.1 mmol) in acetonitrile (0.34 mL) was flushed with argon and stirred in a sealed vial at 80° C. overnight. The mixture was filtered, concentrated, and purified by reverse-phase chromatography 5-95% MeCN/water with 0.1% TFA as modifier. Fractions containing product were pooled, frozen, and lyophilized to give N-((1-(dimethylamino)cyclobutyl)methyl)-8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-amine (6 mg, 30% yield) as the bis TFA salt. LCMS (MM-ES+APCI, Pos): m/z 597.3 [M+H].

Example 28

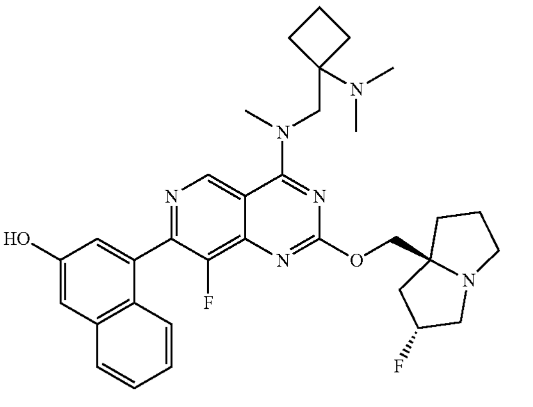

4-(4-(((1-(dimethylamino)cyclopropyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol Synthesized according to Example 1, substituting N,N-dimethyl-1-((methylamino)methyl)cyclobutan-1-amine in place of 1-(aminomethyl)-N,N-dimethylcyclobutan-1-amine in Step B to give product as the bis TFA salt. LCMS (MM-ES+APCI, Pos): m/z 589.1 [M+H].

Example 29

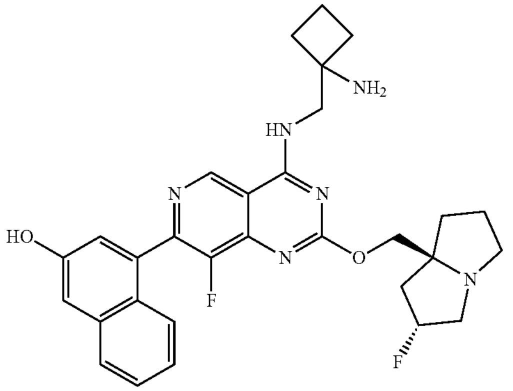

4-(4-(((1-aminocyclobutyl)methyl)amino)-8-fluoro-2-(((2R, 7aS)-2-fluorotetrahydro-1H-pyrrolizin-7a(5H)-yl)methoxy)pyrido[4,3-d]pyrimidin-7-yl)naphthalen-2-ol

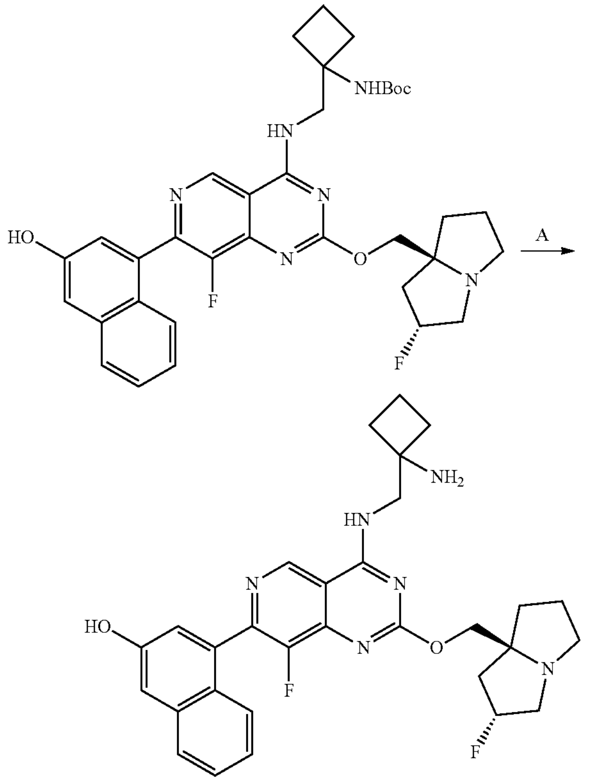

tert-butyl (1-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)cyclobutyl)carbamate. Synthesized according to Example 1, substituting tert-butyl (1-(aminomethyl)cyclobutyl)carbamate in place of 1-(aminomethyl)-N,N-dimethylcyclobutan-1-amine in Step B.

Step A. 4-(4-(((1-aminocyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate). To a solution of tert-butyl (1-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)cyclobutyl)carbamate (16 mg, 0.03 mmol) in DCM (1 mL) was added TFA (0.5 mL). The mixture was stirred at ambient temperature for 1 hour and concentrated in vacuo. The residue was purified by reverse phase HPLC (Gilson, 5-95% ACN/water with 0.1% TFA) and lyophilized to afford 4-(4-(((1-aminocyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate) (3.9 mg, 20% yield). LCMS (MM-ES+APCI, Pos): m/z 547 [M+H].

Example 30

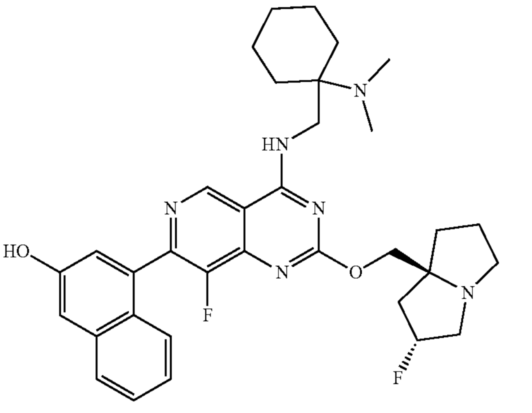

4-(4-(((1-(dimethylamino)cyclohexyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol Synthesized according to Example 1, substituting 1-(aminomethyl)-N,N-dimethylcyclohexan-1-amine dihydrochloride in place of 1-(aminomethyl)-N,N-dimethylcyclobutan-1-amine in Step B to give the title compound as the bis TFA salt. LCMS (MM-ES+APCI, Pos): m/z 603 [M+H].

Example 31

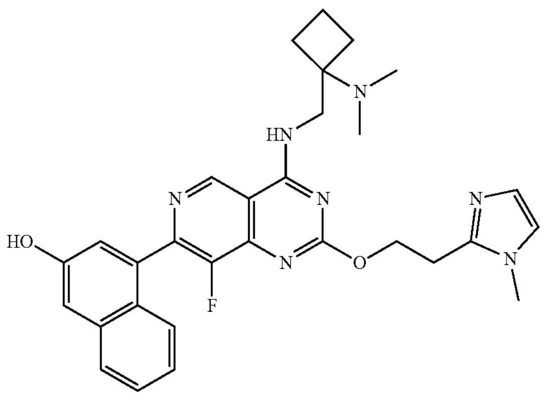

4-(4-(((1-(dimethylamino)cyclobutyl)methyl)amino)-8-fluoro-2-(2-(1-methyl-1H-imidazol-2-yl)ethoxy)pyrido[4,3-d]pyrimidin-7-yl)naphthalen-2-ol Synthesized according to Example 1, substituting 2-(1-methyl-1H-imidazol-2-yl)ethan-1-ol in place of ((2S,7aR)-2-fluorotetrahydro-1H-pyrrolizin-7a(5H)-yl)methanol in Step C to give the title compound as the bis TFA salt. LCMS (MM-ES+APCI, Pos): m/z 542.2 [M+H].

Example 32

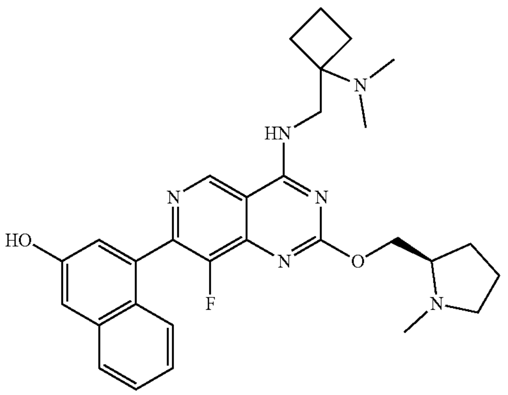

(R)-4-(4-(((1-(dimethylamino)cyclobutyl)methyl)amino)-8-fluoro-2-((1-methylpyrrolidin-2-yl)methoxy)pyrido[4,3-d]pyrimidin-7-yl)naphthalen-2-ol Synthesized according to Example 1, substituting (R)-(1-methylpyrrolidin-2-yl)methanol in place of ((2S,7aR)-2-fluorotetrahydro-1H-pyrrolizin-7a(5H)-yl)methanol in Step C to give the title compound as the bis TFA salt. LCMS (MM-ES+APCI, Pos): m/z 531.2 [M+H].

Example 33

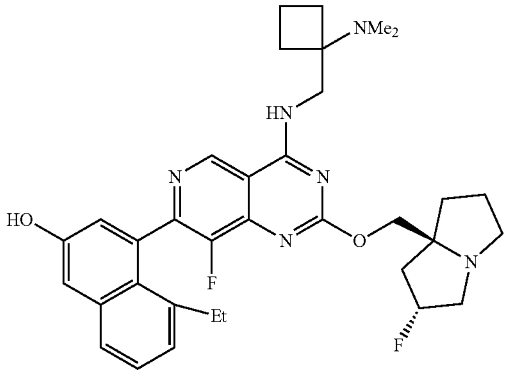

4-(4-(((1-(dimethylamino)cyclobutyl)methyl)amino)-8-fluoro-2-(((2R, 7aS)-2-fluorotetrahydro-1H-pyrrolizin-7a(5H)-yl)methoxy)pyrido[4,3-d]pyrimidin-7-yl)-5-ethylnaphthalen-2-ol

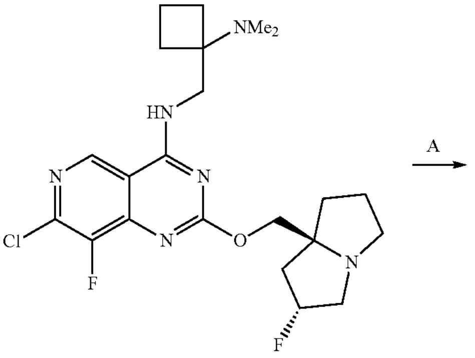

-continued

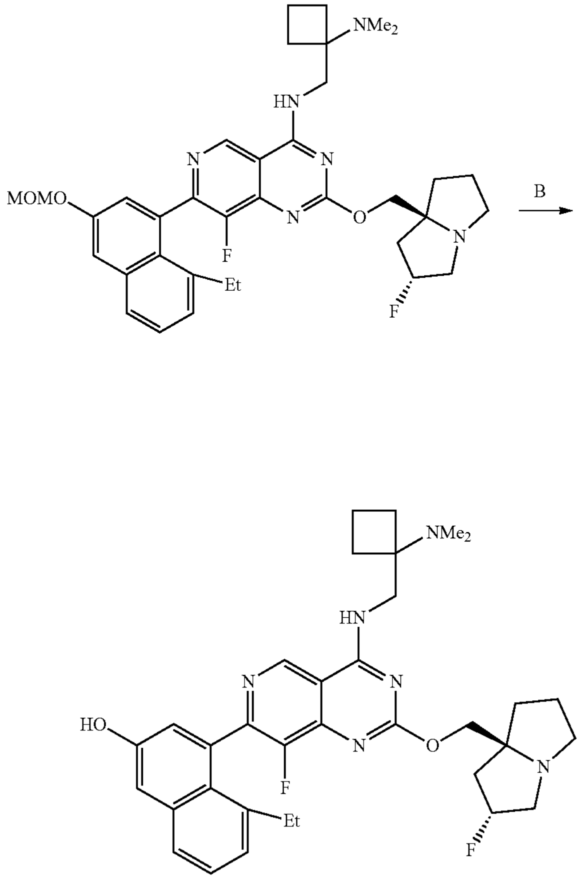

Step A. 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol. Synthesized according to Example 3, Step A substituting 2-(8-ethyl-3-(methoxymethoxy)naphthalen-1-yl)-4,4,5,5-tetramethyl-1,3,2-dioxaborolane in place of 4,4,5,5-tetramethyl-2-(8-(trifluoromethyl)naphthalen-1-yl)-1,3,2-dioxaborolane to afford N-((1-(dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (46 mg, 58%). LCMS (MM-ES+APCI, Pos): m/z 647.3 [M+H].

Step B. 4-(4-(((1-(dimethylamino)cyclobutyl)methyl)amino)-8-fluoro-2-(((2R,7aS)-2 fluorotetrahydro-1H-pyrrolizin-7a(5H)-yl)methoxy)pyrido[4,3-d]pyrimidin-7-yl)-5-ethylnaphthalen-2-ol dihydrochloride. To a solution of N-((1-(dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (46 mg, 0.07 mmol) in DCM (1.5 mL) was added a 4 N mixture of HCl in 1,4-dioxane (1.5 mL, 6.0 mmol). The suspension was stirred for 30 minutes at room temperature then condensed in vacuo to afford 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol dihydrochloride (22 mg, 45%). LCMS (MM-ES+APCI, Pos): m/z 603.3 [M+H].

Example 34

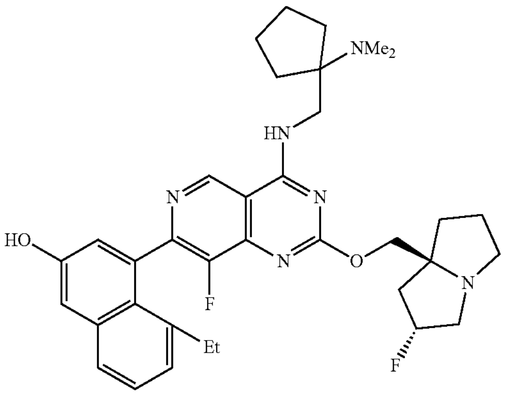

4-(4-(((1-(dimethylamino)cyclopentyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol

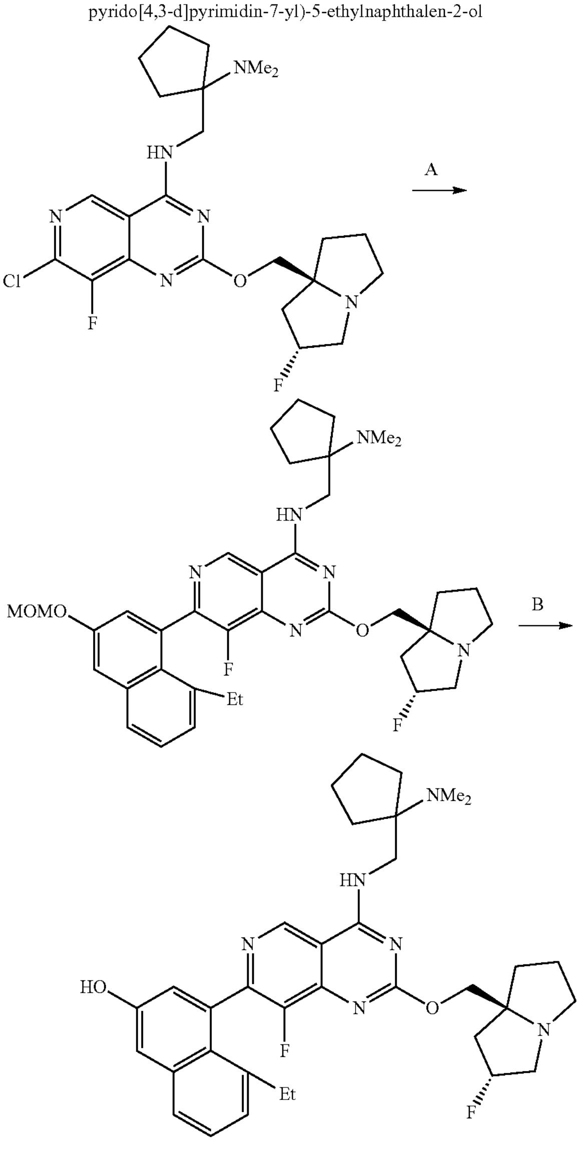

7-chloro-N-((1-(dimethylamino)cyclopentyl)methyl)-8-fluoro-2-(((2R,7aS)-2-fluorotetrahydro-1H-pyrrolizin-7a (5H)-yl)methoxy)pyrido[4,3-d]pyrimidin-4-amine. Synthesized according to Example 2, Step A-C substituting 1-(aminomethyl)-N,N-dimethylcyclopentan-1-amine for 1-(aminomethyl)-N,N-dimethylcyclobutan-1-amine in Step A. LCMS (MM-ES+APCI, Pos): m/z 481.0 [M+H].

Step A. N-((1-(dimethylamino)cyclopentyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine. Synthesized according to Example 3, Step A substituting 2-(8-ethyl-3-(methoxymethoxy)naphthalen-1-yl)-4,4,5,5-tetramethyl-1,3,2-dioxaborolane in place of 4,4,5,5-tetramethyl-2-(8-(trifluoromethyl)naphthalen-1-yl)-1,3,2-dioxaborolane and 7-chloro-N-((1-(dimethylamino)cyclopentyl)methyl)-8-fluoro-2-(((2R,7aS)-2-fluorotetrahydro-1H-pyrrolizin-7a(5H)-yl)methoxy)pyrido[4,3-d]pyrimidin-4-amine in place of 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine to afford N-((1-(dimethylamino)cyclopentyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (33 mg, 55%). LCMS (MM-ES+APCI, Pos): m/z 661.4 [M+H].

Step B. 4-(4-(((1-(dimethylamino)cyclopentyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol dihydrochloride. Synthesized according to Example 33, Step B substituting N-((1-(dimethylamino)cyclopentyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine in place of 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol to afford 4-(4-(((1-(dimethylamino)cyclopentyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol dihydrochloride (26 mg, 74%). LCMS (MM-ES+APCI, Pos): m/z 617.3 [M+H].

Example 35

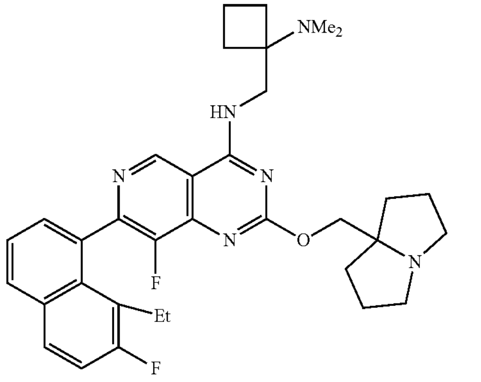

N-((1-(dimethylamino)cyclobutyl)methyl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-amine -continued

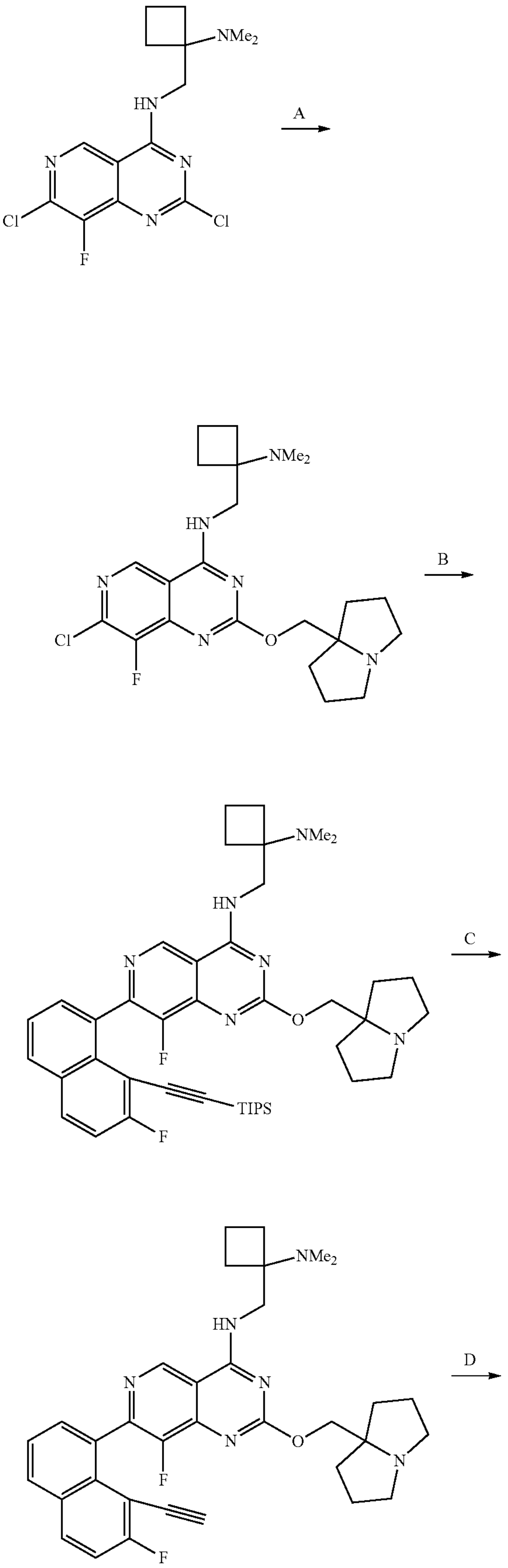

-continued

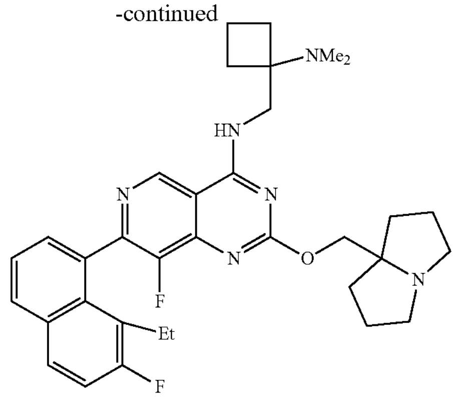

Step A. 7-chloro-N-((1-(dimethylamino)cyclobutyl)methyl)-8-fluoro-2-((tetrahydro-1H-pyrrolizin-7a(5H)-yl)methoxy)pyrido[4,3-d]pyrimidin-4-amine. Synthesized according to Example 1, Step C substituting (tetrahydro-1H-pyrrolizin-7a(5H)-yl)methanol in place of ((2S,7aR)-2-fluorotetrahydro-1H-pyrrolizin-7a(5H)-yl)methanol to afford 7-chloro-N-((1-(dimethylamino)cyclobutyl)methyl)-8-fluoro-2-((tetrahydro-1H-pyrrolizin-7a(5H)-yl)methoxy)pyrido[4,3-d]pyrimidin-4-amine (0.10 g, 38%). LCMS (MM-ES+APCI, Pos): m/z 448.9 [M+H].

Step B. N-((1-(dimethylamino)cyclobutyl)methyl)-8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-amine. Synthesized according to Example 3, Step A substituting ((2-fluoro-8-(4,4,5,5-tetramethyl-1,3,2-dioxaborolan-2-yl)naphthalen-1-yl)ethynyl)triisopropylsilane in place of 4,4,5,5-tetramethyl-2-(8-(trifluoromethyl)naphthalen-1-yl)-1,3,2-dioxaborolane to afford N-((1-(dimethylamino)cyclobutyl)methyl)-8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-amine (17 mg, 21%). LCMS (MM-ES+APCI, Pos): m/z 739.0 [M+H].

Step C. N-((1-(dimethylamino)cyclobutyl)methyl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-amine. N-((1-(dimethylamino)cyclobutyl)methyl)-8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-amine (17 mg, 0.02 mmol) was dissolved in THE (1 mL). A 1 N solution of tetrabutylammonium fluoride (0.12 mL, 0.12 mmol) was added and the solution was stirred at room temperature for 30 minutes. The reaction mixture was diluted with DCM and quenched by addition of water. The organics were washed with water, brine, dried over $MgSO_4$, filtered, and condensed to afford N-((1-(dimethylamino)cyclobutyl)methyl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-amine (13 mg, quantitative). LCMS (MM-ES+APCI, Pos): m/z 583.0 [M+H].

Step D. N-((1-(dimethylamino)cyclobutyl)methyl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-amine bis(2,2,2-trifluoroacetate). A solution of N-((1-(dimethylamino)cyclobutyl)methyl)-7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-amine (13 mg, 0.02 mmol) in methanol (1 mL) was degassed with argon and 10% $Pd(OH)_2$ on carbon (6 mg, 0.004 mmol) was added. After purged with hydrogen, the mixture was stirred at room temperature for 1 hour. The suspension was filtered through Celite and concentrated. The residue was purified by prep HPLC (5-95% $MeCN/H_2O$ with 0.1% TFA as modifier) and lyophilized to afford N-((1-(dimethylamino)cyclobutyl)methyl)-7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-amine bis(2,2,2-trifluoroacetate) (4 mg, 25%). LCMS (MM-ES+APCI, Pos): m/z 587.3 [M+H].

Example 36

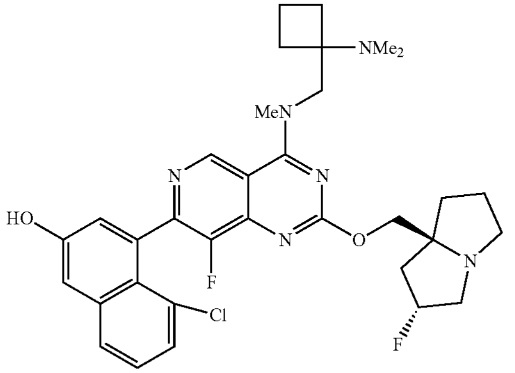

5-chloro-4-(4-(((1-(dimethylamino)cyclobutyl)methyl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol

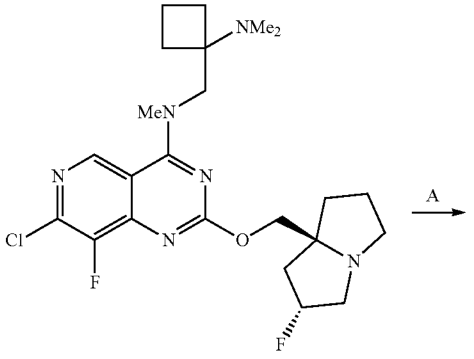

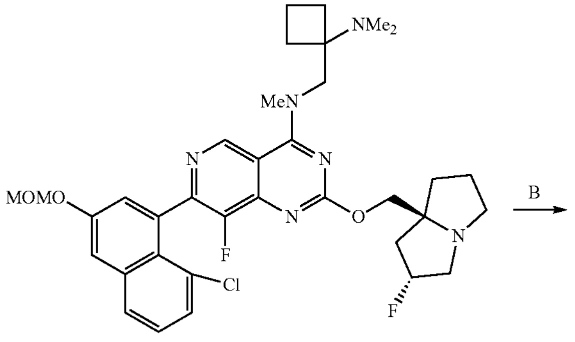

-continued

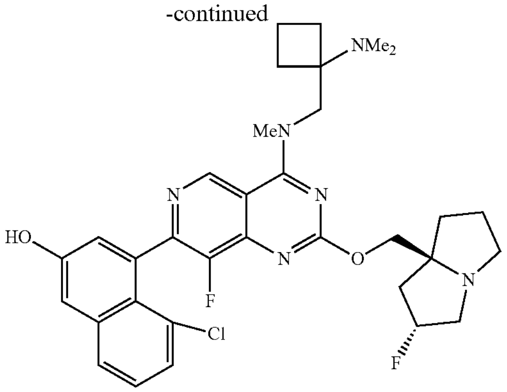

Step A. 7-(8-chloro-3-(methoxymethoxy)naphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)-N-methylpyrido[4,3-d]pyrimidin-4-amine. 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)-N-methylpyrido[4,3-d]pyrimidin-4-amine (50 mg, 0.1 mmol), (8-chloro-3-(methoxymethoxy)naphthalen-1-yl)trimethylstannane (60 mg, 0.16 mmol), 2,2'-bis(diphenylphosphino)-1,1'-binaphthyl (13 mg, 0.02 mmol), copper(I) iodide (5.9 mg, 0.03 mmol), and dichloro[1,1'-bis(diphenylphosphino)ferrocene]palladium dichloromethane adduct (8.5 mg, 0.01 mmol) were suspended in toluene (4 mL). The suspension was degassed with argon and heated to 90° C. for 20 hours. The mixture was filtered through Celite and concentrated. The residue was purified by prep HPLC (5-95% MeCN/$H_2O$ with 0.1% TFA as modifier). The organic phase was partitioned between DCM and saturated aqueous $NaHCO_3$. The organic layer was dried over magnesium sulfate and concentrated to afforded 7-(8-chloro-3-(methoxymethoxy)naphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)-N-methylpyrido[4,3-d]pyrimidin-4-amine (18 mg, 26%). LCMS (MM-ES+APCI, Pos): m/z 667.3 [M+H].

Step B. 5-chloro-4-(4-(((1-(dimethylamino)cyclobutyl)methyl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol. Synthesized according to Example 33, Step B substituting 7-(8-chloro-3-(methoxymethoxy)naphthalen-1-yl)-N-((1-(dimethylamino)cyclobutyl)methyl)-8-fluoro-2-(((2R,7aS)-2-fluorotetrahydro-1H-pyrrolizin-7a(5H)-yl)methoxy)-N-methylpyrido[4,3-d]pyrimidin-4-amine in place of to afford 5-chloro-4-(4-(((1-(dimethylamino)cyclobutyl)methyl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol dihydrochloride (19 mg, 99%). LCMS (MM-ES+APCI, Pos): m/z 623 [M+H].

Example 37

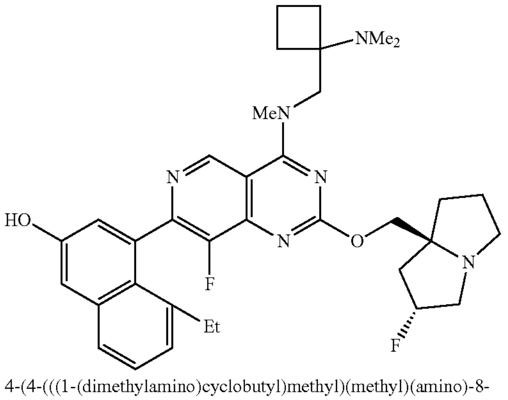

4-(4-(((1-(dimethylamino)cyclobutyl)methyl)(methyl)(amino)-8-fluoro-2-(((2R, 7aS)-2-fluorotetrahydro-1H-pyrrolizin-7a(5H)-yl)methoxy)pyrido[4,3-d]pyrimidin-7-yl)-5-ethylnaphthalen-2-ol

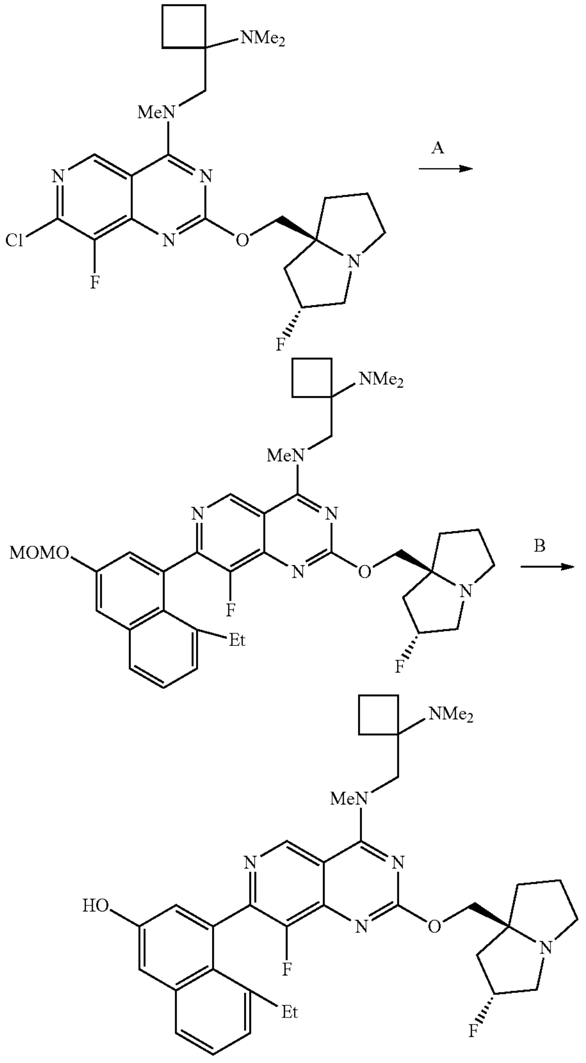

Step A. N-(((dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine. Synthesized according to Example 3, Step A substituting 2-(8-ethyl-3-(methoxymethoxy)naphthalen-1-yl)-4,4,5,5-tetramethyl-1,3,2-dioxaborolane in place of 4,4,5,5-tetramethyl-2-(8-(trifluoromethyl)naphthalen-1-yl)-1,3,2-dioxaborolane to afford N-((1-(dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (30 mg, 42%). LCMS (MM-ES+APCI, Pos): m/z 661.4 [M+H].

Step B. 4-(4-(((1-(dimethylamino)cyclobutyl)methyl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol dihydrochloride. Synthesized according to Example 33, Step B substituting N-((1-(dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine in place of N-((1-(dimethylamino)cyclobutyl)methyl)-7-(8-ethyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine to afford 4-(4-(((1-(dimethylamino)cyclobutyl)methyl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethylnaphthalen-2-ol dihydrochloride (14 mg, 44%). LCMS (MM-ES+APCI, Pos): m/z 617.3 [M+H].

Example 38

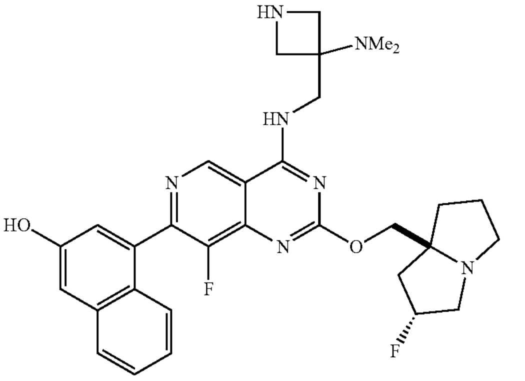

3-(((8-fluoro-2-(((2R, 7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)azetidin-3-ol (racemic, trans)

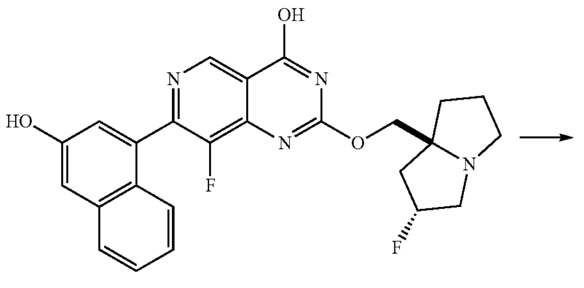

-continued

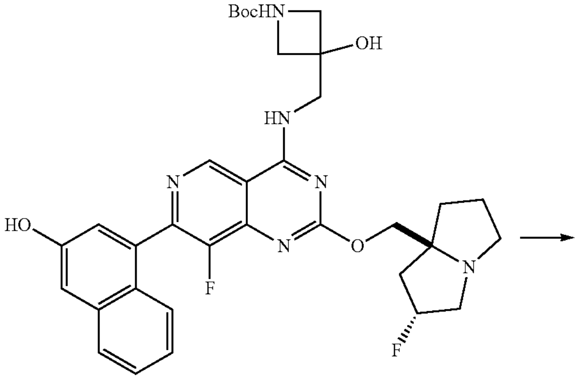

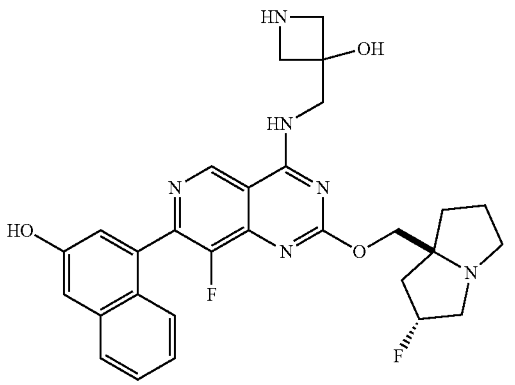

Step A. Tert-butyl 3-(((8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-hydroxyazetidine-1-carboxylate. Synthesized according to Example 41, substituting tert-butyl 3-(aminomethyl)-3-hydroxyazetidine-1-carboxylate in place of 4-(aminomethyl)-N,N-dimethyltetrahydro-2H-pyran-4-amine to afford tert-butyl 3-(((8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-hydroxyazetidine-1-carboxylate (11 mg, 16%). LCMS (MM-ES+APCI, Pos): m/z 649.3 [M+H].

Step B. 3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)azetidin-3-ol bis(2,2,2-trifluoroacetate). To a solution of tert-butyl 3-(((8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)-3-hydroxyazetidine-1-carboxylate (11 mg, 0.02 mmol) in DCM (1 mL) was added a 4 N solution of HCl in 1,4-dioxane (1 mL). The suspension was stirred for 30 minutes at room temperature and concentration in vacuo. The residue was purified by prep HPLC (5-50% MeCN/$H_2O$/0.1% TFA in 15 minutes) and lyophilized to afford 3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)amino)methyl)azetidin-3-ol bis(2,2,2-trifluoroacetate) (5 mg, 45%). LCMS (MM-ES+APCI, Pos): m/z 549.0 [M+H].

Example 39

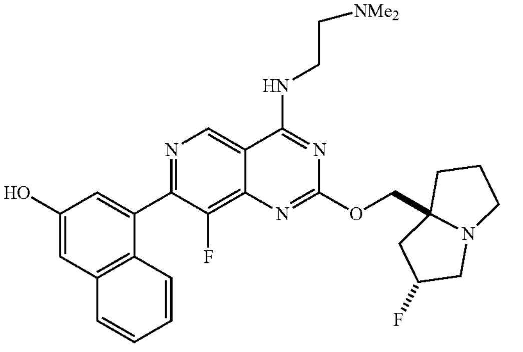

4-(4-((2-(dimethylamino)ethyl)amino)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol (racemic, trans)

Synthesized according to Example 41, substituting N,N-dimethylethylenediamine in place of 4-(aminomethyl)-N,N-dimethyltetrahydro-2H-pyran-4-amine to afford 4-(4-((2-(dimethylamino)ethyl)amino)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate) (20 mg, 49%). LCMS (MM-ES+APCI, Pos): m/z 535.3 [M+H].

Example 40

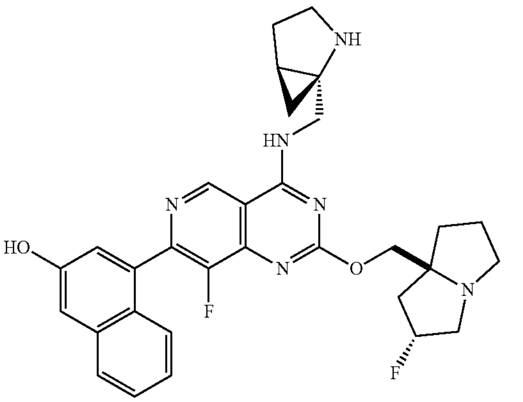

4-(4-((((1S, 5R)-2-azabicyclo[3.1.0]hexan-1-yl)methyl)amino)-8-fluoro-2-(((2R, 7aS)-2-fluorotetrahydro-1H-pyrrolizin-7a(5H)-yl)methoxy)pyrido[4,3-d]pyrimidin-7-yl)naphthalen-2-ol -continued

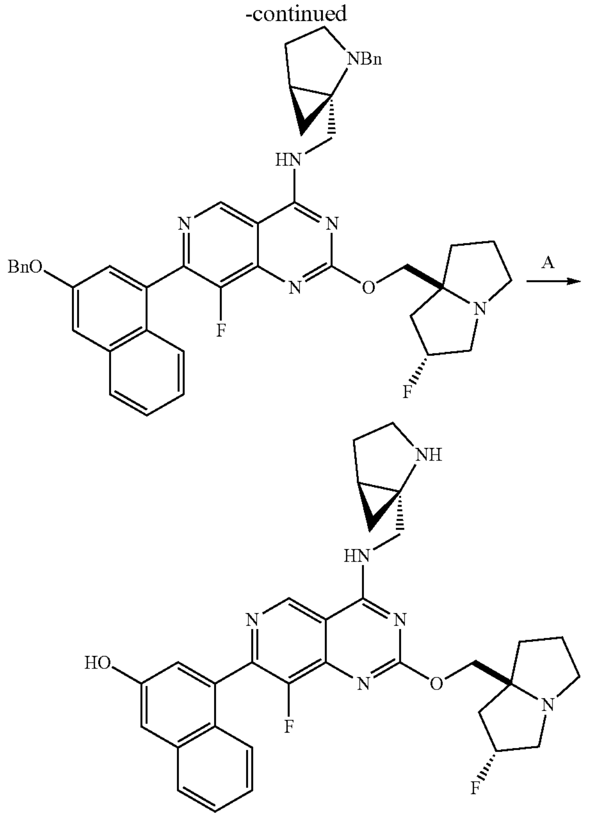

N-(((1S,5R)-2-benzyl-2-azabicyclo[3.1.0]hexan-1-yl)methyl)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine. Synthesized according to Example 1, Step B-D substituting ((1S,5R)-2-benzyl-2-azabicyclo[3.1.0]hexan-1-yl)methanamine dihydrochloride in place of 1-(aminomethyl)-N,N-dimethylcyclobutan-1-amine to afford N-(((1S,5R)-2-benzyl-2-azabicyclo[3.1.0]hexan-1-yl)methyl)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (15 mg, 22%). LCMS (MM-ES+APCI, Pos): m/z 738.9 [M+H].

Step A. 4-(4-((((1S,5R)-2-azabicyclo[3.1.0]hexan-1-yl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate). A solution of N-(((1S,5R)-2-benzyl-2-azabicyclo[3.1.0]hexan-1-yl)methyl)-7-(3-(benzyloxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (15 mg, 0.02 mmol) in methanol (1 mL) was degassed with argon, followed by addition of 10% $Pd(OH)_2$ on Carbon (5.7 mg, 0.004 mmol). After purged with hydrogen, the suspension was stirred at room temperature for 1 hour. The mixture was filtered through Celite and condensed. The residue was purified by prep HPLC (5-95% $MeCN/H_2O$ with 0.1% TFA as modifier) and then lyophilized to afford 4-(4-((((1S,5R)-2-azabicyclo[3.1.0]hexan-1-yl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis (2,2,2-trifluoroacetate) (5 mg, 37%). LCMS (MM-ES+APCI, Pos): m/z 559.3 [M+H].

Example 41

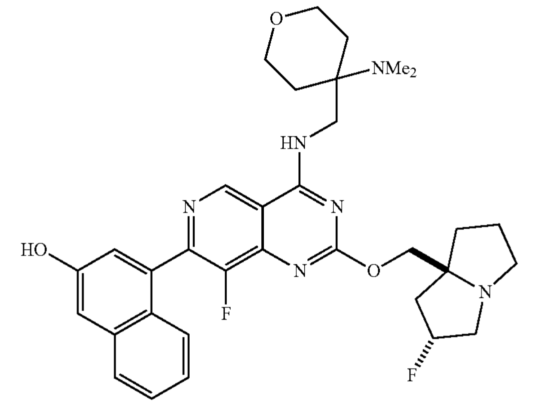

4-(4-(((4-(dimethylamino)tetrahydro-2H-pyran-4-yl)methyl)amino)-8-fluoro-2-(((2R, 7aS)-2-fluorotetrahydro-1H-pyrrolizin-7a(5H)-yl)methoxy)pyrido[4,3-d]pyrimidin-7-yl)naphthalen-2-ol (racemic,trans)

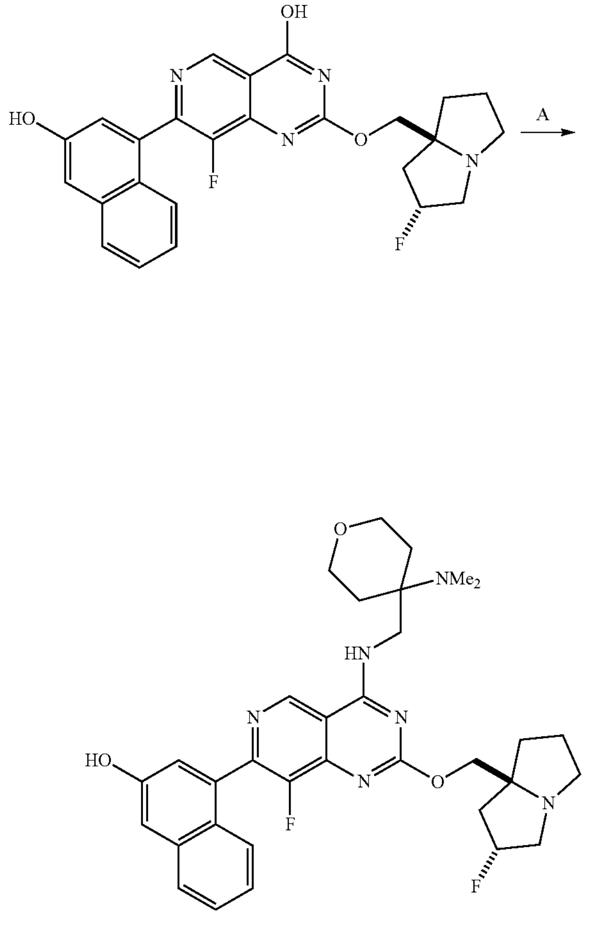

Step A. 4-(4-(((4-(dimethylamino)tetrahydro-2H-pyran-4-yl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol. To a solution of 8-fluoro-2-(((2S,7aR)-2-fluorotetrahydro-1H-pyrrolizin-7a(5H)-yl)methoxy)-7-(3-hydroxynaphthalen-1-yl)pyrido[4,3-d]pyrimidin-4-ol (30 mg, 0.07 mmol) in N,N-dimethylacetamide (1 mL) were added N,N-diisopropylethylamine (80 μL, 0.45 mmol) and 2-(3H-[1,2,3]triazolo[4,5-b]pyridin-3-yl)-1,1,3,3-tetramethylisouronium hexafluorophosphate (98 mg, 0.26 mmol). After stirring at room temperature for 15 minutes, 4-(aminomethyl)-N,N-dimethyltetrahydro-2H-pyran-4-amine (31 mg, 0.19 mmol) was added and the reaction stirred 2 hours. The reaction was diluted with saturated aqueous $NaHCO_3$ and the suspension was stirred for 3 hours. The mixture was partitioned between water and EtOAc, the layers were separated and the aqueous was washed 3× with EtOAc. The combined organics were dried over sodium sulfate, filtered, and concentrated. The residue was purified by prep HPLC (5-95% $MeCN/H_2O$ with 0.1% TFA as modifier). Lyophilization afforded 4-(4-(((4-(dimethylamino)tetrahydro-2H-pyran-4-yl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate) (15 mg, 32%). LCMS (MM-ES+APCI, Pos): m/z 604.9 [M+H].

Example 42

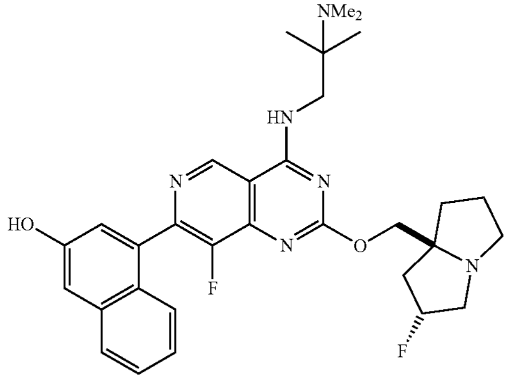

4-(4-((2-(dimethylamino)-2-methylpropyl)amino)-8-fluoro-2-(((2R, 7aS)-2-fluorotetrahydro-1H-pyrrolizin-7a(5H)-yl)methoxy)pyrido[4,3-d]pyrimidin-7-yl)naphthalen-2-ol (trans racemic)

Synthesized according to Example 41, substituting (1-amino-2-methylpropan-2-yl)dimethylamine in place of 4-(aminomethyl)-N,N-dimethyltetrahydro-2H-pyran-4-amine to afford 4-(4-((2-(dimethylamino)-2-methylpropyl)amino)-8-fluoro-2-(((2S,7aR)-2-fluorotetrahydro-1H-pyrrolizin-7a(5H)-yl)methoxy)pyrido[4,3-d]pyrimidin-7-yl)naphthalen-2-ol bis(2,2,2-trifluoroacetate) (16 mg, 37%). LCMS (MM-ES+APCI, Pos): m/z 563 [M+H].

Example 43
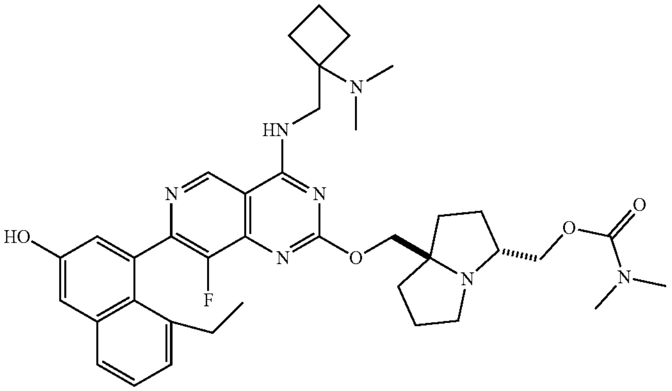
((3R, 7aR)-7a-(((4-(((1-(dimethylamino)cyclobutyl)methyl)amino)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate (racemic trans)
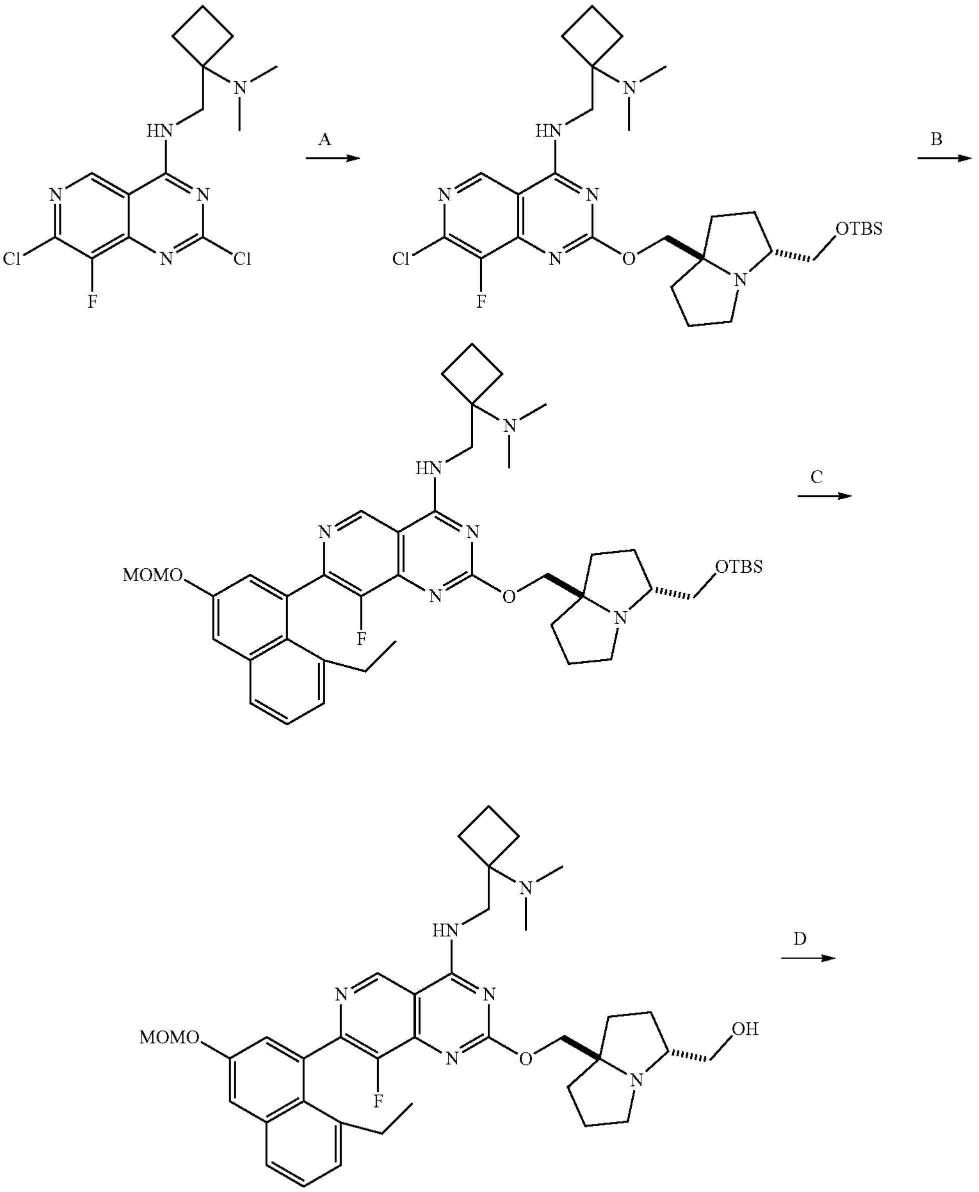

-continued

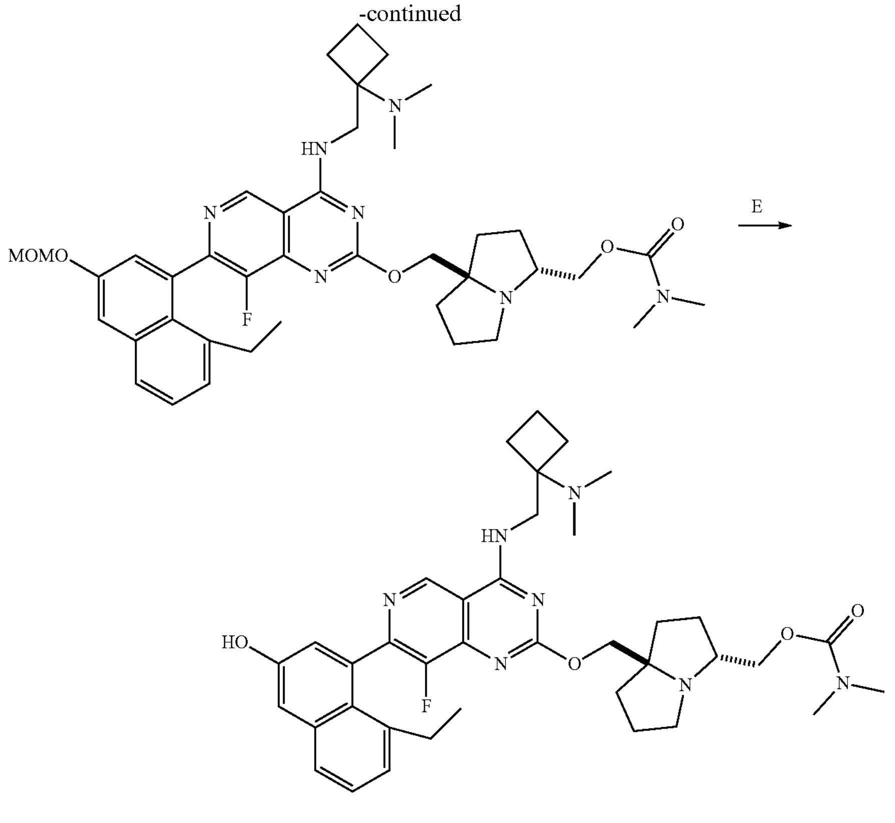

Step A. 2-(((3R,7aR)-3-(((tert-butyldimethylsilyl)oxy)methyl)tetrahydro-1H-pyrrolizin-7a(5H)-yl)methoxy)-7-chloro-N-((1-(dimethylamino)cyclobutyl)methyl)-8-fluoropyrido[4,3-d]pyrimidin-4-amine. To a solution of 2,7-dichloro-N-((1-(dimethylamino)cyclobutyl)methyl)-8-fluoropyrido[4,3-d]pyrimidin-4-amine (83 mg, 0.24 mmol, synthesized according to Example 1, Step A-B) and ((3R,7aR)-3-(((tert-butyldimethylsilyl)oxy)methyl)tetrahydro-1H-pyrrolizin-7a(5H)-yl)methanol (60 mg, 0.21 mmol) in THE (2 mL) at 0° C. was added sodium hydride (25 mg, 0.63 mmol). The mixture was warmed to ambient temperature and stirred for 16 hours. The mixture was partitioned between sat. $NH_4Cl$ (20 mL) and EtOAc (20 mL). The aqueous layer was extracted with EtOAc (2×10 mL) and the combined organic phases were washed with brine (10 mL), dried over $Na_2SO_4$, filtered and concentrated in vacuo. The residue was purified by silica column chromatography eluting with 0→20% MeOH/DCM to afford 2-(((3R,7aR)-3-(((tert-butyldimethylsilyl)oxy)methyl)tetrahydro-1H-pyrrolizin-7a(5H)-yl)methoxy)-7-chloro-N-((1-(dimethylamino)cyclobutyl)methyl)-8-fluoropyrido[4,3-d]pyrimidin-4-amine (69 mg, 55% yield). LCMS (MM-ES+APCI, Pos): m/z 594.3 [M+H].

Step B. 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-7-(8-ethyl-3-(methoxymethoxy)naphthalen-1-yl)-8-fluoropyrido[4,3-d]pyrimidin-4-amine. 2-(8-ethyl-3-(methoxymethoxy)naphthalen-1-yl)-4,4,5,5-tetramethyl-1,3,2-dioxaborolane (95 mg, 0.28 mmol), 2-(((3R,7aR)-3-(((tert-butyldimethylsilyl)oxy)methyl)tetrahydro-1H-pyrrolizin-7a(5H)-yl)methoxy)-7-chloro-N-((1-(dimethylamino)cyclobutyl)methyl)-8-fluoropyrido[4,3-d]pyrimidin-4-amine (0.14 g, 0.23 mmol), and Mesylate[(di(1-adamantyl)-n-butylphosphine)-2-(2'-amino-1,1'-biphenyl)]palladium(II) (34 mg, 0.046 mmol) were suspended in Phosphoric acid, potassium salt (0.70 mL, 0.70 mmol) and THE (2 mL). After degassing with argon, the mixture was heated to 60° C. for 16 hours. The cooled mixture was partitioned between water (10 mL) and EtOAc (10 mL). The layers were separated, and the aqueous layer was extracted with EtOAc (2×5 mL). The combined organic phases were washed with brine (10 mL), dried over $Na_2SO_4$, filtered and concentrated in vacuo. The residue was purified by silica column chromatography eluting with 0-20% MeOH/DCM+0.1% $NH_4OH$ as modifier to afford 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-7-(8-ethyl-3-(methoxymethoxy)naphthalen-1-yl)-8-fluoropyrido[4,3-d]pyrimidin-4-amine (0.17 g, 92% yield). LCMS (MM-ES+APCI, Pos): m/z 774.4 [M+H].

Step C. ((3R,7aR)-7a-(((4-(((1-(dimethylamino)cyclobutyl)methyl)amino)-7-(8-ethyl-3-(methoxymethoxy)naphthalen-1-yl)-8-fluoropyrido[4,3-d]pyrimidin-2-yl)oxy)methyl)hexahydro-1H-pyrrolizin-3-yl)methanol. To a solution of 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-7-(8-ethyl-3-(methoxymethoxy)naphthalen-1-yl)-8-fluoropyrido[4,3-d]pyrimidin-4-amine (0.17 g, 0.21 mmol) in THE (5 mL) was added TBAF (0.64 mL, 0.64 mmol). The mixture was stirred at ambient temperature for 1 hour then partitioned between sat. $NaHCO_3$ (10 mL) and EtOAc (10 mL). The aqueous layer was extracted with EtOAc (2×5 mL) and the combined organic phases were washed with brine (10 mL), dried over $Na_2SO_4$, filtered and concentrated to afford ((3R,7aR)-7a-(((4-(((1-(dimethylamino)cyclobutyl)methyl)amino)-7-(8-ethyl-3-(methoxymethoxy)naphthalen-1-yl)-8-fluoropyrido

[4,3-d]pyrimidin-2-yl)oxy)methyl)hexahydro-1H-pyrrolizin-3-yl)methanol which was used in the next reaction. LCMS (MM-ES+APCI, Pos): m/z 659.3 [M+H].

Step D. ((3R,7aR)-7a-(((4-(((1-(dimethylamino)cyclobutyl)methyl)amino)-7-(8-ethyl-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate. To a solution of ((3R,7aR)-7a-(((4-(((1-(dimethylamino)cyclobutyl)methyl)amino)-7-(8-ethyl-3-(methoxymethoxy)naphthalen-1-yl)-8-fluoropyrido[4,3-d]pyrimidin-2-yl)oxy)methyl)hexahydro-1H-pyrrolizin-3-yl)methanol (70 mg, 0.05 mmol) in THE (2 mL) was added triethylamine (44 μL, 0.3 mmol) followed by p-nitrophenylchloroformate (22 mg, 0.11 mmol). The mixture was stirred for 30 min then dimethylamine (0.53 mL, 1.1 mmol) was added. The mixture was partitioned between sat. $NaHCO_3$ (10 mL) and EtOAc (10 mL). The layers was separated and the aqueous layer was extracted with EtOAc (2×5 mL). The combined organic phases were washed with brine (5 mL), dried over $Na_2SO_4$, filtered and concentrated in vacuo. The residue was purified by silica column chromatography eluting with 0-20% MeOH/DCM+0.1% $NH_4OH$ to afford ((3R,7aR)-7a-(((4-(((1-(dimethylamino)cyclobutyl)methyl)amino)-7-(8-ethyl-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate (26 mg, 34% yield). LCMS (MM-ES+APCI, Pos): m/z 730.4 [M+H].

Step E. ((3R,7aR)-7a-(((4-(((1-(dimethylamino)cyclobutyl)methyl)amino)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate. To a solution of ((3R,7aR)-7a-(((4-(((1-(dimethylamino)cyclobutyl)methyl)amino)-7-(8-ethyl-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate (26 mg, 0.04 mmol) in DCM (1 mL) was added 4N HCl/dioxane (1 mL). The mixture was stirred at ambient temperature for 1 hour then concentrated in vacuo. The residue was purified by prep HPLC (Gilson, 5-95% ACN/water+0.1% TFA as modifier) and lyophilized to afford the product as the TFA salt (17 mg, 52% yield). LCMS (MM-ES+APCI, Pos): m/z 686.4 [M+H].

Example 44

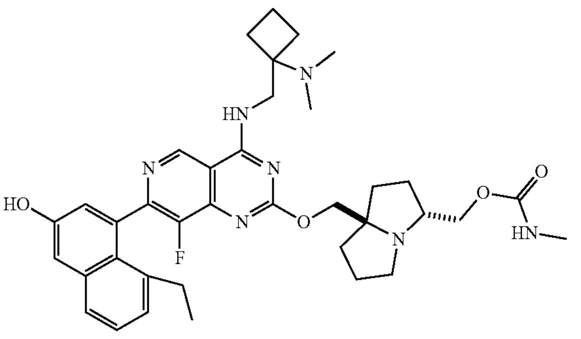

((3R, 7aR)-7a-(((4-(((1-(dimethylamino)cyclobutyl)methyl)amino)-7-(8-ethyl-3-hydroxynaphthalen-1-yl)-8-fluoropyrido[4,3-d]pyrimidin-2-yl)oxy)methyl)hexahydro-1H-pyrrolizin-3-yl)methyl methylcarbamate (racemic trans)

Synthesized according to Example 43, substituting methylamine in place of dimethylamine in Step D to give product as the TFA salt. LCMS (MM-ES+APCI, Pos): m/z 672.4 [M+H].

Example 45

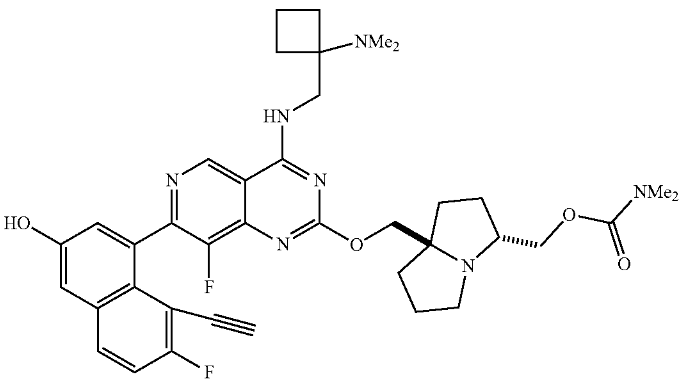

((3R, 7aR)-7a-(((4-(((1-(dimethylamino)cyclobutyl)methyl)amino)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate (racemic trans)

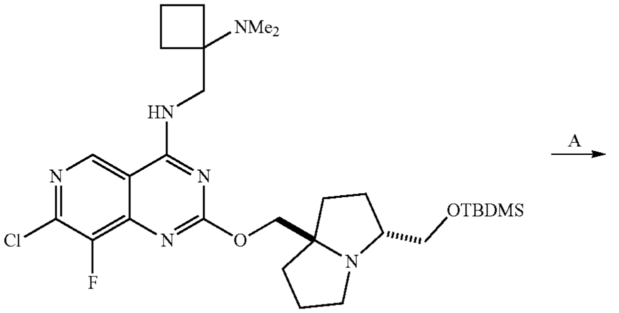

-continued

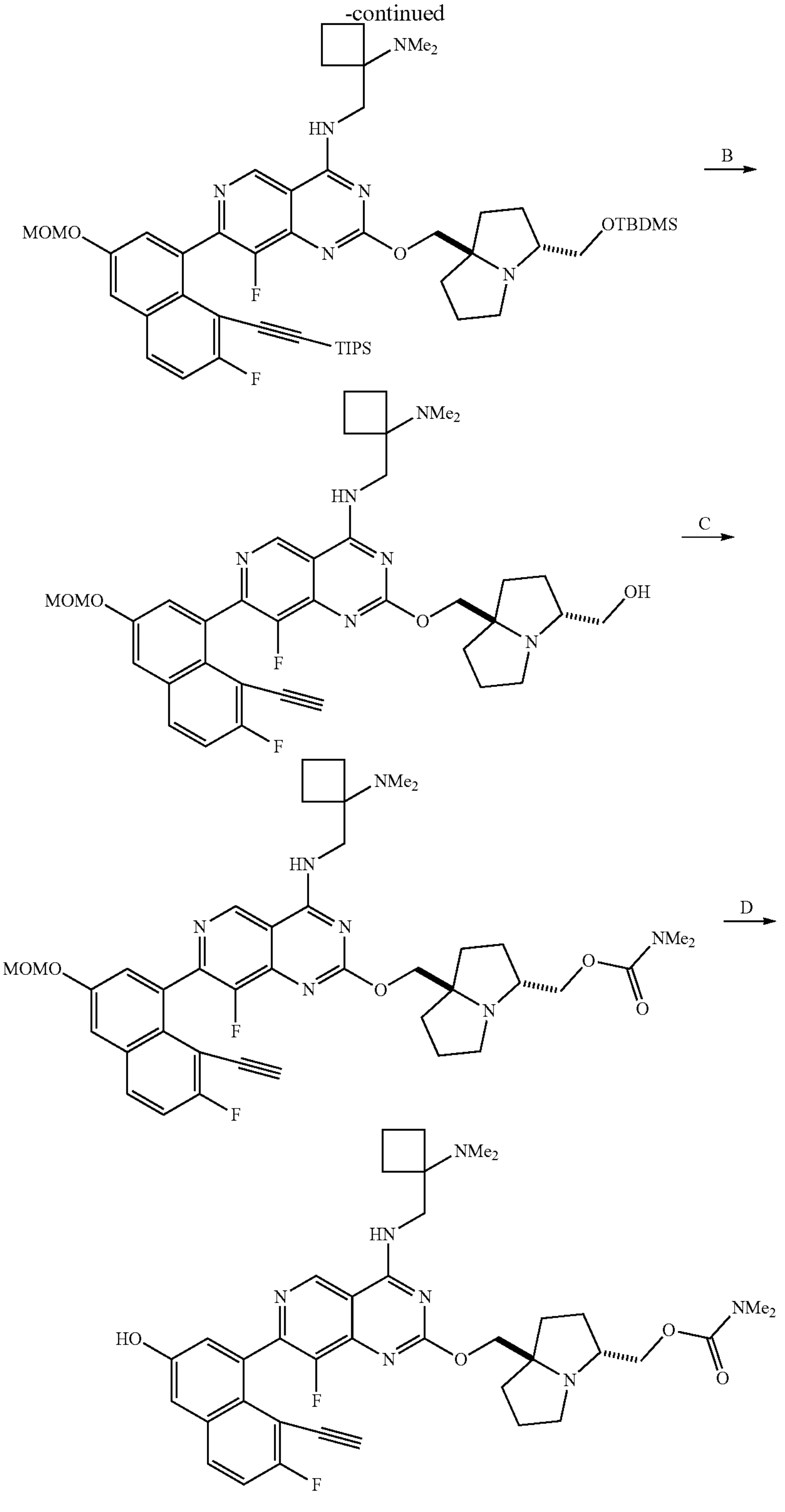

Step A. 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-8-fluoro-7-(7-fluoro-3-(methoxymethoxy)-8-((triisopropylsilyl)ethynyl)naphthalen-1-yl)pyrido[4,3-d]pyrimidin-4-amine. 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-8-fluoro-7-(7-fluoro-3-(methoxymethoxy)-8-((triisopropylsilyl)ethynyl)naphthalen-1-yl)pyrido[4,3-d]pyrimidin-4-amine (0.14 g, 0.24 mmol), ((2-fluoro-6-(methoxymethoxy)-8-(4,4,5,5-tetramethyl-1,3,2-dioxaborolan-2-yl)naphthalen-1-yl)ethynyl)triisopropylsilane (0.15 g, 0.29 mmol), and mesylate[(di(1-adamantyl)-n-butylphosphine)-2-(2'-amino-1,1'- biphenyl)]palladium(II) (35 mg, 0.049 mmol) were suspended in THE (3.0 mL). A 1 N aqueous solution of $K_3PO_4$ (0.73 mL, 0.73 mmol) was added, and the mixture was degassed with argon. After heated to 60° C. for 16 hours, the mixture was cooled and diluted with EtOAc. The organics were washed with water, and the aqueous was further washed with EtOAc. The combined organics were dried over $Na_2SO_4$ and condensed in vacuo. The residue was purified by flash chromatography eluting with 0-100% (20% MeOH/DCM)/DCM to afford 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-8-fluoro-7-(7-fluoro-3-(methoxymethoxy)-8-((triisopropylsilyl)ethynyl)naphthalen-1-yl)pyrido[4,3-d]pyrimidin-4-amine (0.15 g, 67%). LCMS (MM-ES+APCI, Pos): m/z 944.5 (M+H).

Step B. ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol. 2-(((3R,7aR)-3-(((tert-butyldimethylsilyl)oxy)methyl)tetrahydro-1H-pyrrolizin-7a(5H)-yl)methoxy)-N-((1-(dimethylamino)cyclobutyl)methyl)-8-fluoro-7-(7-fluoro-3-(methoxymethoxy)-8-((triisopropylsilyl)ethynyl)naphthalen-1-yl)pyrido[4,3-d]pyrimidin-4-amine (0.15 g, 0.16 mmol) was dissolved in THE (3 mL) and a 1 N THE solution of tetra-n-butylammonium fluoride (0.49 mL, 0.49 mmol) was added. After stirred at room temperature for 30 minutes, the mixture was condensed in vacuo and the residue suspended in DCM. The organics were washed with saturated aqueous $NaHCO_3$ followed by saturated aqueous NaCl. The organics were dried over $Na_2SO_4$ and concentrated in vacuo to afford ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol (0.11 g, 100%). LCMS (MM-ES+APCI, Pos): m/z 673.3 (M+H).

Step C. ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate. ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol (65 mg, 0.097 mmol) was dissolved in THE (1.5 mL), and triethylamine (0.13 mL, 0.97 mmol) was added. After stirred for 5 minutes at room temperature, 4-nitrophenyl chloroformate (29 mg, 0.14 mmol) was added. The suspension was stirred for 1 hour, and then a 2 N THE solution of dimethylamine (0.48 mL, 0.96 mmol) was added. The mixture was stirred for 1 hour and condensed in vacuo. The residue was purified by prep HPLC eluting with 5-95% $MeCN/H_2O$ with 0.1% TFA as modifier. The fractions containing product were partitioned between DCM and saturated aqueous $NaHCO_3$, and the aqueous was washed twice with DCM. The combined organics were dried over $Na_2SO_4$ and condensed in vacuo to afford ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate (33 mg, 46%). LCMS (MM-ES+APCI, Pos): m/z 744.3 (M+H).

Step D. ((3R,7aR)-7a-(((4-(((1-(dimethylamino)cyclobutyl)methyl)amino)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate. ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate (33 mg, 0.044 mmol) was dissolved in DCM (1.0 mL). A 4 N dioxane solution of HCl (1.0 mL, 4.0 mmol) was added and the mixture was stirred at room temperature for 30 minutes before condensing in vacuo. The residue was purified by prep HPLC eluting with 5-50% $MeCN/H_2O$ with 0.1% TFA as modifier. Fractions containing product were pooled and lyophilized to afford ((3R,7aR)-7a-(((4-(((1-(dimethylamino)cyclobutyl)methyl)amino)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (17 mg, 41%). LCMS (MM-ES+APCI, Pos): m/z 700.3 (M+H).

Example 46

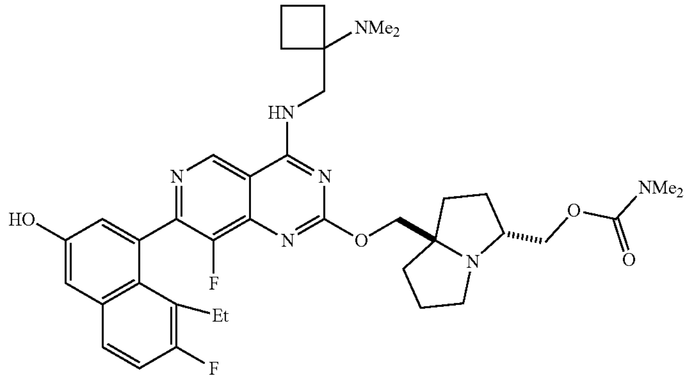

((3R, 7aR)-7a-(((4-(((1-(dimethylamino)cyclobutyl)methyl)amino)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate -continued

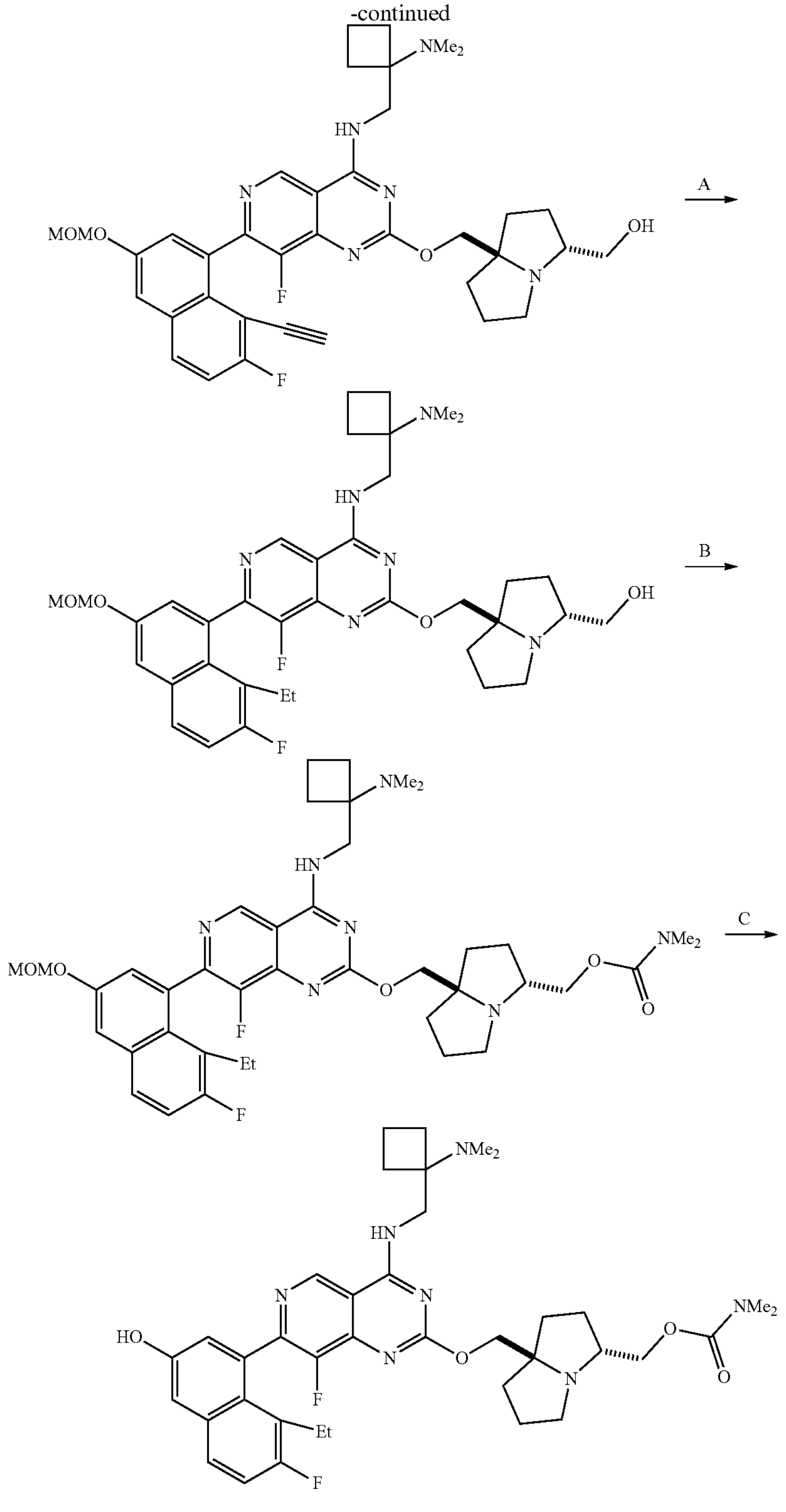

Step A. ((3R,7aR)-7a-(((4-(((1-(dimethylamino)cyclobutyl)methyl)amino)-7-(8-ethyl-7-fluoro-3-(metho xymethoxy)naphthalen-1-yl)-8-fluoropyrido[4,3-d]pyrimidin-2-yl)oxy)methyl)hexahydro-1H-pyrrolizin-3-yl)methanol. ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol (65 mg, 0.097 mmol) was dissolved in methanol (3.0 mL). The mixture was degassed with argon, and 10% $Pd(OH)_2/C$ (14 mg, 0.0097 mmol) was added. The suspension was purged with a hydrogen balloon and stirred under hydrogen atmosphere for 2 hours at room temperature. The mixture was filtered through Celite and condensed in vacuo to afford ((3R,7aR)-7a-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol (65 mg, quantitative). LCMS (MM-ES+APCI, Pos): m/z 677.3 (M+H).

Step B. ((3R,7aR)-7a-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate. Synthesized according to Example 45, Step C substituting ((3R,7aR)-7a-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol in place of ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methanol to afford ((3R,7aR)-7a-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate (24 mg, 33%). LCMS (MM-ES+APCI, Pos): m/z 748.3 (M+H).

Step C. ((3R,7aR)-7a-(((4-(((1-(dimethylamino)cyclobutyl)methyl)amino)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate. Synthesized according to Example 45, Step D substituting ((3R,7aR)-7a-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate in place of ((3R,7aR)-7a-(((4-(((1-(dimethylamino)cyclobutyl)methyl)amino)-7-(8-ethynyl-7-fluoro-3-(methoxymethoxy)naphthalen-1-yl)-8-fluoropyrido[4,3-d]pyrimidin-2-yl)oxy)methyl)hexahydro-1H-pyrrolizin-3-yl)methyl dimethylcarbamate to afford ((3R,7aR)-7a-(((4-(((1-(dimethylamino)cyclobutyl)methyl)amino)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl dimethylcarbamate as the TFA salt (18 mg, 44%). LCMS (MM-ES+APCI, Pos): m/z 704.4 (M+H).

Example 47

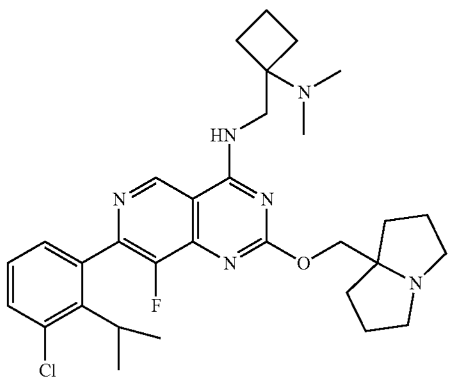

7-(3-chloro-2-isopropylphenyl)-N-((1-(dimethylamino)cyclobutyl)methyl)-8-fluoro-2-((tetrahydro-1H-pyrrolizin-7a(5H)-yl)methoxy)pyrido[4,3-d]pyrimidin-4-amine Synthesized according to Example 1, Steps A-D substituting (tetrahydro-1H-pyrrolizin-7a(5H)-yl)methanol in place of ((2S,7aR)-2-fluorotetrahydro-1H-pyrrolizin-7a(5H)-yl)methanol in Step C and substituting 2-(3-chloro-2-isopropylphenyl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step D to afford 7-(3-chloro-2-isopropylphenyl)-N-((1-(dimethylamino)cyclobutyl)methyl)-8-fluoro-2-((tetrahydro-1H-pyrrolizin-7a(5H)-yl)methoxy)pyrido[4,3-d]pyrimidin-4-amine as the TFA salt (4.1 mg, 0.005 mmol, 7% yield). LCMS (MM-ES+APCI, Pos): m/z 567.3 (M+H).

Example 48

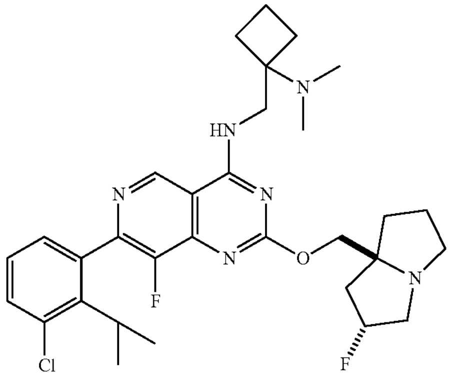

7-(3-chloro-2-isopropylphenyl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (racemic, trans)

Synthesized according to Example 1, Steps A-D substituting 2-(3-chloro-2-isopropylphenyl)-4,4,5,5-tetramethyl-1,3,2-dioxaborolane in place of 2-(3-(benzyloxy)naphthalen-1-yl)-4,4,5,5-tetramethyl-1,3,2-dioxaborolane in Step D to afford 7-(3-chloro-2-isopropylphenyl)-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine as the TFA salt (35 mg, 0.043 mmol, 67% yield). LCMS (MM-ES+APCI, Pos): m/z 585.3 (M+H).

Example 49

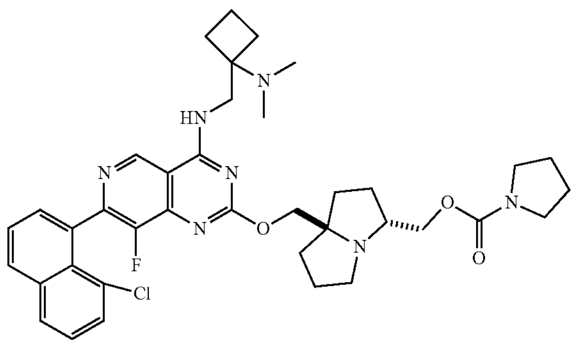

((3R, 7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl-pyrrolidine-1-carboxylate (racemic trans)

-continued

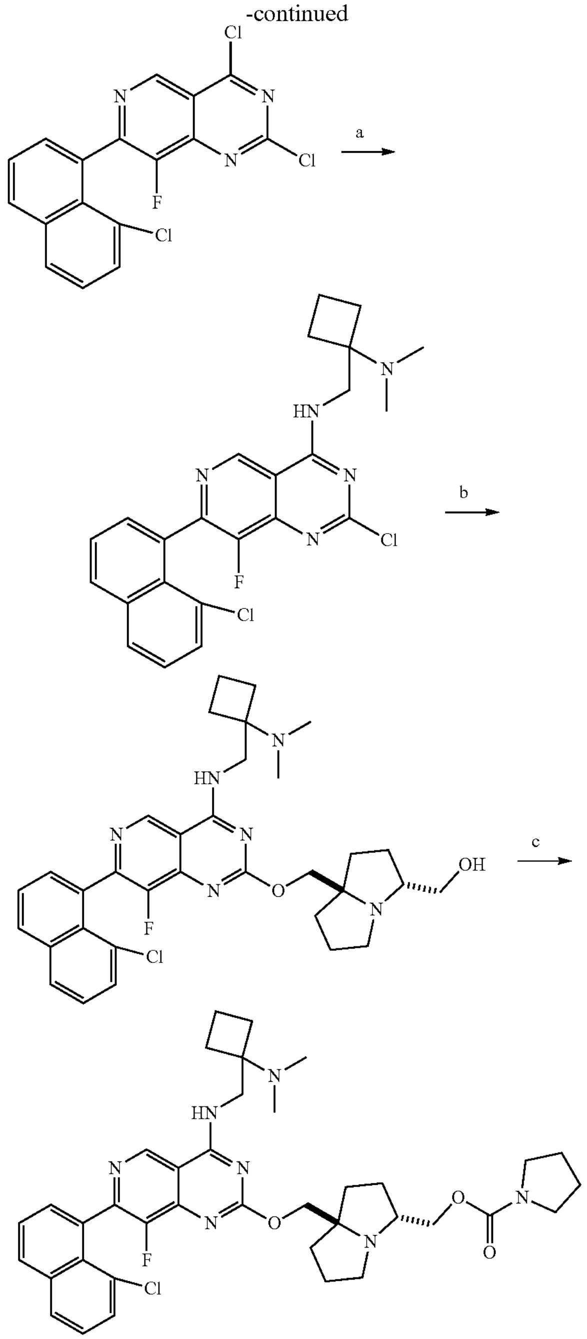

Step A. 2-chloro-7-(8-chloronaphthalen-1-yl)-N-((1-(dimethylamino)cyclobutyl)methyl)-8-fluoropyrido[4,3-d]pyrimidin-4-amine. To a solution of 2,4-dichloro-7-(8-chloronaphthalen-1-yl)-8-fluoropyrido[4,3-d]pyrimidine (0.25 g, 0.66 mmol) in dichloromethane (5 mL) at 0° C. was added N,N-diisopropylethylamine (0.12 mL, 0.66 mmol) followed by dropwise addition of 1-(aminomethyl)-N,N-dimethylcyclobutan-1-amine (80 mg, 0.63 mmol) in dichloromethane (3 mL). The mixture was stirred at 0° C. for 1 hr under nitrogen. The reaction mixture was warmed to ambient temperature and stirred under nitrogen for 14 hrs. The mixture was concentrated under vacuum. The crude oil was purified by flash chromatography eluting with 0-80% MeOH/DCM with 0.5% $NH_4OH$ as modifier to afford 2-chloro-7-(8-chloronaphthalen-1-yl)-N-((1-(dimethylamino)cyclobutyl)methyl)-8-fluoropyrido[4,3-d]pyrimidin-4-amine (71 mg, 23%). LCMS (MM-ES+APCI, Pos): m/z 471.2 [M+H].

Step B. 2-chloro-7-(8-chloronaphthalen-1-yl)-N-((1-(dimethylamino)cyclobutyl)methyl)-8-fluoropyrido[4,3-d]pyrimidin-4-amine. To a solution of 2,4-dichloro-7-(8-chloronaphthalen-1-yl)-8-fluoropyrido[4,3-d]pyrimidine (0.25 g, 0.66 mmol) in dichloromethane (5 mL) at 0° C. was added N,N-diisopropylethylamine (0.12 mL, 0.66 mmol) followed by dropwise addition of 1-(aminomethyl)-N,N-dimethylcyclobutan-1-amine (80 mg, 0.63 mmol) in dichloromethane (3 mL). The mixture was stirred at 0° C. for 1 hr under nitrogen. The reaction mixture was warmed to ambient temperature and stirred under nitrogen for 14 hrs. The mixture was concentrated under vacuum. The crude oil was purified by flash chromatography eluting with 0-80% MeOH/DCM with 0.5% $NH_4OH$ as modifier to afford 2-chloro-7-(8-chloronaphthalen-1-yl)-N-((1-(dimethylamino)cyclobutyl)methyl)-8-fluoropyrido[4,3-d]pyrimidin-4-amine (71 mg, 23%). LCMS (MM-ES+APCI, Pos): m/z 471.2 [M+H].

Step C. ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl pyrrolidine-1-carboxylate. To a solution of ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methanol (8.4 mg, 0.014 mmol) and triethylamine (3 μl, 0.02 mmol) in anhydrous THE (0.3 mL) was added 4-nitrophenyl carbonochloridate (2.5 mg, 0.013 mmol). The reaction was stirred at ambient temperature for 30 mins under $N_2$. To the solution was added pyrrolidine (3 μL, 0.04 mmol) and stirred at ambient temperature for 2 hrs. Additional pyrrolidine (6 μL) was added to the reaction mixture followed by stirring at ambient temperature for 16 hrs. The mixture was concentrated and the residue purified by reverse phase HPLC eluting with 5-95% ACN/water with 0.1% TFA as modifier to afford ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl pyrrolidine-1-carboxylate as the TFA salt (0.92 mg, 8.5%). LCMS (MM-ES+APCI, Pos): m/z 702.4 [M+H].

Example 50

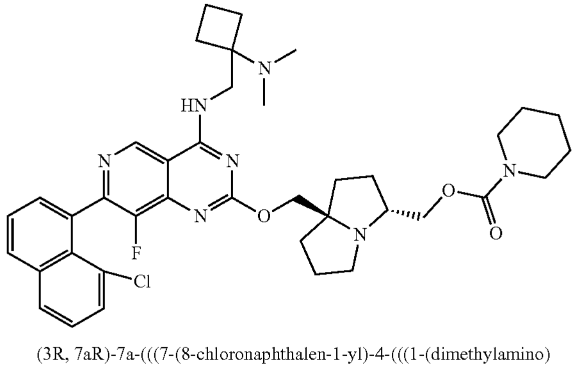

(3R, 7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methylpiperidine-1-carboxylate (racemic trans)

-continued

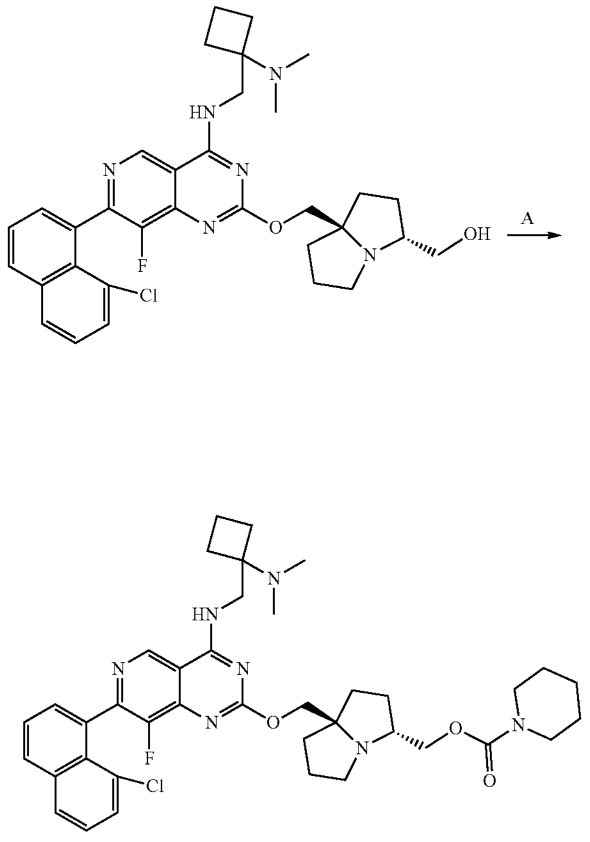

Step A. ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl piperidine-1-carboxylate. To a solution of ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methanol (40 mg, 0.066 mmol) and triethylamine (27 μl, 0.19 mmol) in anhydrous THE (1.6 mL) and DCM (0.4 mL) was added 4-nitrophenyl carbonochloridate (12 mg, 0.062 mmol). The reaction was stirred at ambient temperature for 16 hours under $N_2$. To the solution was added piperidine (16 μl, 0.16 mmol) and the reaction was stirred at ambient temperature for 2 hrs. The mixture was concentrated and the residue was purified by reverse phase HPLC eluting with 5-95% ACN/water with 0.1% TFA as modifier to afford ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl piperidine-1-carboxylate as the TFA salt (3.5 mg, 15% yield). LCMS (MM-ES+APCI, Pos): m/z 716.4 [M+H].

Example 51

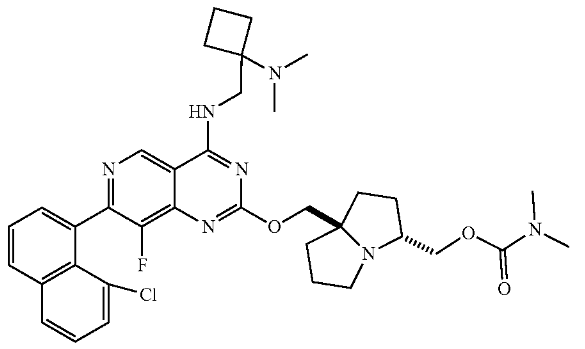

((3R, 7aR)-7a-(((7-(8-chloronaphthalen-1-yl)-4-(((1-dimethylamino)cyclobutyl)methyl)amino)-8-fluoropyrido[4,3-d]pyrimidin-2-yl)oxy)methyl)hexahydro-1H-pyrrolizin-3-yl)methyldimethylcarbamate (racemic trans)

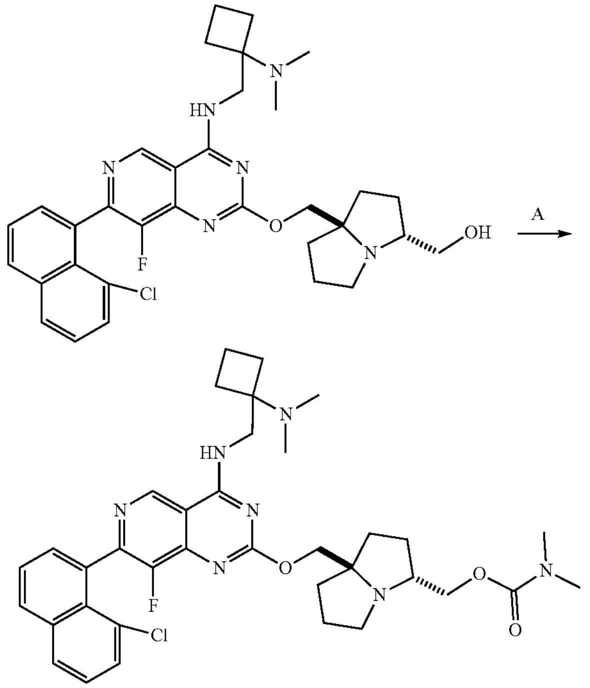

Step A. ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl dimethylcarbamate. To a solution of ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methanol (40 mg, 0.066 mmol) and triethylamine (27 μl, 0.19 mmol) in anhydrous THE (1.6 mL) and DCM (0.4 mL) was added 4-nitrophenyl carbonochloridate (12 mg, 0.062 mmol). The reaction was stirred at ambient temperature for 16 hrs under $N_2$. To the solution was added dimethylamine (0.16 mL, 0.324 mmol) and the reaction was stirred at ambient temperature for 2 hrs. The mixture was concentrated and the residue was purified by reverse phase HPLC eluting with 0→100% ACN/water+0.1% TFA as modifier to afford ((3R,7aR)-7a-(((7-(8-chloronaphthalen-1-yl)-4-(((1-(dimethylamino)cyclobutyl)methyl)amino)-8-fluoropyrido[4,3-d]pyrimidin-2-yl)oxy)methyl)hexahydro-1H-pyrrolizin-3-yl)methyl dimethylcarbamate as the TFA salt (1 mg, 5.8% yield). LCMS (MM-ES+APCI, Pos): m/z 676.3 [M+H].

Example 52

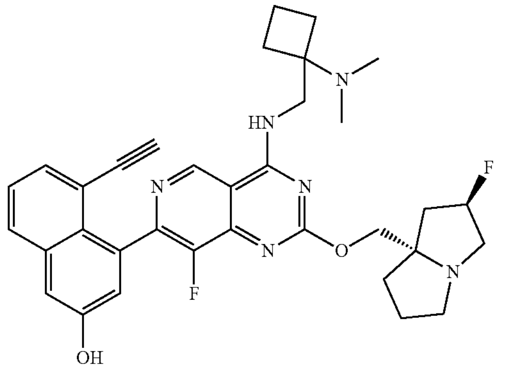

4-(4-(((1-(dimethylamino)cyclobutyl)methyl)amino)-8-fluoro-2-(((2R, 7aS)-2-fluorotetrahydro-1H-pyrrolizin-7a(5H)-yl)methoxy) pyrido[4,3-d]pyrimidin-7-yl)-5-ethynylnaphthalen-2-ol

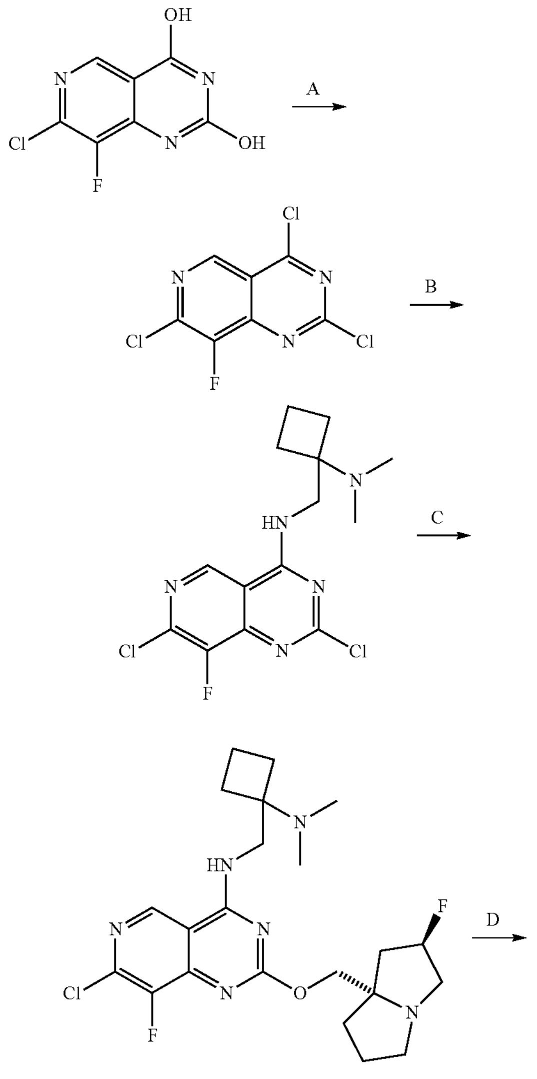

-continued

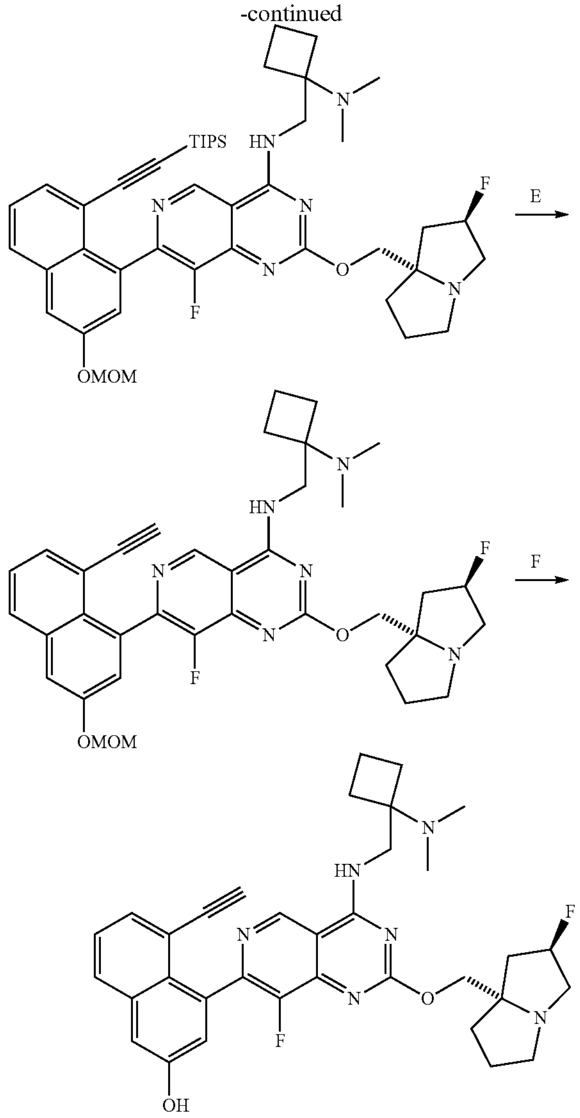

Step A. 2,4,7-trichloro-8-fluoro-pyrido[4,3-d]pyrimidine. A mixture of 7-chloro-8-fluoropyrido[4,3-d]pyrimidine-2,4-diol (0.75 g, 3.48 mmol, 1.0 eq) and DIEA (2.25 g, 17.4 mmol, 3.03 mL, 5.0 eq) in $POCl_3$ (18.6 g, 121 mmol, 11.3 mL, 35 eq) was stirred at 110° C. for 1 hour. After completion, the mixture was concentrated under vacuum to give the title compound (0.88 g, crude) which was used in the next step without further purification. Brown oil. LCMS [ESI, M+1]: 252.0.

Step B. 2,7-dichloro-N-[[1-(dimethylamino)cyclobutyl] methyl]-8-fluoro-pyrido[4,3-d]pyrimidin-4-amine. To a mixture of 2,4,7-trichloro-8-fluoro-pyrido[4,3-d]pyrimidine (0.88 g, 3.49 mmol, 1.0 eq) in dichloromethane (15 mL) were added DIEA (4.51 g, 35 mmol, 6.07 mL, 10 eq) and 1-(aminomethyl)-N,N-dimethylcyclobutanamine (894 mg, 6.97 mmol, 2.0 eq) at −40° C. The mixture was stirred at 25° C. for 2 hours. After completion, the mixture was diluted with water (20 mL) and then the organic layer was separated. The aqueous phase was extracted with dichloromethane (2×15 mL). The combined organic layer was washed with saturated brine (20 mL), dried over $Na_2SO_4$, filtered and concentrated under vacuum. The residue was purified by reversed phase flash chromatography [water (FA, 0.1%)/ acetonitrile] to give the title compound (339 mg, two steps 28% yield). Yellow solid. LCMS [ESI, M+1]: 344.2.

Step C. 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine. To a mixture of 2,7-dichloro-N-[[1-(dimethylamino)cyclobutyl]methyl]-8-fluoro-pyrido[4,3-d]pyrimidin-4-amine (470 mg, 1.37 mmol, 1.0 eq) and ((2R,7aS)-2-fluorohexahydro-1H-pyrrolizin-7a-yl)methanol (261 mg, 1.64 mmol, 1.2 eq) in dioxane (10 mL) was added DIEA (529 mg, 4.10 mmol, 713 μL, 3.0 eq). The mixture was stirred at 100° C. for 22 hours. After completion, the mixture was diluted with ethyl acetate (8 mL) and water (10 mL) and then the organic layer was separated. The aqueous phase was extracted with ethyl acetate (2×8 mL). The combined organic layer was washed with brine (10 mL), dried over $Na_2SO_4$, filtered and concentrated under vacuum. The residue was purified by reversed phase flash chromatography [water (FA, 0.10%)/acetonitrile] to give the title compound (213 mg, 31% yield). Yellow solid. LCMS [ESI, M+1]: 467.4.

Step D. N-((1-(dimethylamino)cyclobutyl)methyl)-8-fluoro-2-(((2R,7aS)-2-fluorotetrahydro-1H-pyrrolizin-7a(5H)-yl)methoxy)-7-(3-(methoxymethoxy)-8-((triisopropylsilyl)ethynyl)naphthalen-1-yl)pyrido[4,3-d]pyrimidin-4-amine. To a mixture of 7-chloro-N-((1-(dimethylamino)cyclobutyl)methyl)-8-fluoro-2-(((2R,7aS)-2-fluorotetrahydro-1H-pyrrolizin-7a(5H)-yl)methoxy)pyrido[4,3-d]pyrimidin-4-amine (207 mg, 443 μmol, 1.0 eq), triisopropyl ((6-(methoxymethoxy)-8-(4,4,5,5-tetramethyl-1,3,2-dioxaborolan-2-yl)naphthalen-1-yl)ethynyl)silane (438 mg, 887 μmol, 2.0 eq) and $K_3PO_4$ aqueous solution (1.5 M, 887 μL, 3.0 eq) in THE (6 mL) was added [2-(2-aminophenyl)phenyl]palladium(1+);bis(1-adamantyl)-butyl-phosphane; methanesulfonate (32.28 mg, 44.33 μmol, 0.1 eq) under $N_2$. The mixture was stirred under $N_2$ at 60° C. for 1 hour. After completion, the mixture was concentrated under vacuum. The residue was purified by reversed phase flash chromatography [water (FA, 0.1%)/acetonitrile] to give the title compound (226 mg, 55% yield). Brown solid. $^1$H NMR (400 MHz, $CDCl_3$) δ=8.84 (s, 1H), 7.81 (br d, J=8.4 Hz, 1H), 7.66 (br d, J=7.2 Hz, 1H), 7.51 (br d, J=2.4 Hz, 1H), 7.40 (br t, J=7.6 Hz, 1H), 7.15-7.07 (m, 1H), 5.39-5.19 (m, 3H), 4.41-4.12 (m, 2H), 3.86-3.72 (m, 2H), 3.51 (s, 3H), 3.31-3.15 (m, 3H), 3.03-2.92 (m, 1H), 2.44-2.35 (m, 2H), 2.31 (s, 6H), 2.28-2.10 (m, 4H), 1.98-1.76 (m, 6H), 0.89 (br t, J=7.6 Hz, 21H). LCMS [ESI, M+1, M/2+1]: 799.5, 400.5.

Step E. N-((1-(dimethylamino)cyclobutyl)methyl)-7-(8-ethynyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine. To a mixture of N-((1-(dimethylamino)cyclobutyl)methyl)-8-fluoro-2-(((2R,7aS)-2-fluorotetrahydro-1H-pyrrolizin-7a(5H)-yl)methoxy)-7-(3-(methoxymethoxy)-8-((triisopropylsilyl)ethynyl)naphthalen-1-yl)pyrido[4,3-d]pyrimidin-4-amine (198 mg, 248 μmol, 1.0 eq) in DMF (4 mL) was added CsF (301 mg, 1.98 mmol, 73.1 μL, 8.0 eq). The mixture was stirred at 25° C. for 2 hours. After completion, the residue was purified by reversed phase flash chromatography [water (FA, 0.1%)/acetonitrile] directly to give the title compound (131 mg, 81% yield). Brown solid. LCMS [ESI, M+1, M/2+1]: 643.3, 322.4.

Step F. 4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethynylnaphthalen-2-ol. To a mixture of N-((1-(dimethylamino)cyclobutyl)methyl)-7-(8-ethynyl-3-(methoxymethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-amine (80 mg, 124 μmol, 1.0 eq) in MeCN (1 mL) was added HCl·dioxane (4 M, 2 mL, 64 eq) at 0° C. The mixture was stirred at 0° C. for 0.5 hour. After completion, the mixture was concentrated under vacuum. The residue was purified by prep-HPLC (column: Shim-pack C18 150*25*10 μm; mobile phase: [water (0.225% FA)-ACN]; B %: 9%-29%, 9 min) to give the title compound (38.7 mg, 48% yield, FA). Yellow solid. $^1$H NMR (400 MHz, METHANOL-d4) δ=9.22 (s, 1H), 7.83 (d, J=8.4 Hz, 1H), 7.53-7.49 (m, 1H), 7.40 (t, J=7.8 Hz, 1H), 7.34 (d, J=2.86 Hz, 1H), 7.18-7.14 (m, 1H), 5.56-5.37 (m, 1H), 4.61-4.52 (m, 2H), 4.34-4.25 (t, J=15.2 Hz, 1H), 4.19-4.10 (t, J=14.4 Hz, 1H), 3.75-3.56 (m, 3H), 3.35-3.25 (m, 1H), 3.01 (s, 1H), 2.76 (s, 6H), 2.57-2.37 (m, 4H), 2.33-2.17 (m, 5H), 2.10-1.92 (m, 3H). LCMS [ESI, M+1, M/2+1]: 599.3, 300.4.

Example 53

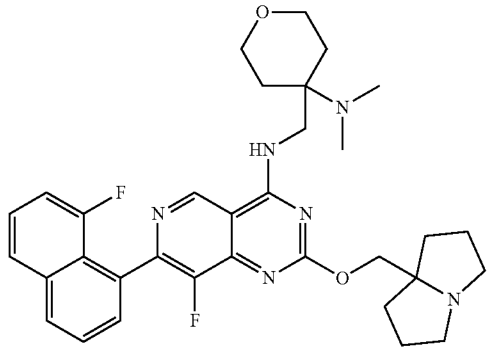

N-((4-(dimethylamino)tetrahydro-2H-pyran-4-yl)methyl)-8-fluoro-7-(8-fluoronaphthalen-1-yl)-2-((hexahydro-1H-pyrrolizin-7a-yl)methoxy)pyrido[4.3-d]pyrimidin-4-amine

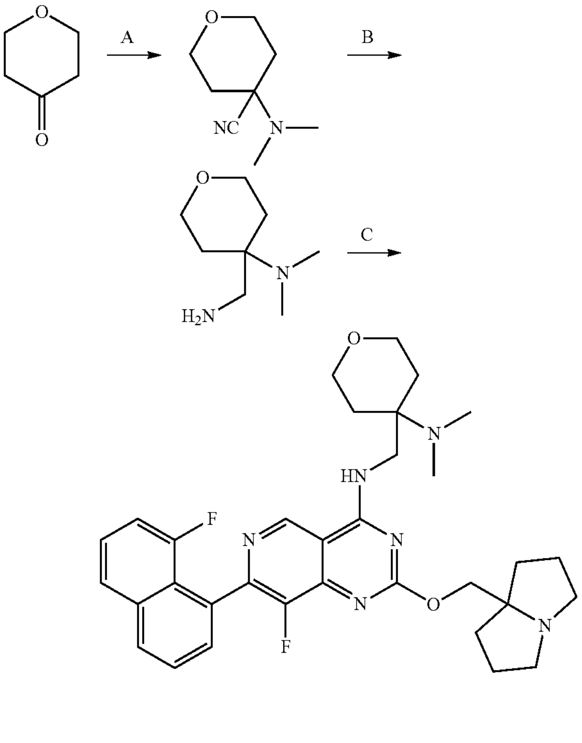

Step A. 4-(dimethylamino) tetrahydro-2H-pyran-4-carbonitrile. To a mixture of KCN (3.25 g, 49.9 mmol, 2.14 mL, 1.0 eq) and dihydro-2H-pyran-4(3H)-one (5 g, 49.9 mmol, 4.59 mL, 1.0 eq) was added a solution of $(CH_3)_2NH$ (4.07 g, 49.9 mmol, 4.58 mL, 1.0 eq, HCl) in $H_2O$ (40 mL). The mixture was stirred at 20° C. for 12 hours. Upon completion, the reaction mixture was diluted with water (40 mL) and extracted with ethyl acetate (3×50 mL). The combined organic layers were washed with brine (30 mL), dried over $Na_2SO_4$, filtered and concentrated under reduced pressure to give the title compound (4.4 g, 57% yield). White Solid; $^1$H NMR (400 MHz, 400 MHz, $CDCl_3$) δ=4.00 (dt, J=3.2, 12.0 Hz, 2H), 3.64 (td, J=2.0, 12.4 Hz, 2H), 2.34 (s, 6H), 2.12-2.02 (m, 2H), 1.78-1.66 (m, 2H).

Step B. 4-(aminomethyl)-N,N-dimethyltetrahydro-2H-pyran-4-amine. To a mixture of 4-(dimethylamino) tetrahydro-2H-pyran-4-carbonitrile (2 g, 13.0 mmol, 1.0 eq) in THE (20 mL) was added $LiAlH_4$ (1.97 g, 51.9 mmol, 4.0 eq) in one portion at 0° C. under $N_2$. The mixture was stirred at 0° C. for 1 hour. Upon completion, the reaction mixture was quenched with $H_2O$ (2 mL), 15% NaOH aqueous (2 mL), and $H_2O$ (6 mL) successively, and the mixture was dried over $Na_2SO_4$, then filtered. The filter cake was washed with ethyl acetate (3×30 mL). The organic layer was washed with brine (30 mL), dried over $Na_2SO_4$, filtered and concentrated under reduced pressure to give the title compound (1.6 g, 78% yield). Colorless oil; $^1$H NMR (400 MHz, $CDCl_3$) δ=3.87-3.78 (m, 2H), 3.58-3.53 (m, 2H), 2.84 (s, 2H), 2.29 (s, 6H), 1.79-1.73 (m, 2H), 1.47-1.45 (m, 2H).

Step C. N-((4-(dimethylamino)tetrahydro-2H-pyran-4-yl) methyl)-8-fluoro-7-(8-fluoronaphthalen-1-yl)-2-((hexahydro-1H-pyrrolizin-7a-yl)methoxy)pyrido[4,3-d]pyrimidin-4-amine. To a mixture of 8-fluoro-7-(8-fluoronaphthalen-1-yl)-2-((hexahydro-1H-pyrrolizin-7a-yl) methoxy)-4-(2,2,2-trifluoroethoxy)pyrido[4,3-d]pyrimidine (100 mg, 188 μmol, 1.0 eq) and 4-(aminomethyl)-N,N-dimethyltetrahydro-2H-pyran-4-amine (89.5 mg, 565 μmol, 3.0 eq) in DMF (2 mL) was added DIEA (73.1 mg, 565 μmol, 98.5 μL, 3 eq) and 4 Å MS (50 mg). Then the mixture was degassed and purged with $N_2$ for 3 times, heated to 40° C. and stirred for 2 hours. Upon completion, the mixture was purified by prep-HPLC (column: Waters Xbridge 150*25 mm*5 μm; mobile phase: [water (10 mM $NH_4HCO_3$)–ACN]; B %: 30%-60%, 10 min). The desired fraction was collected and concentrated under vacuum to remove acetonitrile. The mixture was lyophilized to give the title compound (43.4 mg, 38% yield). White solid; $^1$H NMR (400 MHz, DMSO-d6) δ=9.36 (s, 1H), 8.68-8.63 (m, 1H), 8.17 (br d, J=8.0 Hz, 1H), 7.93 (d, J=8.4 Hz, 1H), 7.76-7.71 (m, 1H), 7.66-7.52 (m, 2H), 7.30 (dd, J=7.6, 12.8 Hz, 1H), 4.13 (s, 2H), 3.82-3.72 (m, 2H), 3.69-3.62 (m, 2H), 3.61-3.53 (m, 2H), 3.01-2.88 (m, 2H), 2.63-2.55 (m, 2H), 2.37 (s, 6H), 1.94-1.86 (m, 2H), 1.84-1.72 (m, 6H), 1.67-1.55 (m, 4H); LCMS [ESI, M+1]: 589.4.

Example 54

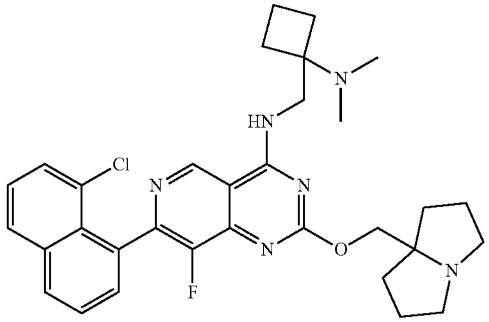

7-(8-chloronaphthalen-1-yl)-N-((1-(dimethylamino) cyclobutyl)methyl)-8-fluoro-2-((tetrahydro-1H-pyrrolizin-7a(5H)-yl)methoxy)pyrido[4,3-d]pyrimidin-4-amine

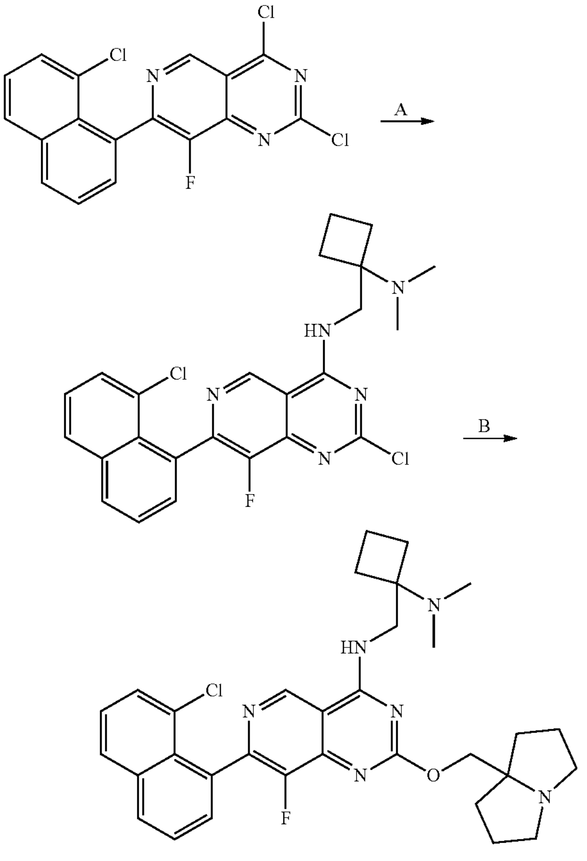

Step A. 2-chloro-7-(8-chloronaphthalen-1-yl)-N-((1-(dimethylamino)cyclobutyl)methyl)-8-fluoropyrido[4,3-d]pyrimidin-4-amine. To a solution of 2,4-dichloro-7-(8-chloro-1-naphthyl)-8-fluoro-pyrido[4,3-d]pyrimidine (100 mg, 264 μmol, 1.0 eq) in dichloromethane (2.0 mL) was added DIEA (341 mg, 2.64 mmol, 460 μL, 10 eq) and 1-(aminomethyl)-N,N-dimethylcyclobutanamine (40.6 mg, 317 μmol, 1.2 eq) at −40° C. The mixture was stirred at −40° C. for 1 hour. The reaction mixture was diluted with water (5.0 mL) and the organic layer was separated. The aqueous phase was extracted with ethyl acetate (3×5.0 mL). The combined organic layers were washed with brine (5.0 mL), dried over $Na_2SO_4$, filtered and concentrated under reduced pressure. The residue was purification by column chromatography ($Al_2O_3$, petroleum ether/ethyl acetate=1/0 to ethyl acetate/methanol=1/1). The residue was purified by reversed phase flash chromatography [water (0.1% formic acid)/acetonitrile)] to give the title compound (50 mg, 35% yield). Yellow solid. LCMS [ESI, M+1]: 470.1.

Step B. 7-(8-chloronaphthalen-1-yl)-N-((1-(dimethylamino)cyclobutyl)methyl)-8-fluoro-2-((tetrahydro-1H-pyrrolizin-7a(5H)-yl)methoxy)pyrido[4,3-d]pyrimidin-4-amine. A mixture of 2-chloro-7-(8-chloro-1-naphthyl)-N-[[1-(dimethylamino)cyclobutyl]methyl]-8-fluoro-pyrido[4,3-d]pyrimidin-4-amine (45 mg, 95.7 μmol, 1.0 eq), (hexahydro-1H-pyrrolizin-7a-yl)methanol (27.0 mg, 191 μmol, 2.0 eq), DIEA (37.1 mg, 287 μmol, 50 μL, 3.0 eq) in dioxane (2.0 mL) was degassed and purged with $N_2$ for 3 times, and then the mixture was stirred at 90° C. for 12 hours under $N_2$ atmosphere. The reaction mixture was diluted with water (5.0 mL) and extracted with ethyl acetate (3x5.0 mL). The combined organic layers were dried over $Na_2SO_4$, filtered and concentrated under reduced pressure. The residue was purified by reversed phase flash chromatography [water (0.1% formic acid)/acetonitrile)] to give the title compound (9.59 mg, 17% yield). Off-white solid. $^1H$ NMR (400 MHz, methanol-$d_4$) δ=9.22 (s, 1H), 8.17-8.12 (m, 1H), 8.05-7.99 (m, 1H), 7.72-7.66 (m, 1H), 7.62-7.57 (m, 2H), 7.54-7.48 (m, 1H), 4.54-4.46 (m, 2H), 4.14-4.01 (m, 2H), 3.44-3.33 (m, 2H), 3.05-2.94 (m, 2H), 2.39 (s, 6H), 2.27-2.15 (m, 4H), 2.12-1.98 (m, 6H), 1.98-1.84 (m, 4H). LCMS [ESI, M+1]: 575.2.

Example 55

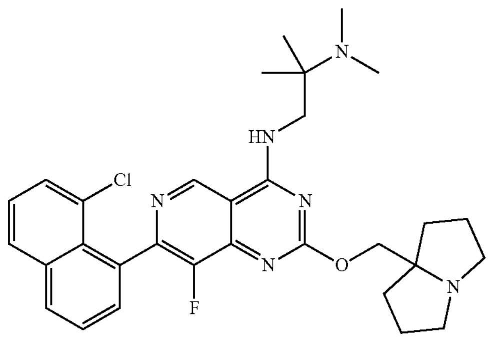

N1-(7-(8-chloronaphthalen-1-yl)-8-fluoro-2-((tetrahydro-1H-pyrrolizin-7a(5H)-yl)methoxy)pyrido[4.3-d]pyrimidin-4-yl)-N2,N2,2-trimethylpropane-1,2-diamine

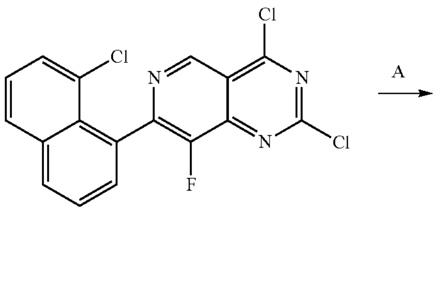

-continued

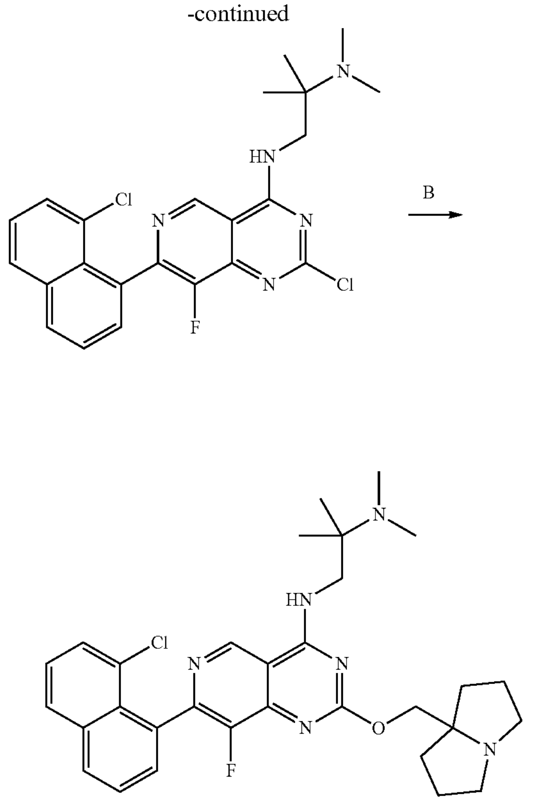

Step A. $N^1$-(2-chloro-7-(8-chloronaphthalen-1-yl)-8-fluoropyrido[4,3-d]pyrimidin-4-yl-$N^2$,$N^2$,2-trimethylpropane-1,2-diamine. To a solution of 2,4-dichloro-7-(8-chloro-1-naphthyl)-8-fluoro-pyrido[4,3-d]pyrimidine (554 mg, 1.46 mmol, 1.0 eq) in DCM (5 mL) were added DIEA (566 mg, 4.38 mmol, 763 μL, 3.0 eq) and $N^2$,$N^2$,2-trimethylpropane-1,2-diamine (254 mg, 2.19 mmol, 1.5 eq). The mixture was stirred at −40° C. for 2 hours. The reaction mixture was concentrated under reduced pressure. The residue was purified by reversed phase flash chromatography (C18, 0.1% FA in water, 0-40% ACN) affording the title compound (120 mg, 18% yield). Yellow solid; LCMS [ESI, M+1]: 459.1.

Step B. $N^1$-(7-(8-chloronaphthalen-1-yl)-8-fluoro-2-((hexahydro-1H-pyrrolizin-7a-yl)methoxy)pyrido[4,3-d]pyrimidin-4-yl)-$N^2$,$N^2$,2-trimethylpropane-1,2-diamine. To a solution of $N^1$-(2-chloro-7-(8-chloronaphthalen-1-yl)-8-fluoropyrido[4,3-d]pyrimidin-4-yl)-$N^2$,$N^2$,2-trimethylpropane-1,2-diamine (30.0 mg, 65.4 μmol, 1.0 eq) and (hexahydro-1H-pyrrolizin-7a-yl)methanol (27.7 mg, 196 μmol, 3.0 eq) in dioxane (1 mL) were added DIEA (33.8 mg, 262 μmol, 45.6 μL, 4.0 eq) and 4 A MS (20 mg, 63.4 μmol). The mixture was stirred at 120° C. for 12 hours. The reaction mixture was filtered and concentrated under reduced pressure. The residue was purified by prep-HPLC (column: Waters Xbridge C18 150*50 mm*10 μm; mobile phase: [water (10 mM $NH_4HCO_3$)-ACN]; B %: 30%-60%, 10 min) affording the title compound. (7.80 mg, 21% yield). White solid; $^1H$ NMR (400 MHz, $CDCl_3$) δ 8.90 (s, 1H), 7.99 (dd, J=1.2, 8.0 Hz, 1H), 7.87 (dd, J=1.2, 8.0 Hz, 1H), 7.63-7.58 (m, 1H), 7.57-7.51 (m, 2H), 7.47-7.33 (m, 2H), 4.26 (s, 2H), 3.54 (s, 2H), 3.19-3.07 (m, 2H), 2.72-2.58 (m, 2H), 2.30 (s, 6H), 2.18-2.10 (m, 2H), 1.91-1.84 (m, 4H), 1.72-1.62 (m, 2H), 1.16 (d, J=5.2 Hz, 6H); LCMS [ESI, M+1]: 563.2.

Example 56

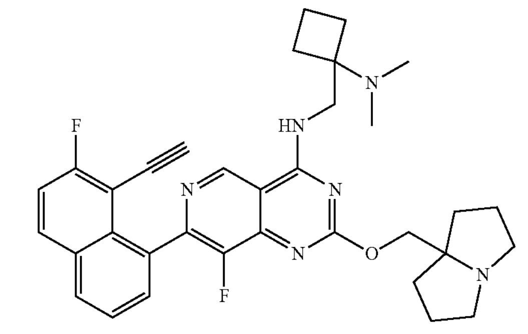

N-((1-(dimethylamino)cyclobutyl)methyl)-7-(8-ethynyl-7-fluoronaphthalen-1-yl)-8-fluoro-2-((hexahydro-1H-pyrrolizin-7a-yl)methoxy)pyrido[4,3-d]pyrimidin-4-amine

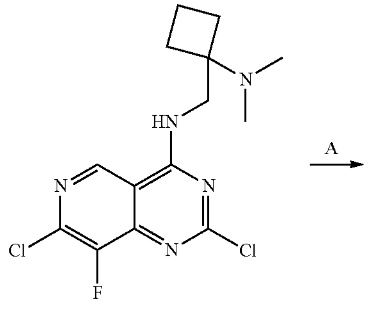

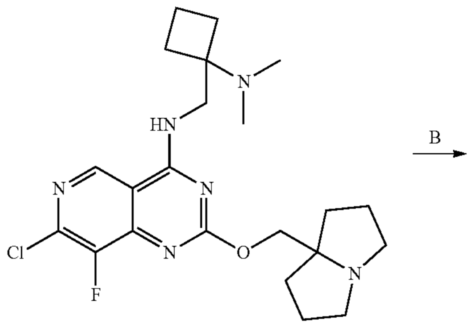

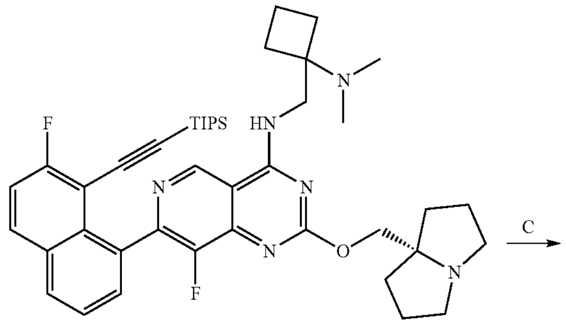

-continued

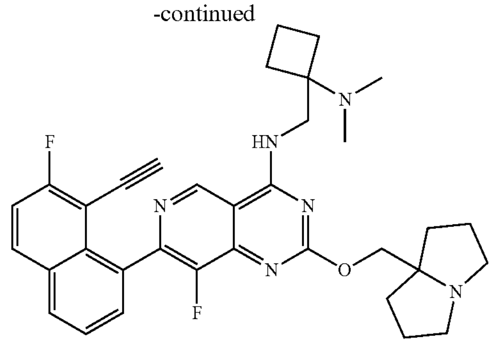

Step A. 7-chloro-N-((1-(dimethylamino)cyclobutyl)methyl)-8-fluoro-2-((hexahydro-1H-pyrrolizin-7a-yl)methoxy)pyrido[4,3-d]pyrimidin-4-amine. To a mixture of 2,7-dichloro-N-((1-(dimethylamino)cyclobutyl)methyl)-8-fluoropyrido[4,3-d]pyrimidin-4-amine (600 mg, 1.74 mmol, 1.0 eq, synthesized according to Example 52, Step A-B) and (hexahydro-1H-pyrrolizin-7a-yl)methanol (738 mg, 5.23 mmol, 3.0 eq) in dioxane (10.0 mL) was added DIEA (676 mg, 5.23 mmol, 911 μL, 3.0 eq). The mixture was stirred at 90° C. for 16 hours. After completion, the reaction mixture was diluted with $H_2O$ (10 mL) and extracted with ethyl acetate (3×10 mL). The combined organic layers were washed with saturated brine (30 mL), dried over $Na_2SO_4$, filtered and concentrated under reduced pressure to give a residue. The residue was purified by column chromatography ($SiO_2$, petroleum ether:ethyl acetate=5:1 to dichloromethane:methanol=20: 1) affording the title compound (420 mg, 48% yield). Yellow solid; $^1$H NMR (400 MHz, $CDCl_3$-d) δ=8.58 (s, 1H), 7.10 (br s, 1H), 4.24 (s, 2H), 3.75 (d, J=3.6 Hz, 2H), 3.19-3.06 (m, 2H), 2.70-2.58 (m, 2H), 2.41-2.32 (m, 2H), 2.28 (s, 6H), 2.14-2.07 (m, 2H), 1.92-1.84 (m, 4H), 1.83-1.72 (m, 2H), 1.71-1.59 (m, 4H).

Step B. N-((1-(dimethylamino)cyclobutyl)methyl)-8-fluoro-7-(7-fluoro-8-((triisopropylsilyl)ethynyl)naphthalen-1-yl)-2-((hexahydro-1H-pyrrolizin-7a-yl)methoxy)pyrido[4,3-d]pyrimidin-4-amine. A mixture of 7-chloro-N-((1-(dimethylamino)cyclobutyl)methyl)-8-fluoro-2-((hexa hydro-1H-pyrrolizin-7a-yl)methoxy)pyrido[4,3-d]pyrimidin-4-amine (200 mg, 445 μmol, 1.0 eq), ((2-fluoro-8-(4,4,5,5-tetramethyl-1,3,2-dioxaborolan-2-yl)naphthalen-1-yl)ethynyl)triisopropylsilane (1.01 g, 2.23 mmol, 5.0 eq), [2-(2-aminophenyl)phenyl]palladium(1+);bis(1-adamantyl)-butyl-phosphane; methanesulfonate (64.9 mg, 89.1 μmol, 0.2 eq) and $K_3PO_4$ (1.5 M, 1.00 mL, 3.37 eq) in THE (4.00 mL) was degassed and purged with $N_2$ for 3 times, and then the mixture was stirred at 60° C. for 2 hours under $N_2$ atmosphere. After completion, the reaction mixture was diluted with $H_2O$ (10 mL) and extracted with ethyl acetate (3×20 mL). The combined organic layers were washed with saturated brine (50 mL), dried over $Na_2SO_4$, filtered and concentrated under reduced pressure to give a residue. The residue was purified by reversed phase flash chromatography [C18, 0.1% FA in water, 0-40% MeCN] affording the title compound (175 mg, 50% yield). Yellow solid; LCMS [ESI, M+1]: 739.5.

Step C. N-((1-(dimethylamino)cyclobutyl)methyl)-7-(8-ethynyl-7-fluoronaphthalen-1-yl)-8-fluoro-2-((hexahydro-1H-pyrrolizin-7a-yl)methoxy)pyrido[4,3-d]pyrimidin-4-amine. To a solution of N-((1-(dimethylamino)cyclobutyl)methyl)-8-fluoro-7-(7-fluoro-8-((triisopropylsilyl)ethynyl)naphthalen-1-yl)-2-((hexahydro-1H-pyrrolizin-7a-yl)methoxy)pyrido[4,3-d]pyrimidin-4-amine (150 mg, 203

μmol, 1.0 eq) in DMF (2 mL) was added CsF (308 mg, 2.03 mmol, 74.8 μL, 10.0 eq). The mixture was stirred at 15° C. for 2 hours. After completion, the reaction mixture was filtered. The filtrate was purified by flash silica gel chromatography (column: Phenomenex Synergi C18 150*25*10 um; mobile phase: [water (0.225% FA)-ACN]; B %: 8%-35%, 9 min) and lyophilized affording the title compound (76.3 mg, 56% yield, 1.9 FA). Yellow solid; $^{1}H$ NMR (400 MHz, methanol-$d_4$) δ=9.28 (s, 1H), 8.17-8.10 (m, 2H), 7.71-7.62 (m, 2H), 7.46 (t, J=8.8 Hz, 1H), 4.70 (s, 2H), 4.35 (d, J=14.8 Hz, 1H), 4.18 (d, J=15.2 Hz, 1H), 3.72-3.62 (m, 2H), 3.46 (s, 1H), 3.30-3.23 (m, 2H), 2.79 (s, 6H), 2.51-2.40 (m, 2H), 2.36-2.27 (m, 4H), 2.26-2.07 (m, 6H), 2.05-1.93 (m, 2H); LCMS [ESI, M+1]: 583.3.

Example 57

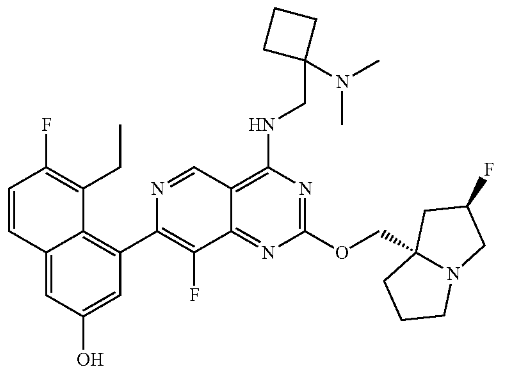

4-(4-(((1-(dimethylamino)cyclobutyl)methyl)amino)-8-fluoro-2-(((2R,7aS)-2-fluorotetrahydro-1H-pyrrolizin-7a(5H)-yl)methoxy)pyrido[4,3-d]pyrimidin-7-yl)-5-ethyl-6-fluoronaphthalen-2-ol

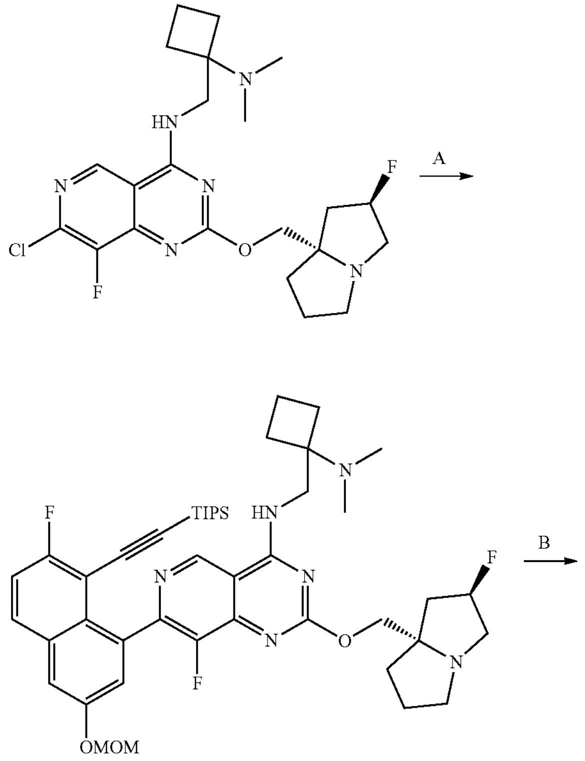

-continued

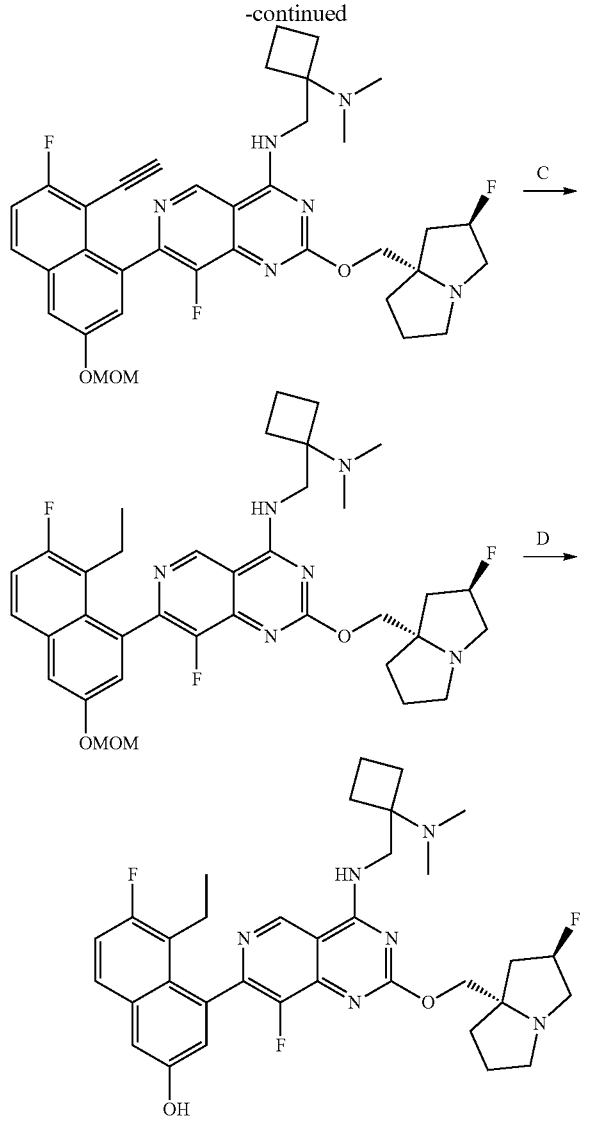

Step A. N-((1-dimethylamino)cyclobutyl)methyl)-8-fluoro-7-(7-fluoro-3-(methoxymethoxy)-8-((triisopropylsilyl)ethynyl)naphthalen-1-yl)-2-(((2R,7aS)-2-fluorohexahydro-1H-pyrrolizin-7a-yl)methoxy)pyrido[4,3-d]p yrimidin-4-amine. A mixture of 7-chloro-N-((1-(dimethylamino)cyclobutyl)methyl)-8-fluoro-2-(((2R,7aS)-2-fluorohexahydro-1H-pyrrolizin-7a-yl)methoxy)pyrido[4,3-d]pyrimidin-4-amine (180 mg, 385 μmol, 1.0 eq, synthesized according to Example 52, Step A-C), ((2-fluoro-6-(methoxymethoxy)-8-(4,4,5,5-tetramethyl-1,3,2-dioxaborolan-2-yl)naphthalen-1-yl)ethynyl)triisopropylsilane (296 mg, 578 μmol, 1.5 eq), [2-(2-aminophenyl)phenyl]palladium(1+);bis(1-adamantyl)-butyl-phosphane; methanesulfonate (42.1 mg, 57.8 μmol, 0.15 eq) and $K_3PO_4$ (1.5 M, 0.80 mL, 3.11 eq) in THE (3.20 mL) was degassed and purged with $N_2$ for 3 times, and then the mixture was stirred at 60° C. for 2 hours under $N_2$ atmosphere. After completion, the reaction mixture was diluted with $H_2O$ (10 mL) and extracted with ethyl acetate (3×20 mL). The combined organic layers were washed with saturated brine (50 mL), dried over $Na_2SO_4$, filtered and concentrated under reduced pressure to give a residue. The residue was purified by reversed phase flash chromatography [C18, 0.1% FA in water, 0-40% MeCN] affording the title compound (240 mg, 75% yield). Yellow solid; LCMS [ESI, M/2+1, M+1]: 409.4, 817.5.

Step B. N-((1-(dimethylamino)cyclobutyl)methyl)-7-(8-ethynyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine. To a solution of N-((1-(dimethylamino)cyclobutyl)methyl)-8-fluoro-7-(7-fluoro-3-(methoxymethoxy)-8-((triisopropylsilyl)ethynyl) naphthalen-1-yl)-2-(((2R,7aS)-2-fluorohexahydro-1H-pyrrolizin-7a-yl)methoxy)pyrido[4,3-d]pyrimidin-4-amine (230 mg, 281 μmol, 1.0 eq) in DMF (4 mL) was added CsF (428 mg, 2.81 mmol, 10.0 eq). The mixture was stirred at 15° C. for 2 hours. After completion, the reaction mixture was diluted with $H_2O$ (10 mL) and extracted with ethyl acetate (3×10 mL). The combined organic layers were washed with saturated brine (30 mL), dried over $Na_2SO_4$, filtered and concentrated under reduced pressure to give a residue. The residue was purified by reversed phase flash chromatography [C18, 0.1% FA in water, 0-60% MeCN] affording the title compound (120 mg, 64% yield). Yellow solid; LCMS [ESI, M+1]: 661.4.

Step C. N-((1-(dimethylamino)cyclobutyl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine. To a solution of N-((1-(dimethylamino)cyclobutyl)methyl)-7-(8-ethynyl-7-fluoro-3-(methoxymethoxy)naphthalen-1-yl)-8-fluoro-2-(((2R,7aS)-2-fluorohexahydro-1H-pyrrolizin-7a-yl) methoxy)pyrido[4,3-d]pyrimidin-4-amine (100 mg, 151 μmol, 1.0 eq) in MeOH (4.00 mL) was added Pd/C (100 mg, 10% purity, 1.00 eq) under $N_2$ atmosphere. The mixture was stirred at 40° C. for 3 hours under $H_2$ (15 psi). After completion, the reaction mixture was filtered through celite and the filtrate was concentrated affording the title compound (95 mg, 86% yield). Yellow oil; LCMS [ESI, M+1]: 665.7.

Step D. 4-(4-(((1-(dimethylamino)cyclobutyl)methyl) amino)-8-fluoro-2-(((2R,7aS)-2-fluorohexahydro-1H-pyrrolizin-7a-yl)methoxy)pyrido[4,3-d]pyrimidin-7-yl)-5-ethyl-6-fluoronaphthalen-2-ol. To a solution of N-((1-(dimethylamino)cyclobutyl)methyl)-7-(8-ethyl-7-fluoro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-amine (80.0 mg, 120 μmol, 1.0 eq) in ACN (1.00 mL) was added HCl·dioxane (4.0 M, 1.00 mL) at 0° C. The mixture was stirred at 0° C. for 15 minutes. After completion, the reaction mixture was diluted with saturated $Na_2CO_3$ aqueous (5 mL) and extracted with ethyl acetate (3×10 mL). The combined organic layers dried over $Na_2SO_4$, filtered and concentrated under reduced pressure to give a residue. The residue was purified by prep-HPLC (column: Waters Xbridge 150*25 mm*5 μm; mobile phase: [water (10 mM $NH_4HCO_3$)-ACN]; B %: 50%-80%, 10 min) and lyophilized affording the title compound (19.7 mg, 26% yield). White solid; $^1H$ NMR (400 MHz, $CDCl_3$) δ=8.87 (d, J=1.6 Hz, 1H), 7.54-7.48 (m, 1H), 7.26-7.13 (m, 2H), 7.12-7.08 (m, 1H), 7.01-6.94 (m, 1H), 5.39-5.17 (m, 1H), 4.36-4.20 (m, 2H), 3.87-3.70 (m, 2H), 3.34-3.14 (m, 3H), 3.05-2.94 (m, 1H), 2.51-2.35 (m, 3H), 2.34-2.26 (m, 7H), 2.25-2.21 (m, 1H), 2.20-2.10 (m, 2H), 1.92-1.62 (m, 7H), 0.80 (t, J=7.2 Hz, 3H); LCMS [ESI, M+1]: 621.7.

Example 58

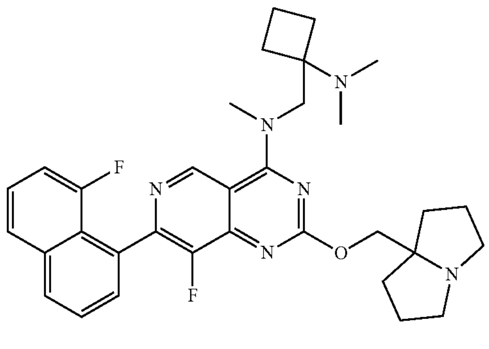

N-((1-(dimethylamino)cyclobutyl)methyl)-8-fluoro-7-(8-fluoronaphthalen-1-yl)-N-methyl-2-((tetrahydro-1H-pyrrolizin-7a(5H)-yl)methoxy)pyrido[4, 3-d]pyrimidin-4-amine

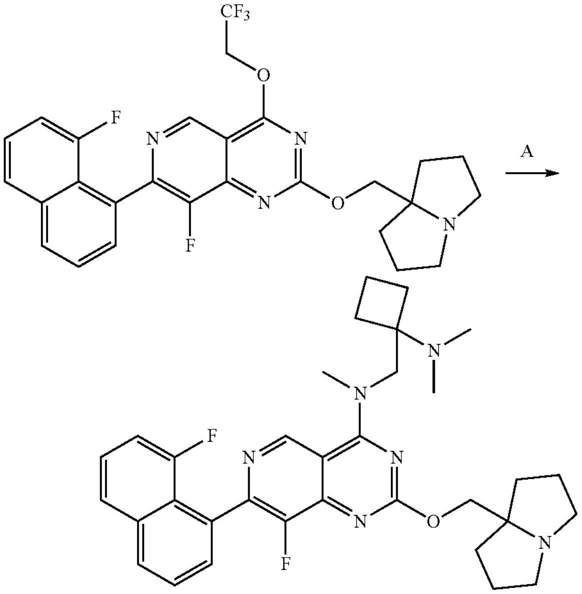

Step A. N-((1-(dimethylamino)cyclobutyl)methyl)-8-fluoro-7-(8-fluoronaphthalen-1-yl)-2-((hexahydro-1H-pyrrolizin-7a-yl)methoxy)-N-methylpyrido[4,3-d]pyrimidin-4-amine. To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 μmol, 1.0 eq), 4 Å molecular sieve (50.0 mg) and N,N-dimethyl-1-(methylaminomethyl)cyclobutanamine (40.2 mg, 283 μmol, 1.5 eq) in DMF (2.0 mL) was added DIEA (73.1 mg, 565 μmol, 98.5 μL, 3.0 eq). The mixture was stirred at 60° C. for 2 hours. After completion, the reaction mixture was diluted with $H_2O$ (10 mL) and extracted with ethyl acetate (3×10 mL). The combined organic layers were washed with saturated brine (20 mL), dried over $Na_2SO_4$, filtered and concentrated under reduced pressure to give a residue. The filtrate was purified by prep-HPLC (column: Waters Xbridge 150*25 mm*5 μm; mobile phase: [water (10 mM $NH_4HCO_3$)-ACN]; B %: 28%-58%, 10 min) and lyophilized affording the title compound (31.4 mg, 29% yield). White solid; $^1H$ NMR (400 MHz, $CDCl_3$) δ 9.18 (s, 1H), 7.98 (dt, J=2.0, 7.6 Hz, 1H), 7.77-7.70 (m, 1H), 7.66-7.57 (m, 2H), 7.46-7.40 (m, 1H), 7.13-7.09 (m, 1H), 4.44-4.34 (m, 1H), 4.27-4.18 (m, 2H), 4.17-4.08 (m, 1H), 3.70 (s, 3H), 3.15-3.04 (m, 2H), 2.67-2.58 (m, 2H), 2.32 (s, 6H), 2.24-2.14 (m, 2H), 2.12-2.02 (m, 2H), 2.02-1.94 (m, 2H), 1.88-1.78 (m, 6H), 1.69-1.60 (m, 2H); LCMS [ESI, M+1]: 573.3.

Example 59

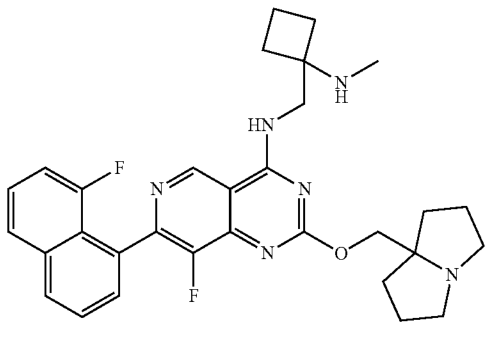

8-fluoro-7-(8-fluoronaphthalen-1-yl)-2-((hexahydro-lH-pyrrolizin-7a-yl)methoxy)-N-((1-(methylamino)cyclobutyl)methyl)pyrido[4, 3-d] pyrimidin-4-amine

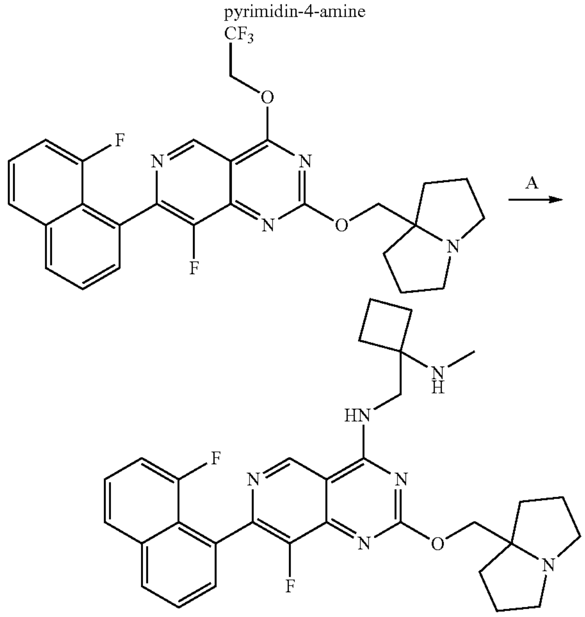

Step A: 8-fluoro-7-(8-fluoronaphthalen-1-yl)-2-((hexahydro-1H-pyrrolizin-7a-yl)methoxy)-N-((1-(methylamino) cyclobutyl)methyl)pyrido[4,3-d]pyrimidin-4-amine. To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 μmol, 1.0 eq), 4 Å molecular sieve (50.0 mg) and 1-(aminomethyl)-N-methyl-cyclobutanamine (21.5 mg, 188 μmol, 1.0 eq) in DMF (2.0 mL) was added DIEA (31.7 mg, 245 μmol, 42.7 μL, 1.3 eq). The mixture was stirred at 15° C. for 1 hour. After completion, the reaction mixture was diluted with $H_2O$ (10 mL) and extracted with ethyl acetate (3×10 mL). The combined organic layers were washed with saturated brine (20 mL), dried over $Na_2SO_4$, filtered and concentrated under reduced pressure to give a residue. The filtrate was purified by prep-HPLC (column: Waters Xbridge 150*25 mm*5 μm; mobile phase: [water (10 mM $NH_4HCO_3$)-ACN]; B %: 28%-58%, 10 min) and lyophilized affording the title compound (47.5 mg, 46% yield). White solid; $^1H$ NMR (400 MHz, $CDCl_3$) δ 8.88 (s, 1H), 7.98 (dt, J=1.6, 8.4 Hz, 1H), 7.76-7.70 (m, 1H), 7.65-7.59 (m, 1H), 7.58-7.53 (m, 1H), 7.48-7.39 (m, 1H), 7.13-7.08 (m, 1H), 7.01 (br s, 1H), 4.27 (s, 2H), 3.72 (d, J=3.6 Hz, 2H), 3.17-3.07 (m, 2H), 2.70-2.60 (m, 2H), 2.30 (s, 3H), 2.17-2.10 (m, 2H), 2.07-1.98 (m, 2H), 1.97-1.81 (m, 8H), 1.72-1.65 (m, 2H). [ESI, M+1]: 545.2.

Example 60

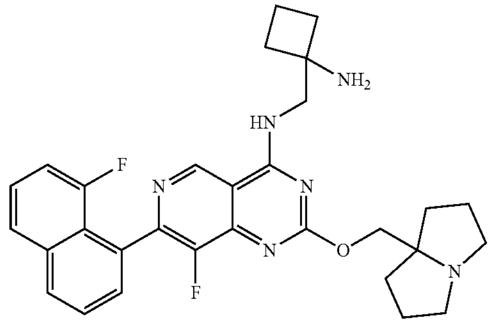

N-1((1-aminocyclobutl)methyl)-8-fluoro-7-(8-fluoronaphthalen-1-yl)-2-((hexahydro-1H-pyrrolizin-7a-yl)methoxy)pyrido[4,3-d]pyrimidin-4-amine

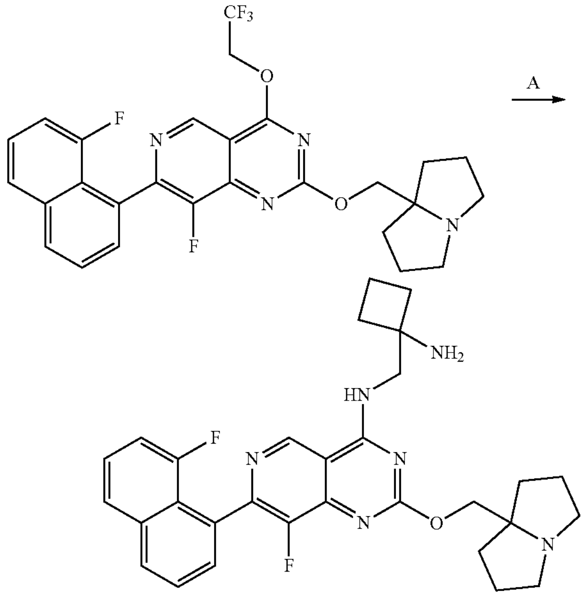

Step A. N-((1-aminocyclobutyl)methyl)-8-fluoro-7-(8-fluoronaphthalen-1-yl)-2-((hexahydro-1H-pyrrolizin-7a-yl) methoxy)pyrido[4,3-d]pyrimidin-4-amine. To a solution of 8-fluoro-7-(8-fluoronaphthalen-1-yl)-2-((hexahydro-1H-pyrrolizin-7a-yl)methoxy)-4-(2,2,2-trifluoroethoxy)pyrido [4,3-d]pyrimidine (100 mg, 188 μmol, 1.00 eq), 4 Å molecular sieve (50.0 mg) and 1-(aminomethyl)cyclobutanamine (32.6 mg, 188 μmol, 1.00 eq, 2HCl) in DMF (1.0 mL) was added DIEA (36.5 mg, 283 μmol, 49.2 μL, 1.50 eq). The mixture was stirred at 20° C. for 4 hours. After completion, the reaction mixture was filtered. The filtrate was purified by prep-HPLC (column: Shim-pack C18 150*25*10 μm; mobile phase: [water (0.225% FA)-ACN]; B %: 10%-30%, 10 min) and lyophilized affording the title compound (37.5 mg, 31% yield, 1.4 FA). White solid; $^1H$ NMR (400 MHz, methanol-$d_4$) δ=9.29 (s, 1H), 8.13 (d, J=8.0 Hz, 1H), 7.86 (d, J=8.0 Hz, 1H), 7.74-7.68 (m, 1H), 7.60 (dd, J=1.2, 7.2 Hz, 1H), 7.57-7.51 (m, 1H), 7.25-7.13 (m, 1H), 4.69 (s, 2H), 4.22-4.04 (m, 2H), 3.73-3.64 (m, 2H), 3.29-3.22 (m, 2H), 2.45-2.28 (m, 6H), 2.27-2.13 (m, 4H), 2.13-2.05 (m, 4H). [ESI, M+1]: 531.

Example 61

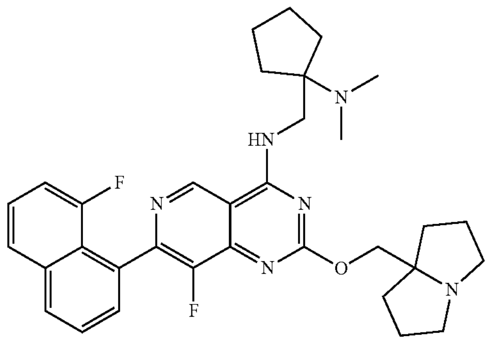

N-((1-(dimethylamino)cyclopentyl)methyl)-8-fluoro-7-(8-fluoronaphthalen-1-yl)-2-((hexahydro-1H-pyrrolizin-7a-yl)methoxy)pyrido[4,3-d]pyrimidin-4-amine

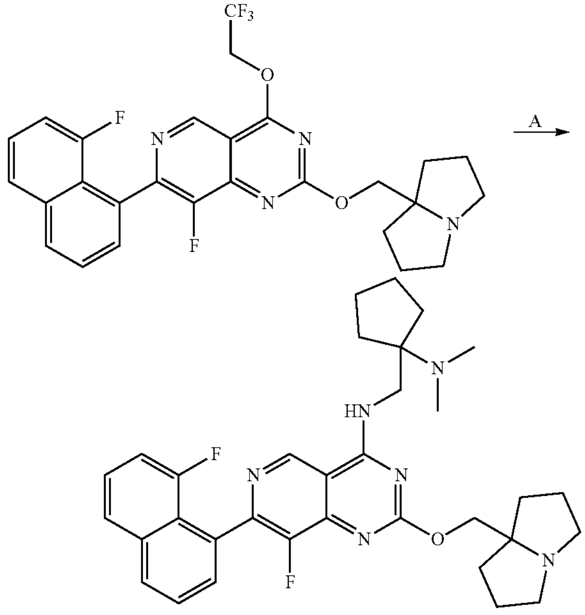

Step A. N-((1-(dimethylamino)cyclopentyl)methyl)-8-fluoro-7-(8-fluoronaphthalen-1-yl)-2-((hexahydro-1H-pyrrolizin-7a-yl)methoxy)pyrido[4,3-d]pyrimidin-4-amine. To a solution of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 μmol, 1.00 eq), 4 Å molecular sieve (50.0 mg) and 1-(aminomethyl)-N,N-dimethyl-cyclopentanamine (53.6 mg, 377 μmol, 2.00 eq) in DMF (2.0 mL) was added DIEA (73.1 mg, 565 μmol, 98.5 μL, 3 eq). The mixture was stirred at 40° C. for 2 hours. After completion, the reaction mixture was filtered. The filtrate was purified by prep-HPLC (column: Shim-pack C18 150*25*10 μm; mobile phase: [water (0.225% FA)–ACN]; B %: 11%-31%, 10 min) and lyophilized affording the title compound (46.7 mg, 38% yield, 1.3 FA). Yellow solid; $^{1}H$ NMR (400 MHz, methanol-$d_4$) δ=9.32 (s, 1H), 8.12 (d, J=8.4 Hz, 1H), 7.86 (d, J=8.0 Hz, 1H), 7.75-7.68 (m, 1H), 7.60 (dd, J=1.2, 7.2 Hz, 1H), 7.57-7.50 (m, 1H), 7.25-7.14 (m, 1H), 4.67 (s, 2H), 4.10-3.96 (m, 2H), 3.71-3.59 (m, 2H), 3.29-3.20 (m, 2H), 2.75 (m, 6H), 2.36-2.26 (m, 2H), 2.25-2.04 (m, 6H), 2.03-1.90 (m, 4H), 1.89-1.80 (m, 4H); [ESI, M+1]: 573.0.

Example 62

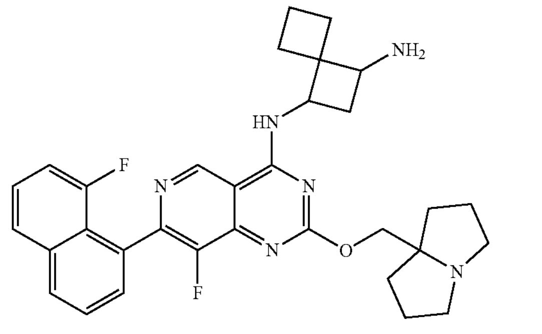

N$^{1}$-(8-fluoro-7-(8-fluoronaphthalen-1-yl)-2-((hexahydro-1H-pyrrolizin-7a-yl)methoxy)pyrido[4,3-d]pyrimidin-4-yl)spiro[3.3]heptane-1,3-diamine

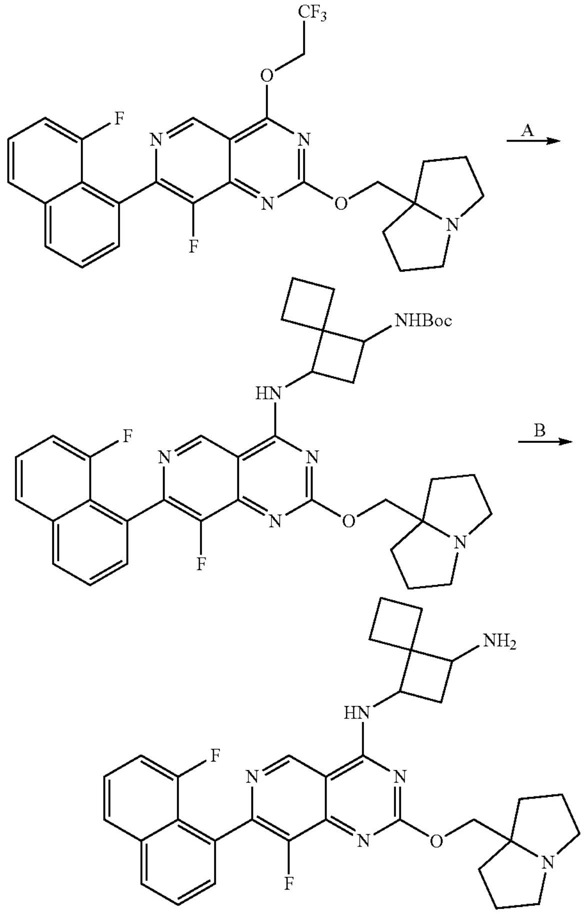

Step A. tert-butyl(3-((8-fluoro-7-(8-fluoronaphthalen-1-yl)-2-((hexahydro-1H-pyrrolizin-7a-yl)methoxy)pyrido[4,3-d]pyrimidin-4-yl)amino)spiro[3.3]heptan-1-yl)carbamate. To a mixture of 8-fluoro-7-(8-fluoronaphthalen-1-yl)-2-((hexahydro-1H-pyrrolizin-7a-yl)methoxy)-4-(2,2,2-trifluoroethoxy)pyrido[4,3-d]pyrimidine (100 mg, 188 μmol, 1.0 eq) and tert-butyl N-(1-aminospiro[3.3]heptan-3-yl)carbamate (51.2 mg, 226 μmol, 1.2 eq) in DMF (3 mL) was added DIEA (73.1 mg, 565 μmol, 98.5 μL, 3.0 eq) and 4 Å MS (100 mg) in one portion at 25° C. The mixture was heated to 40° C. and stirred for 12 hours under $N_2$. Upon completion, the mixture was filtered and the filtrate was concentrated in vacuum to give a residue. The residue was purified by reversed phase flash chromatography (0.1% FA condition) affording the title compound (80 mg, 65% yield). Yellow solid. [ESI, M+1]: 657.3.

Step B. $N^1$-(8-fluoro-7-(8-fluoronaphthalen-1-yl)-2-((hexahydro-1H-pyrrolizin-7a-yl)methoxy)pyrido[4,3-d]pyrimidin-4-yl)spiro[3.3]heptane-1,3-diamine. To a mixture of tert-butyl (3-((8-fluoro-7-(8-fluoronaphthalen-1-yl)-2-((hexahydro-1H-pyrrolizin-7a-yl)methoxy)pyrido[4,3-d]pyrimidin-4-yl)amino)spiro[3.3]heptan-1-yl)carbamate (70 mg, 106 μmol, 1.0 eq) and $CH_3CN$ (0.5 mL) was added HCl·dioxane (4 M, 0.5 mL, 18.7 eq) in one portion at 0° C. The mixture was stirred at 25° C. for 20 minutes under $N_2$. Upon completion, the mixture was concentrated in vacuum to give a residue. The mixture was purified by prep-HPLC (column: Phenomenex Luna C18 150*25 mm*10 μm; mobile phase: [water (0.225% FA)–ACN]; B %: 7%-37%, 11 min) affording the title compound (22.2 mg, 32% yield, 2 FA). White solid; $^1$H NMR (400 MHz, methanol-$d_4$) δ=9.39-9.36 (m, 1H), 8.14 (d, J=8.8 Hz, 1H), 7.87 (d, J=8.4 Hz, 1H), 7.76-7.71 (m, 1H), 7.61 (dd, J=0.8 Hz, 7.2 Hz, 1H), 7.57-7.51 (m, 1H), 7.24-7.16 (m, 1H), 5.14-4.69 (m, 2H), 4.67-4.60 (m, 1H), 3.73-3.36 (m, 3H), 3.29-3.25 (m, 2H), 2.74-2.66 (m, 1H), 2.57-2.40 (m, 1H), 2.32-2.20 (m, 3H), 2.19-2.07 (m, 8H), 2.01-1.76 (m, 3H). [ESI, M+1]: 557.2.

Example A

KRas G12D Surface Plasmon Resonance (SPR) Binding Assay

This Example illustrates that exemplary compounds of the present invention bind to KRas G12D as measured by surface plasmon resonance (SPR).

Briefly, 1 L of 1.05×HBS-Mg buffer (262.5 mM BioUltra Hepes, pH 7.5, 157.5 mM NaCl, 105 mM $MgCl_2$, 0.525 mM TCEP, 0.0305% Brij-35) was prepared and filter sterilized using a 0.22 μm bottle top filter. Approximately 50 mL of 1.05×HBS-Mg buffer was removed and saved for future dilutions. A 50 mL aliquot of DMSO (Sigma Aldrich DMSO Lot. #SHBK2079) was added and continued to stir for 10 minutes, creating the final 1.0×HBS-Mg buffer (250 mM BioUltra Hepes pH 7.5, 150 mM NaCl, 100 mM $MgCl_2$, 0.5 mM TCEP, 0.03% Brij-35).

Biacore T200 instrument was primed using 1.0×HBS-Mg buffer before docking a GE Streptavidin (SA) chip and then primed two additional times prior to beginning the immobilization step. All immobilized protein mixtures were created using 3-5 mg/mL Biotinylated Avidin-tagged KRAS protein using the following immobilization settings: SA chip type, 1 flow cells per cycle, 720 second contact time, and 5 μL/min flow rate. Normalization of the detector was also performed during the immobilization step using the GE BiaNormalize solution.

All compounds were diluted to 10 mM in 100% DMSO prior to being diluted 20× in 1.05× buffer. Another 10λ dilution was created using 1.0× buffer prior to performing a series of 3× dilutions to create a compound concentration curve using the following assay settings: 20 C analysis temperature, General Settings=10 Hz data collection rate and multi-detection; Assay Steps=all set to LMW kinetics; Cycle Types=LMW kinetics (60 s contact time, 120 s dissociation time, 100 μL/min flow rate, extra wash after injection with 50% DMSO, flow path 1,2,3,4); Flow path detection=2-1, 4-3). Data evaluation was performed using the Biacore T200 Evaluation software and data fit to 1:1 binding model.

The results for exemplary compounds of Formula (I) are shown in Table 1.

TABLE 1

Determination of KRas G12D $K_D$ for Exemplary Compounds of Formula (I)

| Example No. | $K_D$ (nM) |
|---|---|
| 1 | 14.7 |
| 7 | 12.2 |
| 8 | 66.8 |
| 36 | 135.2 |
| 52 | 0.04 |

Example B

KRas G12D Binding Assay

This Example illustrates that exemplary compounds of the present invention bind to KRas G12D and are capable of displacing a labeled tracer ligand occupying the KRas G12D binding site.

The ability of a compound to bind to KRAS G12D was measured using a TR-FRET displacement assay. Biotinylated GDP-loaded recombinant human KRAS G12D (corresponding to amino acids 1:169, produced at Array BioPharma Inc.) was incubated with a custom-made Cy5 labelled tracer, europium labelled streptavidin and compound (2% DMSO final) in buffer (50 mM HEPES [pH 7.5], 5 mM $MgCl_2$, 0.005% Tween-20 & 1 mM DTT). After a 60 minute incubation at 22° C., the reaction was measured using a PerkinElmer EnVision multimode plate reader via TR-FRET dual wavelength detection, and the percent of control (POC) calculated using a ratiometric emission factor. 100 POC is determined using no test compound and 0 POC is determined using a concentration of control compound that completely inhibits binding of the tracer to KRAS. The POC values were fit to a 4-parameter logistic curve and the $IC_{50}$ value was determined as the concentration where the curve crosses 50 POC.

The results for exemplary compounds of Formula (I) are shown in Table 2.

TABLE 2

Binding to KRas G12D by Exemplary Compounds of Formula (I)

| Example No. | $IC_{50}$ (nM) |
|---|---|
| 1 | 19.6 |
| 2 | 269.1 |
| 3 | 238.9 |
| 4 | 957.7 |
| 5 | 2258.9 |
| 6 | 117.0 |
| 7 | 10.0 |
| 8 | 39.9 |
| 9 | 2170.0 |
| 10 | 3721.0 |
| 11 | 98.0 |
| 12 | 100.0 |
| 13 | 165.0 |
| 14 | 306.1 |
| 15 | 3148.1 |
| 16 | 146.1 |
| 17 | 80.9 |

TABLE 2-continued

| Binding to KRas G12D by Exemplary Compounds of Formula (I) | |
|---|---|
| Example No. | $IC_{50}$ (nM) |
| 18 | 46.5 |
| 19 | 245.3 |
| 20 | 22.0 |
| 21 | 59.2 |
| 22 | 1319.2 |
| 23 | 582.9 |
| 24 | 954.2 |
| 25 | 1638.2 |
| 26 | 343.5 |
| 27 | 1879.0 |
| 28 | 609.2 |
| 29 | 62.8 |
| 30 | 1576.6 |
| 31 | 856.8 |
| 32 | 381.1 |
| 33 | 0.9 |
| 34 | 1.1 |
| 35 | 30.4 |
| 36 | 76.5 |
| 37 | 26.1 |
| 38 | 389.3 |
| 39 | 521.4 |
| 40 | 5148.9 |
| 41 | 684.3 |
| 42 | 210.9 |
| 43 | 1.1 |
| 44 | 0.7 |
| 45 | 0.4 |
| 46 | 0.7 |
| 47 | 513.1 |
| 48 | 1078.8 |
| 49 | 231.7 |
| 50 | 89.6 |
| 51 | 102.1 |
| 52 | 0.6 |
| 53 | 7158.9 |
| 54 | 79.3 |
| 55 | 938.2 |
| 56 | 2.6 |
| 57 | 1.1 |
| 58 | 9092.3 |
| 59 | 1032.4 |
| 60 | 2118.0 |
| 61 | 479.8 |
| 62 | 202.7 |

Example C

Inhibition of KRas G12D-mediated Phosphorylation of ERK by Exemplary Compounds of Formula (I)

This Example illustrates that exemplary compounds of the present invention inhibit the phosphorylation of ERK downstream of KRAS G12D.

AGS cells (ATCC CRL-1739) expressing G12D were grown in DMEM medium supplemented with 10% fetal bovine serum, 10 mM HEPES, and Penicillin/Streptomycin. Cells were plated in tissue culture treated 96 well plates at a density of 40,000 cells/well and allowed to attach for 12-14 hours. Diluted compounds were then added in a final concentration of 0.5% DMSO. After 3 hours, the medium was removed, 150 µl of 4.0% formaldehyde was added and the plates incubated at room temperature for 20 minutes. The plates were washed with PBS, and permeabilized with 150 µL of ice cold 100% methanol for 10 minutes. Non-specific antibody binding to the plates was blocked using 100 µL Licor blocking buffer (Li-Cor Biotechnology, Lincoln NE) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling cs-9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 both in Licor block+0.05% Tween20, and were incubated for 1 hour at room temperature. The plates were washed with PBS+0.05% Tween 20. A 100 µl aliquot of PBS was added to each well and the plates were read on a Li-Cor Odyssey CLX plate reader.

The phospho-ERK(Thr202/Tyr204 signal was normalized to the GAPDH signal for each well and percent of DMSO control values were calculated. IC50 values were generated using a 4-parameter fit of the dose response curve The results for exemplary compounds of Formula (I) are shown in Table 3. ND is not determined.

TABLE 3

| Inhibition of KRas G12D-mediated Phosphorylation of ERK by Exemplary Compounds of Formula (I) | |
|---|---|
| Example No. | $IC_{50}$ (nM) |
| 1 | 692.3 |
| 7 | 711.3 |
| 8 | >16666.7 |
| 17 | >16666.7 |
| 18 | >16666.7 |
| 20 | 2508.4 |
| 21 | >16666.7 |
| 29 | 1559.3 |
| 36 | 3288.6 |
| 43 | 53.5 |
| 44 | 220.2 |
| 45 | 38.3 |
| 46 | 38.7 |
| 50 | 10671.4 |
| 51 | >16666.7 |
| 52 | 12.0 |
| 54 | >16666.7 |
| 56 | 349.6 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound of Formula (I):

Formula (I)

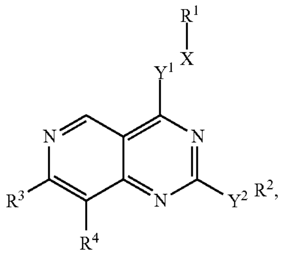

or pharmaceutically acceptable salt thereof, wherein:

$R^1$ is hydroxy, —$N(R^5)_2$, cycloalkyl, or heterocyclyl, wherein the cycloalkyl or the heterocyclyl is optionally substituted with one or more $R^X$;

X is a bond or C1-C4 alkylene;

$Y^1$ is O or $NR^5$;

$Y^2$ is a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(═NH)$NH_2$, -L-C(O)$N(R^5)_2$, -L-C1-C6 haloalkyl, -L-$OR^5$, -L-$NR^5$C(O)-aryl, or -L-COOH, wherein the heterocyclyl the aryl portion of -L-$NR^5$C(O)-aryl, the heterocyclyl portion of -L-heterocyclyl, and the cycloalkyl portion of the -L-cycloalkyl may each be optionally substituted with one or more $R^6$, and wherein the aryl or heteroaryl of the -L-aryl and the -L-heteroaryl may be optionally substituted with one or more $R^7$;

each L is independently a C1-C4 alkylene optionally substituted with hydroxy, C1-C4 hydroxyalkyl or heteroaryl;

$R^3$ is aryl or heteroaryl, wherein the aryl or the heteroaryl is optionally substituted with one or more $R^8$;

$R^4$ is hydrogen, halogen or C1-C3 alkyl;

each $R^5$ is independently hydrogen or C1-C3 alkyl;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2F$, —NHC(O)phenyl, —NHC(O)phenyl$SO_2F$, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(═O)—, oxo, (C1-C3 haloalkyl)C(═O)—, —$SO_2F$, (C1-C3 alkoxy)C1-C3 alkoxy, -L-OC(O)$N(R^5)_2$ or -L-OC(O)heterocyclyl;

each Q is independently a bond or O;

each $R^7$ is independently halogen, hydroxy, HC(═O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, cycloalkyl, C1-C3 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, or —S—C1-C3 haloalkyl; and each $R^X$ is independently C1-C3 alkyl, hydroxy, —$N(R^5)_2$, —$CH_2N(R^5)_2$, cyanomethyl, or heterocyclyl.

2. The compound or pharmaceutically acceptable salt according to claim 1, wherein $Y^1$ is $NR^5$.

3. The compound or pharmaceutically acceptable salt according to claim 1, wherein X is methylene or ethylene.

4. The compound or pharmaceutically acceptable salt according to claim 1, wherein $R^1$ is —$N(R^5)_2$.

5. The compound or pharmaceutically acceptable salt according to claim 1, wherein $R^1$ is cycloalkyl optionally substituted with one or more $R^X$.

6. The compound or pharmaceutically acceptable salt according to claim 5, wherein the cycloalkyl is cyclopropyl, cyclobutyl, cyclopentyl, cyclohexyl, or spiro[3.3]heptanyl each optionally substituted with one $R^X$.

7. The compound or pharmaceutically acceptable salt according to claim 6, wherein $R^X$ is —$N(R^5)_2$, hydroxy, C1-C3 alkyl, or heterocyclyl.

8. The compound or pharmaceutically acceptable salt according to claim 5, wherein the cycloalkyl is cyclobutyl.

9. The compound or pharmaceutically acceptable salt according to claim 1, wherein $R^1$ is heterocyclyl optionally substituted with one or more $R^X$.

10. The compound or pharmaceutically acceptable salt according to claim 9, wherein the heterocyclyl is azetidinyl, pyrrolidinyl, piperidinyl, piperazinyl, tetrahydropyranyl, 2-azabicyclo[3.1.0]hexanyl or diazapanyl, each optionally substituted with one or more $R^X$.

11. The compound or pharmaceutically acceptable salt according to claim 10, wherein the heterocyclyl is substituted with one $R^x$, wherein the one $R^X$ is hydroxy, C1-C3 alkyl, —$N(R^5)_2$, —$CH_2N(R^5)_2$, or cyanomethyl.

12. The compound or pharmaceutically acceptable salt according to claim 11, wherein the heterocyclyl is pyrrolidinyl and the one $R^X$ is C1-C3 alkyl.

13. The compound or pharmaceutically acceptable salt according to claim 11, wherein the heterocyclyl is azetidinyl and the one $R^X$ is hydroxyl.

14. The compound or pharmaceutically acceptable salt according to claim 11, wherein the heterocyclyl is tetrahydropyranyl and the one $R^X$ is —$N(R^5)_2$.

15. The compound or pharmaceutically acceptable salt according to claim 1, wherein X is a bond.

16. The compound or pharmaceutically acceptable salt according to claim 15, wherein $R^1$ is heterocyclyl optionally substituted with one or more $R^X$.

17. The compound or pharmaceutically acceptable salt according to claim 16, wherein the heterocyclyl is 3-azabicyclo[3.2.0]hexanyl.

18. The compound or pharmaceutically acceptable salt according to claim 1, wherein X is butylene and $R^1$ is hydroxy.

19. The compound or pharmaceutically acceptable salt according to claim 1, wherein $Y^1$ is O.

20. The compound or pharmaceutically acceptable salt according to claim 19, wherein X is a bond, and $R^1$ is heterocyclyl.

21. The compound or pharmaceutically acceptable salt according to claim 20, wherein the heterocyclyl is 3,8-diazabicyclo[3.2.1]octanyl.

22. The compound or pharmaceutically acceptable salt according to claim 1, wherein $Y^2$ is O.

23. The compound or pharmaceutically acceptable salt according to claim 22, wherein $R^2$ is -L-heterocyclyl optionally substituted with one or more $R^6$.

24. The compound or pharmaceutically acceptable salt according to claim 23, wherein L is methylene and the heterocyclyl is pyrrolidinyl or hexahydro-1H-pyrrolizinyl, each optionally substituted with one or more $R^6$.

25. The compound or pharmaceutically acceptable salt according to claim 24, wherein L is methylene and the heterocyclyl is pyrrolidinyl optionally substituted with one or more $R^6$.

26. The compound or pharmaceutically acceptable salt according to claim 25, wherein the pyrrolidinyl is optionally substituted with one $R^6$, wherein $R^6$ is C1-C3 alkyl.

27. The compound or pharmaceutically acceptable salt according to claim 24, wherein the heterocyclyl is hexahydro-1H-pyrrolizinyl optionally substituted with one or more $R^6$.

28. The compound or pharmaceutically acceptable salt according to claim 27, wherein the hexahydro-1H-pyrrolizinyl is optionally substituted with one $R^6$, wherein $R^6$ is halogen, -L-OC(O)N($R^5$)$_2$ or -L-OC(O)heterocyclyl.

29. The compound or pharmaceutically acceptable salt according to claim 28, wherein $R^6$ is halogen.

30. The compound or pharmaceutically acceptable salt according to claim 28, wherein $R^6$ is -L-OC(O)N($R^5$)$_2$, and wherein the -L- of the -L-OC(O)N($R^5$)$_2$ is methylene and each of the $R^5$ groups is C1-C3 alkyl.

31. The compound or pharmaceutically acceptable salt according to claim 28, wherein $R^6$ is -L-OC(O)heterocyclyl, and wherein the -L- of the -L-OC(O)heterocyclyl is methylene and the heterocyclyl portion is pyrrolidinyl or piperidinyl.

32. The compound or pharmaceutically acceptable salt according to claim 22, wherein $R^2$ is -L-heteroaryl optionally substituted with one or more $R^7$.

33. The compound or pharmaceutically acceptable salt according to claim 32, wherein L is ethylene and the heteroaryl is pyrazolyl substituted with one $R^7$.

34. The compound or pharmaceutically acceptable salt according to claim 1, wherein $R^3$ is aryl optionally substituted with one or more $R^8$.

35. The compound or pharmaceutically acceptable salt according to claim 34, wherein the aryl is naphthyl optionally substituted with one or more $R^8$.

36. The compound or pharmaceutically acceptable salt according to claim 35, wherein the naphthyl is substituted with one $R^8$, wherein the one $R^8$ is hydroxy, halogen, C1-C3 alkyl, C1-C3 haloalkyl, cycloalkyl, C2-C4 alkenyl or C2-C4 alkynyl.

37. The compound or pharmaceutically acceptable salt according to claim 35, wherein the naphthyl is substituted with two $R^8$, wherein one $R^8$ is hydroxy and the other $R^8$ is C1-C3 alkyl, halogen or C2-C4 alkynyl, or one $R^8$ is halogen and the other $R^8$ is C1-C3 alkyl or C2-C4 alkynyl.

38. The compound or pharmaceutically acceptable salt according to claim 35, wherein the naphthyl is substituted with three $R^8$, wherein the first $R^8$ is hydroxy, the second $R^8$ is halogen and the third $R^8$ is C1-C3 alkyl or C2-C4 alkynyl.

39. The compound or pharmaceutically acceptable salt according to claim 34, wherein the aryl is phenyl optionally substituted with one or more $R^8$.

40. The compound or pharmaceutically acceptable salt according to claim 39, wherein the phenyl is substituted with one $R^8$, wherein the $R^8$ is C1-C3 alkyl.

41. The compound or pharmaceutically acceptable salt according to claim 39, wherein the phenyl is substituted with two $R^8$, wherein one $R^8$ is halogen and the other $R^8$ is C1-C3 alkyl.

42. The compound or pharmaceutically acceptable salt according to claim 39, wherein the phenyl is substituted with two $R^8$, wherein one $R^8$ is halogen and the other $R^8$ is cycloalkyl.

43. The compound or pharmaceutically acceptable salt according to claim 1, wherein $R^3$ is heteroaryl.

44. The compound or pharmaceutically acceptable salt according to claim 43, wherein the heteroaryl is indazolyl optionally substituted with one or more $R^8$.

45. The compound or pharmaceutically acceptable salt according to claim 44, wherein the indazolyl is substituted with two $R^8$, wherein one $R^8$ is halogen and the other $R^8$ is C1-C3 alkyl.

46. The compound or pharmaceutically acceptable salt according to claim 1, wherein $R^4$ is halogen.

47. The compound or pharmaceutically acceptable salt according to claim 46, wherein the halogen is fluorine.

48. A compound or pharmaceutically acceptable salt, wherein the compound is:

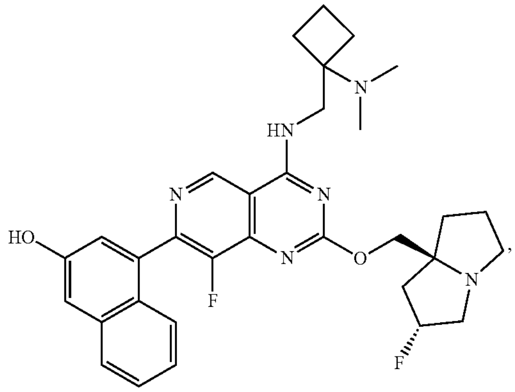

,

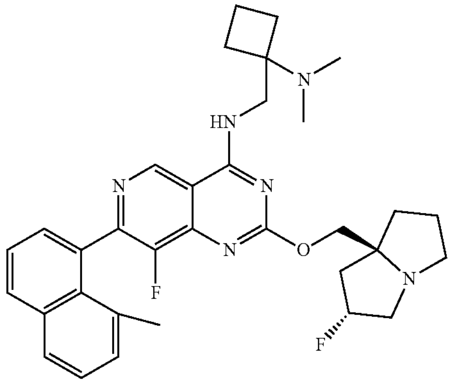

,

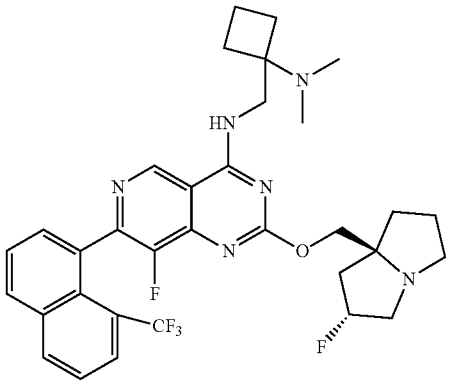

,

-continued
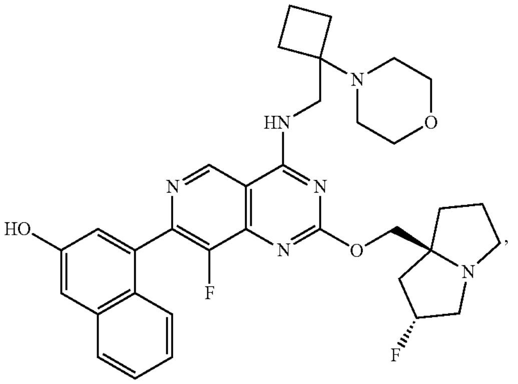
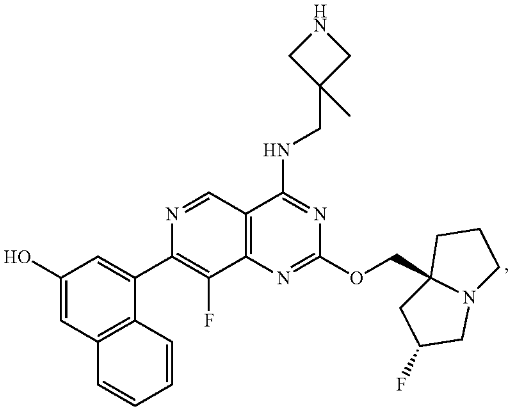
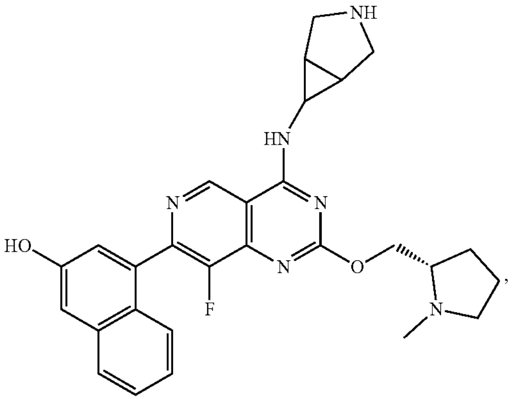
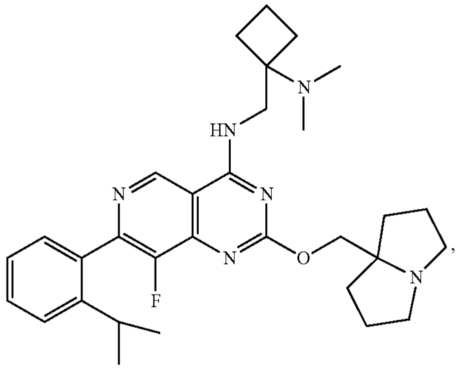
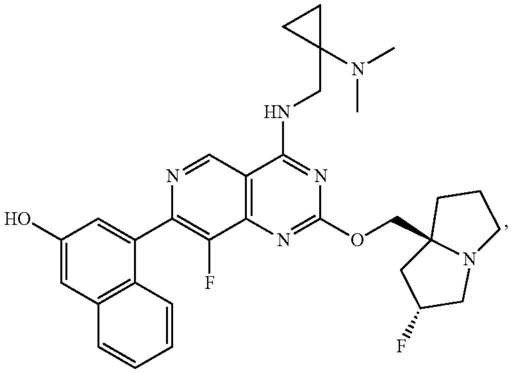
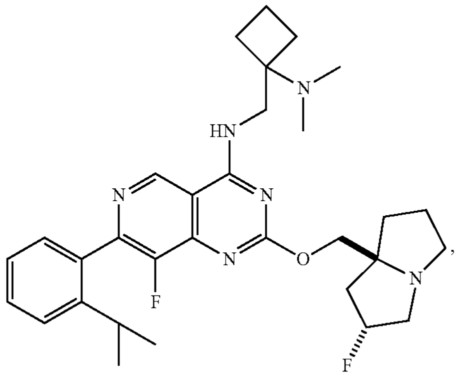
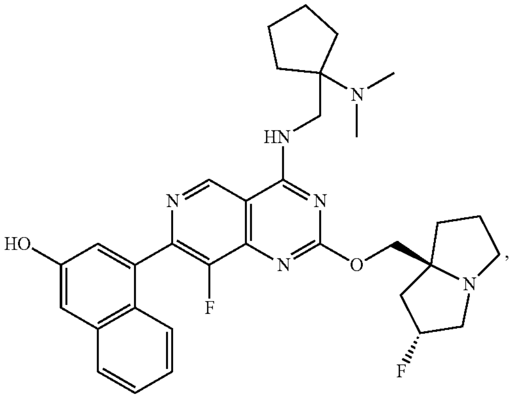
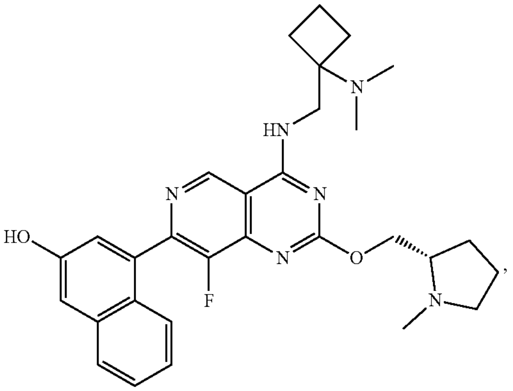
-continued -continued
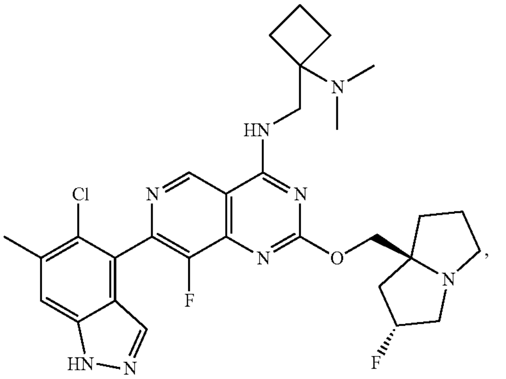
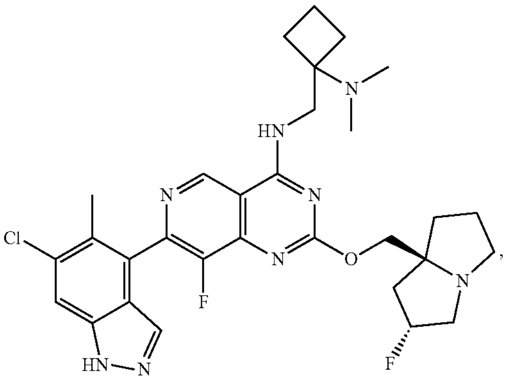
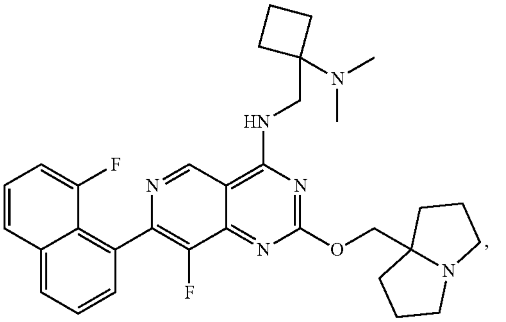
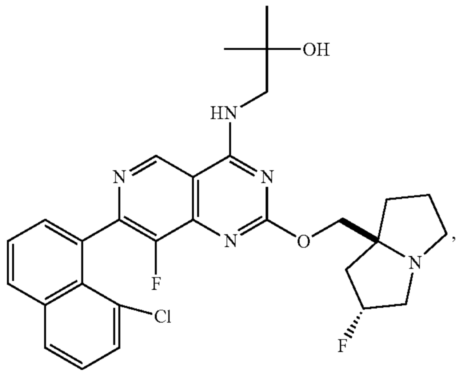
-continued
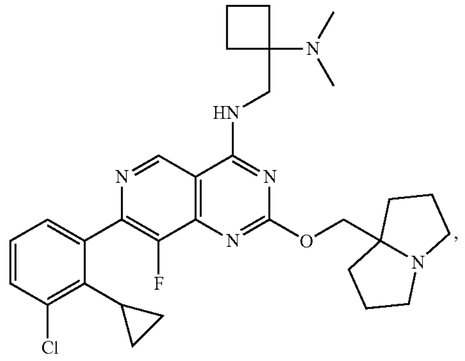
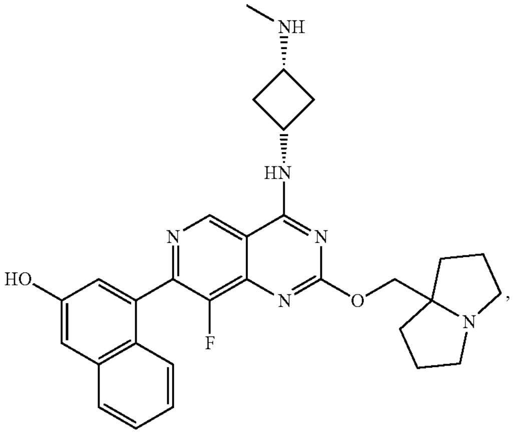
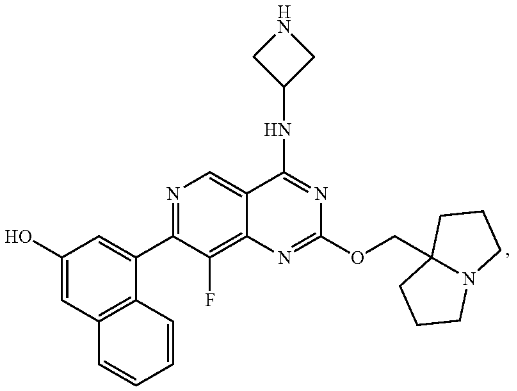
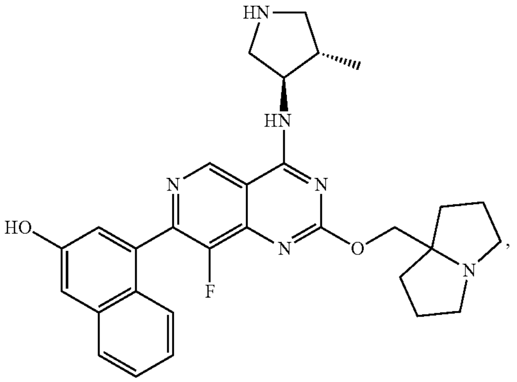

-continued
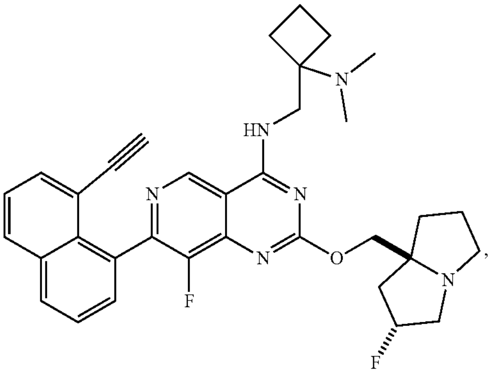
,
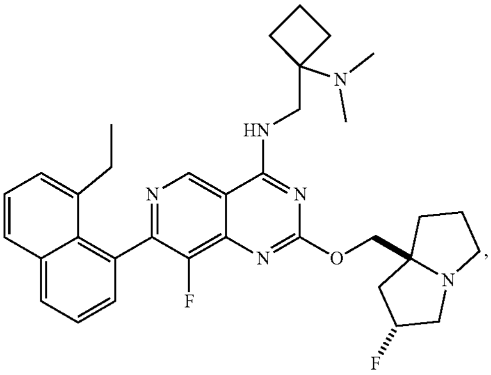
,
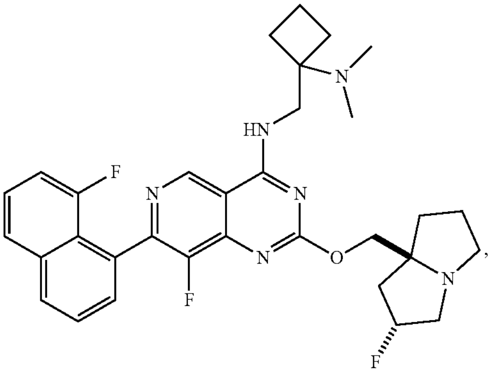
,
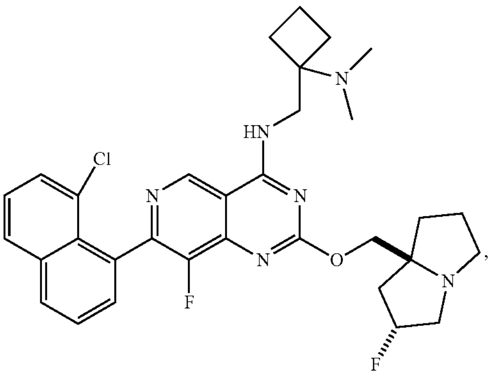
,
-continued
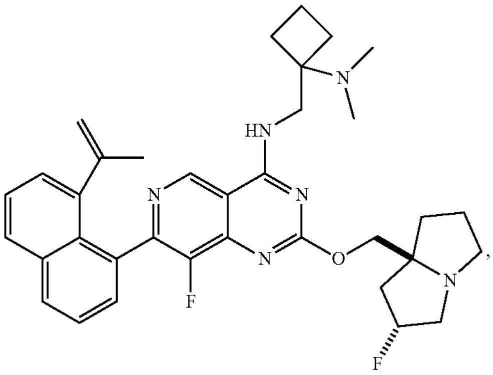
,
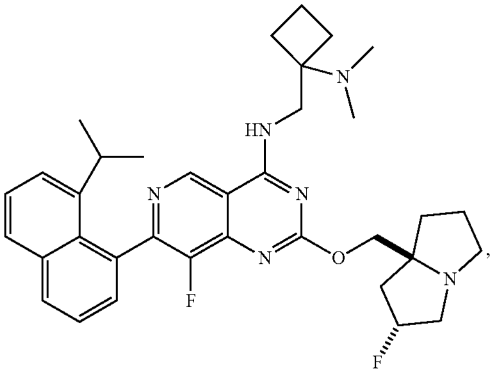
,
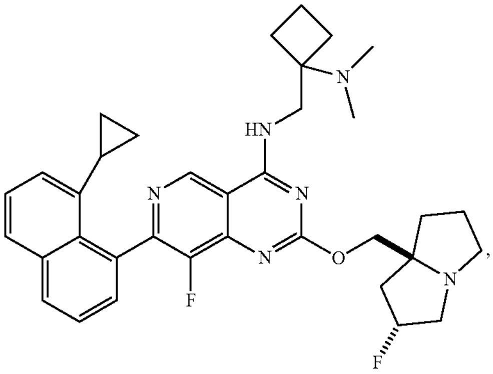
,
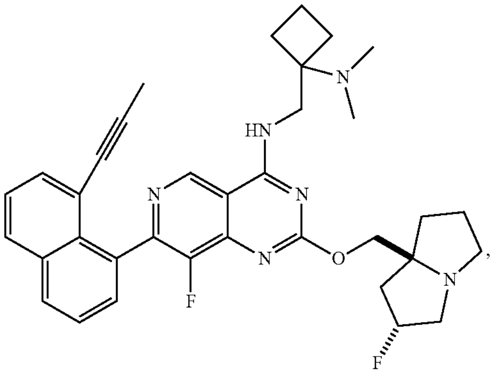
, -continued
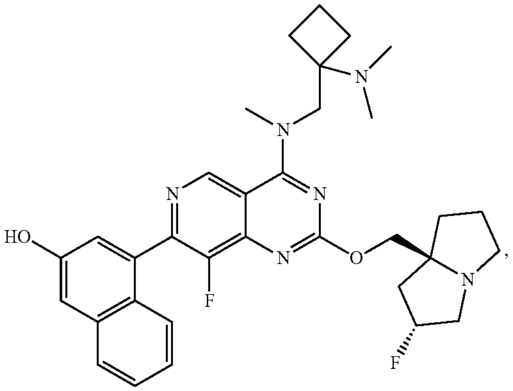,
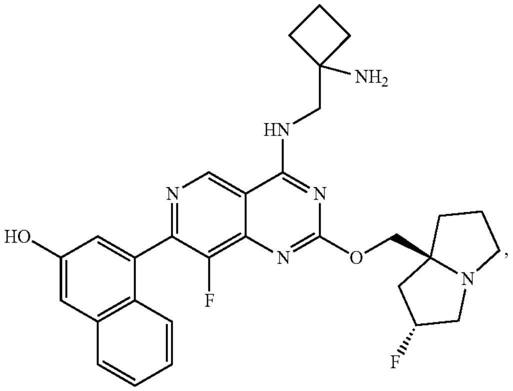,
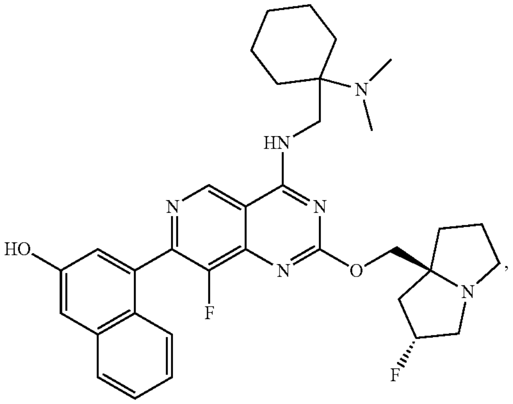,
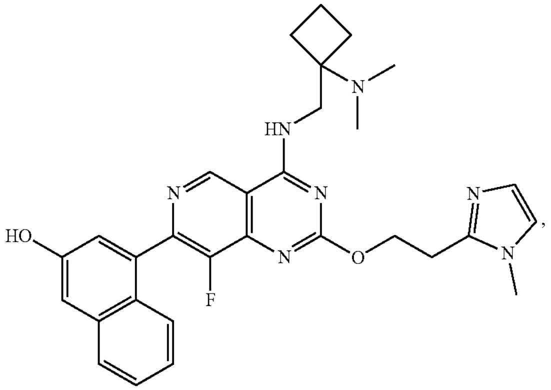,
-continued
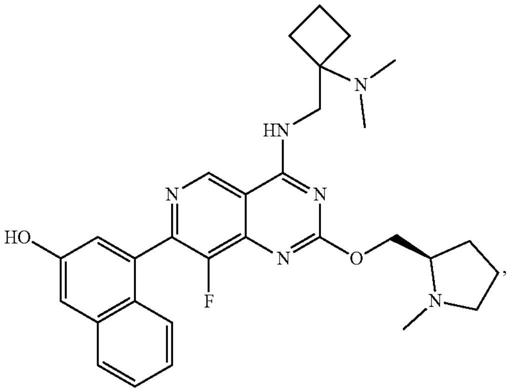,
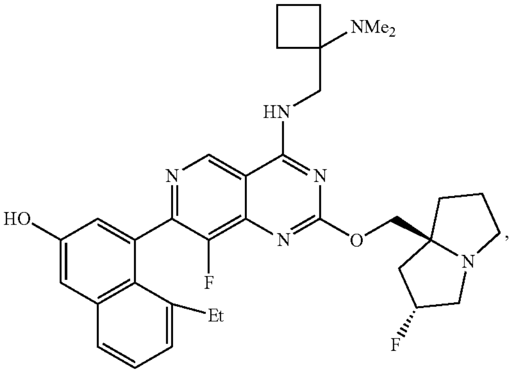,
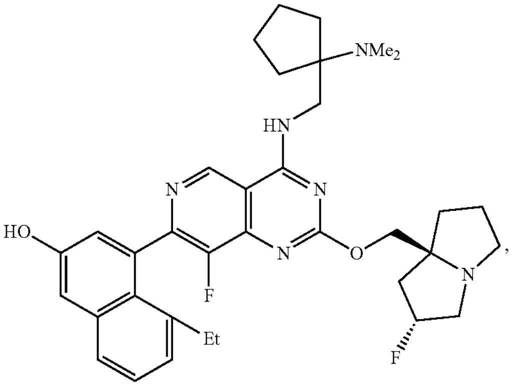,
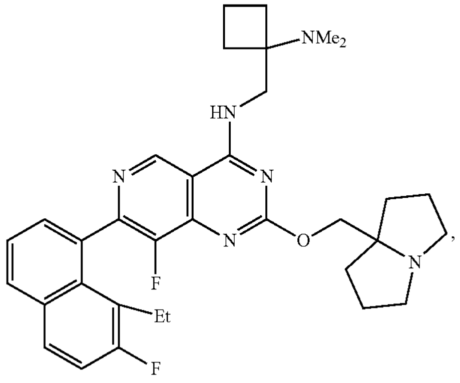, -continued
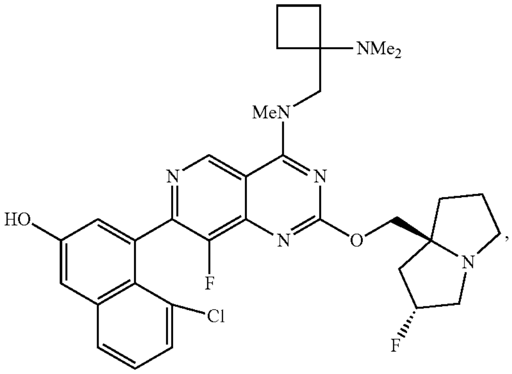,
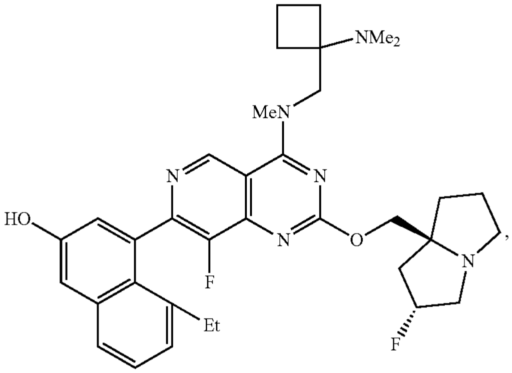,
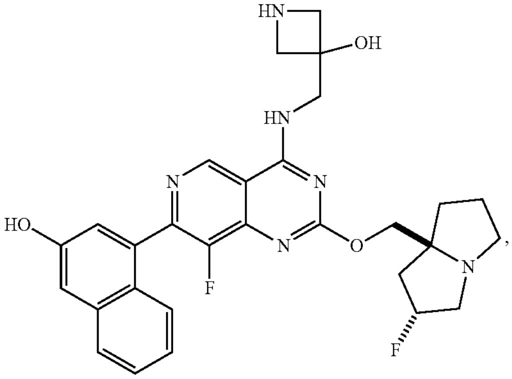,
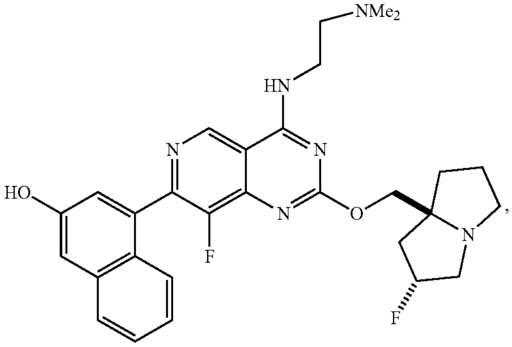,
-continued
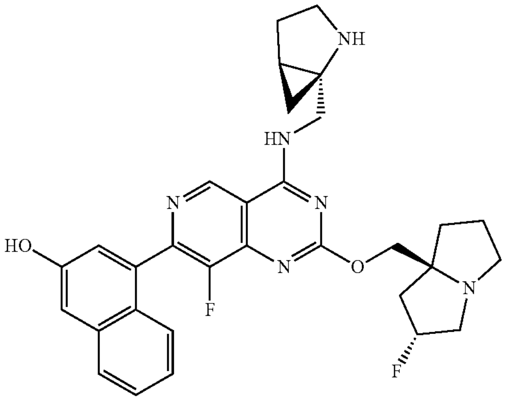,
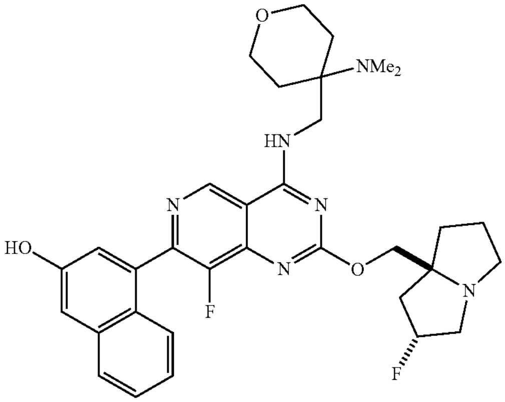,
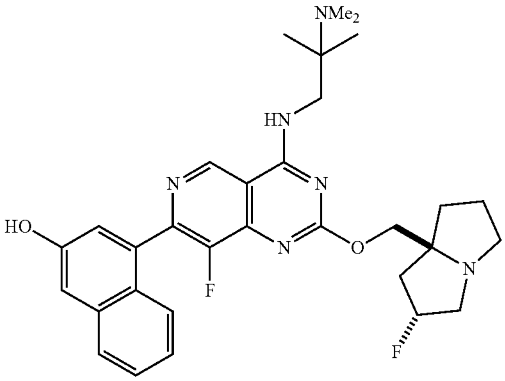,
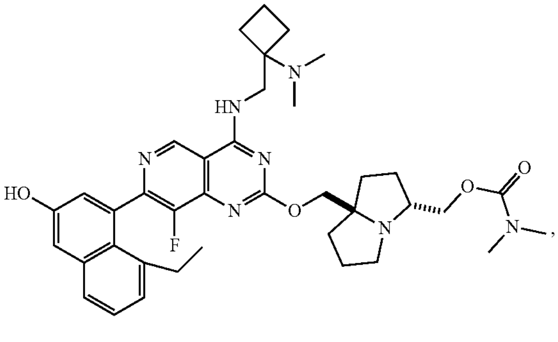, -continued
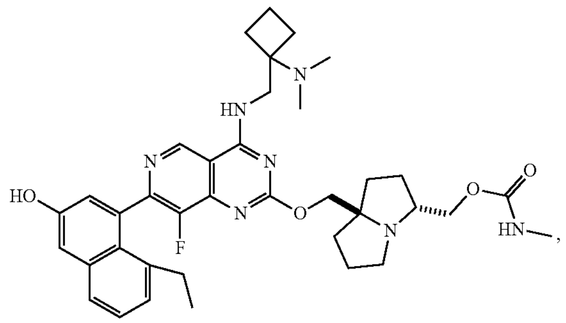
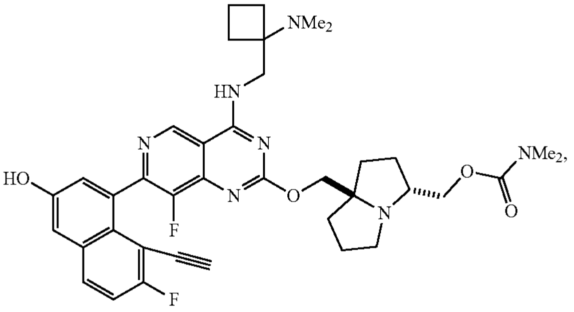
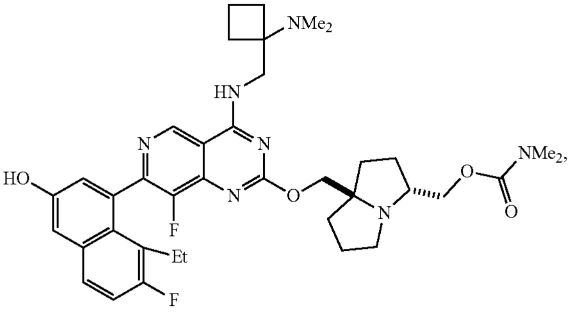
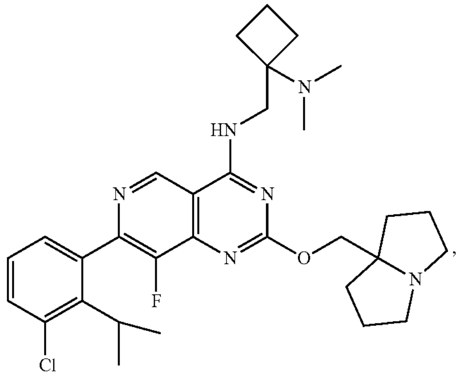
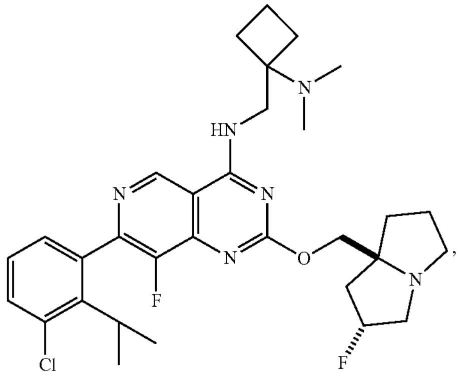
-continued
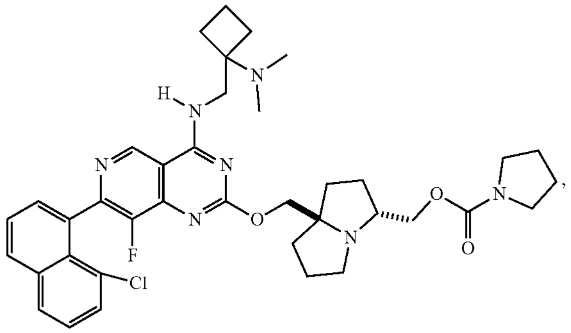
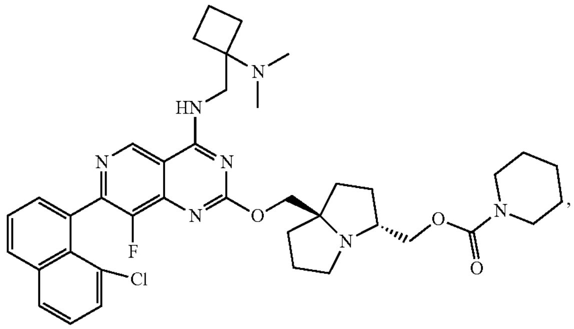
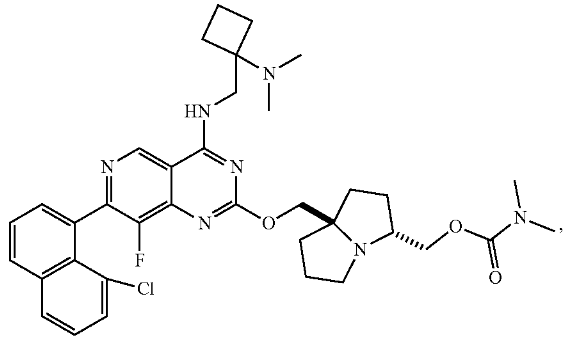
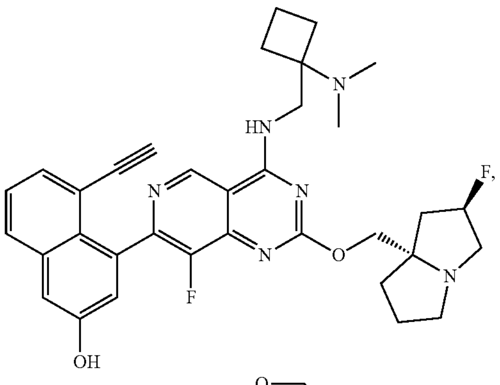
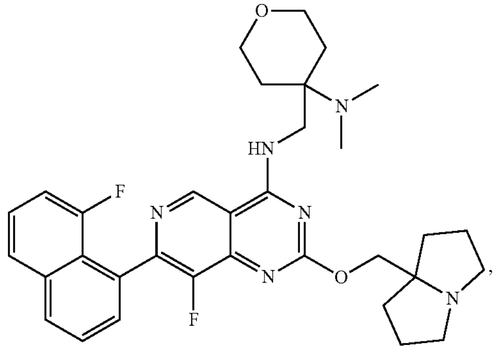

-continued
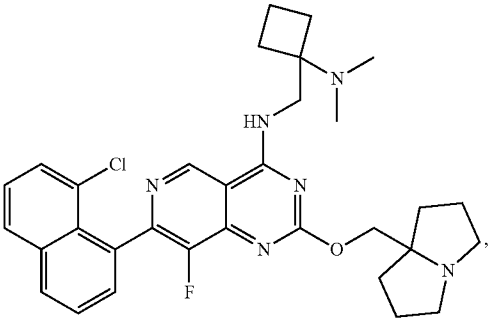
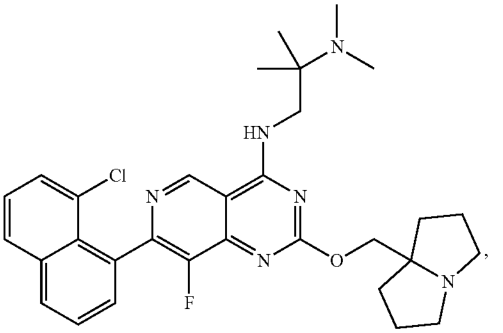
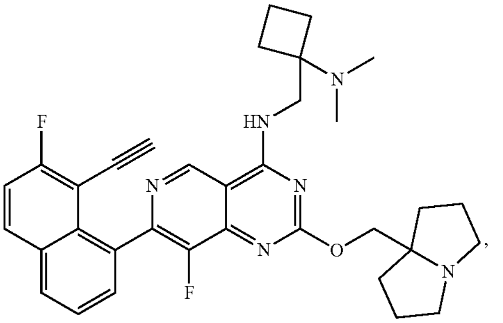
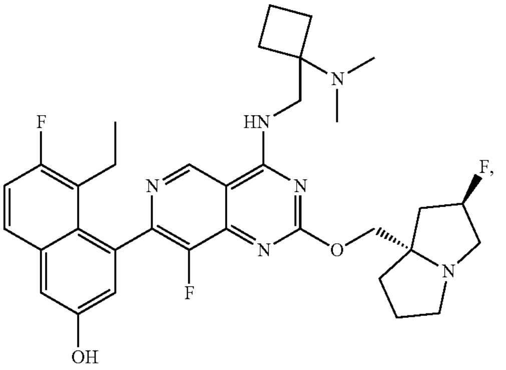
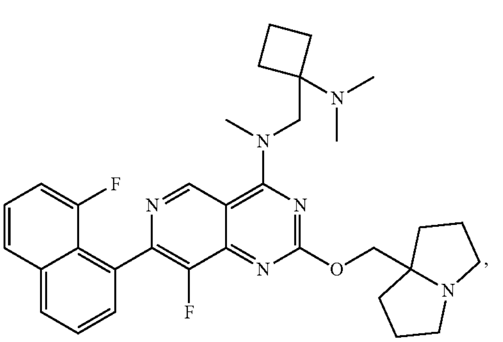
-continued
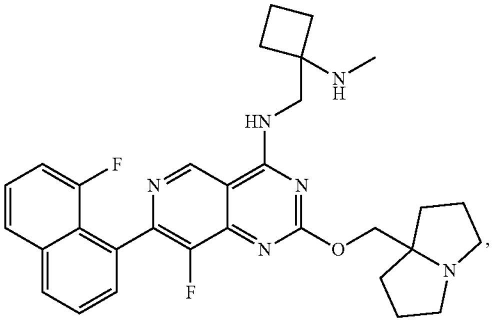
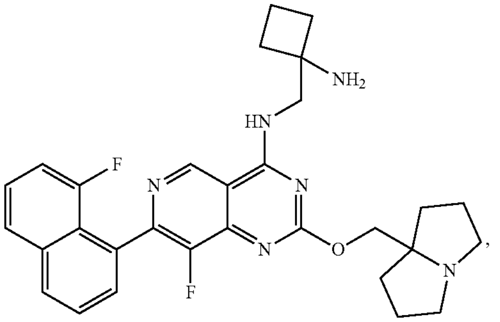
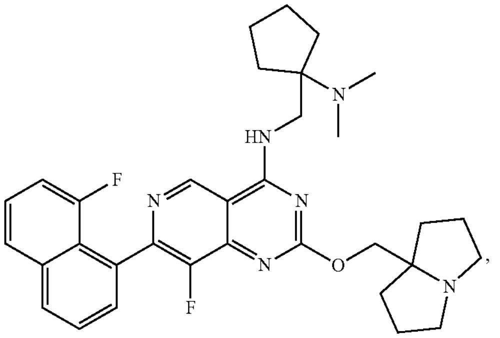
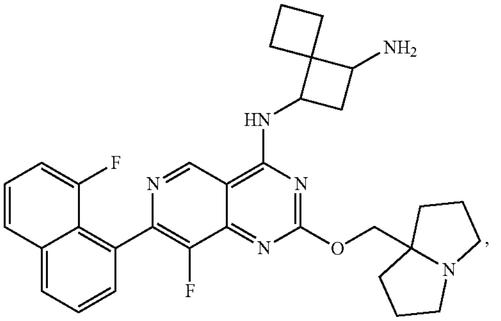
or
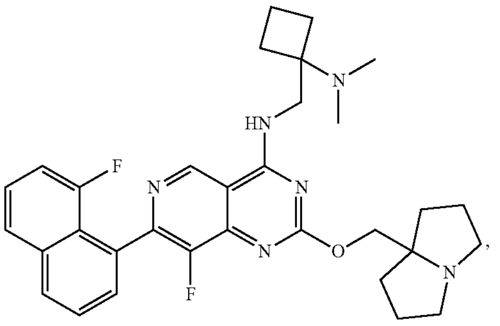
or a pharmaceutically acceptable salt thereof.

49. A pharmaceutical composition, comprising a therapeutically effective amount of a compound of claim 1 or a pharmaceutically acceptable salt thereof, and a pharmaceutically acceptable excipient.

50. A method for inhibiting KRas G12D activity in a cell, comprising contacting the cell in which inhibition of KRas G12D activity is desired with an effective amount of a compound of according to claim 1 or a pharmaceutically acceptable salt thereof.

* * * * *